United States Patent
Crooks et al.

(10) Patent No.: US 12,297,452 B2
(45) Date of Patent: *May 13, 2025

(54) METHODS OR GENERATING T-CELLS FROM STEM CELLS AND IMMUNOTHERAPEUTIC METHODS USING THE T-CELLS

(71) Applicant: The Regents of the University of California, Oakland, CA (US)

(72) Inventors: Gay M. Crooks, Sherman Oaks, CA (US); Amélie Montel-Hagen, Los Angeles, CA (US); Christopher Seet, Santa Monica, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 655 days.

This patent is subject to a terminal disclaimer.

(21) Appl. No.: 17/478,875

(22) Filed: Sep. 17, 2021

(65) Prior Publication Data

US 2022/0096553 A1 Mar. 31, 2022

Related U.S. Application Data

(63) Continuation of application No. 15/772,224, filed as application No. PCT/US2016/059375 on Oct. 28, 2016, now Pat. No. 11,154,573.

(60) Provisional application No. 62/359,456, filed on Jul. 7, 2016, provisional application No. 62/265,204, filed on Dec. 9, 2015, provisional application No. 62/248,931, filed on Oct. 30, 2015.

(51) Int. Cl.
| | | |
|---|---|---|
| *C12N 5/00* | (2006.01) | |
| *A61K 39/00* | (2006.01) | |
| *A61P 35/00* | (2006.01) | |
| *C07K 14/705* | (2006.01) | |
| *C12N 5/0735* | (2010.01) | |
| *C12N 5/074* | (2010.01) | |
| *C12N 5/077* | (2010.01) | |
| *C12N 5/0775* | (2010.01) | |
| *C12N 5/0783* | (2010.01) | |

(52) U.S. Cl.
CPC ........ *C12N 5/0062* (2013.01); *A61K 39/4611* (2023.05); *A61K 39/4631* (2023.05); *A61K 39/4632* (2023.05); *A61K 39/4644* (2023.05); *A61P 35/00* (2018.01); *C07K 14/705* (2013.01); *C12N 5/00* (2013.01); *C12N 5/0037* (2013.01); *C12N 5/0606* (2013.01); *C12N 5/0636* (2013.01); *C12N 5/0663* (2013.01); *C12N 5/0669* (2013.01); *C12N 5/0696* (2013.01); *C07K 2317/622* (2013.01); *C07K 2319/03* (2013.01); *C12N 2500/22* (2013.01); *C12N 2500/24* (2013.01); *C12N 2500/32* (2013.01); *C12N 2500/38* (2013.01); *C12N 2500/90* (2013.01); *C12N 2501/125* (2013.01); *C12N 2501/145* (2013.01); *C12N 2501/15* (2013.01); *C12N 2501/2302* (2013.01); *C12N 2501/2304* (2013.01); *C12N 2501/2306* (2013.01); *C12N 2501/2307* (2013.01); *C12N 2501/2315* (2013.01); *C12N 2501/2321* (2013.01); *C12N 2501/25* (2013.01)

(58) Field of Classification Search
None
See application file for complete search history.

(56) References Cited

U.S. PATENT DOCUMENTS

| | | |
|---|---|---|
| 5,389,640 A | 2/1995 | Gerster et al. |
| 6,110,929 A | 8/2000 | Gerster et al. |
| 6,331,539 B1 | 12/2001 | Crooks et al. |
| 6,451,810 B1 | 9/2002 | Coleman et al. |
| 7,795,404 B1 | 9/2010 | Lin et al. |
| 8,021,867 B2 | 9/2011 | Smith et al. |
| 8,377,886 B2 | 2/2013 | Susztak et al. |
| 10,350,243 B2 | 7/2019 | Zakrzewski et al. |
| 2003/0109042 A1 | 6/2003 | Wu et al. |
| 2004/0171086 A1 | 9/2004 | Fink et al. |
| 2004/0171148 A1 | 9/2004 | Schmitt et al. |
| 2005/0123522 A1 | 6/2005 | Punnonen et al. |
| 2006/0073591 A1 | 4/2006 | Abitorabi et al. |
| 2009/0253622 A1 | 10/2009 | Van Noort et al. |
| 2010/0279403 A1 | 11/2010 | Rajesh et al. |
| 2011/0052554 A1 | 3/2011 | Zakrzewski et al. |
| 2011/0236363 A1 | 9/2011 | Chang et al. |
| 2015/0299656 A1 | 10/2015 | Gattinoni et al. |
| 2018/0155688 A1 | 6/2018 | Seet et al. |

(Continued)

FOREIGN PATENT DOCUMENTS

| | | |
|---|---|---|
| EP | 2906684 | 7/2020 |
| JP | 2012-509659 | 4/2012 |
| WO | 98/30679 | 7/1998 |

(Continued)

OTHER PUBLICATIONS

Office Action issued in corresponding Mexican Application No. MX/a/2018/005274 dated Apr. 21, 2023.

(Continued)

*Primary Examiner* — Michail A Belyavskyi
(74) *Attorney, Agent, or Firm* — Norton Rose Fulbright US LLP

(57) ABSTRACT

Methods and composition for production of T cells are provided. Also provided are therapeutic methods using engineered T cells. For example, in certain aspects methods include preparing three dimensional cell culture compositions comprising stroma cells and hematopoietic stem or progenitor cells in a serum-free medium for producing T cells.

10 Claims, 134 Drawing Sheets
Specification includes a Sequence Listing.

(56) References Cited

U.S. PATENT DOCUMENTS

2019/0231817 A1  8/2019  Crooks et al.

FOREIGN PATENT DOCUMENTS

| WO | 2000/076518 | 12/2000 |
|---|---|---|
| WO | 2007/027226 | 3/2007 |
| WO | 2011/101468 | 8/2011 |
| WO | 2011/131944 | 10/2011 |
| WO | 2012/027017 | 3/2012 |
| WO | 2014/138315 | 9/2014 |
| WO | WO 2014/186469 | 11/2014 |

OTHER PUBLICATIONS

Zeleniak, et al., "A tissue-engineered artificial human thymus from human iPSCs to study T cell immunity", *Nat. Methods*, vol. 19, pp. 1191-1192, 2022.
Chen et al., "The role of BCL11B in regulating the proliferation of human naive T cells," *Human Immunology* 2012, 73(5), 456-464.
Ellmeier et al., "Transcriptional control of CD4 and CD8 coreceptor expression during T cell development," *Cell. Mol. Life Sci.* 2013, 18 pages.
Ha et al., "The T-ALL related gene BCL11B regulates the initial stages of human T-cell differentiation," *Leukemia* 2017, 31, 2503-2514.
Ho et al., "CD4-CD8αα Subset of CD1d-Restricted NKT Cells Controls T Cell Expansion," *J Immunol* 2004; 172:7350-7358.
International Search Report and Written Opinion issued in Corresponding PCT Application No. PCT/US2020/039414, date Sep. 8, 2020.
Li et al., "Molecular Analysis of T-lineage Commitment: a possible role for Bcl11b," *The FASEB Journal* 2008, 22(S1), 844.6-844.6.
Office Action issued in Corresponding Eurasian Application No. 201891059, dated Mar. 28, 2022 (English Translation provided).
Permatasari et al., "BCL11B is frequently downregulated in HTLV-1-infected T-cells through Tax-mediated proteasomal degradation" *Biochemical and Biophysical Research Communications* 2017, 490(3), 1086-1092.
Sakamaki et al., "Bcl11b SWI/SNF-complex subunit modulates intestinal adenoma and regeneration after y-irradiation through Wnt/β-catenin pathway" *Carcinogenesis* 2015, 36(6):622-31.
Seet et al., "Generation of mature T cells from human hematopoietic stem/progenitor cells in artificial thymic organoids" *Nat Methods* 2017, 14(5): 521-530.
Brile, C. et al., "Engineering the human thymic microenvironment to support thymopoiesis in vivo", *Stem Cells*, 32(9), pp. 2386-2396, 2014.
Office Action issued in corresponding Canadian Application No. 3003145, dated Sep. 27, 2023.
Alexopoulou, et al., "Recognition of Double-Stranded RNA and Activation of NF-KB by Toll-Like Receptor 3," *Nature*, 413 (6857), pp. 732-738. (2001).
Anderson et al., "Cellular Interactions in Thymocyte Development" *Annu Rev. Immunol.*, 1996,14:73-99.
Awong et al., "Human CD8 T cells generated in vitro from hematopoietic stem cells are functionally mature" *BMC Immunol*, 2011, 12:22.
Balan, et al., "Human XCR 1 + Dendritic Cells Derived in Vitro from CD34+ Progenitors Closely Resemble Blood Dendritic Cells, Including Their Adjuvant Responsiveness, Contrary to Monocyte-Derived Dendritic Cells," *The Journal of Immunology*, 193(4); 1622-1635, 2014.
Baurain, et al., "High Frequency of Autologous Anti-Melanoma CTL Directed Against an Antigen Generated by a Point Mutation in a New Helicase Gene," *Journal of Immunology*, 164 pp. 6057-6066. (2000).
Brandle, et al., "A Mutated HLA-A2 Molecule Recognized by Autologous Cytotoxic T Lymphocytes on a Human Renal Cell Carcinoma," *Journal of Experimental Medicine*, 183, pp. 2501-2508. (1996).

Calvo, Julien et al., Assessment of Human Multi-Potent Hematopoietic Stem/Progenitor Cell Potential Using a Single In Vitro Screening System. *PLOS One*, vol. 7, Issue 11, pp. 1-12, (2012).
Caminschi, et al., "The Dendritic Cell Subtype-Restricted C-type Lectin Clec9 A is a Target for Vaccine Enhancement," *Blood*, 112(8), pp. 3264-3273. (2008).
Cheever, et al., "The Prioritization of Cancer Antigens: A National Cancer Institute Pilot Project for the Acceleration of Translational Research," *Clinical Cancer Research*, 15(17), pp. 5323-5337. (2009).
Chen et al., "NS21: re-defined and modified supplement B27 for neuronal cultures" *J. Neurosci Methods*, 2008, 171(2):239-247.
Cheng, et al., "Notch Signaling in Differentiation and Function of Dendritic Cells," *Immunologic Research*, 41(1), pp. 1-14. (2008). NIH Public Access Author Manuscript Retrieved from https://www.ncbi.nlm.nih.gov/pmc/articles/PMC2709100/pdf/nihms13342.pdf.
Chiari, et al., "Two Antigens Recognized by Autologous Cytolytic T Lymphocytes on a Melanoma Result from a Single Point Mutation in an Essential Housekeeping Gene," *Cancer Research*, 59, pp. 5785-5792. (1999).
Chung et al., "Engineering the human thymic microenvironment to support thymopoiesis in vivo", *Stem Cells*, 32(9):2386-2396, (2014).
Corbiere, et al., "Antigen Spreading Contributes to MAGE Vaccination-Induced Regression of Melanoma Metastases," *Cancer Research*, 71, pp. 1253-1262. (2011).
Coulie, et al., "A Mutated Intron Sequence Codes for an Antigenic Peptide Recognized by Cytolytic T Lymphocytes on a Human Melanoma," *Proceedings of the National Academy of Sciences of the United States of America*, 92(17), pp. 7976-7980. (1995).
Dallas et al., "Density of the Notch Ligand Delta1 determines generations of B and T cell precursors from hematopoietic stem cells", *The Journal of Experimental Medicine*, 201(9):1361-1366, (2005).
De Smedt et al., "T-lymphoid differentiation potential measured in vitro is higher in CD34 +cn38-1o hematopoietic stem cells from umbilical cord blood than from bone marrow and is an intrinsic property of the cells" *Haematologica*, 2011, 96(5):646-654.
Deniger, et al., "Bispecific T-Cells Expressing Polyclonal Repertoire of Endogenous γδ T-Cell Receptors and Introduced CD19-Specific Chimeric Antigen Receptor," *Molecular Therapy*, 21(3): 638-647, 2013.
Echchakir, et al., "A Point Mutation in the a-Actinin-4 Gene Generates an Antigenic Peptide Recognized by Autologous Cytolytic T Lymphocytes on a Human Lunch Carcinoma," *Cancer Research*, 61, pp. 4078-4083. (2001).
European Search Report Issued in European Application No. 16797322.1, dated Sep. 28, 2018.
Evseenko et al., "Mapping the first stages of mesoderm commitment during differentiation of human embryonic stem cells" *Proc Natl Acad Sci U.S.A.*, 2010, 107(31):13742-7.
Extended European Search report issued in European Patent Application No. 16860902, Mar. 22, 2019.
Gaudin, et al., "A hsp70-2 Mutation Recognized by CTL on a Human Renal Cell Carcinoma," *Journal of Immunology*, 162(3), pp. 1730-1738. (1999).
Hogan, et al., "The Peptide Recognized by HLA-A68.2-Restricted, Squamous Cell Carcinoma of the Lung-Specific Cytotoxic T Lymphocytes is Derived From a Mutated Elongation Factor 2 Gene1 ," *Cancer Research*, 58, pp. 5144-5150. (1998).
Huang, et al., "T Cells Associated with Tumor Regression Recognize Frameshifted Products of the CDKN2A Tumor Suppressor Gene Locus and a Mutated HLA Class I Gene Product," *Journal of Immunology*, 172(10), pp. 6057-6064. (2005).
International Preliminary Report on Patentability Issued in Corresponding PCT Application No. PCT/US2016/033339, mailed Nov. 21, 2017.
International Search Report and Written Opinion Issued in Corresponding PCT Application. No. PCT/US2016/033339, mailed Sep. 6, 2016.
International Search Report and Written Opinion issued in International Application No. PCT/US2016/059375, dated Feb. 8, 2017.
Itoh, K., et al., Reproducible Establishment of Hemopoietic Supportive Stromal Cell Lines from Murine Bone Marrow. Exp. Hematol., vol. 17, pp. 145-153 (1989).

(56) References Cited

OTHER PUBLICATIONS

Karanikas, et al., "High Frequency of Cytolytic T Lymphocytes Directed Against a Tumor-Specific Mutated Antigen Detectable with HLA Tetramers in the Blood of a Lunch Carcinoma Patient with Long Survival," *Cancer Research*, 61, pp. 3718-3724. (2001).
Kawakami, et al., "Isolation of a New Melanoma Antigen, MART-2, Containing a Mutated Epitope Recognized by Autologous Tumor-Infiltrating T Lymphocytes," *Journal of Immunology*, 166, pp. 2871-2877. (2001).
Kokatla, et al., "Structure-Based Design of Novel Human Toll-Like Receptor 8 Antagonists," *ChemMedChem*, 9(4), pp. 719-723. (2014). NIH Public Access Author Manuscript Retrieved from https://www.ncbi.nlm.nih.gov/pmc/articles/PMC4105021/pdf/nihms-577383.pdf.
LaMott-Mohs, et al., "Induction of T-Cell Development from Human Cord Blood Hematopoietic Stem Cells by Delta-like 1 In Vitro," *Blood*, 105( 4 ), pp. 1431-1439. (2005).
Lee et al., "Restricted Dendritic Cell and Monocyte Progenitors in Human Cord Blood and Bone Marrow," *Journal of Experimental Medicine*, 212(3), pp. 385-399. (2015).
Lei, et al., "Aire-Dependent Production of XCL 1 Mediates Medullary Accumulation of Thymic Dendritic Cells and Contributes to Regulatory T Cell Development," *Journal of Experimental Medicine*, 208(2), pp. 383-394. (2011).
Lennerz, et al., "The Response of Autlogous T Cells to a Human Melanoma is Dominated by Mutated Neoantigens," *Proceedings of the National Academy of Sciences of the United States of America*, 102(44), pp. 16013-16018. (2005).
Lu & Robbins, "Cancer Immunotherapy Targeting Neoantigens," Seminars Immunol., 28(1), pp. 22-27. (2016). Retrieved from HHS Public Access, Author Manuscript Retrieved from https://www.ncbi.nlm.nih.gov/pmc/articles/PMC4862880/pdf/nihms-737023.pdf.
Lu, et al., "Mutated PPP1R3B is Recognized by T Cells Used to Treat a Melanoma Patient Who Experienced a Durable Complete Tumor Regression," *Journal of Immunology*. 190, pp. 6034-6042. (2013).
Ludwig et al., "Derivation of human embryonic stem cells in defined conditions," *Nat Biotechnol*, 2006, 24(2):1S5-7.
Ludwig et al., "Feeder-independent culture of human embryonic stem cells," *Nat Methods*, 3(S):637-646.
Mandruzzato, et al., "A CASP-8 Mutation Recognized by Cytolytic T Lymphocytes on a Human head and Neck Carcinoma," *Journal of Experimental Medicine*, 186, pp. 785-793. (1997).
Manning J., et al., Vitamins C Promotes Maturation of T-Cells. *Antioxidants & Redox Signaling*, vol. 19, No. 17, pp. 2054-2067 (2013).
Martin, et al., "Differences in Lymphocyte Developmental Potential Between Human Embryonic Stem Cell and Umbilical Cord Blood-Derived Hematopoietic Progenitor Cells," *Blood*, 112(7): 2730-2737, 2008.
Mori, K., et al., Development of Stromal Cell Colonies in Bone Marrow Cell Culture. *Gann*, Vo. 69, pp. 689-693, (1978).
Novellino., et al., "Identification of a Mutated Receptor-Like Protein Tyrosine Phosphatase K as a Novel, Class II HLA-Restricted Melanoma Antigen," *Journal of Immunology*, 170(12), pp. 6363-6370. (2003).
Office Action Issued in Corresponding Eurasian Patent Application No. 201891059, dated Apr. 30, 2021.
Office Action Issued in Corresponding Japanese Patent Application No. 2018-522655, dated Nov. 30, 2020.
Ohishi, et al., "The Notch Ligand, Delta-1, Inhibits the Differentiation of Monocytes in Macrophages but Permits Their Differentiation into Dendritic Cells," *Blood*, 98(5), pp. 1402-1407. (2001).
Olivier, et al., "The Notch Ligand Delta-1 is a Hematopoietic Development Cofactor for Plasmacytoid Dendritic Cells," *Blood*, 107(7), pp. 2694-2701. (2006).
Palucka & Banchereau, "Cancer Immunotherapy Via Dendritic Cells," *Nature Reviews Cancer*, 12( 4 ), pp. 265-277. (2012). NIH Public Access Author Manuscript Retrieved from https://wwwncbi.nlm.nih.gov/pmc/articles/PMC3433802/pdf/nihms397786.pdf.

Pieper, et al., "Biochemical Identification of a Mutated Human Melanoma Antigen Recognized by CD4+ T Cells," *Journal of Experimental Medicine*, 189(5), pp. 757-765. (1999).
Poulin, et al., "Characterization of Human DNGR-1 + BDCA +Leukocytes as Putative Equivalents of Mouse CD8a+ Dendritic Cells," *Journal of Experimental Medicine*, 207(6), pp. 1261-1271. (2010).
Poznansky et al., "Efficient generation of human T cells from a tissue-engineered thymic organoid" *Nature Biology*, 2000, 18:729-734.
Proietto, et al., "The Equivalents in Human Blood and Spleen Dendritic Cell Subtypes can be Generated In Vitro from Human Stem Cells in the Presence of FMS-Like Tyrosine Kinase 3 Ligand and Thrombopoietin," *Cellular & Molecular Immunology*, 9, pp. 446-454. (2012).
Robbins, et al., "A Mutated Beta-Catenin Gene Encodes a Melanoma-Specific Antigen Recognized by Tumor Infiltrating Lymphocytes," *Journal of Experimental Medicine*, 183(3), pp. 1185-1192. (1996).
Schmitt et al., "Induction of T Cell Development from Hematopoietic Progenitor Cells by Delta-like-1 In Vitro" *Immunity*, 2002, 17:749-756.
Search Report Issued in Corresponding Singapore Patent Application No. 11201803419P, dated Oct. 2, 2019.
Seet et al., "Artificial Thymic Organoids permit Allelic Exclusion and Efficient Generation of Naive TCR-Engineered T-Cells from Human Hematopoietic Stem Cells In Vitro" *Blood*, 2016, 128:4553.
Sensi, et al., "Immunogenicity Without Immunoselection, A Mutant but Functional Antoxidant Enzyme Retained in a Human Metastatic Melanoma and Targeted by CDS8+ T Cells with a Memory Phenotype," *Cancer Research*, 65(2), pp. 632-640. (2005).
Singapore Written Opinion dated Jul. 19, 2021 issued in Singapore Application No. 11201803419P.
Smith, et al., "Genetic Engineering of Hematopoietic Stem Cells to Generate Invariant Natural Killer T Cells," *PNAS*, 112(5): 1523-1528, 2015.
Snauwaert et al., "In vitro generation of mature, naive antigen-specific CD8+ T cells with a single T-cell receptor by agonist selection" *Leukemia*, 2014, 28:830-841.
Sotiropoulou, et al., "Characterization of the Optimal Culture Conditions for Clinical Scale Production of Human Mesenchymal Stem Cells," *Stem Cell*, 24: 462-471, 2006.
Takenoyama, et al., "A Point Mutation in the NFYC Gene Generates an Antigenic Peptide Recognized by Autlogous Cytolytic T Lymphocytes on a Human Squamous Cell Lung Carcinoma," *International Journal of Cancer*, 118, pp. 1992-1997. (2006).
Tebas et al., "Antiviral effects of autologous CD4 T cells genetically modified with a conditionally replicating lentiviral vector expressing long antisense to HIV", *Blood*, 121(9):1524-1533, (2013).
Themeli et al., "New Cell Sources for T Cell Engineering and Adoptive Immunotherapy," *Cell Stem Cell*, 2015, 16(4):357-366.
Thordadottir, et al., "The Aryl Hydrocarbon Receptor Antagonist StemReginin 1 Promotes Human Plasmacytoid and Myeloid Dendritic Cell Development from CD34 Hematopoietic Progenitor Cells," *Stem Cells and Development*, 23(9), pp. 955-967. (2014).
Tullett, et al., "Harnessing Human Cross-Presenting CLEC9A+ XRC1 + Dendritic Cells for Immunotherapy," *Frontiers in Immunology*, 5(239), pp. 1-4. (2014).
Van Coppernolle et al., "Functionally Mature CD4 and CD8 TCRab Cells are Generated in OP9-DL1 Cultures from Human CD34+ Hematopoietic Cells" *J. Immunol*, 2009, 183(8):4859-70.
Van Der Aa, et al., "BDCA3+CLEC9A+ Human Dendritic Cell Function and Development," *El Sevier, Seminars in Cell & Developmental Biology*, 41, pp. 39-48.(2014).
Vatakis, et al., "Introduction to Exogenous T-Cell Receptors in Human Hematopoietic Progenitors Results in Exclusion of Endogenous T-Cell Receptor Expression," *Molecular Therapy*, 21(5): 1055-6063, 2013.
Viardot, et al., "Potential Antiinflammatory Role of Insulin Via the Preferential Polarization of Efffector T Cells Toward a T Helper 2 Phenotype," *Endocrinology*, 148(1): 346-353, 2007.
Vigneron, et al., "Identification of a New Peptide Recognized by Autologous Cytolytic T Lymphocytes on a Human Melanoma,"

(56) References Cited

OTHER PUBLICATIONS

*Cancer Immunity*, 2, pp. 9. (2002). Retrieved from https://pdfs.sematicscholar.org/b9lc/57a60dfc33ed4d5103e25277b204dcc9e3e0.pdf.

Wang, et al., "Cloning Genes Encoding MHC Class II-Restricted Antigens: Mutated CDC27 As a Tumor Antigen," *Science*, 284, pp. 1351-1354. (1999).

Wang, et al., "Identification of a Mutated Fibronectin As a Tumor Antigen Recognized by CD4+T Cells," *Journal of Experimental Medicine*, 195(11), pp. 1397-1406. (2002).

Wolfel, et al., "A p16INK4a-Insensitive CDK4 Mutant Targeted by Cytolytic T Lymphocytes in a Human Melanoma," *Science*, 269(5228), pp. 1281-1284. (1995).

Written Opinion Issued in Corresponding Singapore Patent Application No. 11201803419P, dated Oct. 16, 2019.

Yost, et al., "Defined, Serum-Free Conditions for In-Vitro Culture of Primary Human T-ALL Blasts," *Leukemia*, 27(6): 1437-1440, 2013.

Yui et al., "Developmental gene networks: a triathlon on the course to T cell identity" *Nature Reviews Immunology*, 2014, 14(8):529-545.

Zeng, et al., "Human Dendritic Cells Derived From Embryonic Stem Cells Stably Modified With CD1d Efficiently Stimulate Anti-tumor Invariant Natural Killer T Cell Response," *Stem Cell Translational Medicine*, 3: 69-80, 2014.

Zhou, et al., "Diverse CD8+ T-Cell Responses to Renal Cell Carcinoma Antigens in Patients Treated with an Autologous Granulocyte-Macrophage Colony-Stimulating Factor Gene-Transduced Renal Tumor Cell Vaccine," *Cancer Research*, 65(3), pp. 1079-1088. (2005).

Zhou, et al., "Persistence of Multiple Tumor-Specific T-Cell Clones is Associated with Complete Tumor Regression in a Melanoma Patient Receiving Adoptive Cell Transfer Therapy," *Journal of Immunology*, 28, pp. 53-62. (2005). NIH Public Access Author Manuscript Retrieved from https://ncbi.nlm.nih.gov/pmc/articles/PMC2175172/pdf/nihms36125.pdf.

Zuniga-Pflucker, T-Cell Development Made Simple, *Nature Review Immunology*, 4: 67-72, 2004.

Wen, L., "Health food processing technology and formula." *Jiangxi Science and Technology Press*, p. 35, 2002.

Cui, H., "Pathology of Poultry Nutrition and Metabolism Diseases." *Sichuan Science and Technology Press*, pp. 30-31, 2007.

Office Action issued in corresponding Eurasian Application No. 201891059, dated Nov. 7, 2022.

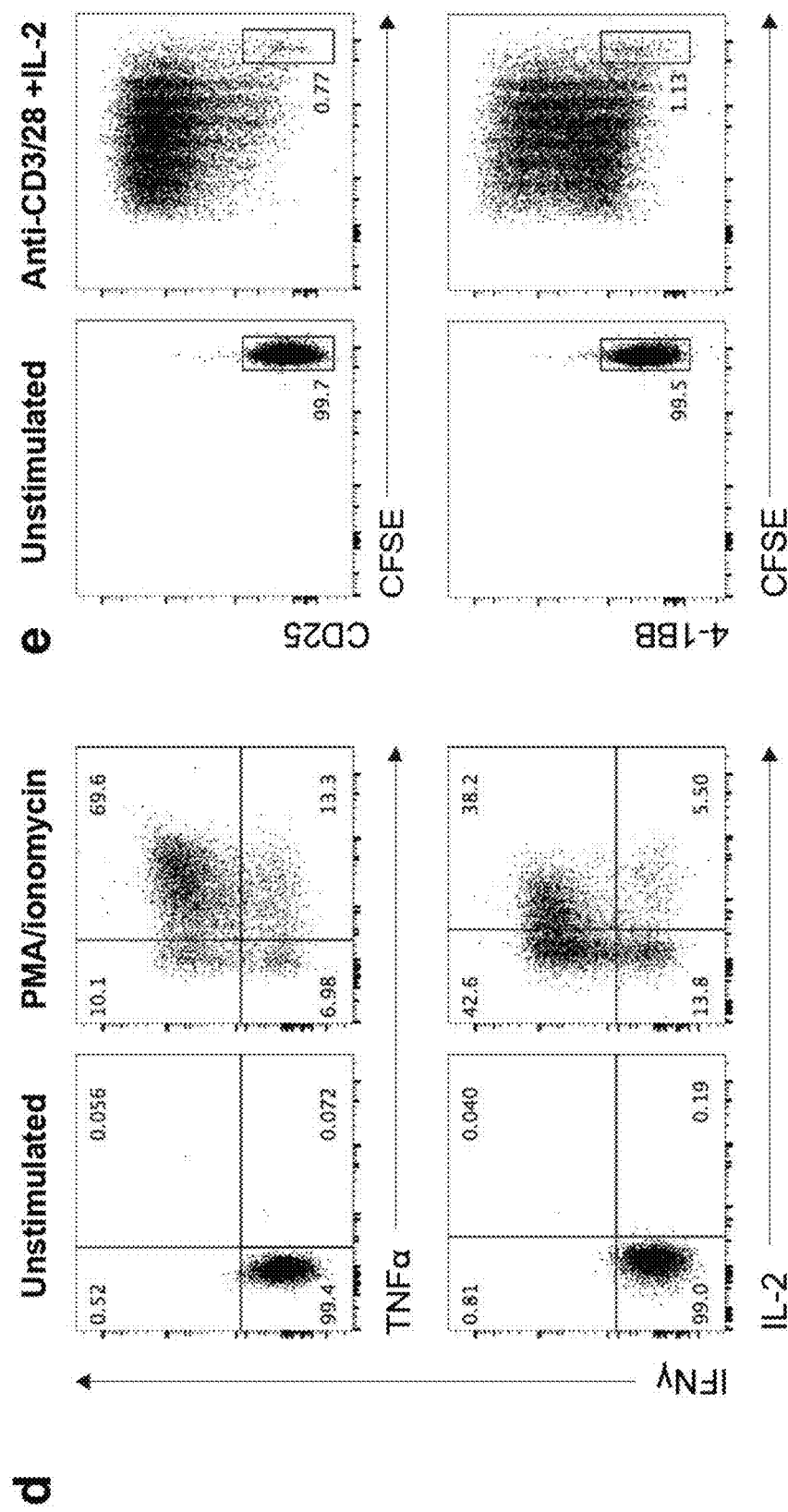
FIG. 16D-E

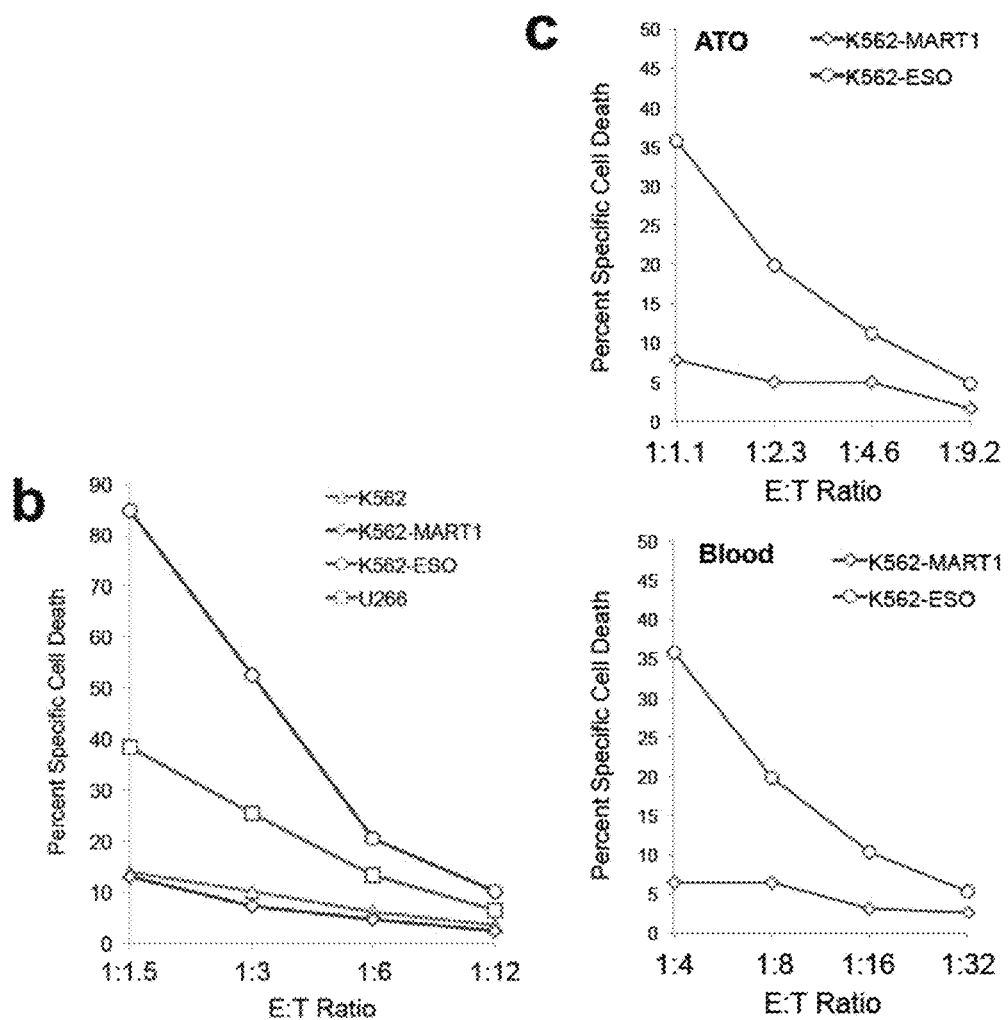
FIG. 18B-C

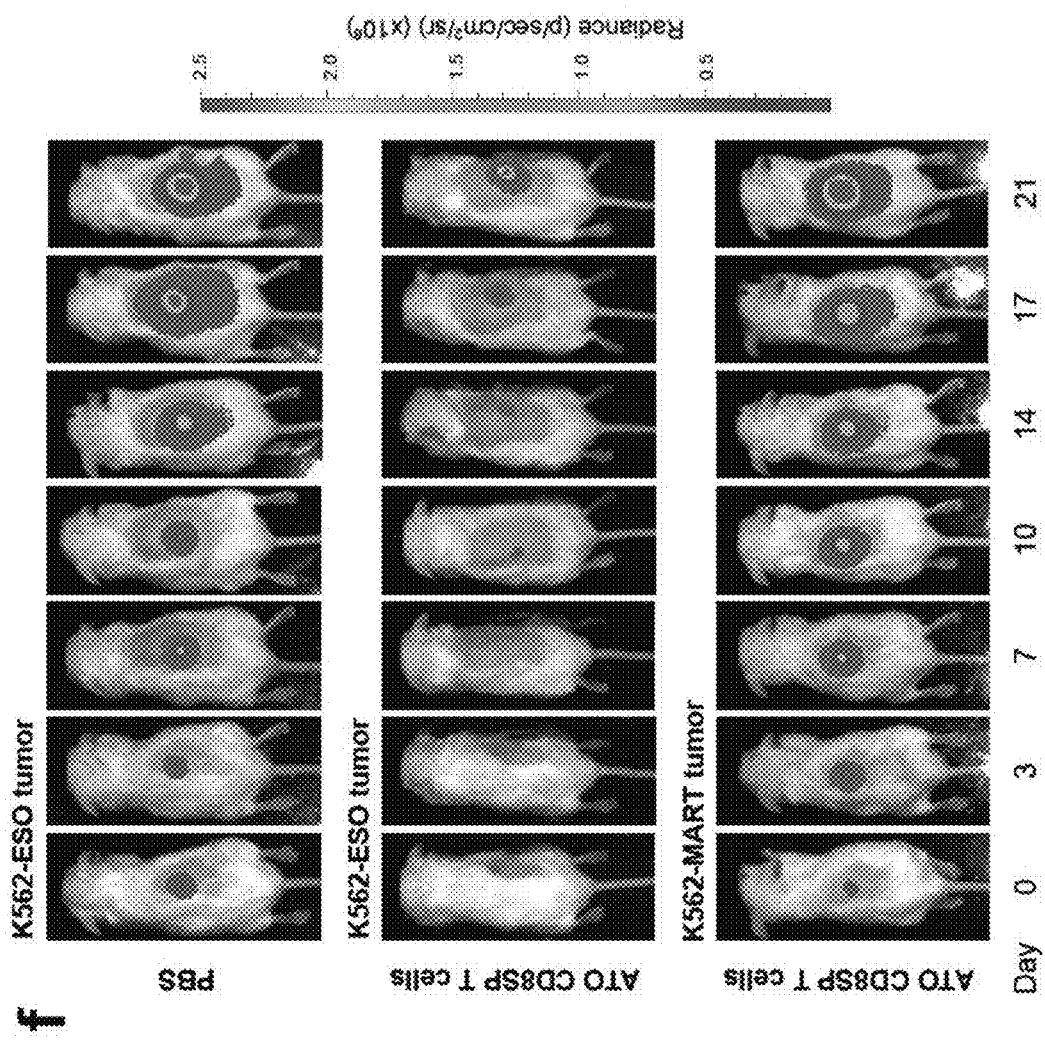
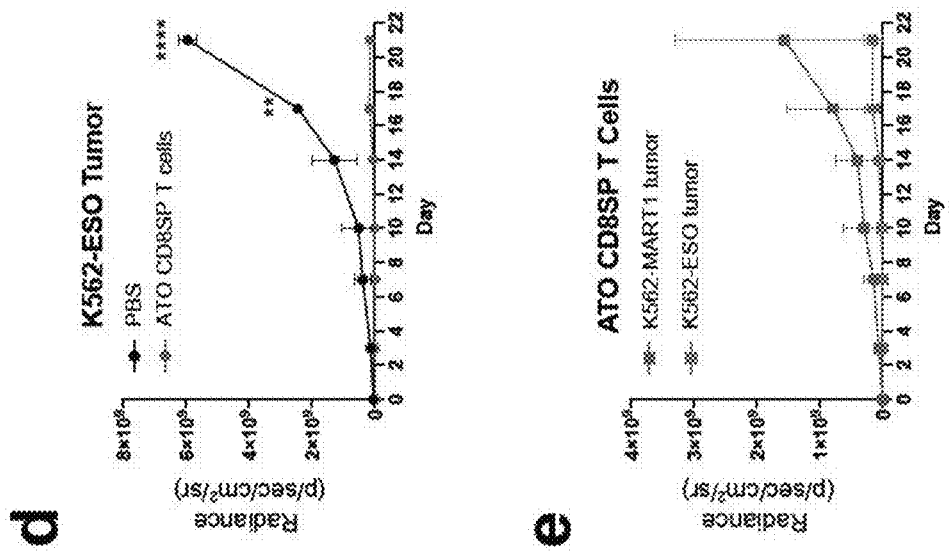
FIG. 18D-F

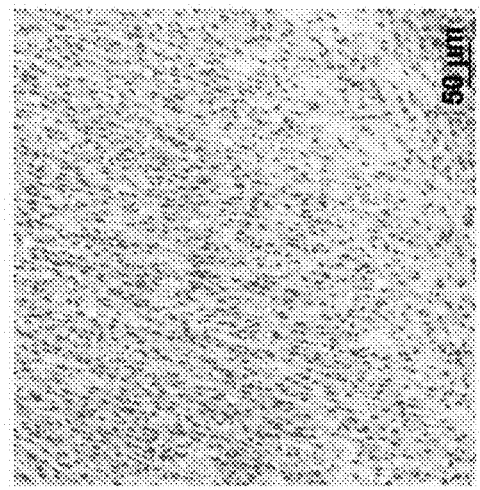
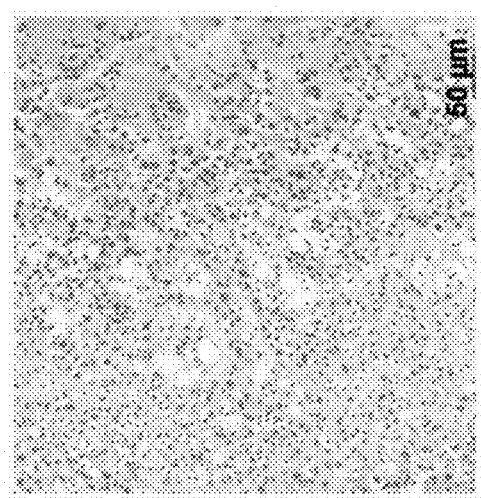
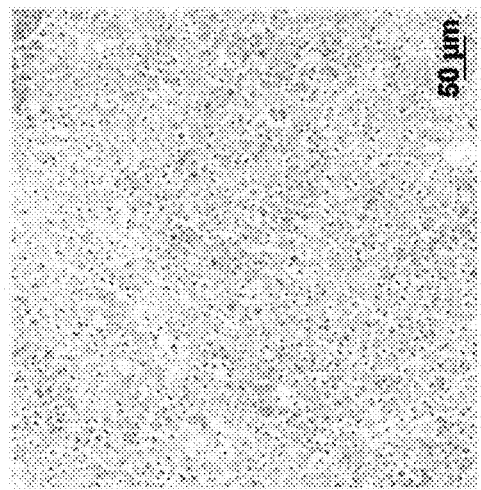
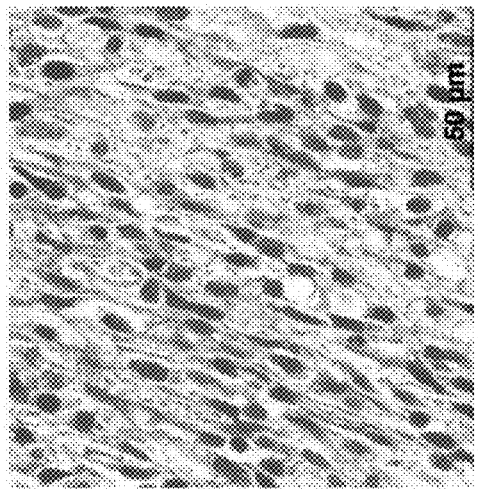
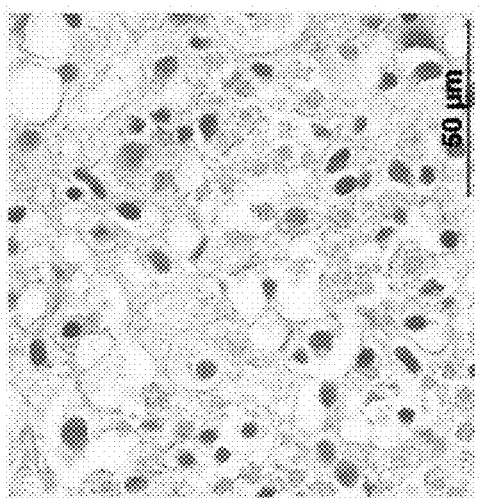
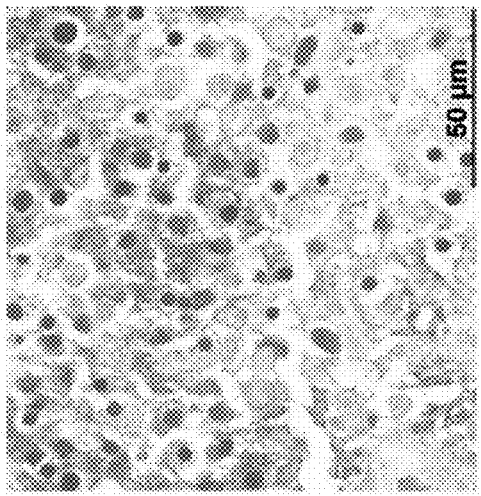
FIG. 19

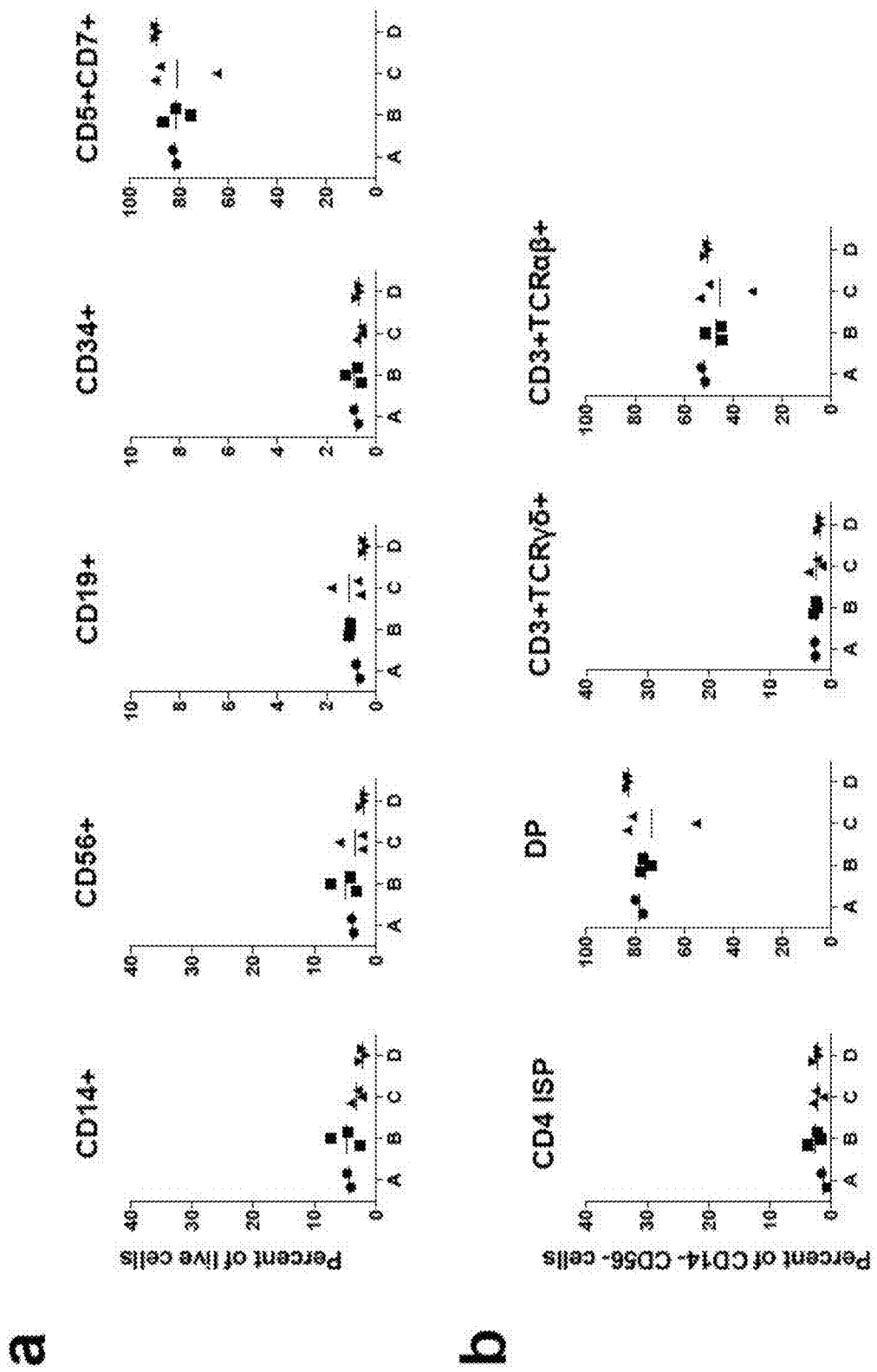
FIG. 21A-B

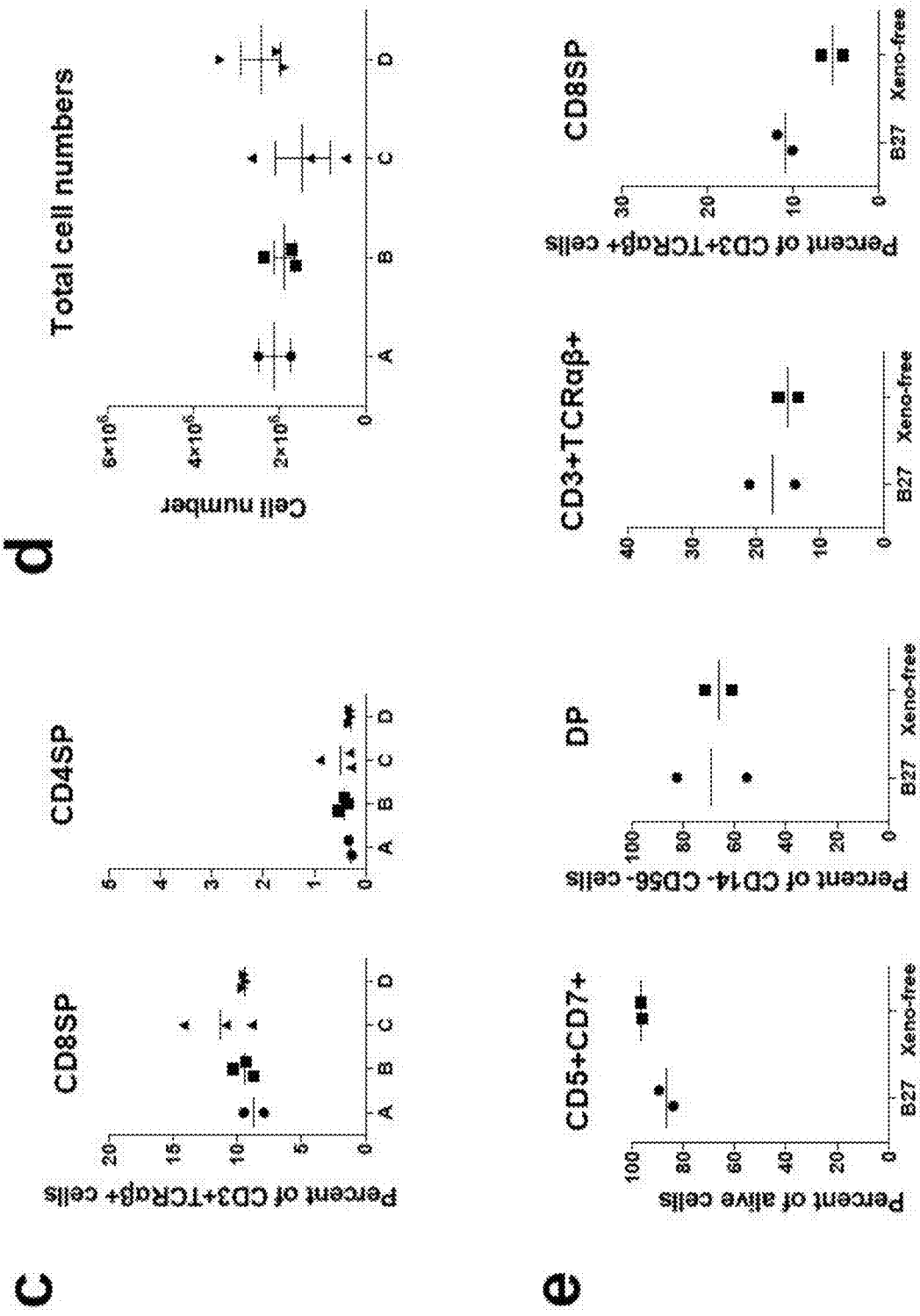
FIG. 21C-E

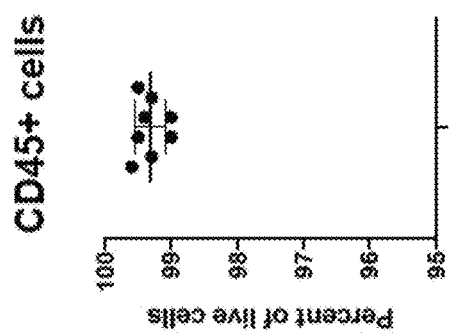
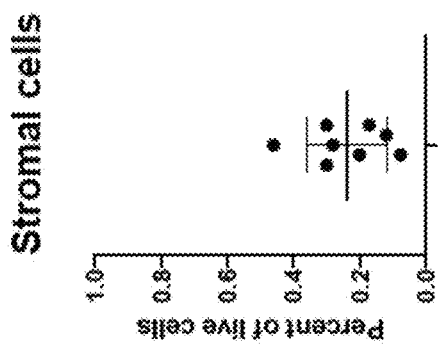
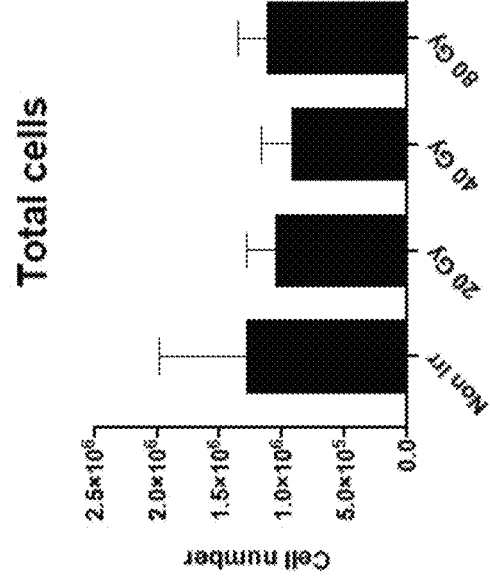
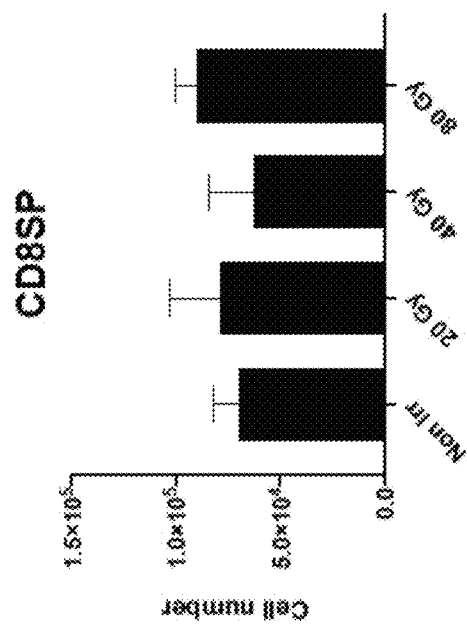
FIG. 21J-K

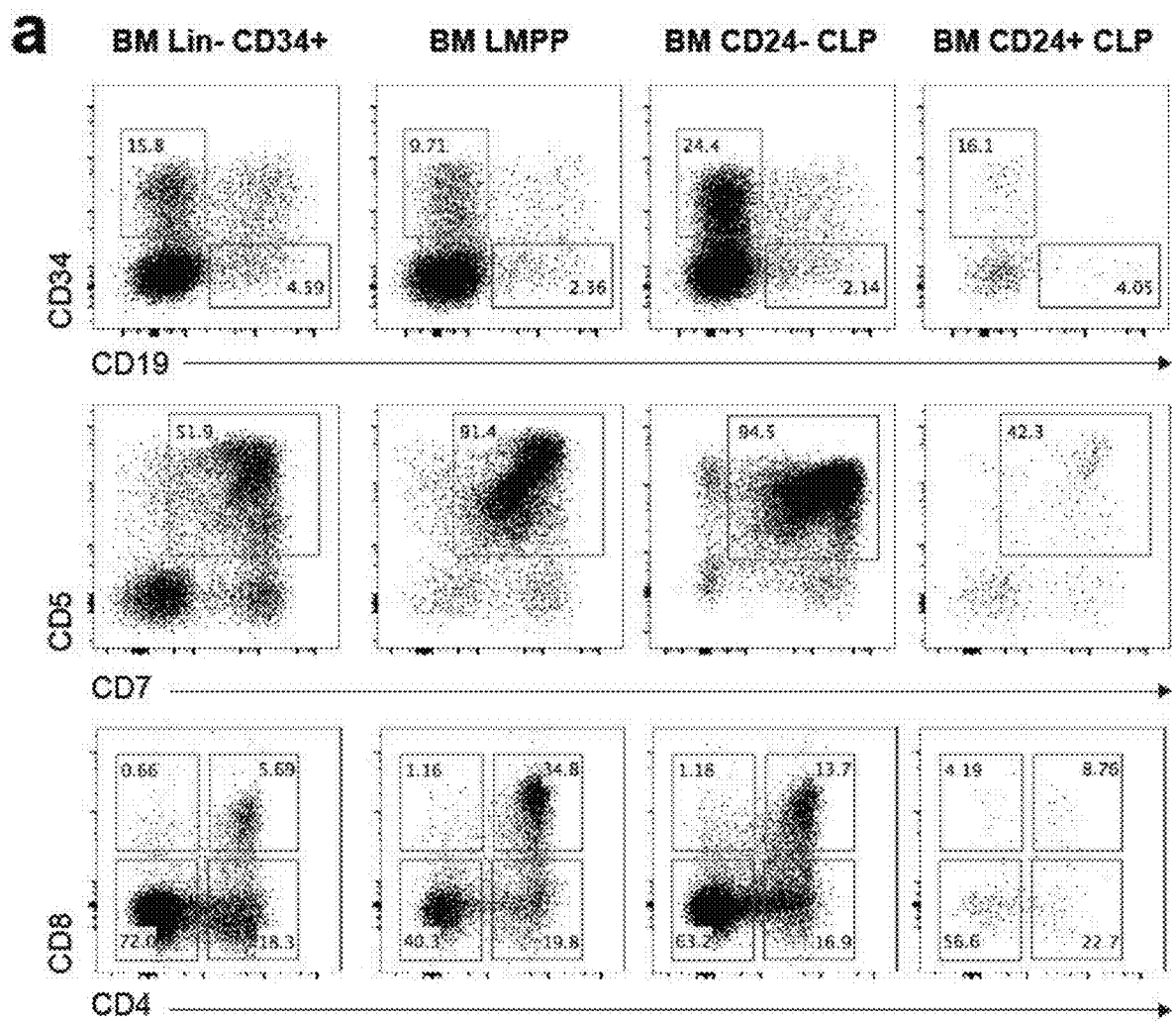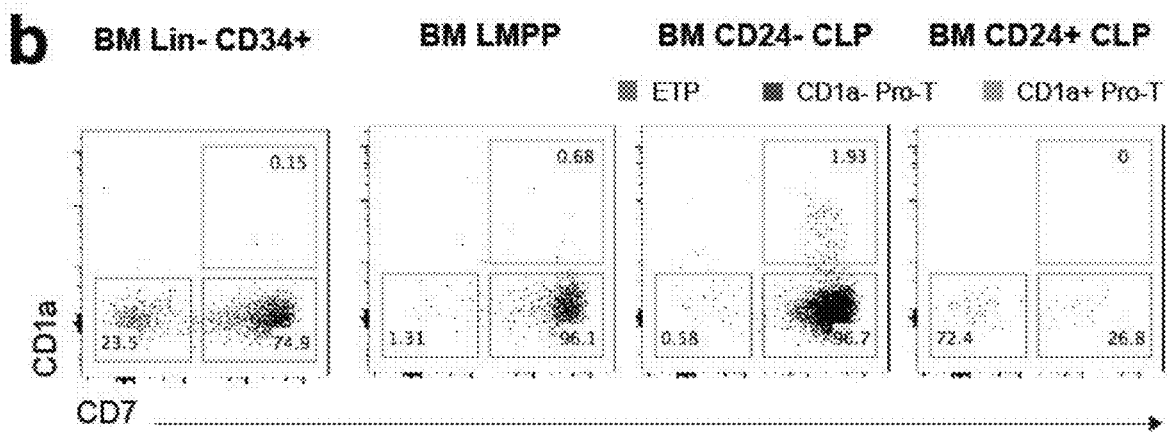
FIG. 24A-B

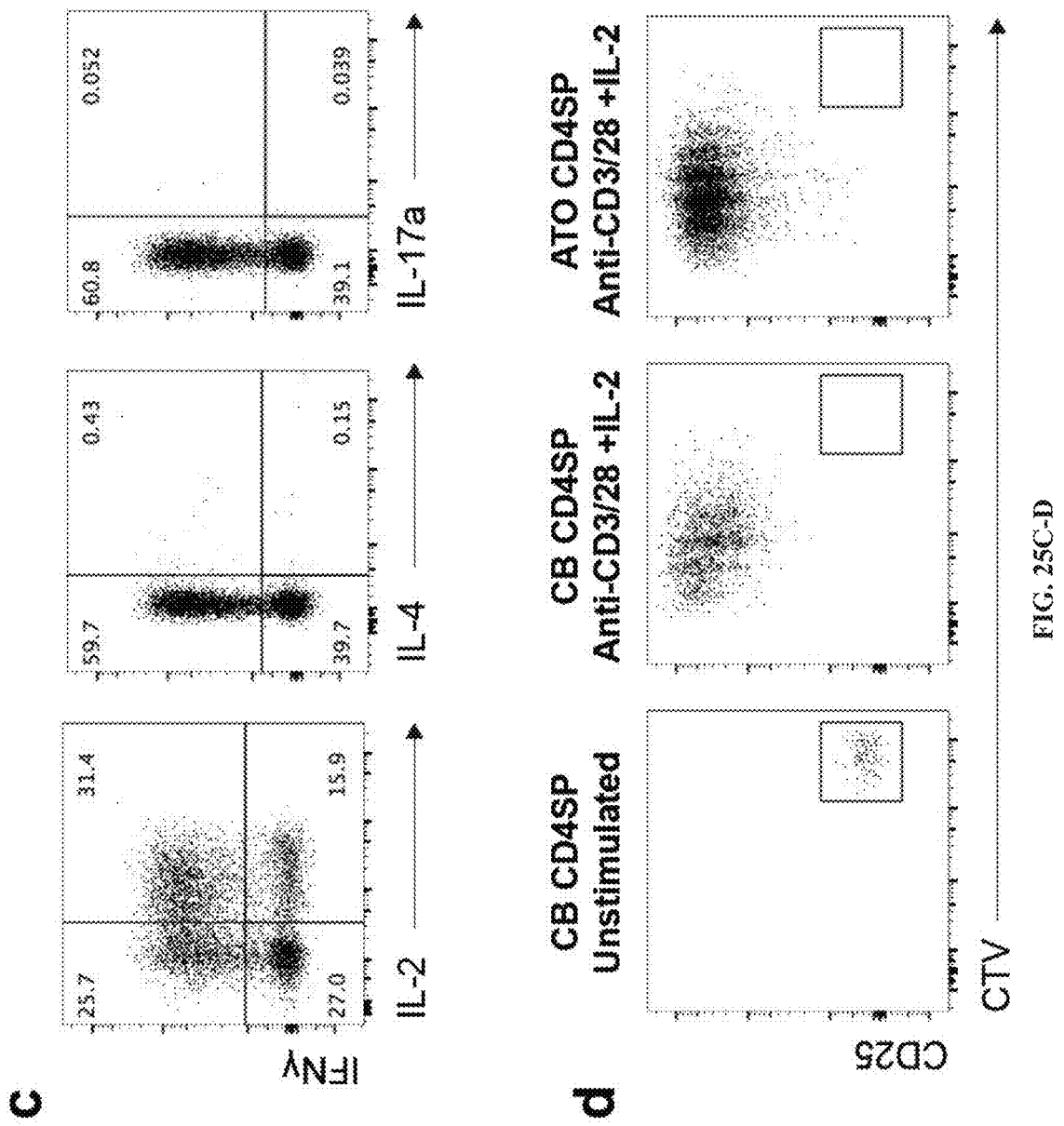
FIG. 25C-D

METHODS OR GENERATING T-CELLS FROM STEM CELLS AND IMMUNOTHERAPEUTIC METHODS USING THE T-CELLS

CROSS-REFERENCE TO RELATED APPLICATIONS

This application is a continuation application of U.S. patent application Ser. No. 15/772,224, filed on Apr. 30, 2018 (now U.S. Pat. No. 11,154,573), which is a national phase under 35 U.S.C. § 371 of International Application No. PCT/US2016/059375, filed Oct. 28, 2016, which claims the benefit of priority of U.S. Provisional Patent Application No. 62/248,931 filed Oct. 30, 2015, U.S. Provisional Patent Application No. 62/265,204 filed Dec. 9, 2015, and U.S. Provisional Patent Application No. 62/359,456 filed Jul. 7, 2016. The entire contents of each of the above-referenced disclosures are specifically incorporated herein by reference without disclaimer.

This invention was made with Government support under HL066992 awarded by the National Institutes of Health. The Government has certain rights in the invention.

BACKGROUND OF THE INVENTION

1. Field of the Invention

The present invention relates generally to the field of cell culture and development. More particularly, it concerns the production of T cells from stem cells or progenitor cells.

2. Description of Related Art

Current engineered T cell therapies (including TCR-engineered and CAR-T approaches) rely on genetically modifying autologous peripheral blood T cells, (i.e. T cells for modification are isolated from the same patient who will receive them). The autologous approach is required due to alloreactivity of donor T cells when transplanted into allogeneic (non-self) recipients that may result in a syndrome of tissue damage in the recipient known as graft-versus-host disease (GVHD). The use of patient-specific autologous engineered T cell therapies however is extremely labor and cost-intensive, and of uncertain scalability, despite the rapid push to commercialization of autologous cell therapies currently in late-stage clinical trials. Furthermore, the use of autologous engineered T cell therapies is precluded or of decreased efficacy in patients from whom normal T cells cannot be adequately collected (e.g., lymphopenic patients) or those whose T cells are functionally impaired (e.g., HIV/AIDS patients; elderly patients as a result of age-related immune dysfunctions). Given these many concerns, methods to generate non-alloreactive, off-the-shelf engineered T cells therapies is a great unmet commercial need in the field of adoptive cellular therapy.

SUMMARY OF THE INVENTION

Described herein are methods for generating engineered T cells and compositions of the resultant T cells. In some embodiments, the T cells are non-alloreactive and express an exogenous TCR and/or CAR. These T cells are useful for "off the shelf" T-cell therapies and do not require the use of the patient's own T cells. Therefore, the current methods provide for a more cost-effective, less labor-intensive T cell immunotherapy. Also described are immunotherapeutic methods using these T cells.

Aspects of the disclosure relate to a novel three dimensional cell culture system to produce T cells from less differentiated cells such as embryonic stem cells, pluripotent stem cells, hematopoietic stem or progenitor cells, or stem or progenitor cells described herein and known in the art. In particular embodiments, the system involves using serum-free medium. In certain aspects, the novel system uses a serum-free medium that is suitable for neural cell development for culturing of a three-dimensional cell aggregate including stroma cells and stem or progenitor cells produces T cells, or more specifically, antigen-specific T cells or T cells that have undergone positive or negative selection in vitro. In embodiments of the disclosure, the 3D cell aggregate is cultured in a serum-free medium comprising insulin for a time period sufficient for the in vitro differentiation of stem or progenitor cells to T cells. In some embodiments, the T cells undergo positive selection, which provides for T cells with high avidity to specific antigens.

Accordingly, aspects of the disclosure relate to a cell culture composition, comprising a three-dimensional (3D) cell aggregate and media. In some embodiments, the 3D cell aggregate comprise: a) a selected population of stromal cells; and/or b) a selected population of stem or progenitor cells. It is specifically contemplated that a) or b) may be excluded or substantially excluded in particular embodiments. In certain embodiments, one or more of the cells, particularly stroma cells, may express a Notch ligand. In some embodiments, the Notch ligand is exogenous. In some embodiments, the Notch ligand is endogenous. In other embodiments, the medium may comprise an externally added Notch ligand. In further embodiments, an externally added Notch ligand may be attached to a solid support or immobilized. For example, in some embodiments the stromal cells have an exogenous nucleotide sequence encoding a Notch ligand that may be introduced (or have been previously introduced) into the cells by transfection or transduction. In certain embodiments, the culture composition may not comprise a Notch ligand, or may not comprise an externally added Notch ligand.

The term "notch ligand" as used herein includes intact (full-length), partial (a truncated form), or modified (comprising one or more mutations, such as conservative mutations) notch ligands as well as Notch ligands from any species or fragments thereof that retain at least one activity or function of a full-length Notch ligand. Also included are peptides that mimic notch ligands. Notch ligands can be "canonical notch ligands" or "non-canonical notch ligands." Canonical notch ligands are characterized by extracellular domains typically comprising an N-terminal (NT) domain followed by a Delta/Serrate/LAG-2 (DSL) domain and multiple tandemly arranged Epidermal Growth Factor (EGF)-like repeats. The DSL domain together with the flanking NT domain and the first two EGF repeats containing the Delta and OSM-11-like proteins (DOS) motif are typically required for canonical ligands to bind Notch. The intracellular domains of some canonical ligands contain a carboxy-terminal PSD-95/Dlg/ZO-1-ligand (PDZL) motif that plays a role independent of Notch signaling. *C. elegans* DSL ligands lack a DOS motif but have been proposed to cooperate with DOS-only containing ligands to activate Notch signaling. Illustrative canonical notch ligands include, but are not limited to, Delta-like ligand 4 (DLL4), Delta-like ligand 1 (DLL1), Jagged 1 (JAG1), Jagged 2

(JAG2), Delta-like ligand 3 (DLL3), and X-delta 2; other similar illustrative canonical ligands are contemplated in additional embodiments.

Non-canonical notch ligands lack a DSL domain (Delta/Serrate/LAG-2), are structurally diverse, and include integral- and GPI-linked membrane proteins as well as various secreted proteins. Where a "notch ligand fragment" or a "canonical notch ligand fragment" is referenced herein, it is contemplated that the fragment is a fragment that binds notch. Examples of non-canonical notch ligands include, but are not limited to, Contactin-1, NOV/CCN3, Contactin-6, Periostin/OSF-2, DLK2/EGFL9, Pref-1/DLK1/FA1, DNER, Thrombospondin-2, MAGP-1/MFAP2, Thrombospondin-3, MAGP-2/MFAP5, Thrombospondin-4, and Netrin-1.

In some embodiments, the medium further comprises vitamins. In some embodiments, the medium comprises 1, 2, 3, 4, 5, 6, 7, 8, 9, 10, 11, 12, or 13 of the following (and any range derivable therein): biotin, DL alpha tocopherol acetate, DL alpha-tocopherol, vitamin A, choline chloride, calcium pantothenate, pantothenic acid, folic acid nicotinamide, pyridoxine, riboflavin, thiamine, inositol, vitamin B12, or the medium includes combinations thereof or salts thereof. In some embodiments, the medium comprises or consists essentially of biotin, DL alpha tocopherol acetate, DL alpha-tocopherol, vitamin A, choline chloride, calcium pantothenate, pantothenic acid, folic acid nicotinamide, pyridoxine, riboflavin, thiamine, inositol, and vitamin B12. In some embodiments, the vitamins include or consist essentially of biotin, DL alpha tocopherol acetate, DL alpha-tocopherol, vitamin A, or combinations or salts thereof. In some embodiments, the medium further comprises proteins. In some embodiments, the proteins comprise albumin or bovine serum albumin, a fraction of BSA, catalase, insulin, transferrin, superoxide dismutase, or combinations thereof. In some embodiments, the medium further comprises one or more of the following: corticosterone, D-Galactose, ethanolamine, glutathione, L-carnitine, linoleic acid, linolenic acid, progesterone, putrescine, sodium selenite, or triodo-I-thyronine, or combinations thereof. In some embodiments, the medium comprises one or more of the following: a B-27® supplement, xeno-free B-27® supplement, GS21™ supplement, or combinations thereof. In some embodiments, the medium comprises or further comprises amino acids, monosaccharides, inorganic ions. In some embodiments, the amino acids comprise arginine, cystine, isoleucine, leucine, lysine, methionine, glutamine, phenylalanine, threonine, tryptophan, histidine, tyrosine, or valine, or combinations thereof. In some embodiments, the inorganic ions comprise sodium, potassium, calcium, magnesium, nitrogen, or phosphorus, or combinations or salts thereof. In some embodiments, the medium further comprises one or more of the following: molybdenum, vanadium, iron, zinc, selenium, copper, or manganese, or combinations thereof. In certain embodiments, the medium comprises or consists essentially of one or more vitamins discussed herein and/or one or more proteins discussed herein, and/or one or more of the following: corticosterone, D-Galactose, ethanolamine, glutathione, L-carnitine, linoleic acid, linolenic acid, progesterone, putrescine, sodium selenite, or triodo-I-thyronine, a B-27® supplement, xeno-free B-27® supplement, GS21™ supplement, an amino acid (such as arginine, cystine, isoleucine, leucine, lysine, methionine, glutamine, phenylalanine, threonine, tryptophan, histidine, tyrosine, or valine), monosaccharide, inorganic ion (such as sodium, potassium, calcium, magnesium, nitrogen, and/or phosphorus) or salts thereof, and/or molybdenum, vanadium, iron, zinc, selenium, copper, or manganese.

The medium in certain aspects can be prepared using a medium used for culturing animal cells as their basal medium, such as any of AIM V, X-VIVO-15, NeuroBasal, EGM2, TeSR, BME, BGJb, CMRL 1066, Glasgow MEM, Improved MEM Zinc Option, IMDM, Medium 199, Eagle MEM, αMEM, DMEM, Ham, RPMI-1640, and Fischer's media, as well as any combinations thereof, but the medium may not be particularly limited thereto as far as it can be used for culturing animal cells. Particularly, the medium may be xeno-free or chemically defined.

The medium can be a serum-containing or serum-free medium, or xeno-free medium. From the aspect of preventing contamination with heterogeneous animal-derived components, serum can be derived from the same animal as that of the stem cell(s). The serum-free medium refers to medium with no unprocessed or unpurified serum and accordingly, can include medium with purified blood-derived components or animal tissue-derived components (such as growth factors).

The medium may contain or may not contain any alternatives to serum. The alternatives to serum can include materials which appropriately contain albumin (such as lipid-rich albumin, bovine albumin, albumin substitutes such as recombinant albumin or a humanized albumin, plant starch, dextrans and protein hydrolysates), transferrin (or other iron transporters), fatty acids, insulin, collagen precursors, trace elements, 2-mercaptoethanol, 3'-thiolglycerol, or equivalents thereto. The alternatives to serum can be prepared by the method disclosed in International Publication No. 98/30679, for example (incorporated herein in its entirety). Alternatively, any commercially available materials can be used for more convenience. The commercially available materials include knockout Serum Replacement (KSR), Chemically-defined Lipid concentrated (Gibco), and Glutamax (Gibco).

In further embodiments, the medium may be a serum-free medium that is suitable for cell development. For example, the medium may comprise B-27® supplement, xeno-free B-27® supplement (available at world wide web at thermofisher.com/us/en/home/technical-resources/media-formulation.250.html), NS21 supplement (Chen et al., J Neurosci Methods, 2008 Jun. 30; 171(2): 239-247, incorporated herein in its entirety), GS21™ supplement (available at world wide web at amsbio.com/B-27.aspx), or a combination thereof at a concentration effective for producing T cells from the 3D cell aggregate.

In certain embodiments, the medium may comprise one, two, three, four, five, six, seven, eight, nine, ten, 11, 12, 13, 14, 15, 16, 17, 18, 19, 20 or more of the following: Vitamins such as biotin; DL Alpha Tocopherol Acetate; DL Alpha-Tocopherol; Vitamin A (acetate); proteins such as BSA (bovine serum albumin) or human albumin, fatty acid free Fraction V; Catalase; Human Recombinant Insulin; Human Transferrin; Superoxide Dismutase; Other Components such as Corticosterone; D-Galactose; Ethanolamine HCl; Glutathione (reduced); L-Carnitine HCl; Linoleic Acid; Linolenic Acid; Progesterone; Putrescine 2HCl; Sodium Selenite; and/or T3 (triodo-I-thyronine).

In further embodiments, the medium may comprise externally added ascorbic acid. The medium can also contain one or more externally added fatty acids or lipids, amino acids (such as non-essential amino acids), vitamin(s), growth factors, cytokines, antioxidant substances, 2-mercaptoethanol, pyruvic acid, buffering agents, and/or inorganic salts.

One or more of the medium components may be added at a concentration of at least, at most, or about 0.1, 0.5, 1, 2, 3, 4, 5, 10, 15, 20, 25, 30, 35, 40, 45, 50, 55, 60, 65, 70, 75, 80, 85, 90, 95, 100, 150, 180, 200, 250 ng/L, ng/ml, µg/ml, mg/ml, or any range derivable therein.

The medium used may be supplemented with at least one externally added cytokine at a concentration from about 0.1 ng/mL to about 500 ng/mL, more particularly 1 ng/mL to 100 ng/mL, or at least, at most, or about 0.1, 0.5, 1, 2, 3, 4, 5, 10, 15, 20, 25, 30, 35, 40, 45, 50, 55, 60, 65, 70, 75, 80, 85, 90, 95, 100, 150, 180, 200, 250 ng/L, ng/ml, µg/ml, mg/ml, or any range derivable therein. Suitable cytokines, include but are not limited to, FLT3 ligand (FLT3L), interleukin 7 (IL-7), stem cell factor (SCF), thrombopoietin (TPO), IL-2, IL-4, IL-6, IL-15, IL-21, TNF-alpha, TGF-beta, interferon-gamma, interferon-lambda, TSLP, thymopentin, pleotrophin, and/or midkine. Particularly, the culture medium may include at least one of FLT3L and IL-7. More particularly, the culture may include both FLT3L and IL-7.

In certain embodiments, the 3D cell aggregate may comprise a defined or undefined exogenous extracellular matrix, such as collagen, gelatin, poly-L-lysine, poly-D-lysine, laminin, and fibronectin and mixtures thereof for example Matrigel™, and lysed cell membrane preparations. In other embodiments, the 3D cell aggregate does not comprise a exogenous matrix or a scaffold.

Other culturing conditions can be appropriately defined. For example, the culturing temperature can be about 20 to 40° C., such as at least, at most, or about 20, 21, 22, 23, 24, 25, 26, 27, 28, 29, 30, 31, 32, 33, 34, 35, 36, 37, 38, 39, 40° C. (or any range derivable therein), though the temperature may be above or below these values. The $CO_2$ concentration can be about 1, 2, 3, 4, 5, 6, 7, 8, 9, or 10% (or any range derivable therein), such as about 2% to 10%, for example, about 2 to 5%, or any range derivable therein. The oxygen tension can be at least or about 1, 5, 8, 10, 20%, or any range derivable therein.

The stromal cells and stem or progenitor cells may be present at any ratio, for example, from about 100:1, 80:1, 40:1, 20:1, 10:1, 5:1, 1:1, 1:5, 1:10, 1:20, 1:40, 1:80, and/or 1:100, or any range derivable therein.

In some embodiments, the stroma cells may be a murine stromal cell line, a human stromal cell line, a selected population of primary stromal cells, a selected population of stromal cells differentiated from pluripotent stem cells in vitro, or a combination thereof. In some embodiments, the stromal cells are differentiated from the same population of stem or progenitor cells as that used as the starting material in the methods described herein. In some embodiments, the stromal cells are differentiated from human cells. In some embodiments, the stromal cells are differentiated from human pluripotent stem cells. In some embodiments, the stromal cells are differentiated from human or non-human HSPC or PSC cells.

In further embodiments, the stromal cells or progenitors thereof may be genetically modified. For example, stromal cells may express an exogenous human major histocompatibility complex (MHC). In further embodiments, the stroma cells may express an exogenous antigen-specific costimulatory molecule, cytokine, antigen, or extracellular matrix protein, or any T cell regulator like any bioactive molecule or genes that modulate T cell differentiation, proliferation, or function. In some embodiments, the stromal cells (or progenitor) is engineered to express an antigen or HLA molecule.

In some embodiments, the cell aggregate comprises or further comprises tumor cells or tumor antigen. In some embodiments, the cell aggregate comprises exogenous major histocompatibility complex (MHC). In some embodiments, the MHC is a human MHC. In some embodiments, the cell aggregate comprises exogenous antigen-specific costimulatory molecule, cytokine, antigen, or extracellular matrix protein, or any T cell regulator like any bioactive molecule or genes that modulate T cell differentiation, proliferation, or function. In some embodiments, the stromal cells (or progenitor) is engineered to express an antigen or HLA molecule.

In certain embodiments, the stem or progenitor cells may be selected from embryonic stem cells, hematopoietic stem or progenitor cells, cells isolated from bone marrow, cord blood, peripheral blood, thymus, or the stem or progenitor cells may have been differentiated from embryonic stem cells (ESC) or induced pluripotent stem cells (iPSC) in vitro. Stem or progenitor cells from primary tissue or ESC or iPSC may be from human or non-human animals (e.g., mouse) in origin.

In further embodiments, the stem or progenitor cells may be genetically modified. For example, the stem or progenitor cells may express an exogenous T cell receptor (TCR) or a chimeric antigen receptor (CAR), or both. In further embodiments, the stem or progenitor cells may express an exogenous invariant natural killer T cell (iNKT) associated TCR. In still further embodiment, the stem or progenitor cells express an exogenous antigen-specific TCR or have an exogenous genetic modification of genes that modulate T cell differentiation, expansion or function.

In some embodiments, the stem or progenitor cells or stroma cells used in the culturing compositions and methods described herein are cells that have previously been frozen. In some embodiments, the cells have never been frozen. In some embodiments, the cells have been passaged for at least, at most, or exactly 0, 1, 2, 3, 4, 5, 6, 7, 8, 9, 10, 15, 20, 25, 30, 35, 40, 45, or 50 times (or any range derivable therein).

In certain embodiments, any of the cell population, such as the stroma cells, the stem or progenitor cells or the T cell produced therein may comprise at least, about, or at most, 1, 2, 3, 4, 5, 6, 7, 8, 9, 10, 11, 12, 13, 14, 15, 16, 17, 18, 19, 20, 21, 22, 23, 24, 25, 50, 60, 70, 80, 90, 100, 200, 300, 400, 500, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^3$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, or $2\times10^6$ cells (or any range derivable therein). In particular embodiments, the stem or progenitor cells are from 1 to 200,000.

Aspects of the disclosure also relate to a method for preparing a composition of T cells from stem or progenitor cells, the method comprising culturing a three-dimensional (3D) cell aggregate comprising: a) a selected population of stromal cells that express a Notch ligand; b) a selected population of stem or progenitor cells; wherein the 3D cell aggregate is cultured in a serum-free medium comprising insulin for a time period sufficient for the in vitro differentiation of the stem or progenitor cells to T cells. The culturing composition may include any embodiments described herein as components to the culturing composition and culture medium. Furthermore, the cells used in the method aspects of the disclosure may be any stem or progenitor cells or stroma cells described herein as suitable for use in the culturing composition.

The compositions and methods described herein may be modified so that the method is for preparing a T cell with a certain phenotype. In some embodiments, the methods are for preparing a T cell with the phenotype: CD4+CD8− T cells, CD4−CD8+ T cells, CD34+ CD7+ CD1a+ cells, CD3+ TCRab+, CD3+ TCRgd+, CD3+ TCRab+ CD4+ CD8−, CD3+ TCRab+ CD8+ CD4−, CD3+ TCRab+ CD4+ CD8− CD45RO− CD45RA+, CD3+ TCRab+ CD8+ CD4−

CD45RO− CD45RA+, CD3+ TCRab+ CD4+ CD8− CD45RO− CD45RA+ CCR7+, CD3+ TCRab+ CD8+ CD4− CD45RO− CD45RA+ CCR7+, CD3+ TCRab+ CD4+ CD8− CD45RO− CD45RA+ CD27+, CD3+ TCRab+ CD8+ CD4− CD45RO− CD45RA+ CD27+, CD34$^+$ CD7$^+$ CD1a$^+$ cells, CD34+CD5+CD7+, CD34+CD5+CD7−, natural killer T cells, regulatory T cells, antigen-specific T cells, intraepithelial lymphocyte T cells, or cells that are CD45+, CD11b+, CD11b−, CD15+, CD15−, CD24+, CD24−, CD114+, CD114−, CD182+, CD182−, CD4+, CD4−, CD14+, CD14−, CD11a+, CD11a−, CD91+, CD91−, CD16+, CD16−, CD3+, CD3−, CD25+, CD25−, Foxp3+, Fox3p−, CD8+, CD8−, CD19+, CD19−, CD20+, CD20−, CD24+, CD24, CD38+, CD38−, CD22+, CD22−, CD61+, CD61−, CD16+, CD16−, CD56+, CD56−, CD31+, CD31−, CD30+, CD30−, CD38+, and/or CD38− or combinations thereof. By way of example, intraepithelial lymphocytes (IEL) may be prepared by expressing cognate antigen in the stromal cells.

In some embodiments, the method further comprises centrifugation of the stem or progenitor cells and the stromal cells to form a 3D cell aggregate. The methods may comprise culturing a three-dimensional (3D) cell aggregate. The 3D cell aggregate comprises a selected population of stromal cells that express an exogenous Notch ligand; and a selected population of stem or progenitor cells. Any of the alternatives of the medium ingredients may be as described above.

In further embodiments, the culturing may comprise using centrifugation to form the 3D cell aggregate. The culturing may be for any length of time, such as at least, at most, or exactly about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hours, days or weeks or any range derivable therein. In additional embodiments, the culturing may or may not involve cell passaging.

In some embodiments, the methods further comprise endogenously-expressed TCRs from the in vitro differentiated T cells. In some embodiments, the method further comprises priming the T cells. In some embodiments, the T cells are primed with antigen presenting cells. In some embodiments, the antigen presenting cells present tumor antigens.

In further embodiments, there may be provided methods or steps comprising administering the T cells from the 3D cell aggregate to a subject in need thereof or further differentiating the T cells from the 3D cell aggregate.

In some embodiments, the T cells from the 3D cell aggregate do not express an endogenous TCR through allelic exclusion. In other embodiments, the T cells from the 3D cell aggregate express an exogenous TCR or CAR.

There may be provided methods for producing T cells, comprising culturing the cell culture composition as described above, thereby producing T cells. There may be also provided methods as described above, which may be further defined as a method for producing antigen-specific T cells, wherein the progenitor cells express an exogenous antigen-specific TCR or CAR.

There may be provided methods for producing T cells or any of the culturing methods may produce T cells from the 3D cell aggregate. Methods in certain aspects may further comprise detecting the number of, selecting for or against, or increasing the number of CD4$^+$CD8$^-$ T cells, CD4$^-$CD8$^+$ T cells, CD34$^+$ CD7$^+$ CD1a$^+$ cells, CD3+ TCRab+, CD3+ TCRab+ TCRgd+, CD3+ TCRab+ CD4+ CD8−, CD3+ TCRab+ CD8+ CD4−, CD3+ TCRab+ CD4+ CD8− CD45RO− CD45RA+, CD3+ TCRab+ CD8+ CD4− CD45RO− CD45RA+, CD3+ TCRab+ CD4+ CD8− CD45RO− CD45RA+ CCR7+, CD3+ TCRab+ CD8+ CD4− CD45RO− CD45RA+ CCR7+, CD3+ TCRab+ CD4+ CD8− CD45RO− CD45RA+ CD27+, CD3+ TCRab+ CD8+ CD4− CD45RO− CD45RA+ CD27+, CD34$^+$ CD7$^+$ CD1a$^+$ cells, CD34+ CD5+CD7+, CD34+CD5+CD7−, natural killer T cells, regulatory T cells, antigen-specific T cells using tetramer or anti-TCR antibodies, CAR T cells using modified antigens, transduced T cells using fluorescent markers, or a combination thereof. In some embodiments, the intraepithelial lymphocytes are CD4− CD8+, CD4+ CD8−, CD4+ CD8+, CD4− CD8−, TCRab+, TCRgd+, CD5+CD7+, CD5+CD7+ CD3−CD4−CD8−, CD5+CD7+CD3−CD4−CD8aa, or combinations thereof. In some embodiments, intraepithelial lymphocytes such as CD4− CD8+, CD4+ CD8−, CD4+ CD8+, CD4− CD8−, TCRab+, TCRgd+, CD5+CD7+, CD5+CD7+ CD3−CD4−CD8−, and/or CD5+CD7+CD3−CD4−CD8aa are excluded.

There may be provided methods for increasing the number of T cells in a subject or for treating a disease or condition in a subject, the method comprising administering to a subject an effective amount of T cells or antigen-specific T cells, prepared as described herein or any T cells of the disclosure, such as those comprising an exogenous TCR. In some embodiments, the T cells have a cell-surface marker described herein.

The subject may be any animal, in particular a mouse, non-human primate, or human. In further aspects, the subject may have been determined to have or be at risk for an autoimmune disease, a cancer, an infection, an immunodeficiency, or a combination thereof.

In further embodiments, there may be provided a method for producing T cells that do not react with a self-antigen, comprising culturing a three-dimensional (3D) cell aggregate with a serum-free medium at a concentration effective for producing T cells from the 3D cell aggregate. In certain aspects, the 3D cell aggregate comprises: a) a selected population of stromal cells that express an exogenous Notch ligand and b) a selected population of stem or progenitor cells, wherein one or more cells of a) or b) express an exogenous self-antigen; thereby the 3D cell aggregate produce T cells that do not reach with a self-antigen. In further aspects, wherein one or more of the cells of a) or b) express or do not express an exogenous self-MHC.

Aspects of the disclosure relate to T cells made by the methods described herein. In some embodiments, the T cells have a specific phenotype, cell surface marker, or characteristic described throughout this disclosure.

Accordingly, aspects of the disclosure relate to an isolated T cell or population of T cells comprising a chimeric antigen receptor (CAR), wherein the T cells have an intraepithelial lymphocyte phenotype. In some embodiments, the T cells are TCR−. In some embodiments, the T cells are CD4− CD8+, CD4+ CD8−, CD4+ CD8+, CD4− CD8−, TCRab+, TCRgd+, CD5+CD7+, CD5+CD7+CD3−CD4−CD8−, CD5+CD7+CD3−CD4−CD8aa, or combinations thereof. In some embodiments, the T cells are CD5+CD7+CD3−CD4−CD8−. In some embodiments, the T cells are CD5+CD7+ CD3−CD4−CD8aa. In some embodiments, the CAR comprises a CD19 CAR. In some embodiments, the T cells further comprise an exogenous TCR. In some embodiments, the T cells are CD3+. In some embodiments, the T cells are CD4$^+$CD8$^-$ T cells, CD4$^-$CD8$^+$ T cells, CD34$^+$ CD7$^+$ CD1a$^+$ cells, CD3+ TCRab+, CD3+ TCRgd+, CD3+ TCRab+ CD4+ CD8−, CD3+ TCRab+ CD8+ CD4−, CD3+ TCRab+ CD4+ CD8− CD45RO− CD45RA+, CD3+ TCRab+ CD8+ CD4− CD45RO− CD45RA+, CD3+ TCRab+ CD4+ CD8− CD45RO− CD45RA+ CCR7+, CD3+

TCRab+ CD8+ CD4−CD45RO− CD45RA+ CCR7+, CD3+ TCRab+ CD4+ CD8− CD45RO− CD45RA+ CD27+, CD3+ TCRab+ CD8+ CD4− CD45RO− CD45RA+ CD27+, CD34$^+$ CD7$^+$ CD1a$^+$ cells, CD34+CD5+CD7+, CD34+ CD5+CD7−, natural killer T cells, regulatory T cells, antigen-specific T cells, intraepithelial lymphocyte T cells, or cells that are CD45+, CD11b+, CD11b−, CD15+, CD15−, CD24+, CD24−, CD114+, CD114−, CD182+, CD182−, CD4+, CD4−, CD14+, CD14−, CD11a+, CD11a−, CD91+, CD91−, CD16+, CD16−, CD3+, CD3−, CD25+, CD25−, Foxp3+, Fox3p−, CD8+, CD8−, CD19+, CD19−, CD20+, CD20−, CD24+, CD24, CD38+, CD38−, CD22+, CD22−, CD61+, CD61−, CD16+, CD16−, CD56+, CD56−, CD31+, CD31−, CD30+, CD30−, CD38+, or CD38− or combinations thereof. Further aspects relate to an isolated T cell or population of T cells, wherein the T cells express an exogenous TCR or CAR and wherein the T cells are CD4$^+$CD8$^-$ T cells, CD4$^-$CD8$^+$ T cells, CD34$^+$ CD7$^+$ CD1a$^+$ cells, CD3+ TCRab+, CD3+ TCRgd+, CD3+ TCRab+ CD4+ CD8−, CD3+ TCRab+ CD8+ CD4−, CD3+ TCRab+ CD4+ CD8− CD45RO− CD45RA+, CD3+ TCRab+ CD8+ CD4− CD45RO− CD45RA+, CD3+ TCRab+ CD4+ CD8− CD45RO− CD45RA+ CCR7+, CD3+ TCRab+ CD8+ CD4− CD45RO− CD45RA+ CCR7+, CD3+ TCRab+ CD4+ CD8− CD45RO− CD45RA+ CD27+, CD3+ TCRab+ CD8+ CD4− CD45RO− CD45RA+ CD27+, CD34$^+$ CD7$^+$ CD1a$^+$ cells, CD34+CD5+CD7+, CD34+CD5+CD7−, natural killer T cells, regulatory T cells, antigen-specific T cells, intraepithelial lymphocyte T cells, cells that are CD45+, CD11b+, CD11b−, CD15+, CD15−, CD24+, CD24−, CD114+, CD114−, CD182+, CD182−, CD4+, CD4−, CD14+, CD14−, CD11a+, CD11a−, CD91+, CD91−, CD16+, CD16−, CD3+, CD3−, CD25+, CD25−, Foxp3+, Fox3p−, CD8+, CD8−, CD19+, CD19−, CD20+, CD20−, CD24+, CD24, CD38+, CD38−, CD22+, CD22−, CD61+, CD61−, CD16+, CD16−, CD56+, CD56−, CD31+, CD31−, CD30+, CD30−, CD38+, or CD38− or combinations thereof. In some embodiments, the T cells are a population of T cells and wherein the population of T cell comprises at least 50% of the cells are mature naïve CD8 or CD4 single positive cells. In some embodiments, the T cells comprise at least, at most, or exactly 5, 10, 15, 20, 25, 30, 35, 40, 45, 50, 55, 60, 65, 70, 75, 80, 85, 90, 91, 92, 93, 94, 95, 96, 97, 98, 99, or 100% mature naïve CD8 single positive and/or CD4 single positive cells (or any range derivable therein). In some embodiments, the cells express an exogenous invariant natural killer T cell (iNKT) associated TCR. In some embodiments, the cells have been differentiated in vitro from stem or progenitor cells. In some embodiments, the stem or progenitor cells are selected from embryonic stem cells, induced pluripotent stem cells, human mesodermal progenitor cells, mesodermal progenitor cells, human embryonic mesodermal progenitor cells, hematopoietic stem or progenitor cells, cells isolated from bone marrow, cells isolated from cord blood, cells isolated from peripheral blood, cells isolated from thymus, or cells that have been differentiated from embryonic stem cells (ESC) or induced pluripotent stem cells (iPSC) in vitro. In some embodiments, the endogenous TCR has been suppressed through allelic exclusion.

In additional embodiments, any genetic modification compositions or methods may be used to introduce exogenous nucleic acids into cells or to edit the genomic DNA, such as gene editing, homologous recombination or non-homologous recombination, RNA-mediated genetic delivery or any conventional nucleic acid delivery methods. Non-limiting examples of the genetic modification methods may include gene editing methods such as by CRISPR/CAS9, zinc finger nuclease, or TALEN technology.

Genetic modification may also include the introduction of a selectable or screenable marker that aid selection or screen or imaging in vitro or in vivo. Particularly, in vivo imaging agents or suicide genes may be expressed exogenously or added to starting cells or progeny cells. In further aspects, the methods may involve image-guided adoptive cell therapy.

Aspects of the disclosure relate to a method for treating a patient comprising administering to the patient an in vitro differentiated T cell or T cell precursor comprising an exogenous TCR and/or CAR. In some embodiments, the use of an in vitro differentiated T cell or T cell precursor comprising an exogenous TCR and/or CAR is contemplated. The exogenous TCR may be of any defined antigen specificity. In some embodiments, it will be selected based on absent or reduced alloreactivity to the intended recipient (examples include certain virus-specific TCRs, xeno-specific TCRs, or cancer-testis antigen-specific TCRs). In the example where the exogenous TCR is non-alloreactive, during T cell differentiation the exogenous TCR suppresses rearrangement and/or expression of endogenous TCR loci through a developmental process called allelic exclusion, resulting in T cells that express only the non-alloreactive exogenous TCR and are thus non-alloreactive. In some embodiments, the choice of exogenous TCR may not necessarily be defined based on lack of alloreactivity. In some embodiments, the endogenous TCR genes have been modified by genome editing so that they do not express a protein. Methods of gene editing such as methods using the CRISPR/Cas9 system are known in the art and described herein.

In some embodiments, the methods described herein relate to stem and progenitor cells expressing an exogenous TCR and wherein the method, composition, or cells further comprise an embodiment disclosed herein. In this case, the stem cells or progenitor cells may be differentiated in vitro. In some embodiments, the stem or progenitor cells are CD34+ cells.

In some embodiments, the T cell comprises the exogenous TCR and an additional antigen or ligand recognition receptor. In some embodiments, the additional antigen recognition receptor is a CDR—(complementarity determining region) based antigen recognition receptor. In some embodiments, the exogenous TCR comprises proteins expressed from TCR-alpha and TCR-beta genes. In some embodiments, the exogenous TCR comprises proteins expressed from TCR-gamma and TCR-delta genes. In some embodiments, the exogenous TCR comprises proteins expressed from TCR-alpha and TCR-beta genes and the antigen recognition receptor comprises proteins expressed from the TCR-gamma and TCR-delta genes. In some embodiments, the exogenous TCR comprises proteins expressed from TCR-gamma and TCR-delta genes and the antigen recognition receptor comprises proteins expressed from the TCR-alpha and TCR-beta genes.

In some embodiments, the additional antigen recognition receptor is not a TCR molecule. In some embodiments, the additional antigen recognition receptor is a chimeric antigen receptor molecule (CAR). In some embodiments, the CAR is a tumor antigen-specific CAR (i.e. a CAR that recognizes a tumor antigen). In some embodiments, the CAR is a virus antigen-specific CAR (i.e. a CAR that recognizes a viral antigen). In these embodiments, the exogenous TCR mediates allelic exclusion during T cell development, but upon transplantation into patients the intended anti-tumor or anti-viral reactivity is mediated by the CAR, and the exogenous TCR is an inert "passenger".

In some embodiments, the exogenous TCR is specific for a first antigen and the additional antigen recognition receptor is specific for a second antigen. This creates a T cell with duel specificity, one specificity conferred by the additional antigen receptor, and one specificity conferred by the exogenous TCR. In some embodiments, the first and second antigens are cancer cell antigens expressed by the cancer cells of the patient. For example, a patient may have a cancer that is known or the antigens of the patient's cancer may be experimentally determined. In some embodiments, the antigens are known in the art to be associated with the cancer. In some embodiments, the antigens are experimentally determined. For example, a patient's cancerous cells may be isolated and analyzed for expression of cell surface proteins, or for immunogenic neoantigens. When the first and second antigens are cancer antigens expressed by the cancer cells of the patient, the T cells exhibit duel specificity for the same cancer cells. This is advantageous in that it limits immune evasion by the cancer when one of the antigens is lost by antigen downregulation (or other mechanisms). The exogenous TCR used to induce allelic exclusion therefore imparts functional anti-tumor or anti-viral specificity, resulting in the generation of T cells with dual target specificity. An example is an engineered non-alloreactive CAR-T cell in which the CAR mediates specificity to tumor antigen A, and the non-alloreactive TCR mediates specificity to tumor antigen B (the latter in an MHC-restricted manner). Targeting more than one antigen expressed by a target cell population may improve efficacy and reduce the escape of resistant clones.

In some embodiments, the exogenous TCR is a virus-specific TCR, a xeno-specific TCR, a cancer cell-specific TCR, a bacteria-specific TCR, or a cancer-testis antigen-specific TCR. The antigens that bind the exogenous TCR may be known in the art or experimentally determined from analysis of T cell responses to cells expressing such antigens.

In some embodiments, the T cells are allogeneic to the recipient.

In some embodiments, the patient has cancer. In some embodiments, the method is for treating cancer in the subject. In some embodiments, the cancer is selected from lung cancer, prostate cancer, ovarian cancer, testicular cancer, brain cancer, skin cancer, melanoma, colon cancer, rectal cancer, gastric cancer, esophageal cancer, tracheal cancer, head & neck cancer, pancreatic cancer, liver cancer, breast cancer, ovarian cancer, lymphoid cancers including lymphoma and multiple myeloma, leukemia, sarcomas of bone or soft tissue, cervical cancer, and vulvar cancer.

In some embodiments, the method further comprises administration of an antigen, which may be purified, conjugated to other molecules, or presented by a cell or cell-like vehicle, wherein the antigen is recognized by the exogenous TCR. This may be done to cause the in vivo expansion of the administered engineered T cells.

In some embodiments, the methods further comprise contacting the T cells with an activating composition prior to administration to the patient. For example, T cells may be activated according to the following:

| T cell subsets | CTL | Th1 | Th1/Th2 | Th1 | Th17 | Treg | Th2/Th9 |
|---|---|---|---|---|---|---|---|
| Activated by | Anti-CD3/28; anti-CD2; IL-2, IL-21, IL-15, IL-7, PMA; ionomycin; PHA; pervanadate | Anti-CD3/CD28; IL-2; PMA; ionomycin; PHA; pervanadate | Anti-CD3/CD28; IL-2; PMA; ionomycin; PHA; pervandadate | IFN-α | IL6; IL-21 | IL-2; IL-7; IL-15 | IL-4 |

Kits for activation of T cells are also commercially available. Example kits include anti-Biotin Particles (e.g. MACSiBead or DYNABEADS®) and biotinylated antibodies against human CD2, CD3, and CD28. Anti-Biotin Particles loaded with the biotinylated antibodies are used to mimic antigen-presenting cells and activate resting T cells from PBMCs as well as purified T cells. T cell expansion is achieved by culturing and reactivation at day 14 of culture. Other kits may include directly-conjugated anti-CD3/28 microbeads; multimeric antibody complexes; or use antibodies targeting alternative T cell proteins such as CD2. T cells may also be activated by mitogens such as ConA, PHA, and PWM, for example.

In some embodiments, the exogenous TCR is non-alloreactive. The term "non-alloreactive" refers to a protein that does not cause immunoreactivity when transplanted into the recipient. In some embodiments, the exogenous TCR is inert, meaning that it does not cause clinically significant toxicity.

In some embodiments, the patient has or is at risk of having a microbial infection. In certain embodiments, the patient has been tested for a microbial infection. In some embodiments, the first and second antigens are virus antigens expressed by the same virus type or by cells infected with the said virus type. In some embodiments, the first and second antigens are bacterial cell antigens expressed by the same bacterium or in cells infected with said bacterium. In some embodiments, the first and second antigens are microbial cell antigens expressed by cells of the same microbe, or cells infected with said microbe.

In some embodiments, the exogenous TCR is a NY-ESO-1 specific TCR.

In some embodiments, the method further comprises administration of an antigen presenting cell to the patient. In some embodiments, the antigen presenting cell is a dendritic cell. In some embodiments, the antigen presenting cell is an artificial antigen presenting cell. In some embodiments, the antigen presenting cell is loaded with an antigen that is recognized by the exogenous TCR. Methods of loading antigen presenting cells with antigen are known in the art. In some embodiments, the antigen presenting cells are autologous. Isolated antigen presenting cells (which may be isolated from the patient being treated) are typically treated with a maturation agent such as IL-4 and/or GM-CSF. The antigen presenting cells may then be pulsed with antigen (such as antigen specific for the exogenous TCR) to produce antigen-loaded APCs. In some embodiments, the antigen-loaded APCs are cultured (contacted with) pro-inflammatory cytokines such as LPS, interferon gamma, TNF-α, IL-1, IL-6 and/or PGE2. The method may further comprise freezing the antigen-loaded APCs, thawing antigen-loaded APCs, and administering antigen-loaded APCs to the patient.

The exogenous TCR can also be used to direct allelic exclusion and/or impart antigen specificity or additional functions to engineered regulator/suppressor T cells generated from stem and progenitor cells, irrespective of transduction with an additional antigen or ligand receptor.

In some embodiments, the in vitro differentiated T cell is engineered to be a T regulatory cell. In some embodiments, the T cell further comprises expression of FOXP3. In some embodiments, the T cell is engineered or selected to express FOXP3. In some embodiments, the FOXP3 expression is constitutive. The expression of FOXP3 may impart regulatory functionality to the T cell. Therefore, the T cells may be suppressor T cells that are useful for suppressing autoimmune or alloreactivity in the patient. Examples of this approach would be the introduction of an exogenous TCR into stem and progenitor cells which are also engineered to produce allelically excluded FOXP3 T regulatory cells; in this case the exogenous TCR may not necessarily be selected based on reduced alloreactivity.

In some embodiments of any of the above-disclosed methods, the subject has or is at risk of having an autoimmune disease, graft versus host disease (GVHD), or graft rejection. The subject may be one diagnosed with such disease or one that has been determined to have a predisposition to such disease based on genetic or family history analysis. The subject may also be one that is preparing to or has undergone a transplant. In some embodiments, the method is for treating an autoimmune disease, GVHD, or graft rejection.

Also within the scope of this disclosure are engineered T cells such as those described in the methods described herein. Accordingly, certain aspects relate to an in vitro differentiated T cell comprising an exogenous TCR. In some embodiments, the TCR is a virus-specific TCR, a xeno-specific TCR, a cancer cell-specific TCR, a bacteria-specific TCR, or a cancer-testis antigen-specific TCR. In some embodiments, the T cells further comprise an additional antigen or ligand recognition receptor. In some embodiments, the exogenous TCR comprises proteins expressed from a TCR-alpha and TCR-beta genes. In some embodiments, the exogenous TCR comprises proteins expressed from a TCR-gamma and TCR-delta genes. In some embodiments, the exogenous TCR is an engineered molecule that mimics TCR signaling. In some embodiments, the exogenous TCR comprises proteins expressed from a TCR-alpha and TCR-beta genes and the antigen recognition receptor comprises proteins expressed from the TCR-gamma and TCR-delta genes. In some embodiments, the exogenous TCR comprises proteins expressed from a TCR-gamma and TCR-delta genes and the antigen recognition receptor comprises proteins expressed from the TCR-alpha and TCR-beta genes. In some embodiments, the additional antigen recognition receptor is not a TCR molecule. In some embodiments, the additional antigen recognition receptor is a chimeric antigen receptor (CAR). In some embodiments, the CAR is a tumor antigen-specific CAR. In some embodiments, the CAR is a viral antigen-specific CAR. In some embodiments, the exogenous TCR is specific for a first antigen and the additional antigen recognition receptor is specific for a second antigen. In some embodiments, the first and second antigens are cancer cell antigens expressed by cells of a cancer. In some embodiments, the first and second antigens are viral antigens expressed by a virus or cells infected with said virus. In some embodiments, the first and second antigens are bacteria cell antigens expressed by cells of a bacterium or cells infected with said bacterium. In some embodiments, the exogenous TCR is a NY-ESO-1 specific TCR. In some embodiments, the T cell further comprises expression of FOXP3. In some embodiments, the T cell is engineered or selected to express FOXP3. In some embodiments, the FOXP3 expression is constitutive.

In some embodiments, the cells comprise: CD4$^+$CD8$^-$ T cells, CD4$^-$CD8$^+$ T cells, CD34$^+$ CD7$^+$ CD1a$^+$ cells, CD3+ TCRab+, CD3+ TCRgd+, CD3+ TCRab+ CD4+ CD8−, CD3+ TCRab+ CD8+ CD4−, CD3+ TCRab+ CD4+ CD8− CD45RO− CD45RA+, CD3+ TCRab+ CD8+ CD4− CD45RO− CD45RA+, CD3+ TCRab+ CD4+ CD8− CD45RO− CD45RA+ CCR7+, CD3+ TCRab+ CD8+ CD4− CD45RO− CD45RA+ CCR7+, CD3+ TCRab+ CD4+ CD8− CD45RO− CD45RA+ CD27+, CD3+ TCRab+ CD8+ CD4− CD45 RO− CD45RA+ CD27+, CD34$^+$ CD7$^+$ CD1a$^+$ cells, CD34+CD5+CD7+, CD34+CD5+CD7−, natural killer T cells, or regulatory T cells, antigen-specific T cells. In some embodiments, CD4$^+$CD8$^-$ T cells, CD4$^-$CD8$^+$ T cells, CD34$^+$ CD7$^+$ CD1a$^+$ cells, CD3+ TCRab+, CD3+ TCRgd+, CD3+ TCRab+ CD4+ CD8−, CD3+ TCRab+ CD8+ CD4−, CD3+ TCRab+ CD4+ CD8− CD45RO− CD45RA+, CD3+ TCRab+ CD8+ CD4− CD45RO− CD45RA+, CD3+ TCRab+ CD4+ CD8− CD45RO− CD45RA+ CCR7+, CD3+ TCRab+ CD8+ CD4− CD45RO− CD45RA+ CCR7+, CD3+ TCRab+ CD4+ CD8− CD45RO− CD45RA+ CD27+, CD3+ TCRab+ CD8+ CD4− CD45RO− CD45RA+ CD27+, CD34$^+$ CD7$^+$ CD1a$^+$ cells, CD34+CD5+CD7+, CD34+CD5+CD7−, natural killer T cells, regulatory T cells, antigen-specific T cells are excluded. In some embodiments, the cells comprise a cell surface marker described herein or the cells do not express a cell surface marker described herein. In some embodiments, the cells comprise intraepithelial lymphocytes (IELs). In some embodiments, the intraepithelial lymphocytes are CD4− CD8+, CD4+ CD8−, CD4+ CD8+, CD4− CD8−, TCRab+, TCRgd+, CD5+CD7+, CD5+ CD7+CD3−CD4−CD8−, CD5+CD7+CD3−CD4−CD8aa, or combinations thereof. In some embodiments, intraepithelial lymphocytes such as CD4− CD8+, CD4+ CD8−, CD4+ CD8+, CD4− CD8−, TCRab+, TCRgd+, CD5+CD7+, CD5+ CD7+CD3−CD4−CD8−, and/or CD5+CD7+CD3−CD4− CD8aa are excluded.

Further aspects relate to a method for delivery of an agent to exogenous TCR-expressing T cells in a patient with said exogenous TCR-expressing T cells comprising administering to the patient an agent conjugated to an antigen, wherein the antigen is recognized by the exogenous TCR. In some embodiments, the exogenous TCR is inert. In some embodiments, the agent is an elimination agent. For example, the agent may be a cytotoxic agent that eliminates the cell upon contact of the agent-antigen with the TCR on the surface of the cell. Elimination agents include, but are not limited to, for example, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); antimytotic agents such as the vinca alkaloids, vincristine and vinblastine, paclitaxel (taxol), ricin, pseudomonas exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these elimination agents. Further elimination agents include, but are not limited to chemotherapeutic agents such as carboplatin, cisplatin, paclitaxel, gemcitabine, calicheamicin, doxorubicin, 5-fluorouracil, mitomycin C, actinomycin D, cyclophosphamide, vincristine and bleomycin.

Further aspects relate to a method for the in vitro selection and isolation of the engineered T cells of the disclosure (i.e. the in vitro differentiated T cell expressing the exogenous TCR). The method comprises contacting a composition comprising the T cells with an agent that specifically binds to the exogenous TCR to make an agent-TCR expressing cell complex and purifying the agent-TCR expressing cell complex from the composition. The agent may be an antibody that specifically binds to the exogenous TCR, a peptide-MHC multimer, or any other molecule that specifically recognizes the exogenous TCR. In some embodiments, the agent is attached to a solid support. The solid support may be a bead (e.g. magnetic or sepharose), a plate such as a tissue culture dish, a coverslip, or array. The solid support may also be a purification column. In some embodiments, the method further comprises administration of a secondary molecule that specifically binds to the agent. The secondary molecule may be, for example, a secondary antibody that binds to the primary antibody. In some embodiments, the secondary molecule is attached to a solid support. In some embodiments, the method further comprises separation of the solid support and bound molecules from the composition. The separation may be done by washing unbound molecules from the solid support, and/or other separation techniques such as centrifugation or column separation. In some embodiments, the method further comprises washing the solid support and associated molecules one or more times. In some embodiments, the primary or secondary molecule may be conjugated to a fluorescent molecule method, and the separation may be done by flow cytometry/fluorescence-activated cell sorting. In some embodiments, the method further comprises dissociating the agent from the agent-TCR expressing cell complex. In some embodiments, the method further comprises further purifying the TCR expressing cells based on inclusion or exclusion of other T cell markers, for example CD4, CD8, CD45RA, CD45RO, CCR7/CD197, CD62L, CD27, CD28, and CD1a. In some embodiments, the method further comprises culturing the purified TCR expressing cells. In some embodiments, the method further comprises freezing the purified TCR expressing cells.

Further aspects relate to a method of making an in vitro differentiated T cell expressing an exogenous TCR described herein, the method comprising transferring an exogenous TCR or TCR-derivative into a stem cell or immune progenitor cell; and differentiating the stem or immune progenitor cell into a T cell or T cell precursor. The differentiation may be performed to methods known in the art or according to the differentiation/culturing methods described herein. In some embodiments, the stem or immune progenitor cell is contacted with cognate MHC and/or peptide molecules prior to, simultaneously, and/or after contact with a differentiating agent.

In some embodiments, differentiating the stem or immune progenitor cell into a T cell comprises co-culturing stem or immune progenitor cells with stromal cells ectopically expressing a Notch ligand. In some embodiments, the stromal cells are OP9 cells. In some embodiments, the Notch ligand is Delta-like 1 (Dll1). In some embodiments, the Notch ligand is one described herein or in the art, such as in U.S. Pat. No. 7,795,404, which is herein incorporated by reference. In some embodiments, the method further comprises contacting the co-cultured stem or immune progenitor cells and stromal cells with Flt-3 ligand and/or IL-7 and/or Stem Cell Factor/Kit ligand and/or thrombopoietin. In some embodiments, differentiating the stem or immune progenitor cell into a T cell comprises: culturing a three-dimensional (3D) cell aggregate, comprising: a) a selected population of stromal cells that express an exogenous Notch ligand; b) a selected population of stem or progenitor cells; with a serum-free medium comprising B-27® supplement, xeno-free B-27® supplement, GS21TM supplement, ascorbic acid, Flt-3 ligand, IL-7, or a combination thereof at a concentration effective for producing T cells from the 3D cell aggregate, wherein the 3D cell aggregate produce T cells. In some embodiments, the method further comprises one or more of the embodiments described below.

In some embodiments, the T cell population or composition of cells comprises: $CD4^+CD8^-$ T cells, $CD4^-CD8^+$ T cells, $CD34^+$ $CD7^+$ $CD1a^+$ cells, CD3+ TCRab+, CD3+ TCRgd+, CD3+ TCRab+ CD4+ CD8−, CD3+ TCRab+ CD8+ CD4−, CD3+ TCRab+ CD4+ CD8− CD45RO− CD45RA+, CD3+ TCRab+ CD8+ CD4− CD45RO− CD45RA+, CD3+ TCRab+ CD4+ CD8− CD45RO− CD45RA+ CCR7+, CD3+ TCRab+ CD8+ CD4− CD45RO− CD45RA+ CCR7+, CD3+ TCRab+ CD4+ CD8− CD45RO− CD45RA+ CD27+, CD3+ TCRab+ CD8+ CD4− CD45RO− CD45RA+ CD27+, $CD34^+$ $CD7^+$ $CD1a^+$ cells, CD34+ CD5+CD7+, CD34+CD5+CD7−, natural killer T cells, or regulatory T cells, and/or antigen-specific T cells. In some embodiments, $CD4^+CD8^-$ T cells, $CD4^-CD8^+$ T cells, $CD34^+$ $CD7^+$ $CD1a^+$ cells, CD3+ TCRab+, CD3+ TCRgd+, CD3+ TCRab+ CD4+ CD8−, CD3+ TCRab+ CD8+ CD4−, CD3+ TCRab+ CD4+ CD8− CD45RO− CD45RA+, CD3+ TCRab+ CD8+ CD4− CD45RO− CD45RA+, CD3+ TCRab+ CD4+ CD8− CD45RO− CD45RA+ CCR7+, CD3+ TCRab+ CD8+ CD4− CD45RO− CD45RA+ CCR7+, CD3+ TCRab+ CD4+ CD8− CD45RO− CD45RA+ CD27+, CD3+ TCRab+ CD8+ CD4− CD45RO− CD45RA+ CD27+, $CD34^+$ $CD7^+$ $CD1a^+$ cells, CD34+CD5+CD7+, CD34+CD5+CD7−, natural killer T cells, regulatory T cells, and/or antigen-specific T cells are excluded. In some embodiments, the intraepithelial lymphocytes are CD4− CD8+, CD4+ CD8−, CD4+ CD8+, CD4− CD8−, TCRab+, TCRgd+, CD5+CD7+, CD5+CD7+CD3−CD4−CD8−, CD5+CD7+ CD3−CD4−CD8aa, or combinations thereof. In some embodiments, intraepithelial lymphocytes such as CD4− CD8+, CD4+ CD8−, CD4+ CD8+, CD4− CD8−, TCRab+, TCRgd+, CD5+CD7+, CD5+CD7+CD3−CD4−CD8−, and/or CD5+CD7+CD3−CD4−CD8aa are excluded.

In some embodiments, the T cell population or composition of cells comprises at least or at most 5, 10, 15, 20, 25, 30, 35, 40, 45, 50, 55, 60, 65, 70, 75, 80, 85, 90, 95, or 100% (or any range derivable therein) of live cells having a phenotype and/or cell marker described herein. The cells may be from week 1, 1.5, 2, 2.5, 3, 3.5, 4, 4.5, 5, 5.5, 6, 6.5, 7, 8, 9, 10, 11, 12, 13, 14, 15, or 16 (or any derivable range therein) ATOs.

In some embodiments, the T cell population or composition of cells comprises a ratio of at least or at most 1:0.1, 1:0.2, 1:0.3, 1:0.4, 1:0.5, 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9, 1:10, 1:10.5, 1:11, 1:11.5, 1:12, 1:12.5, 1:13, 1:13.5, 1:14, 1:14.5, 1:15, 1:20, 1:25, 1:30, 1:35, 1:40, 1:45, or 1:50 (or any range derivable therein) of live cells:cells having a phenotype and/or cell marker described herein or ratio of cells having a phenotype and/or cell marker described herein:live cells.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. It is contemplate that one or more embodiments discussed herein may be specifically excluded in the claims.

Throughout this application, the term "about" is used to indicate that a value includes the inherent variation of error for the device, the method being employed to determine the value, or the variation that exists among the study subjects.

The term "consisting of" or "consisting essentially of" may be substituted for the term "comprising" in any embodiment discussed herein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 16A-F: TCR diversity and function of ATO-derived T cells. (a) Generation of TCR diversity in CD3+TCRαβ+CD8SP T cells from week 7 ATOs (n=5) or human thymi (n=4), as shown by flow cytometric analysis of the frequency of TCR Vβ family expression. (b) TCR clonotype diversity in CD3+TCRαβ+CD8SP T cells from ATOs, thymus, and peripheral blood (PB) naïve T cells by deep sequencing of TCR Vα and (c) TCR Vβ CDR3 regions. Frequency of individual clonotypes is shown. Data are representative of three biological replicates. (d) Polyfunctional cytokine production by ATO-derived CD3+TCRαβ+CD8SP T cells treated with PMA/ionomycin for 6 h. Data are representative of three different experiments. (e) Proliferation (CFSE dilution) and activation (upregulation of CD25 and 4-1BB) of ATO-derived CD3+TCRαβ+CD8SP cells after 5 days in response to anti-CD3/CD28 and IL-2. Data are representative of two individual experiments. (f) Post-ATO expansion of ATO-derived CD3+TCRαβ+CD8SP T cells relative to starting cell number in response to anti-CD3/CD28 and IL-2 after 7 and 14 days. Mean and SD of technical triplicates are shown, and data are representative of three biological replicates.

FIG. 18A-F: Antigen-specific tumor cell killing by ATO-derived TCR-engineered T cells. (a,b) In vitro cytotoxicity of ATO-derived TCR-engineered T cells against antigen-positive tumor cells. CD8SP T cells from HLA-A*02:01/NY-ESO-1157-165-specific TCR-transduced ATOs were activated with anti-CD3/28 +IL-2 for 36 h and co-incubated with K562 cells, K562 cells transduced with HLA-A*02:01 single chain trimers presenting an irrelevant (MART1$_{26-35}$) or cognate (NY-ESO1$_{156-165}$) peptide (K562-MART-1 and K562-ESO, respectively), or the HLA-A*02:01+ NY-ESO-1+ U266 multiple myeloma cell line. (a) Percent early (annexin V+ DAPI−) or late (annexin V+ DAPI+) apoptotic tumor cells was determined by flow cytometry at 9 h. Effector:Target (E:T) ratios were calculated based on percent tetramer+ T cells at the start of co-cultures. Data are representative of two biological replicates. (b) Specific cell death for cytotoxicity assays shown in (a). Total annexin V+ cells were adjusted for spontaneous (non-specific) cell death in wells that did not receive T cells. (c) Retained antigen specificity following prolonged post-ATO activation/expansion of T cells. CD8SP T cells isolated from TCR-transduced ATOs were expanded for 14 days with anti-CD3/28 and IL-2, and cytotoxicity assays performed as described in (a). Assays using TCR-transduced peripheral blood CD8+ donor T cells expanded for 14 days under the same conditions are shown for comparison. (d-f) In vivo tumor control by ATO-derived TCR-engineered T cells. CD8SP T cells from TCR-transduced ATOs were activated/expanded for 14 days, as described in (c). (d) 5.7×10⁶ T cells (including 4.5×10⁶ antigen-specific T cells by tetramer staining) or PBS were injected IV into NSG mice subcutaneously implanted 3 days earlier with 2.5×10⁵ luciferase-transduced K562-ESO or K562-MART tumor cells. (e) Response of K562-ESO vs K562-MART1 tumor cells to ATO CD8SP. Bioluminescence was recorded at the indicated timepoints. Mean and SD for 2-3 mice per group are shown (PBS n=2, TCR-transduced ATOs T cells with K562-ESO n=3, or K562-MART1 n=2) (p=0.00033, **p=0.000066). (f) Bioluminescence imaging of selected mice from assays described in (d) and (e). Note the middle row shows the only mouse of the three total K562-ESO carrying mice treated with ATO CD8SP T cells in which the tumor grew.

FIG. 19: ATOs form solid tissue-like structures. Hematoxylin and eosin staining showing tissue architecture of week 6 3D cultures generated with CB HSPCs and MS5-hDLL1 (i.e. ATO) (left), parental MS-5 cells (center), or MS5-hDLL1 cells alone (right). Magnification is 100× (top row) or 400× (bottom row).

FIG. 21A-K: T cell differentiation in ATOs is highly reproducible and not affected by B27 lot variation, xeno-free B27, or stromal irradiation. No significant effect of B27 lot variation on (a) T-lineage commitment, (b-c) T cell differentiation, or (d) total cell numbers in week 6 ATOs generated from a single CB ($7.5 \times 10^3$ CD34+CD3− HSPCs per ATO) and cultured using 4 different lots of B27 supplement (labeled A-D). Replicate ATOs (n=2-3) are shown for each B27 lot. (e) Substitution of B27 with xeno-free B27 had no significant impact on T cell differentiation or (f) total cell numbers in week 6 ATOs. Irradiation of MS5-hDLL1 stromal cells with 20-80 Gy prior to ATO generation had little impact on (g-i) T cell differentiation, or (j) total cell and CD3+TCRαβ+CD8SP T cell numbers. Mean and SD of triplicate ATOs are shown. Data are representative of two individual experiments. Flow plots in (h) show cells from CD3+TCRαβ+ gate shown in (g). (k) Harvesting cells from ATOs by mechanical disruption at 6 weeks resulted in a suspension of >99% human hematopoietic CD45+ cells (top), and <0.5% GFP+ stroma (bottom). Frequency of human and murine cells is shown for 8 biological replicate ATOs.

FIG. 24A-B: Early onset of T cell commitment from LMPP and CD24− CLP in 3 week ATOs revealed by (a) early appearance of DP and (b) T cell committed CD34+CD7+ progenitors. Data in b) is gated on CD34+ cells as shown in a). Data are representative of two biological replicates.

FIG. 25A-E: TCR diversity and functional validation of ATO-derived T cells. (a) RAG1 and RAG2 are expressed in ATO-derived CD3+CD4+CD8+ (DP) but not mature CD3+CD8SP T cells, similar to human thymocytes. Quantitative RT-PCR for RAG1 and RAG2 are shown relative to expression of B2M in FACS sorted ATO-derived and postnatal thymus-derived T cell populations. Mean and SD of triplicate reactions is shown. (b) Generation of TCR diversity in CD3+TCRαβ+CD4SP T cells isolated from week 7 ATOs (n=5) or human thymi (n=4), as shown by flow cytometric analysis of the frequency of TCR Vβ family expression. (c) Cytokine production by week 12 ATO-derived CD4SP T cells treated with PMA/ionomycin for 6 h. Data are representative of two biological replicates. (d) Proliferation (CTV dilution) and activation (upregulation of CD25) of cord blood (CB) and ATO-derived (week 12) CD4SP T cells after 5 days in response to anti-CD3/CD28 and IL-2. Data are representative of two individual experiments. (e) Post-ATO expansion of ATO-derived CD4SP T cells relative to starting cell number in response to anti-CD3/CD28 and IL-2 after 7 and 14 days. Mean and SD of technical triplicates are shown.

DESCRIPTION OF ILLUSTRATIVE EMBODIMENTS

I. Introduction

Figure 1A:
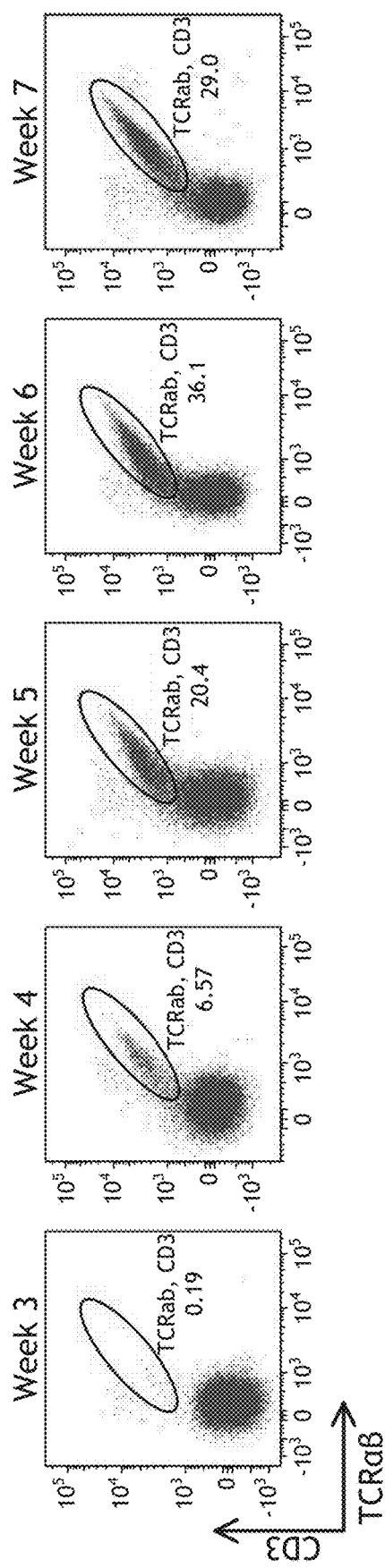
FIG. 1A-1B: Generation of human T cells from cord blood (CB) CD34+ HSPCs in artificial thymic organoids (ATOs). CB CD34+ HSPCs were differentiated for 7 weeks in ATOs. A) Weekly analysis of ATOs showing progressive development of CD3+T CRαβ+ T cells, (gated on CD14−CD56− cells to exclude monocytes and NK cells, respectively). B) Weekly analysis of ATOs gated on CD3+ TCRαβ+ cells showing development of mature CD8+ and CD4+ T cells.

Compositions and methods for producing non-alloreactive T cells that may be allogenic to the recipient patient are described. This is a significant improvement in the art that provides for more cost-effective, less labor-intensive therapies and for immunotherapies in individuals for which autologous T cell therapy is not possible. Furthermore, novel compositions and methods for generation of engineered T cells are provided. These compositions and methods have been provided based on, in part, the discovery of a cell culture composition comprising an artificial thymic organoid (ATO) 3D culture that used highly-standardized, serum-free components and a stromal cell line to facilitate robust and highly reproducible T cell differentiation from human HSPCs. In certain embodiments, it was discovered that T cell differentiation in ATOs closely mimicked endogenous thymopoiesis and, in contrast to monolayer co-cultures, supported efficient positive selection of functional CD3+ TCRαβ+ CD8+ and CD4+ T cells with a diverse TCR repertoire and antigen-naïve phenotype.

As a non-limiting example, the cell culture composition may be used at least in the generation of naive, allelically-excluded, TCR-engineered antigen-specific T cells derived from HSPCs transduced with a TCR specific for an antigen such as the NY-ESO-1 cancer-associated antigen.

In a further embodiment, it was demonstrated with this transgenic TCR system that positive selection in ATOs is driven by self-MHC on autologous hematopoietic cells, but can also be manipulated by stromal cell expression of self-MHC to model or enhance positive selection in vitro.

Thus, 3D cell culture compositions such as ATOs offer a simple, off-the-shelf, and highly standardized model of end-to-end T cell development, with the potential to advance a wide range of studies relating to hematopoiesis, immune regeneration, host immunity, and cellular immunotherapy.

The methods and compositions described herein represent a significant advance in the technology. The artificial thymic organoid embodiment provides several advantages over previously T cell differentiation methods from HSPC. Benefits include but are not limited to one or more of the following:

ATOs generate all the stages of T cell differentiation from hematopoietic stem and progenitor cells (HSPC) including and most importantly, mature naïve T cells (both CD4SP and CD8SP The ability to generate mature T cells from HSPC in ATOs allows the ATO system to be modified to generate engineered T cells by expressing genes (e.g. TCR or CAR) in HSPC The ATO system can also be modified by expressing genes in the stromal compartment (MS5)

ATO cultures may be serum-free and thus do not have the limitation of lot-to-lot variation of fetal calf serum (FCS), or the problems of clinical translation with FCS containing medium.

A comparison with other models of in vitro T cell differentiation of human HSPC illustrates their differences and demonstrates the benefits of the methods and cells provided herein. For example, the OP9-DL1 system had been considered the gold standard for T cell differentiation from human HSPC since around 2005. The system (developed by the lab of Juan Carlos Zuniga-Pflucker, Toronto, Canada) uses a monolayer from a murine stromal cell line (OP9) transduced with the notch ligand Delta like ligand 1 (DLL1 aka DL1) to induce T cell commitment from either mouse (Schmitt et al, Immunity, 2002) or human (La Motte-Mohs, *BLOOD* 2005) HSPC. HSPC are co-cultured on the OP9-DL1 monolayer in medium containing fetal calf serum and cytokines. A variation of this system uses DLL4 instead of DLL1 (OP9-DLL4); results with DLL4 are not significantly different than DLL1.

However, the OP9-DL1 system has problems. For instance, there is negligible production of mature T cells. Although OP9-DL1 (or OP9-DLL4) monolayers can induce early stages of T cell commitment (CD7+CD5+/− cells) from cord blood (CB) HSPC, differentiation past the CD4+CD8+(DP) stage is extremely inefficient with little if any CD8+ or CD4+ single positive (SP) mature T cells (see LaMotte Mohs, *BLOOD* 2005). FIG. 4 from La Motte-Mohs, *Blood* 2005 shows this. A more recent publication from the Zuniga-Pflucker group (Awong et al, *BMC Immunol* 2011) showed data from 60-70 day old OP9-DL1/CB HSPC cultures with at best ~2-4% mature CD8+ cells i.e.

Figure 1B:
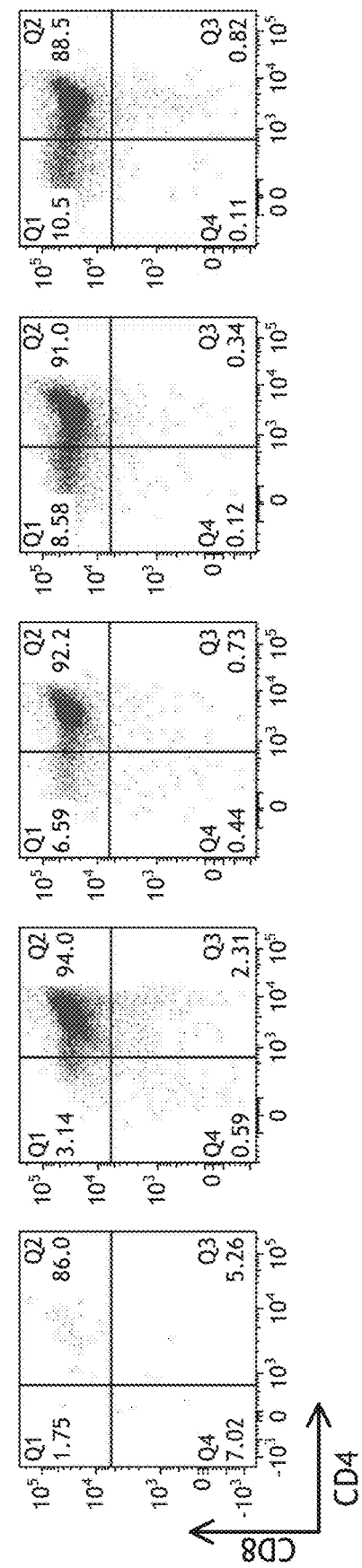

CD8+CD3+CD1a−CD27+ cells (in FIG. 1 from Awong of the 8% CD8+, 40% were CD3+CD27+).

Figures 2A, 2B:
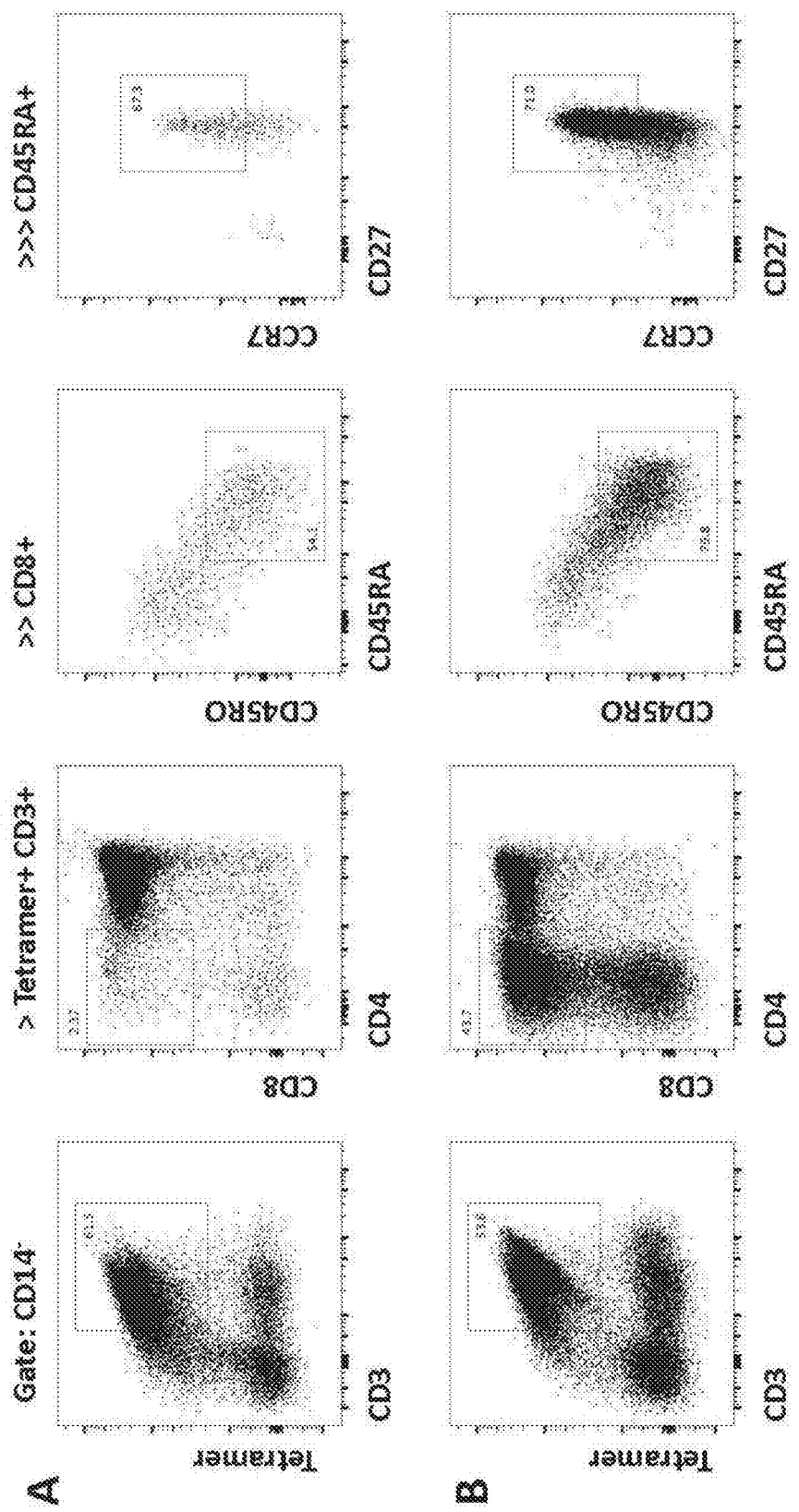
FIG. 2A-2B: Generation of antigen-specific, TCR-engineered T cells from cord blood CD34+ HSPCs in ATOs, and enhancement of positive selection by expression of a human MHC molecule in ATOs. CB CD34+ HSPCs were transduced with a lentivirus encoding a TCR specific for NY-ESO-$1_{157-165}$ in the context of HLA-A*02:01, and differentiated in ATOs for 6 weeks. A) Generation of mature, naïve, antigen-specific CD8+ T cells in ATOs, as demonstrated by expression of the TCR (detected using a HLA-A*02:01/NY-ESO-$1_{157-165}$ tetramer), CD3, CD8, CD45RA, CD27, and CCR7. Each panel represents a sequential gate from the last panel. B) Enhancement of positive selection and mature, antigen-specific T cell generation in ATOs modified to express HLA-A*02:01 in the ATO stromal cell compartment.

The other leading groups publishing on the OP9-DL1 model are from Belgium (papers variously from Vandekerckhove, Plum, Taghon). Similar to the Zuniga-Pflucker group, the Belgian group showed at best 5% CD3+TCRab+ cells and very rare if any SP8 and SP4 when using CB HSPC (de Smedt et al *Haematologica,* 2011). Of note, in another paper by this group, a higher frequency of mature T cells were seen because cultures were initiated with HSPC isolated from human thymus. In thymus, the CD34+ HSPC predominantly comprise pro-T cells that have already been exposed to the thymic signals for T cell differentiation and are thus primed to generate T cells. See FIG. 2A, Van Coppernolle et al, 2009 (HSPC derived from thymus).

As further evidence of the poor differentiation of mature T cells in the OP9-DL1 system, Table 1 in Awong et al, 2011 shows the yield in such cultures: from each single CD34+ CD38− CB HSPC only 0.27 to 1.16 TCRab+CD3+ cells were generated (n=6). In comparison, the ATO system can generate 1,000-2,000 TCRab+CD3+ cells per CB HSPC (Seet et al, 2016).

Other evidence shows that OP9-DL1 performs even worse using other (non-CB) clinical sources of HSPC. Almost all the papers using OP9-DL1 use CB HSPC because other sources (i.e. bone marrow, BM, or mobilized peripheral blood (MPB) are even more inefficient and unreliable than with CB.

The Plum group directly compared CB with BM HSPC on OP9-DL1 stroma (De Smedt et al, *Hematologica* 2011). They show in FIG. 2 of their paper that BM HSPC-initiated cultures have ~10% the frequency of DP and TCRab+CD3+ cells compared to CB (1-2% vs 12% DP and 0.7% vs 5% CD3+TCRab+ from BM vs CB respectively).

In comparison, the ATO system is a highly efficient method of differentiation from all sources of HSPC (BM, MPB, resting PB, thymus, CB) (see Seet et al, 2016).

Furthermore, OP9-DL1 does not survive in serum-free media. The inventors have been unable to reproduce the ATO findings from MS5-DL1 using OP9DL-1 in 3D aggregates and RB27 medium. It appears that OP9-DL1 does not survive the serum-free conditions.

The previously developed Fetal Thymic Organ Culture (FTOC) is is a 3D culture that consists of an intact fragment of human fetal thymus that is seeded with human HSPC and grown in fetal calf serum-containing media using an air fluid interface. There is no transduction required as notch ligand is supplied by the human thymic epithelial cells (TECs). Most of the papers on the FTOC system use this for murine T cell differentiation (Anderson et al, *Annu Rev Immunol.* 1996).

Additionally, FTOCs are not feasible for clinical translation because of the presence of allogeneic human T cells that remain in intact thymus fragment; in additional the assay shows great experimental variability and difficulty with quantitation. The limited availability of human fetal tissue completely precludes clinical translation and makes even experimental use of FTOC very difficult. FTOC have been replaced by OP9-DL1 or OP9-DLL4 because of the above limitations.

Postnatal Thymic organoids were developed by the Crooks group to study the thymic microenvironment (Chung et al, *Stem Cells* 2014). They consist of 3D cultures formed by human TECs and thymic mesenchyme derived from post natal thymus, cultured separately as monolayers for 10-21 days, and then centrifuged along with cord blood HSPC to form 3D aggregates. This model is conceptually similar to the ATOs with the differences being 1. the use of primary thymic tissue 2. The requirement for serum, 3. The dependence on endogenous notch ligand expression from TECs rather than via transduction. However, there is a problem with postnatal thymic_organoids: Primary human thymic tissue is very difficult to obtain as it is acquired from cardiac surgery patients and thus available infrequently and only from a limited number of institutions. In addition, the quality and quantity of thymic stroma is highly variable and so T cell differentiation is inconsistent and yield is poor. As the thymic tissue is allogeneic to the CB HSPC the model creates immunologic challenges. For all these reasons this model is not feasible for clinical use and is problematic for experimental use in terms of quantitation and reproducibility. For reasons discussed in more detail below, the methods and compositions provided have advantages over previously developed methods.

II. Definitions

The term "exogenous TCR" refers to a TCR gene or TCR gene derivative that is transferred (i.e. by way of gene transfer/transduction/transfection techniques) into the cell in vitro. The exogenous TCR genes are inserted into the genome of the recipient cell. In some embodiments, the insertion is random insertion. Random insertion of the TCR gene is readily achieved by methods known in the art. In some embodiments, the TCR genes are inserted into an endogenous loci (such as an endogenous TCR gene loci). In some embodiments, the cells comprise one or more TCR genes that are inserted at a loci that is not the endogenous loci. In some embodiments, the cells further comprise heterologous sequences such as a marker or resistance gene.

The term "chimeric antigen receptor" or "CAR" refers to engineered receptors, which graft an arbitrary specificity onto an immune effector cell. These receptors are used to graft the specificity of a monoclonal antibody onto a T cell; with transfer of their coding sequence facilitated by retroviral or lentiviral vectors. The receptors are called chimeric because they are composed of parts from different sources. The most common form of these molecules are fusions of single-chain variable fragments (scFv) derived from monoclonal antibodies, fused to CD3-zeta transmembrane and endodomain; CD28 or 41BB intracellular domains, or combinations thereof. Such molecules result in the transmission of a signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g. neuroblastoma cells). To target malignant B cells, investigators have redirected the specificity of T cells using a chimeric immunoreceptor specific for the B-lineage molecule, CD19. The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows the scFv to orient in different directions to enable antigen binding. The transmembrane domain is a typical hydrophobic alpha helix usually derived from the original molecule of the signalling endodomain which protrudes into the cell and transmits the desired signal.

The term "antigen" refers to any substance that causes an immune system to produce antibodies against it, or to which a T cell responds. In some embodiments, an antigen is a peptide that is 5-50 amino acids in length or is at least, at most, or exactly 5, 10, 15, 20, 25, 30, 35, 40, 45, 50, 55, 60, 65, 70, 75, 80, 85, 90, 95, 100, 125, 150, 175, 200, 250, or 300 amino acids, or any derivable range therein.

The term "allogeneic to the recipient" is intended to refer to cells that are not isolated from the recipient. In some embodiments, the cells are not isolated from the patient. In some embodiments, the cells are not isolated from a genetically matched individual (such as a relative with compatible genotypes).

The term "inert" refers to one that does not result in unwanted clinical toxicity. This could be either on-target or off-target toxicity. "Inertness" can be based on known or predicted clinical safety data.

The term "xeno-free (XF)" or "animal component-free (ACF)" or "animal free," when used in relation to a medium, an extracellular matrix, or a culture condition, refers to a medium, an extracellular matrix, or a culture condition which is essentially free from heterogeneous animal-derived components. For culturing human cells, any proteins of a non-human animal, such as mouse, would be xeno components. In certain aspects, the xeno-free matrix may be essentially free of any non-human animal-derived components, therefore excluding mouse feeder cells or Matrigel™. Matrigel™ is a solubilized basement membrane preparation extracted from the Engelbreth-Holm-Swarm (EHS) mouse sarcoma, a tumor rich in extracellular matrix proteins to include laminin (a major component), collagen IV, heparin sulfate proteoglycans, and entactin/nidogen.

The term "defined," when used in relation to a medium, an extracellular matrix, or a culture condition, refers to a medium, an extracellular matrix, or a culture condition in which the nature and amounts of approximately all the components are known.

A "chemically defined medium" refers to a medium in which the chemical nature of approximately all the ingredients and their amounts are known. These mediua are also called synthetic media. Examples of chemically defined media include TeSR™

Cells are "substantially free" of certain reagents or elements, such as serum, signaling inhibitors, animal components or feeder cells, exogenous genetic elements or vector elements, as used herein, when they have less than 10% of the element(s), and are "essentially free" of certain reagents or elements when they have less than 1% of the element(s). However, even more desirable are cell populations wherein less than 0.5% or less than 0.1% of the total cell population comprise exogenous genetic elements or vector elements.

A culture, matrix or medium are "essentially free" of certain reagents or elements, such as serum, signaling inhibitors, animal components or feeder cells, when the culture, matrix or medium respectively have a level of these reagents lower than a detectable level using conventional detection methods known to a person of ordinary skill in the art or these agents have not been extrinsically added to the culture, matrix or medium. The serum-free medium may be essentially free of serum.

"Peripheral blood cells" refer to the cellular components of blood, including red blood cells, white blood cells, and platelets, which are found within the circulating pool of blood.

"Hematopoietic stem and progenitor cells" or "hematopoietic precursor cells" refers to cells that are committed to a hematopoietic lineage but are capable of further hematopoietic differentiation and include hematopoietic stem cells, multipotential hematopoietic stem cells (hematoblasts), myeloid progenitors, megakaryocyte progenitors, erythrocyte progenitors, and lymphoid progenitors. "Hematopoietic stem cells (HSCs)" are multipotent stem cells that give rise to all the blood cell types including myeloid (monocytes and macrophages, neutrophils, basophils, eosinophils, erythrocytes, megakaryocytes/platelets, dendritic cells), and lymphoid lineages (T-cells, B-cells, NK-cells).

The hematopoietic stem and progenitor cells may or may not express CD34. The hematopoietic stem cells may co-express CD133 and be negative for CD38 expression, positive for CD90, negative for CD45RA, negative for lineage markers, or combinations thereof. Hematopoietic progenitor/precursor cells include CD34(+)/CD38(+) cells and CD34(+)/CD45RA(+)/lin(−)CD10+(common lymphoid progenitor cells), CD34(+)CD45RA(+)lin(−)CD10(−)CD62L(hi) (lymphoid primed multipotent progenitor cells), CD34(+)CD45RA(+)lin(−)CD10(−)CD123+(granulocyte-monocyte progenitor cells), CD34(+)CD45RA(−)lin(−)CD10(−)CD123+(common myeloid progenitor cells), or CD34(+)CD45RA(−)lin(−)CD10(−)CD123− (megakaryocyte-erythrocyte progenitor cells).

A "vector" or "construct" (sometimes referred to as gene delivery or gene transfer "vehicle") refers to a macromolecule, complex of molecules, or viral particle, comprising a polynucleotide to be delivered to a host cell, either in vitro or in vivo. The polynucleotide can be a linear or a circular molecule.

A "plasmid", a common type of a vector, is an extra-chromosomal DNA molecule separate from the chromosomal DNA which is capable of replicating independently of the chromosomal DNA. In certain cases, it is circular and double-stranded.

By "expression construct" or "expression cassette" is meant a nucleic acid molecule that is capable of directing transcription. An expression construct includes, at the least, a promoter or a structure functionally equivalent to a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial means, or in relation a cell refers to a cell which was isolated and subsequently introduced to other cells or to an organism by artificial means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

A "gene," "polynucleotide," "coding region," "sequence," "segment," "fragment," or "transgene" which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "cell" is herein used in its broadest sense in the art and refers to a living body which is a structural unit of tissue of a multicellular organism, is surrounded by a membrane structure which isolates it from the outside, has the capability of self-replicating, and has genetic information and a mechanism for expressing it. Cells used herein may be naturally-occurring cells or artificially modified cells (e.g., fusion cells, genetically modified cells, etc.).

As used herein, the term "stem cell" refers to a cell capable of self-replication and pluripotency or multipotency. Typically, stem cells can regenerate an injured tissue. Stem cells herein may be, but are not limited to, embryonic stem (ES) cells, induced pluripotent stem cells or tissue stem cells (also called tissue-specific stem cell, or somatic stem cell).

"Embryonic stem (ES) cells" are pluripotent stem cells derived from early embryos. An ES cell was first established in 1981, which has also been applied to production of knockout mice since 1989. In 1998, a human ES cell was established, which is currently becoming available for regenerative medicine.

Unlike ES cells, tissue stem cells have a limited differentiation potential. Tissue stem cells are present at particular locations in tissues and have an undifferentiated intracellular structure. Therefore, the pluripotency of tissue stem cells is typically low. Tissue stem cells have a higher nucleus/cytoplasm ratio and have few intracellular organelles. Most tissue stem cells have low pluripotency, a long cell cycle, and proliferative ability beyond the life of the individual. Tissue stem cells are separated into categories, based on the sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by introducing certain factors, referred to as reprogramming factors.

"Pluripotency" refers to a stem cell that has the potential to differentiate into all cells constituting one or more tissues or organs, or particularly, any of the three germ layers: endoderm (interior stomach lining, gastrointestinal tract, the lungs), mesoderm (muscle, bone, blood, urogenital), or ectoderm (epidermal tissues and nervous system). "Pluripotent stem cells" used herein refer to cells that can differentiate into cells derived from any of the three germ layers, for example, direct descendants of totipotent cells or induced pluripotent cells.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide is particularly chimeric, i.e., composed of heterologous molecules.

III. T Cell Receptor (TCR) and Methods for Generating Exogenous TCRs

The T cell receptor or TCR is a molecule found on the surface of T lymphocytes (T cells) that is responsible for recognizing fragments of antigen as peptides bound to major histocompatibility complex (MHC) molecules. The TCR is composed of two different protein chains (that is, it is a heterodimer). In 95% of T cells in humans, the TCR consists of an alpha ($\alpha$; also referred to herein as "a") and beta ($\beta$—also referred to herein is "b") chain, whereas in 5% of T cells the TCR consists of gamma and delta ($\gamma/\delta$) chains. This ratio changes during ontogeny and in diseased states as well as in different species.

When the TCR engages with antigenic peptide and MHC (peptide/MHC), the T lymphocyte is activated through signal transduction, that is, a series of biochemical events mediated by associated enzymes, co-receptors, specialized adaptor molecules, and activated or released transcription factors. The TCR is a disulfide-linked membrane-anchored heterodimeric protein normally consisting of the highly variable alpha ($\alpha$) and beta ($\beta$) chains expressed as part of a complex with the invariant CD3 chain molecules. T cells expressing this receptor are referred to as $\alpha:\beta$ (or $\alpha\beta$ or ab) T cells, though a minority of T cells express an alternate receptor, formed by variable gamma ($\gamma$—also referred to herein as "g") and delta ($\delta$—also referred to herein as "d") chains, referred as $\gamma\delta$ (or gd) T cells.

Each chain is composed of two extracellular domains: Variable (V) region and a Constant (C) region, both of Immunoglobulin superfamily (IgSF) domain forming antiparallel $\beta$-sheets. The constant region is proximal to the cell membrane, followed by a transmembrane region and a short cytoplasmic tail, while the Variable region binds to the peptide/MHC complex.

The variable domain of both the TCR $\alpha$-chain and $\beta$-chain each have three hypervariable or complementarity determining regions (CDRs), whereas the variable region of the $\beta$-chain has an additional area of hypervariability (HV4) that does not normally contact antigen and, therefore, is not considered a CDR.

The residues are located in two regions of the TCR, at the interface of the $\alpha$- and $\beta$-chains and in the $\beta$-chain framework region that is thought to be in proximity to the CD3 signal-transduction complex. CDR3 is the main CDR responsible for recognizing processed antigen, although CDR1 of the alpha chain has also been shown to interact with the N-terminal part of the antigenic peptide, whereas CDR1 of the $\beta$-chain interacts with the C-terminal part of the peptide. CDR2 is thought to recognize the MHC. CDR4 of the β-chain is not thought to participate in antigen recognition, but has been shown to interact with superantigens. The constant domain of the TCR domain consists of short connecting sequences in which a cysteine residue forms disulfide bonds, which forms a link between the two chains.

The TCR being a member of the IgSF protein means it may be compared to antibodies and BCR. In terms of similarity, TCR is like half an antibody with a heavy and a light chain, except the heavy chain is without its crystallisable fraction (Fc) (Note: ontogenically TCR alpha undergo VJ recombination, so it is like a light chain; TCR beta undergoes VDJ recombination, so it is like a heavy chain). So the TCR is ontologically like one of the antibody-binding fragments of the antibody. The two subunits of TCR are twisted together. Whereas the antibody uses its Fc region to bind to Fc Receptors on innate leukocytes, TCR is already docked onto the cell membrane. However, it is not able to mediate signal transduction itself due to its short cytoplasmic tail, so TCR still requires CD3 and zeta to carry out the signal transduction in its place, just as antibodies requires binding to FcRs to initiate signal transduction. In this way the MHC-TCR-CD3 interaction for T cells is functionally similar to the Ag-Ig-FcR interaction for myeloid leukocytes, and Ag-Ig-CD79 interaction for B cells.

Methods of generating antigen-specific TCRs are known in the art. Methods may include, for example, 1) Synthesizing known or predicted HLA-restricted peptide epitopes derived from proteins of interest (e.g. tumor antigens, neoantigens from sequencing data, etc); 2) presenting these via an antigen-presenting cell (for expansion) or tetramer (for direct sorting) to a pool of T cells from which TCR sequences are to be extracted (e.g. tumor infiltrating lymphocytes in the case of tumor-ag specific T cells); 3) selecting or screening for antigen-specific T cells (eg. FACS sorting antigen-specific T cells based on tetramer binding); 4) cloning (via RT-PCR) and sequencing the TCR genes (i.e. alpha and beta chains or gamma and delta chains of the TCRs); cloning and sequencing may be done either on a population or single cell level; and 5) confirming and analyzing TCR specificity by, for example, testing the function of TCR clones by transducing peripheral blood T cells with these sequences and assessing their reactivity to target cells that express the cognate peptide-MHC complex. Reactivity is usually measured based on cytokine production (e.g. interferon gamma).

IV. Cell Culture Compositions and Methods 3D culture compositions such as artificial thymic organoids (ATO) are an optimized, highly efficient, and highly reproducible off-the-shelf solution for the in vitro generation of human T cells from stem cells. In contrast to existing experimental models for T cell differentiation, certain aspects of the 3D culture compositions use serum-free conditions, avoid the use of human thymic tissue or proprietary scaffold materials, and facilitate positive selection and robust generation of fully functional, mature human T cells from stem cells. As a potentially commercial platform for in vitro T cell development, the 3D culture compositions offer efficiency, reproducibility, scalability, and reduced cost and labor compared to competing technologies. Non-limiting commercial applications may include in vitro experimental modeling of human T cell development, and in vitro production of engineered T cell immunotherapies from a variety of stem cell sources.

In certain embodiments, there may be provided an optimized, three-dimensional (3D) culture system for the in vitro generation of functional T cells from human stem and/or progenitor cells (HSPC). The resulting cellular 3D structures may be called artificial thymic organoids (ATO).

In particular embodiments, this system may comprise the aggregation in a 3D structure of human HSPC with stromal cells expressing a Notch ligand, in the presence of an optimized medium containing FLT3 ligand (FLT3L), interleukin 7 (IL-7), B27, and ascorbic acid. Conditions that permit culture at the air-fluid interface may also be present. It has been determined that combinatorial signaling within ATOs from soluble factors (cytokines, ascorbic acid, B27 components, and stromal cell-derived factors) together with 3D cell-cell interactions between hematopoietic and stromal cells, facilitates human T lineage commitment, positive selection, and efficient differentiation into functional, mature T cells.

In specific embodiments, there may be provided a method of a 3D culture composition (e.g., ATO production), as developed, involves aggregation of the MS-5 murine stromal cell line transduced with human DLL1 (MS-hDLL1, hereafter) with $CD34^+$ HSPCs isolated from human cord blood, bone marrow, or G-CSF mobilized peripheral blood. Up to $1\times10^6$ HSPCs are mixed with MS5-hDLL1 cells at an optimized ratio (typically 1:10 HSPCs to stromal cells).

For example, aggregation is achieved by centrifugation of the mixed cell suspension ("compaction aggregation") followed by aspiration of the cell-free supernatant. In particular embodiments, the cell pellet may then be aspirated as a slurry in 5-10 ul of a differentiation medium and transferred as a droplet onto 0.4 um nylon transwell culture inserts, which are floated in a well of differentiation medium, allowing the bottom of the insert to be in contact with medium and the top with air.

For example, the differentiation medium is composed of RPMI-1640, 5 ng/ml human FLT3L, 5 ng/ml human IL-7, 4% Serum-Free B27 Supplement, and 30 uM L-ascorbic acid. Medium may be completely replaced every 3-4 days from around the culture inserts. During the first 2 weeks of culture, cell aggregates may self-organize as ATOs, and early T cell lineage commitment and differentiation occurs. In certain aspects, ATOs are cultured for at least 6 weeks to allow for optimal T cell differentiation. Retrieval of hematopoietic cells from ATOs is achieved by disaggregating ATOs by pipetting.

Variations in the protocol permit the use of alternative components with varying impact on efficacy, specifically:

Base medium RPMI may be substituted for several commercially available alternatives (e.g. IMDM)

The stromal cell line used is MS-5, a previously described murine bone marrow cell line (Itoh et al, 1989), however MS-5 may be substituted for similar murine stromal cell lines (e.g. OP9, S17), human stromal cell lines (e.g. HS-5, HS-27a), primary human stromal cells, or human pluripotent stem cell-derived stromal cells.

The stromal cell line is transduced with a lentivirus encoding human DLL1 cDNA; however the method of gene delivery, as well as the Notch ligand gene, may be varied. Alternative Notch ligand genes include DLL4, JAG1, JAG2, and others. Notch ligands also include those described in U.S. Pat. Nos. 7,795,404 and 8,377,886, which are herein incorporated by reference. Notch ligands further include Delta 1, 3, and 4 and Jagged 1, 2.

The type and source of HSPCs may include bone marrow, cord blood, peripheral blood, thymus, or other primary sources; or HPSCs derived from human embryonic stem cells (ESC) or induced pluripotent stem cells (iPSC).

Cytokine conditions can be varied: e.g. levels of FLT3L and IL-7 may be changed to alter T cell differentiation kinetics; other hematopoietic cytokines such as Stem Cell Factor (SCF/KIT ligand), thrombopoietin (TPO), IL-2, IL-15 may be added.

Genetic modification may also be introduced to certain components to generate antigen-specific T cells, and to model positive and negative selection. Examples of these modifications include: transduction of HSPCs with a lentiviral vector encoding an antigen-specific T cell receptor (TCR) or chimeric antigen receptor (CAR) for the generation of antigen-specific, allelically excluded naïve T cells; transduction of HSPCs with gene/s to direct lineage commitment to specialized lymphoid cells. For example, transduction of HSPCs with an invariant natural killer T cell (iNKT) associated TCR to generate functional iNKT cells in ATOs; transduction of the ATO stromal cell line (e.g., MS5-hDLL1) with human MHC genes to enhance positive selection and maturation of both TCR engineered or non-engineered T cells in ATOs; and/or transduction of the ATO stromal cell line with an antigen plus costimulatory molecules or cytokines to enhance the positive selection of CAR T cells in ATOs.

V. Cell Culture Conditions

Cell culture conditions may be provided for the culture of 3D cell aggregates described herein and for the production of T cells and/or positive/negative selection thereof. In certain aspects, starting cells of a selected population may comprise at least or about $10^4$, $10^5$, $10^6$, $10^7$, $10^8$, $10^9$, $10^{10}$, $10^{11}$, $10^{12}$, $10^{13}$ cells or any range derivable therein. The starting cell population may have a seeding density of at least or about 10, $10^1$, $10^2$, $10^3$, $10^4$, $10^5$, $10^6$, $10^7$, $10^8$ cells/ml, or any range derivable therein.

B. Culture Containers

A culture vessel used for culturing the 3D cell aggregates or progeny cells thereof can include, but is particularly not limited to: flask, flask for tissue culture, dish, petri dish, dish for tissue culture, multi dish, micro plate, micro-well plate, multi plate, multi-well plate, micro slide, chamber slide, tube, tray, CellSTACK® Chambers, culture bag, and roller bottle, as long as it is capable of culturing the stem cells therein. The stem cells may be cultured in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, or any range derivable therein, depending on the needs of the culture. In a certain embodiment, the culture vessel may be a bioreactor, which may refer to any device or system that supports a biologically active environment. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

The culture vessel can be cellular adhesive or non-adhesive and selected depending on the purpose. The cellular adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used). The substrate for cell adhesion includes collagen, gelatin, poly-L-lysine, poly-D-lysine, laminin, and fibronectin and mixtures thereof for example Matrigel™, and lysed cell membrane preparations.

C. Matrix Components

Various defined matrix components may be used in the culturing methods or compositions. For example, recombinant collagen IV, fibronectin, laminin, and vitronectin in combination may be used to coat a culturing surface as a means of providing a solid support for pluripotent cell growth, as described in Ludwig et al. (2006a; 2006b), which are incorporated by reference in its entirety.

A matrix composition may be immobilized on a surface to provide support for cells. The matrix composition may include one or more extracellular matrix (ECM) proteins and an aqueous solvent. The term "extracellular matrix" is recognized in the art. Its components include one or more of the following proteins: fibronectin, laminin, vitronectin, tenascin, entactin, thrombospondin, elastin, gelatin, collagen, fibrillin, merosin, anchorin, chondronectin, link protein, bone sialoprotein, osteocalcin, osteopontin, epinectin, hyaluronectin, undulin, epiligrin, and kalinin. Other extracellular matrix proteins are described in Kleinman et al., (1993), herein incorporated by reference. It is intended that the term "extracellular matrix" encompass a presently unknown extracellular matrix that may be discovered in the future, since its characterization as an extracellular matrix will be readily determinable by persons skilled in the art.

In some aspects, the total protein concentration in the matrix composition may be about 1 ng/mL to about 1 mg/mL. In some embodiments, the total protein concentration in the matrix composition is about 1 μg/mL to about 300 μg/mL. In more preferred embodiments, the total protein concentration in the matrix composition is about 5 μg/mL to about 200 μg/mL.

The extracellular matrix (ECM) proteins may be of natural origin and purified from human or animal tissues. Alternatively, the ECM proteins may be genetically engineered recombinant proteins or synthetic in nature. The ECM proteins may be a whole protein or in the form of peptide fragments, native or engineered. Examples of ECM protein that may be useful in the matrix for cell culture include laminin, collagen I, collagen IV, fibronectin and vitronectin. In some embodiments, the matrix composition includes synthetically generated peptide fragments of fibronectin or recombinant fibronectin.

In still further embodiments, the matrix composition includes a mixture of at least fibronectin and vitronectin. In some other embodiments, the matrix composition preferably includes laminin.

The matrix composition preferably includes a single type of extracellular matrix protein. In some embodiments, the matrix composition includes fibronectin, particularly for use with culturing progenitor cells. For example, a suitable matrix composition may be prepared by diluting human fibronectin, such as human fibronectin sold by Becton, Dickinson & Co. of Franklin Lakes, N.J. (BD) (Cat #354008), in Dulbecco's phosphate buffered saline (DPBS) to a protein concentration of 5 μg/mL to about 200 μg/mL. In a particular example, the matrix composition includes a fibronectin fragment, such as RetroNectin®. RetroNectin® is a ~63 kDa protein of (574 amino acids) that contains a central cell-binding domain (type III repeat, 8,9,10), a high affinity heparin-binding domain II (type III repeat, 12,13, 14), and CS1 site within the alternatively spliced IIICS region of human fibronectin.

In some other embodiments, the matrix composition may include laminin. For example, a suitable matrix composition may be prepared by diluting laminin (Sigma-Aldrich (St.

Louis, Mo.); Cat #L6274 and L2020) in Dulbecco's phosphate buffered saline (DPBS) to a protein concentration of 5 µg/ml to about 200 µg/ml.

In some embodiments, the matrix composition is xeno-free, in that the matrix is or its component proteins are only of human origin. This may be desired for certain research applications. For example in the xeno-free matrix to culture human cells, matrix components of human origin may be used, wherein any non-human animal components may be excluded. In certain aspects, Matrigel™ may be excluded as a substrate from the culturing composition. Matrigel™ is a gelatinous protein mixture secreted by mouse tumor cells and is commercially available from BD Biosciences (New Jersey, USA). This mixture resembles the complex extracellular environment found in many tissues and is used frequently by cell biologists as a substrate for cell culture, but it may introduce undesired xeno antigens or contaminants.

VI. Selectable or Screenable Markers

In certain embodiments, cells containing an exogenous nucleic acid may be identified in vitro or in vivo by including a marker in the expression vector or the exogenous nucleic acid. Such markers would confer an identifiable change to the cell permitting easy identification of cells containing the expression vector. Generally, a selection marker may be one that confers a property that allows for selection. A positive selection marker may be one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

Selectable markers may include a type of reporter gene used in laboratory microbiology, molecular biology, and genetic engineering to indicate the success of a transfection or other procedure meant to introduce foreign DNA into a cell. Selectable markers are often antibiotic resistance genes; cells that have been subjected to a procedure to introduce foreign DNA are grown on a medium containing an antibiotic, and those cells that can grow have successfully taken up and expressed the introduced genetic material. Examples of selectable markers include: the Abicr gene or Neo gene from Tn5, which confers antibiotic resistance to geneticin.

A screenable marker may comprise a reporter gene, which allows the researcher to distinguish between wanted and unwanted cells. Certain embodiments of the present invention utilize reporter genes to indicate specific cell lineages. For example, the reporter gene can be located within expression elements and under the control of the ventricular- or atrial-selective regulatory elements normally associated with the coding region of a ventricular- or atrial-selective gene for simultaneous expression. A reporter allows the cells of a specific lineage to be isolated without placing them under drug or other selective pressures or otherwise risking cell viability.

Examples of such reporters include genes encoding cell surface proteins (e.g., CD4, HA epitope), fluorescent proteins, antigenic determinants and enzymes (e.g., 0-galactosidase). The vector containing cells may be isolated, e.g., by FACS using fluorescently-tagged antibodies to the cell surface protein or substrates that can be converted to fluorescent products by a vector encoded enzyme.

In specific embodiments, the reporter gene is a fluorescent protein. A broad range of fluorescent protein genetic variants have been developed that feature fluorescence emission spectral profiles spanning almost the entire visible light spectrum (see Table 1 for non-limiting examples). Mutagenesis efforts in the original *Aequorea victoria* jellyfish green fluorescent protein have resulted in new fluorescent probes that range in color from blue to yellow, and are some of the most widely used in vivo reporter molecules in biological research. Longer wavelength fluorescent proteins, emitting in the orange and red spectral regions, have been developed from the marine anemone, *Discosoma striata*, and reef corals belonging to the class Anthozoa. Still other species have been mined to produce similar proteins having cyan, green, yellow, orange, and deep red fluorescence emission. Developmental research efforts are ongoing to improve the brightness and stability of fluorescent proteins, thus improving their overall usefulness.

TABLE 1

Fluorescent Protein Properties

| Protein (Acronym) | Excitation Maximum (nm) | Emission Maximum (nm) | Molar Extinction Coefficient | Quantum Yield | in vivo Structure | Relative Brightness (% of EGFP) |
|---|---|---|---|---|---|---|
| GFP (wt) | 395/475 | 509 | 21,000 | 0.77 | Monomer* | 48 |
| Green Fluorescent Proteins | | | | | | |
| EGFP | 484 | 507 | 56,000 | 0.60 | Monomer* | 100 |
| AcGFP | 480 | 505 | 50,000 | 0.55 | Monomer* | 82 |
| TurboGFP | 482 | 502 | 70,000 | 0.53 | Monomer* | 110 |
| Emerald | 487 | 509 | 57,500 | 0.68 | Monomer* | 116 |
| Azami Green | 492 | 505 | 55,000 | 0.74 | Monomer | 121 |
| ZsGreen | 493 | 505 | 43,000 | 0.91 | Tetramer | 117 |

TABLE 1-continued

Fluorescent Protein Properties

| Protein (Acronym) | Excitation Maximum (nm) | Emission Maximum (nm) | Molar Extinction Coefficient | Quantum Yield | in vivo Structure | Relative Brightness (% of EGFP) |
|---|---|---|---|---|---|---|
| Blue Fluorescent Proteins | | | | | | |
| EBFP | 383 | 445 | 29,000 | 0.31 | Monomer* | 27 |
| Sapphire | 399 | 511 | 29,000 | 0.64 | Monomer* | 55 |
| T-Sapphire | 399 | 511 | 44,000 | 0.60 | Monomer* | 79 |
| Cyan Fluorescent Proteins | | | | | | |
| ECFP | 439 | 476 | 32,500 | 0.40 | Monomer* | 39 |
| mCFP | 433 | 475 | 32,500 | 0.40 | Monomer | 39 |
| Cerulean | 433 | 475 | 43,000 | 0.62 | Monomer* | 79 |
| CyPet | 435 | 477 | 35,000 | 0.51 | Monomer* | 53 |
| AmCyan1 | 458 | 489 | 44,000 | 0.24 | Tetramer | 31 |
| Midori-Ishi Cyan | 472 | 495 | 27,300 | 0.90 | Dimer | 73 |
| mTFP1 (Teal) | 462 | 492 | 64,000 | 0.85 | Monomer | 162 |
| Yellow Fluorescent Proteins | | | | | | |
| EYFP | 514 | 527 | 83,400 | 0.61 | Monomer* | 151 |
| Topaz | 514 | 527 | 94,500 | 0.60 | Monomer* | 169 |
| Venus | 515 | 528 | 92,200 | 0.57 | Monomer* | 156 |
| mCitrine | 516 | 529 | 77,000 | 0.76 | Monomer | 174 |
| YPet | 517 | 530 | 104,000 | 0.77 | Monomer* | 238 |
| PhiYFP | 525 | 537 | 124,000 | 0.39 | Monomer* | 144 |
| Zs Yellow1 | 529 | 539 | 20,200 | 0.42 | Tetramer | 25 |
| mBanana | 540 | 553 | 6,000 | 0.7 | Monomer | 13 |
| Orange and Red Fluorescent Proteins | | | | | | |
| Kusabira Orange | 548 | 559 | 51,600 | 0.60 | Monomer | 92 |
| mOrange | 548 | 562 | 71,000 | 0.69 | Monomer | 146 |
| dTomato | 554 | 581 | 69,000 | 0.69 | Dimer | 142 |
| dTomato-Tandem | 554 | 581 | 138,000 | 0.69 | Monomer | 283 |
| DsRed | 558 | 583 | 75,000 | 0.79 | Tetramer | 176 |
| DsRed2 | 563 | 582 | 43,800 | 0.55 | Tetramer | 72 |
| DsRed-Express (T1) | 555 | 584 | 38,000 | 0.51 | Tetramer | 58 |
| DsRed-Monomer | 556 | 586 | 35,000 | 0.10 | Monomer | 10 |
| mTangerine | 568 | 585 | 38,000 | 0.30 | Monomer | 34 |
| mStrawberry | 574 | 596 | 90,000 | 0.29 | Monomer | 78 |
| AsRed2 | 576 | 592 | 56,200 | 0.05 | Tetramer | 8 |
| mRFP1 | 584 | 607 | 50,000 | 0.25 | Monomer | 37 |
| JRed | 584 | 610 | 44,000 | 0.20 | Dimer | 26 |
| mCherry | 587 | 610 | 72,000 | 0.22 | Monomer | 47 |
| HcRed1 | 588 | 618 | 20,000 | 0.015 | Dimer | 1 |
| mRaspberry | 598 | 625 | 86,000 | 0.15 | Monomer | 38 |
| HcRed-Tandem | 590 | 637 | 160,000 | 0.04 | Monomer | 19 |
| mPlum | 590 | 649 | 41,000 | 0.10 | Monomer | 12 |
| AQ143 | 595 | 655 | 90,000 | 0.04 | Tetramer | 11 |

*Weak Dimer

VII. Exogenous Gene Editing

In certain embodiments, engineered nucleases may be used to introduce exogenous nucleic acid sequences for genetic modification of any cells used herein, particularly the starting cells, such as stroma cells or stem or progenitor cells in the culturing methods or compositions.

Genome editing, or genome editing with engineered nucleases (GEEN) is a type of genetic engineering in which DNA is inserted, replaced, or removed from a genome using artificially engineered nucleases, or "molecular scissors." The nucleases create specific double-stranded break (DSBs) at desired locations in the genome, and harness the cell's endogenous mechanisms to repair the induced break by natural processes of homologous recombination (HR) and nonhomologous end-joining (NHEJ).

Non-limiting engineered nucleases include: Zinc finger nucleases (ZFNs), Transcription Activator-Like Effector Nucleases (TALENs), the CRISPR/Cas9 system, and engineered meganuclease re-engineered homing endonucleases. Any of the engineered nucleases known in the art can be used in certain aspects of the methods and compositions.

It is commonly practiced in genetic analysis that in order to understand the function of a gene or a protein function one interferes with it in a sequence-specific way and monitors its effects on the organism. However, in some organisms it is difficult or impossible to perform site-specific mutagenesis, and therefore more indirect methods have to be used, such as silencing the gene of interest by short RNA interference (siRNA). Yet gene disruption by siRNA can be variable and incomplete. Genome editing with nucleases such as ZFN is different from siRNA in that the engineered nuclease is able to modify DNA-binding specificity and therefore can in principle cut any targeted position in the genome, and introduce modification of the endogenous sequences for genes that are impossible to specifically target by conventional RNAi. Furthermore, the specificity of ZFNs and TALENs are enhanced as two ZFNs are required in the recognition of their portion of the target and subsequently direct to the neighboring sequences.

Meganucleases, found commonly in microbial species, have the unique property of having very long recognition sequences (>14 bp) thus making them naturally very specific. This can be exploited to make site-specific DSB in genome editing; however, the challenge is that not enough meganucleases are known, or may ever be known, to cover all possible target sequences. To overcome this challenge, mutagenesis and high throughput screening methods have been used to create meganuclease variants that recognize unique sequences. Others have been able to fuse various meganucleases and create hybrid enzymes that recognize a new sequence. Yet others have attempted to alter the DNA interacting aminoacids of the meganuclease to design sequence specific meganucelases in a method named rationally designed meganuclease (U.S. Pat. No. 8,021,867 B2, incorporated herein by reference).

Meganuclease have the benefit of causing less toxicity in cells compared to methods such as ZFNs likely because of more stringent DNA sequence recognition; however, the construction of sequence specific enzymes for all possible sequences is costly and time consuming as one is not benefiting from combinatorial possibilities that methods such as ZFNs and TALENs utilize. So there are both advantages and disadvantages.

As opposed to meganucleases, the concept behind ZFNs and TALENs is more based on a non-specific DNA cutting enzyme which would then be linked to specific DNA sequence recognizing peptides such as zinc fingers and transcription activator-like effectors (TALEs). One way was to find an endonuclease whose DNA recognition site and cleaving site were separate from each other, a situation that is not common among restriction enzymes. Once this enzyme was found, its cleaving portion could be separated which would be very non-specific as it would have no recognition ability. This portion could then be linked to sequence recognizing peptides that could lead to very high specificity. An example of a restriction enzyme with such properties is FokI. Additionally FokI has the advantage of requiring dimerization to have nuclease activity and this means the specificity increases dramatically as each nuclease partner would recognize a unique DNA sequence. To enhance this effect, FokI nucleases have been engineered that can only function as heterodimers and have increased catalytic activity. The heterodimer functioning nucleases would avoid the possibility of unwanted homodimer activity and thus increase specificity of the DSB.

Although the nuclease portion of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically happen in repeats that are 3 bp apart and are found in diverse combinations in a variety of nucleic acid interacting proteins such as transcription factors. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Zinc fingers have been more established in these terms and approaches such as modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries among other methods have been used to make site specific nucleases.

VIII. Exogenous Gene Delivery

In certain embodiments, vectors could be constructed to comprise exogenous nucleic acid sequences for genetic modification of any cells used herein, particularly the starting cells, such as stroma cells or stem or progenitor cells in the culturing methods or compositions. Details of components of these vectors and delivery methods are disclosed below.

A. Vector

One of skill in the art would be well equipped to construct a vector through standard recombinant techniques (see, for example, Maniatis et al., 1988 and Ausubel et al., 1994, both incorporated herein by reference).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also might include markers, such as detectable and/or selection markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

B. Regulatory Elements

Eukaryotic expression cassettes included in the vectors particularly contain (in a 5'-to-3' direction) a eukaryotic transcriptional promoter operably linked to a protein-coding sequence, splice signals including intervening sequences, and a transcriptional termination/polyadenylation sequence.

i. Promoter/Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e. g., beta actin promoter (Ng, 1989; Quitsche et al., 1989), GADPH promoter (Alexander et al., 1988, Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007). A specific example could be a phosphoglycerate kinase (PGK) promoter.

ii. Protease Cleavage Sites/Self-Cleaving Peptides and Internal Ribosome Binding Sites Suitable protease cleavages sites and self-cleaving peptides are known to the skilled person (see, e.g., in Ryan et al., 1997; Scymczak et al., 2004). Examples of protease cleavage sites are the cleavage sites of potyvirus NIa proteases (e.g. tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYIF (parsnip yellow fleck virus) 3C-like protease, thrombin, factor Xa and enterokinase. Due to its high cleavage stringency, TEV (tobacco etch virus) protease cleavage sites may be used.

Exemplary self-cleaving peptides (also called "cis-acting hydrolytic elements", CHYSEL; see deFelipe (2002) are derived from potyvirus and cardiovirus 2A peptides. Particular self-cleaving peptides may be selected from 2A peptides derived from FMDV (foot-and-mouth disease virus), equine rhinitis A virus, Thosea asigna virus and porcine teschovirus.

A specific initiation signal also may be used for efficient translation of coding sequences in a polycistronic message. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

iii. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

iv. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

v. Termination Signals

The vectors or constructs may comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, the terminator comprises a signal for the cleavage of the RNA, and the terminator signal promotes polyadenylation of the message. The terminator and/or polyadenylation site elements can serve to enhance message levels and to minimize read through from the cassette into other sequences.

Terminators contemplated include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

vi. Polyadenylation Signals

In expression, particularly eukaryotic expression, one will typically include a polyadenylation signal to effect proper polyadenylation of the transcript. The nature of the polyadenylation signal is not believed to be crucial to the successful practice, and any such sequence may be employed. Exemplary embodiments include the SV40 polyadenylation signal or the bovine growth hormone polyadenylation signal, convenient and known to function well in various target cells. Polyadenylation may increase the stability of the transcript or may facilitate cytoplasmic transport.

vii. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in differentiation programming, which is a specific nucleic acid sequence at which replication is initiated. Alternatively a replication origin of other extra-chromosomally replicating virus as described above or an autonomously replicating sequence (ARS) can be employed.

C. Vector Delivery

Genetic modification or introduction of exogenous nucleic acids into starting cells of the culturing composition or methods may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464, 765, each incorporated herein by reference); by *Agrobacterium*-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

i. Liposome-Mediated Transfection

In a certain embodiment, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a nucleic acid complexed with Lipofectamine (Gibco BRL) or Superfect (Qiagen). The amount of liposomes used may vary upon the nature of the liposome as well as the, cell used, for example, about 5 to about 20 μg vector DNA per 1 to 10 million of cells may be contemplated.

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

ii. Electroporation

In certain embodiments, a nucleic acid is introduced into a cell via electroporation. Electroporation involves the exposure of a suspension of cells and DNA to a high-voltage electric discharge. Recipient cells can be made more susceptible to transformation by mechanical wounding. Also the amount of vectors used may vary upon the nature of the cells used, for example, about 5 to about 20 μg vector DNA per 1 to 10 million of cells may be contemplated.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

iii. Calcium Phosphate

In other embodiments, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

iv. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

IX. Cell Culture Applications

Culture compositions described herein can be used to produce T cells that have commercial or clinical applications as exemplified below.

Method may be provided for in vitro production of antigen-specific T cells from stem cells for immunotherapy. The use of T cells genetically engineered to respond to specific antigens is promising investigational approach to adoptive cell therapy for cancer and infectious diseases. Engineered T cell strategies include transduction with T cell receptors (TCR) and chimeric antigen receptors (CAR) to convey antigen specificity; and gene modifications to improve the efficacy or safety of transferred T cells (for example, by downregulating inhibitory signaling, deleting viral co-receptors, or introducing so-called suicide genes).

To date, investigational therapies of engineered T cells have used peripheral blood T cells. This approach has demonstrated efficacy in clinical trials of several malignant and infectious diseases, however remains problematic for the following reasons. First, adoptively transferred T cells decline in number over time in vivo, resulting in the eventual loss of tumor- or virus-specific immunity. Second, ex vivo activation and expansion of T cells is often required to facilitate efficient gene transduction, and may result in T cell exhaustion and diminished immune potential. Third, in the case of TCR-engineered T cells, mispairing of transgenic and endogenous TCR chains may result in hybrid receptors with diminished antigen recognition or off-target toxicity/autoimmunity (or in the case of CAR T cells, residual expression of an endogenous TCR on highly activated T cells may also lead to off-target toxicity).

The de novo generation of engineered T cells from stem cells using ATOs, has the potential to overcome these limitations of engineered T cells therapies in the following ways: 1) Introduction of a TCR or CAR gene into HSPC (which are pre-thymic) suppresses rearrangement of endogenous TCR loci in developing T cells (alleleic exclusion), resulting in T cells that only express the transgenic antigen receptor, thus mitigating the risk of off-target toxicity from TCR chain mispairing or passenger TCR expression; and 2) HSPC have the potential to generate antigen-specific T cells with a naïve, non-exhausted phenotype, thereby enhancing the quality and longevity of T cells available for adoptive therapy. Furthermore, the generation of allelically-excluded, antigen-specific T cells creates the opportunity to develop off-the-shelf antigen-specific T cell libraries that may be used in allogeneic donors without the risk of graft versus host disease (GVHD) from endogenous donor TCR expression. Despite these advantages, there are currently no commercial approaches for the development of antigen-specific T cells from stem or progenitor cells.

Specific examples of clinical applications in which the ATO system could plausibly be used include:

In vitro production of autologous TCR- and/or CAR-engineered T cells from HSPC for adoptive cellular anti-tumor or anti-viral immunotherapy. Autologous HSPC sources include cord blood, bone marrow and mobilized peripheral blood.

In vitro production of autologous TCR- and/or CAR-engineered T cells from human pluripotent stem cells, including iPSC.

In vitro production of allogeneic (HLA-matched or HLA-modified) TCR- or CAR-engineered T cells from HSPC or pluripotent stem cells as a commercially scalable, off-the-shelf product for adoptive cell therapy. As discussed above, through allelic exclusion T cells produced from TCR and/or CAR transduced pre-thymic HSPC do not express an endogenous TCR, and should not carry the risk of off-target GVHD when transplanted into allogeneic recipients. Stem cells used for this purpose could be further selected or genetically modified to enhance progeny T cell engraftment in allogeneic hosts (for example by using HLA-matched HSPC, or by gene modification of HLA loci or NK cell ligands to decrease alloimmune recognition).

Modification of non-antigen receptor genes in stem cells, with or without introduction of a TCR and/or CAR, to enhance in vivo function of ATO-derived T cells. Examples include genetic inactivation or knock-down of co-inhibitory receptors such as PD-1, TIM-3, or LAG-3; inhibitory signaling pathways such as the TGFβ; or viral entry co-receptors such as CCR5.

Use of the 3D culture aggregates as thymic organoids for modeling the effects of pharmaceutical or biologic compounds on T cell development and function, for example in drug toxicity assays. This could be extended to the use of ATOs with autologous patient cells to model patient-specific pharmacogenomic or disease-specific interactions.

Method and compositions may be provided for the use of a research tool for studying T cell development. As described above, the 3D cell aggregates such as ATOs are a powerful tool for the study of human T cell development from multiple stem cell sources including stem and progenitor cells and hematopoietic stem and progenitor cells (HSPC) and human pluripotent stem cells, including embryonic stem cells (ESC) and induced pluripotent stem cells (iPSC).

Experimental methods currently practiced in laboratories to model T cell development have several important limitations:

OP9-DL1 and similar stromal cell based monolayer systems use immortalized murine bone marrow cells lines transduced with a Notch ligand (typically murine Dll1 or Dll4) as a "feeder layer" for HSPCs. In vitro co-culture of human HSPCs on OP9-DL1 results in commitment to the T cell lineage, however positive selection of T cells is largely impaired resulting in marked deficiency of mature, functional T cells in these systems. Stromal cell co-culture systems are also highly labor intensive, and efficiency and reproducibility are dependent on multiple variables including fetal calf serum lot.

Fetal thymic organ culture (FTOC) methods use intact or reaggregated murine or human fetal thymic tissue depleted of hematopoietic cells as microenvironments to study in vitro T cell development from HSPC. These methods are highly labor-intensive, result in low efficiency T cell generation, provide limited ability for quantitative assays, exhibit high experimental variability due to tissue age and quality, and are limited by accessibility to primary thymic tissue.

Scaffold-based organoids typically use primary thymic stromal cells or similar cells types (e.g. dermal fibroblasts) seeded onto a biomaterial matrix. These systems are limited by low efficiency and scalability, poor reproducibility, and limited availability of proprietary scaffold materials.

Xenogeneic (murine) models of in vivo human T cell development are highly variable in the efficiency of T cell differentiation and poorly quantitative, and many approaches also require implantation of human fetal thymus, liver, and bone marrow cells or fragments into immunodeficient mice.

In contrast to these approaches, ATOs use "off-the-shelf" components and serum-free conditions to reduce biological variability stemming from the use of primary tissue or fetal calf serum; and avoid the use of proprietary scaffold materials. Importantly, ATOs support greatly improved positive selection, allowing the study of mature T cells and T cell positive/negative selection in vitro. Thus, ATOs may be commercialized as a tool for studying T cell development in vitro.

Methods and compositions described herein may also be used as a tool to develop new antigen-specific TCRs to cancer or other therapeutically relevant antigens. For example, the ATO-derived T cells may be selected based on reactivity to tumor-associated antigens or neoantigens using published methods and antigen-specific TCR sequences identified from these responding T cells using published methods. Since we hypothesize the ATO can provide for the generation of T cells with minimal or no negative selection, TCRs with high avidity to self-antigens may be generated, offering a novel TCR repertoire that is distinct from endogenous "thymus-educated" T cell pools. A second method is introducing a tumor-associated antigen during T cell development in ATOs, which should induce agonist selection (and IEL-like differentiation) of reactive T cell clones as they develop within ATOs; these cells and their TCR sequences can then be identified by standard methods. The TCR sequences isolated can also be used in downstream applications and methods described herein for adoptive immunotherapy.

The methods and compositions described herein may also include methods and compositions for expanding embryonic stem cells and/or progenitor cells. Methods known in the art, such as those described in US 20060205072, U.S. Pat. No. 7,344,881, US 20060205071, US 20020076747, and US 20030044978 (which are herein incorporated by reference) may be included in the compositions and methods of the disclosure.

The methods and compositions described herein may also include methods and compositions for increasing the proliferative capacity of cells, such as ES cells, HSPCs/PSC, and/or CD34+ cells. Exemplary compounds include HSC835 (commercialized by Novartis), which achieves expansion of CD34+ cells ex vivo. Other compounds are described in U.S. Pat. No. 8,927,281, which is herein incorporated by reference.

X. Source of Starting Cells

Starting cells such as pluripotent stem cells or hematopoietic stem or progenitor cells may be used in certain compositions or methods for differentiation along a selected T cell lineage. Stromal cells may be used to co-culture with the stem or progenitor cells.

A. Stromal Cells

Stromal cells are connective tissue cells of any organ, for example in the bone marrow, thymus, uterine mucosa (endometrium), prostate, and the ovary. They are cells that support the function of the parenchymal cells of that organ. Fibroblasts (also known as mesenchymal stromal cells/MSC) and pericytes are among the most common types of stromal cells.

The interaction between stromal cells and tumor cells is known to play a major role in cancer growth and progression. In addition, by regulating locally cytokine networks (e.g. M-CSF, LIF), bone marrow stromal cells have been described to be involved in human haematopoiesis and inflammatory processes.

Stromal cells in the bone marrow, thymus, and other hematopoietic organs regulate hematopoietic and immune cell development though cell-cell ligand-receptor interactions and through the release of soluble factors including cytokines and chemokines. Stromal cells in these tissues form niches that regulate stem cell maintenance, lineage specification and commitment, and differentiation to effector cell types.

Stroma is made up of the non-malignant host cells. Stromal cells also provides an extracellular matrix on which tissue-specific cell types, and in some cases tumors, can grow.

B. Hematopoietic Stem and Progenitor Cells

Due to the significant medical potential of hematopoietic stem and progenitor cells, substantial work has been done to try to improve methods for the differentiation of hematopoietic progenitor cells from embryonic stem cells. In the human adult, hematopoietic stem cells present primarily in bone marrow produce heterogeneous populations of hematopoietic (CD34+) progenitor cells that differentiate into all the cells of the blood system. In an adult human, hematopoietic progenitors proliferate and differentiate resulting in the generation of hundreds of billions of mature blood cells daily. Hematopoietic progenitor cells are also present in cord blood. In vitro, human embryonic stem cells may be differentiated into hematopoietic progenitor cells. Hematopoietic progenitor cells may also be expanded or enriched from a sample of peripheral blood as described below. The hematopoietic cells can be of human origin, murine origin or any other mammalian species.

Isolation of hematopoietic progenitor cells include any selection methods, including cell sorters, magnetic separation using antibody-coated magnetic beads, packed columns; affinity chromatography; cytotoxic agents joined to a monoclonal antibody or used in conjunction with a monoclonal antibody, including but not limited to, complement and cytotoxins; and "panning" with antibody attached to a solid matrix, e.g., plate, or any other convenient technique.

The use of separation or isolation techniques include, but are not limited to, those based on differences in physical (density gradient centrifugation and counter-flow centrifugal elutriation), cell surface (lectin and antibody affinity), and vital staining properties (mitochondria-binding dye rho123 and DNA-binding dye Hoechst 33342). Techniques providing accurate separation include but are not limited to, FACS (Fluorescence-activated cell sorting) or MACS (Magnetic-activated cell sorting), which can have varying degrees of sophistication, e.g., a plurality of color channels, low angle and obtuse light scattering detecting channels, impedance channels, etc.

The antibodies utilized in the preceding techniques or techniques used to assess cell type purity (such as flow cytometry) can be conjugated to identifiable agents including, but not limited to, enzymes, magnetic beads, colloidal magnetic beads, haptens, fluorochromes, metal compounds, radioactive compounds, drugs or haptens. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies, see Haugland, Molecular Probes: Handbook of Fluorescent Probes and Research Chemicals (1992-1994). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxygenin, oxazalone, and nitrophenol. The radioactive compounds that can be conjugated or incorporated into the antibodies are known to the art, and include but are not limited to technetium 99m (99TC), 1251 and amino acids comprising any radionuclides, including, but not limited to, 14C, 3H and 35S.

Other techniques for positive selection may be employed, which permit accurate separation, such as affinity columns, and the like. The method should permit the removal to a residual amount of less than about 20%, preferably less than about 5%, of the non-target cell populations.

Cells may be selected based on light-scatter properties as well as their expression of various cell surface antigens. The purified stem cells have low side scatter and low to medium forward scatter profiles by FACS analysis. Cytospin preparations show the enriched stem cells to have a size between mature lymphoid cells and mature granulocytes.

It also is possible to enrich the inoculation population for CD34+ cells prior to culture, using for example, the method of Sutherland et al. (1992) and that described in U.S. Pat. No. 4,714,680. For example, the cells are subject to negative selection to remove those cells that express lineage specific markers. In an illustrative embodiment, a cell population may be subjected to negative selection for depletion of non-CD34+ hematopoietic cells and/or particular hematopoietic cell subsets. Negative selection can be performed on the basis of cell surface expression of a variety of molecules, including T cell markers such as CD2, CD4 and CD8; B cell markers such as CD10, CD19 and CD20; monocyte marker CD14; the NK cell marker CD2, CD16, and CD56 or any lineage specific markers. Negative selection can be performed on the basis of cell surface expression of a variety of molecules, such as a cocktail of antibodies (e.g., CD2, CD3, CD11b, CD14, CD15, CD16, CD19, CD56, CD123, and CD235a) which may be used for separation of other cell types, e.g., via MACS or column separation.

As used herein, lineage-negative (LIN−) refers to cells lacking at least one marker associated with lineage committed cells, e.g., markers associated with T cells (such as CD2, 3, 4 and 8), B cells (such as CD10, 19 and 20), myeloid cells (such as CD14, 15, 16 and 33), natural killer ("NK") cells (such as CD2, 16 and 56), RBC (such as glycophorin A), megakaryocytes (CD41), mast cells, eosinophils or basophils or other markers such as CD38, CD71, and HLA-DR. Preferably the lineage specific markers include, but are not limited to, at least one of CD2, CD14, CD15, CD16, CD19, CD20, CD33, CD38, HLA-DR and CD71. More preferably, LIN− will include at least CD14 and CD15. Further purification can be achieved by positive selection for, e.g., c-kit+ or Thy-1+. Further enrichment can be obtained by use of the mitochondrial binding dye rhodamine 123 and selection for rhodamine+ cells, by methods known in the art. A highly enriched composition can be obtained by selective isolation of cells that are CD34+, preferably CD34+LIN−, and most preferably, CD34+ Thy-1+LIN−. Populations highly enriched in stem cells and methods for obtaining them are well known to those of skill in the art, see e.g., methods described in PCT/US94/09760; PCT/US94/08574 and PCT/US94/10501.

Various techniques may be employed to separate the cells by initially removing cells of dedicated lineage. Monoclonal antibodies are particularly useful for identifying markers associated with particular cell lineages and/or stages of differentiation. The antibodies may be attached to a solid support to allow for crude separation. The separation techniques employed should maximize the retention of viability of the fraction to be collected. Various techniques of different efficacy may be employed to obtain "relatively crude" separations. Such separations are where up to 10%, usually not more than about 5%, preferably not more than about 1%, of the total cells present are undesired cells that remain with the cell population to be retained. The particular technique employed will depend upon efficiency of separation, associated cytotoxicity, ease and speed of performance, and necessity for sophisticated equipment and/or technical skill.

Selection of the progenitor cells need not be achieved solely with a marker specific for the cells. By using a combination of negative selection and positive selection, enriched cell populations can be obtained.

C. Sources of Blood Cells

Hematopoietic stem cells (HSCs) normally reside in the bone marrow but can be forced into the blood, a process termed mobilization used clinically to harvest large numbers of HSCs in peripheral blood. One mobilizing agent of choice is granulocyte colony-stimulating factor (G-CSF).

CD34+ hematopoietic stem cells or progenitors that circulate in the peripheral blood can be collected by apheresis techniques either in the unperturbed state, or after mobilization following the external administration of hematopoietic growth factors like G-CSF. The number of the stem or progenitor cells collected following mobilization is greater than that obtained after apheresis in the unperturbed state. In a particular aspect of the present invention, the source of the cell population is a subject whose cells have not been mobilized by extrinsically applied factors because there is no need to enrich hematopoietic stem cells or progenitor cells in vivo.

Populations of cells for use in the methods described herein may be mammalian cells, such as human cells, non-human primate cells, rodent cells (e.g., mouse or rat), bovine cells, ovine cells, porcine cells, equine cells, sheep cell, canine cells, and feline cells or a mixture thereof. Non-human primate cells include rhesus macaque cells. The cells may be obtained from an animal, e.g., a human patient, or they may be from cell lines. If the cells are obtained from an animal, they may be used as such, e.g., as unseparated cells (i.e., a mixed population); they may have been established in culture first, e.g., by transformation; or they may have been subjected to preliminary purification methods. For example, a cell population may be manipulated by positive or negative selection based on expression of cell surface markers; stimulated with one or more antigens in vitro or in vivo; treated with one or more biological modifiers in vitro or in vivo; or a combination of any or all of these.

Populations of cells include peripheral blood mononuclear cells (PBMC), whole blood or fractions thereof containing mixed populations, spleen cells, bone marrow cells, tumor infiltrating lymphocytes, cells obtained by leukapheresis, biopsy tissue, lymph nodes, e.g., lymph nodes draining from a tumor. Suitable donors include immunized donors, non-immunized (naive) donors, treated or untreated donors. A "treated" donor is one that has been exposed to one or more biological modifiers. An "untreated" donor has not been exposed to one or more biological modifiers.

For example, peripheral blood mononuclear cells (PBMC) can be obtained as described according to methods known in the art. Examples of such methods are discussed by Kim et al. (1992); Biswas et al. (1990); Biswas et al. (1991).

Methods of obtaining precursor cells from populations of cells are also well known in the art. Precursor cells may be expanded using various cytokines, such as hSCF, hFLT3, and/or IL-3 (Akkina et al., 1996), or CD34+ cells may be enriched using MACS or FACS. As mentioned above, negative selection techniques may also be used to enrich CD34+ cells.

It is also possible to obtain a cell sample from a subject, and then to enrich it for a desired cell type. For example, PBMCs and/or CD34+ hematopoietic cells can be isolated from blood as described herein. Cells can also be isolated from other cells using a variety of techniques, such as isolation and/or activation with an antibody binding to an epitope on the cell surface of the desired cell type. Another method that can be used includes negative selection using antibodies to cell surface markers to selectively enrich for a specific cell type without activating the cell by receptor engagement.

Bone marrow cells may be obtained from iliac crest, femora, tibiae, spine, rib or other medullary spaces. Bone marrow may be taken out of the patient and isolated through various separations and washing procedures. An exemplary procedure for isolation of bone marrow cells comprises the following steps: a) centrifugal separation of bone marrow suspension in three fractions and collecting the intermediate fraction, or buffycoat; b) the buffycoat fraction from step (α) is centrifuged one more time in a separation fluid, commonly Ficoll (a trademark of Pharmacia Fine Chemicals AB), and an intermediate fraction which contains the bone marrow cells is collected; and c) washing of the collected fraction from step (b) for recovery of re-transfusable bone marrow cells.

D. Pluripotent Stem Cells

The cells suitable for the compositions and methods described herein may be hematopoietic stem and progenitor cells may also be prepared from differentiation of pluripotent stem cells in vitro. In some embodiments, the cells used in the methods described herein are pluripotent stem cells (embryonic stem cells or induced pluripotent stem cells) directly seeded into the ATOs. In further embodiments, the cells used in the methods and compositions described herein are a derivative or progeny of the PSC such as, but not limited to mesoderm progenitors, hemato-endothelial progenitors, or hematopoietic progenitors.

The term "pluripotent stem cell" refers to a cell capable of giving rise to cells of all three germinal layers, that is, endoderm, mesoderm and ectoderm. Although in theory a pluripotent stem cell can differentiate into any cell of the body, the experimental determination of pluripotency is typically based on differentiation of a pluripotent cell into several cell types of each germinal layer. In some embodiments, a pluripotent stem cell is an embryonic stem (ES) cell derived from the inner cell mass of a blastocyst. In other embodiments, the pluripotent stem cell is an induced pluripotent stem cell derived by reprogramming somatic cells. In certain embodiments, the pluripotent stem cell is an embryonic stem cell derived by somatic cell nuclear transfer.

Embryonic stem (ES) cells are pluripotent cells derived from the inner cell mass of a blastocyst. ES cells can be isolated by removing the outer trophectoderm layer of a developing embryo, then culturing the inner mass cells on a feeder layer of non-growing cells. Under appropriate conditions, colonies of proliferating, undifferentiated ES cells are produced. The colonies can be removed, dissociated into individual cells, then replated on a fresh feeder layer. The replated cells can continue to proliferate, producing new colonies of undifferentiated ES cells. The new colonies can then be removed, dissociated, replated again and allowed to grow. This process of "subculturing" or "passaging" undifferentiated ES cells can be repeated a number of times to produce cell lines containing undifferentiated ES cells (U.S. Pat. Nos. 5,843,780; 6,200,806; 7,029,913). A "primary cell culture" is a culture of cells directly obtained from a tissue such as the inner cell mass of a blastocyst. A "subculture" is any culture derived from the primary cell culture.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson et al., 1998; Thomson and Marshall, 1998; Reubinoff et al, 2000.) In one method, day-5 human blastocysts are exposed to rabbit anti-human spleen cell antiserum, then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigel™ or laminin in the presence of "conditioned" medium containing basic fibroblast growth factor (Xu et al., 2001). The medium is previously conditioned by coculturing with fibroblasts.

Methods for the isolation of rhesus monkey and common marmoset ES cells are also known (Thomson, and Marshall, 1998; Thomson et al., 1995; Thomson and Odorico, 2000).

Another source of ES cells are established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 were established by Thompson et al. In addition, subclones H9.1 and H9.2 of the H9 line have been developed.

The source of ES cells can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

Induced pluripotent stem (iPS) cells are cells which have the characteristics of ES cells but are obtained by the reprogramming of differentiated somatic cells. Induced pluripotent stem cells have been obtained by various methods. In one method, adult human dermal fibroblasts are transfected with transcription factors Oct4, Sox2, c-Myc and Klf4 using retroviral transduction (Takahashi et al., 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF.

Based on cell characteristics, cells of the ES cell-like colonies are induced pluripotent stem cells. The induced pluripotent stem cells are morphologically similar to human ES cells, and express various human ES cell markers. Also, when growing under conditions that are known to result in differentiation of human ES cells, the induced pluripotent stem cells differentiate accordingly. For example, the induced pluripotent stem cells can differentiate into cells having neuronal structures and neuronal markers.

In another method, human fetal or newborn fibroblasts are transfected with four genes, Oct4, Sox2, Nanog and Lin28 using lentivirus transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage and gut epithelium after injection into mice.

Methods of preparing induced pluripotent stem cells from mouse are also known (Takahashi and Yamanaka, 2006). Induction of iPS cells typically require the expression of or exposure to at least one member from Sox family and at least one member from Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc.

IPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of embryonic stem cells can be confirmed by injecting approximately $0.5\text{-}10\times10^6$ cells into the rear leg muscles of 8-12 week old male SCID mice. Teratomas develop that demonstrate at least one cell type of each of the three germ layers.

XI. Genetic Alteration of Differentiated Cells

The cells in certain embodiments can be made to contain one or more genetic alterations by genetic engineering of the cells either before or after differentiation (US 2002/0168766). A cell is said to be "genetically altered", "genetically modified" or "transgenic" when an exogenous nucleic acid or polynucleotide has been transferred into the cell by any suitable means of artificial manipulation, or where the cell is a progeny of the originally altered cell that has inherited the polynucleotide. For example, the cells can be processed to increase their replication potential by genetically altering the cells to express telomerase reverse transcriptase, either before or after they progress to restricted developmental lineage cells or terminally differentiated cells (US 2003/0022367).

In certain embodiments, cells containing an exogenous nucleic acid construct may be identified in vitro or in vivo by including a marker in the expression vector, such as a selectable or screenable marker. Such markers would confer an identifiable change to the cell permitting easy identification of cells containing the expression vector, or help enrich or identify differentiated cardiac cells by using a tissue-specific promoter. For example, in the aspects of cardiomyocyte differentiation, cardiac-specific promoters may be used, such as promoters of cardiac troponin I (cTnI), cardiac troponin T (cTnT), sarcomeric myosin heavy chain (MHC), GATA-4, Nkx2.5, N-cadherin, β1-adrenoceptor, ANF, the MEF-2 family of transcription factors, creatine kinase MB (CK-MB), myoglobin, or atrial natriuretic factor (ANF). In aspects of neuron differentiation, neuron-specific promoters may be used, including but not limited to, TuJ-1, Map-2, Dcx or Synapsin. In aspects of hepatocyte differentiation, definitive endoderm- and/or hepatocyte-specific promoters may be used, including but not limited to, ATT, Cyp3a4, ASGPR, FoxA2, HNF4a or AFP.

Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to blasticidin, neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

XII. Treatment of Disease and Conditions

Methods may be employed with respect to individuals who have tested positive for such disorders, who have one or more symptoms of a disorder, or who are deemed to be at risk for developing such a condition or related condition. In some embodiments, the compositions and methods described herein are used to treat an inflammatory or autoimmune component of a disorder listed herein and/or known in the art.

Certain aspects of the disclosure relate to the treatment of cancer and/or use of cancer antigens. The cancer to be treated or antigen may be an antigen associated with any cancer known in the art or, for example, epithelial cancer, (e.g., breast, gastrointestinal, lung), prostate cancer, bladder cancer, lung (e.g., small cell lung) cancer, colon cancer, ovarian cancer, brain cancer, gastric cancer, renal cell carcinoma, pancreatic cancer, liver cancer, esophageal cancer, head and neck cancer, or a colorectal cancer. In some embodiments, the cancer to be treated or antigen is from one of the following cancers: adenocortical carcinoma, agnogenic myeloid metaplasia, AIDS-related cancers (e.g., AIDS-related lymphoma), anal cancer, appendix cancer, astrocytoma (e.g., cerebellar and cerebral), basal cell carcinoma, bile duct cancer (e.g., extrahepatic), bladder cancer, bone cancer, (osteosarcoma and malignant fibrous histiocytoma), brain tumor (e.g., glioma, brain stem glioma, cerebellar or cerebral astrocytoma (e.g., pilocytic astrocytoma, diffuse astrocytoma, anaplastic (malignant) astrocytoma), malignant glioma, ependymoma, oligodenglioma, meningioma, meningiosarcoma, craniopharyngioma, haemangioblastomas, medulloblastoma, supratentorial primitive neuroectodermal tumors, visual pathway and hypothalamic glioma, and glioblastoma), breast cancer, bronchial adenomas/carcinoids, carcinoid tumor (e.g., gastrointestinal carcinoid tumor), carcinoma of unknown primary, central nervous system lymphoma, cervical cancer, colon cancer, colorectal cancer, chronic myeloproliferative disorders, endometrial cancer (e.g., uterine cancer), ependymoma, esophageal cancer, Ewing's family of tumors, eye cancer (e.g., intraocular melanoma and retinoblastoma), gallbladder cancer, gastric (stomach) cancer, gastrointestinal carcinoid tumor, gastrointestinal stromal tumor (GIST), germ cell tumor, (e.g., extracranial, extragonadal, ovarian), gestational trophoblastic tumor, head and neck cancer, hepatocellular (liver) cancer (e.g., hepatic carcinoma and heptoma), hypopharyngeal cancer, islet cell carcinoma (endocrine pancreas), laryngeal cancer, laryngeal cancer, leukemia, lip and oral cavity cancer, oral cancer, liver cancer, lung cancer (e.g., small cell lung cancer, non-small cell lung cancer, adenocarcinoma of the lung, and squamous carcinoma of the lung), lymphoid neoplasm (e.g., lymphoma), medulloblastoma, ovarian cancer, mesothelioma, metastatic squamous neck cancer, mouth cancer, multiple endocrine neoplasia syndrome, myelodysplastic syndromes, myelodysplastic/myeloproliferative diseases, nasal cavity and paranasal sinus cancer, nasopharyngeal cancer, neuroblastoma, neuroendocrine cancer, oropharyngeal cancer, ovarian cancer (e.g., ovarian epithelial cancer, ovarian germ cell tumor, ovarian low malignant potential tumor), pancreatic cancer, parathyroid cancer, penile cancer, cancer of the peritoneal, pharyngeal cancer, pheochromocytoma, pineoblastoma and supratentorial primitive neuroectodermal tumors, pituitary tumor, pleuropulmonary blastoma, lymphoma, primary central nervous system lymphoma (microglioma), pulmonary lymphangiomyomatosis, rectal cancer, renal cancer, renal pelvis and ureter cancer (transitional cell cancer), rhabdomyosarcoma, salivary gland cancer, skin cancer (e.g., non-melanoma (e.g., squamous cell carcinoma), melanoma, and Merkel cell carcinoma), small intestine cancer, squamous cell cancer, testicular cancer, throat cancer, thymoma and thymic carcinoma, thyroid cancer, tuberous sclerosis, urethral cancer, vaginal cancer, vulvar cancer, Wilms' tumor, and post-transplant lymphoproliferative disorder (PTLD), abnormal vascular proliferation associated with phakomatoses, edema (such as that associated with brain tumors), or Meigs' syndrome.

Certain aspects of the disclosure relate to the treatment of an autoimmune condition and/or use of an autoimmune-associated antigen. The autoimmune disease to be treated or antigen may be an antigen associated with any autoimmune condition known in the art or, for example, diabetes, graft rejection, GVHC, arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, non-granulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), and adult onset diabetes mellitus (Type II diabetes) and autoimmune diabetes. Also contemplated are immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and gianT cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), Addison's disease, autoimmune neutropenia, pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), experimental autoimmune encephalomyelitis, myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, gianT cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyl), and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, gianT cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, asperniogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, graft versus host disease, contact hypersensitivity, asthmatic airway hyperreaction, and endometriosis.

Further aspects relate to the treatment or prevention microbial infection and/or use of microbial antigens. The microbial infection to be treated or prevented or antigen may be an antigen associated with any microbial infection known in the art or, for example, anthrax, cervical cancer (human papillomavirus), diphtheria, hepatitis A, hepatitis B, Haemophilus influenzae type b (Hib), human papillomavirus (HPV), influenza (Flu), japanese encephalitis (JE), lyme disease, measles, meningococcal, monkeypox, mumps, pertussis, pneumococcal, polio, rabies, rotavirus, rubella, shingles (herpes zoster), smallpox, tetanus, typhoid, tuberculosis (TB), varicella (Chickenpox), and yellow fever.

In some embodiments, the methods and compositions may be for vaccinating an individual to prevent infection.

XIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Development of a 3D Organoid System for Producing T Cells

Development of an off-the-shelf 3D organoid system for human T cell development—The aim was to build upon the ability of Notch ligand transduced stromal cell lines, as exemplified by the OP9-DL1 system, to develop a standardized artificial thymic organoid system for studying the role of 3D interactions in T cell differentiation and selection. OP9-DL1 cells are not stable in long term culture, however, requiring cell changes every few days to maintain T supportive potential and prevent adipogenic transformation. As 3D cultures are required to be stable for weeks, it was sought to identify culture and cellular components that would permit prolonged, intact cultures. Furthermore, the efficacy of the OP9-DL1 system is highly sensitive to biological variation in fetal calf serum (FCS) lots and thus we also sought to identify serum-free culture conditions that could reproducibly support T cell differentiation.

It was found that RPMI supplemented with Serum-Free B27 supplement, FLT3L, IL-7 and ascorbic acid (RB27, hereafter) facilitated T cell differentiation within the OP9-DL1 system to a similar extent as standard serum conditions, however stromal cell viability and hematopoietic cell expansion were low. In contrast, the MS-5 murine bone marrow stromal cell line retained long term viability in RB27, however as expected did not support T cell differentiation. We therefore transduced MS-5 cells with full-length human DLL1 cDNA (MS5-hDLL1 hereafter) to create a T-supportive line with long term stability in RB27. DLL1 was selected over DLL1 as it is has been shown to be the physiologically relevant Notch ligand expressed in the human thymus. To test T cell differentiation in these conditions, cord blood (CB) CD34+ HSPCs were FACS-depleted of CD3+ cells and seeded onto MS5-hDLL1 monolayers. MS5-hDLL1 co-cultures in serum-free RB27 supported T lineage commitment and early T cell differentiation from CB HSPCs. Hematopoietic expansion was lower on MS5-hDLL1 in RB27 compared to on OP9-DL1 system in standard media conditions, however the purity and extent of T cell differentiation were similar between systems. MS5-hDLL1 supported β-selection of T cell precursors, resulting in small numbers of CD3+ TCRαβ+ cells, however as in the OP9-DL1 system these were largely arrested at the DP stage, indicating impaired positive selection).

We next used the MS5-hDLL1/serum-free RB27 to create a standardized 3D artificial thymic organoid (ATO) system. To create ATOs, MS5-hDLL1 cells were aggregated with T cell-depleted human cord blood (CB) CD34+ HSPCs. To maximize accessibility and reproducibility, we avoided the use of proprietary scaffold materials or exogenous ECM, instead using a centrifugal reaggregation approach adapted from murine reaggregated thymic organ cultures (RTOC). As data from RTOCs have also demonstrated that air-liquid interface cultures enhance T cell development, ATOs were deployed on commercially-available 0.4 um transwell inserts, the bottom of which permitted contact with media and the top with air. Unlike monolayer co-cultures, which require the serial transfer of hematopoietic cells to new stromal layers, ATOs were cultured intact for up to 10 weeks, with the only intervention being twice-weekly medium and cytokine changes from around the insert. Once deployed, ATOs formed cohesive, 3D structures. ATOs were highly cellular under light microscopy by week 2 and remained stable in appearance through week 10. In some embodiments, the structures are encapsulated.

ATOs initiated with CB CD34+ CD3− HSPCs revealed accelerated kinetics of T lineage differentiation compared with OP9-DL1 or MS5-hDLL1 monolayer co-cultures. T lineage commitment in week 2 ATOs was marked by clear emergence of T-committed CD34+ CD1a+ CD7+ early thymic progenitor (ETP) phenotype, as well as the overlapping pro-T1 and pro-T2 phenotypes. As anticipated, T cell differentiation beyond the CD34+ CD1a+ CD7+ ETP stage was not observed in organoids created with the parental MS-5 cell line, which instead supported myeloid and B cell development. Within ATOs, CD34− CD7+ CD5+ CD4− CD8− ("double negative", DN) T cell precursors represented a majority of cells at week 2, but declined thereafter with reciprocal increases in CD7+ CD4+ CD3− immature single positive (ISP) and CD4+ CD8+ double positive (DP) populations. Taken together, early T cell differentiation in ATOs was orderly and closely resembled that of the native human thymus.

We next examined the efficiency of β-selection and positive selection within ATOs. ATO DP precursors showed surface expression of CD3 and TCRαβ as early as week 2, which increased through week 6, indicating successful transit through β-selection. The frequency of CD3+ TCRαβ+ DP cells in ATOs was comparable to that of the human thymus, both of which were higher compared to OP9-DL1 and MS5-hDLL1 monolayer cultures. Importantly, mature CD3+ TCRαβ+ CD8+ and CD4+ single positive (SP) T cells emerged in ATOs by week 4, increasing in frequency through week 7, consistent with functional positive selection in ATOs. The frequency of CD3+ TCRαβ+ CD8+ and CD4+ SP cells in week 7 ATOs was higher than in specimen-matched OP9-DL1 and MS5-hDLL1 monolayer co-cultures, respectively. While both CD3+ TCRαβ+ CD8+ and CD4+ SP cells were observed in ATOs, the ratio of CD8+ cells to CD4+ cells was higher than in the human thymus, indicating a relative dominance of positively selected CD8+ cells in ATOs. Finally, CD3+ TCRγẟ+ cells were readily identified in ATOs, and were largely CD8− CD4−, similar to in the thymus. Taken together, these data demonstrate that ATOs facilitate rapid and robust T cell differentiation, and greatly improved positive selection of mature human T cells compared with monolayer co-culture systems.

Generation of TCR diversity and functional, naïve T cells in ATOs—We next tested that T cells generated in ATOs expressed a diversity of TCR and were functionally mature. Within CD3+ CD8 SP T cells generated in ATOs, flow cytometry analysis of TCR VB chain segment usage revealed a distribution comparable to that of CD8 SP cells isolated from human thymi, consistent with a diverse, polyclonal TCR repertoire. ATO-derived CD3+ TCRαβ+ SP T cells also demonstrated a mature, naïve phenotype based on downregulation of CD45RO and upregulation of CD45RA, CD27, and CCR7. Of note, a subset of both CD3+ TCRαβ+ CD8 and CD4 SP cells were CD45RO+ CD45RA−, however these were identified as immature T cells emerging from DP precursors, rather than memory T cells, due to their expression of CD1a which, like CD45RO, is downregulated during intrathymic maturation and prior to thymic egress. We next tested the ability of ATO-derived T cells to undergo activation and clonal expansion in response to antigenic stimuli. As anticipated, purified ATO-derived CD8 SP T cells expressed interferon gamma (IFNg) in response to the TCR-signaling mimetics PMA/ionomycin, and underwent activation-induced proliferation in response to CD3/28 ligation and IL-2, as demonstrated by CFSE dilution and upregulation of CD25. Thus, ATOs could generate functional, naïve T cells with a diverse TCR repertoire.

Generation of T cells from multiple hematopoietic tissues—Previous reports have shown that T cell development from adult sources of HSPCs, including mobilized peripheral blood, is highly inefficient within the OP9-DL1 system. Conversely, T cell development may be particularly efficient from CD34+ HSPCs isolated from CB and the postnatal thymus due to a high frequency of lymphoid-committed and T cell-committed progenitors, respectively. We therefore tested the ability of ATOs to support T cells development from purified CD34+ HSPCs isolated from peripheral blood, G-CSF mobilized peripheral blood, and steady-state adult bone marrow. We found that T cell development in ATOs proceeded from all sources analyzed with similar efficiency to cord blood, and resulted in similar numbers of mature CD4+ and CD8+ T cells. Furthermore, purified CD34+ Lin− CD38− CD45RA− HSPCs, which are highly enriched for hematopoietic stem cells, from cord blood, bone marrow, and mobilized peripheral blood, generated T cells with similar efficiency. Thus, ATOs permit development form clinically relevant sources of HSPCs, and can also serve as a valuable investigational tool for studying T lineage potential and T cell differentiation from multiple stem and progenitor cell types.

Structural aspects of ATOs—We next examined structural aspects of T cell differentiation in ATOs. Serial hematoxylin and eosin (H&E) sections of ATOs between weeks 2-6 demonstrated a compact and cellular tissue-like organization. Immunofluorescence staining for CD3 demonstrated that CD3+ cells formed dense clusters preferentially at the outer margin of the ATOs. Thus, T cell development in ATOs occurs within a cellular architecture that facilitates cell-cell contact between multiple hematopoietic cells, resembling conditions within the human thymus.

Differentiation and allelic exclusion of engineered antigen-specific T cells in ATOs—Enforced expression in peripheral blood T cells of a TCR with specificity for a cancer-associated or viral peptide-MHC (pMHC) complex is a promising approach to anti-tumor and anti-viral immunotherapy. The de novo generation of antigen-specific T cells from HSPCs may offer significant advantages in safety and efficacy over TCR transduction of peripheral T cells. As functional T cells were generated in ATOs, we tested the system for the ability to generate TCR-engineered antigen-specific T cells from CD34+ HSPCs.

Cord blood CD34+ HSPCs from healthy donors were transduced with a previously characterized lentiviral TCRαβ construct specific for the cancer-associated NY-ESO-1$_{157-165}$ peptide presented by HLA-A*0201. Differentiation of antigen-specific cells in ATOs was monitored using a HLA-A*0201/NY-ESO-1$_{157-165}$ tetramer and an antibody against the transduced Vβ13.1 segment. In ATOs, there was clear differentiation of tetramer positive cells at the time of initial analysis at week 3, all of which were positive for Vβ13.1 and surface CD3. Interestingly, co-expression of CD3 and the transduced TCR was first seen in CD34− CD7+ CD5+ DN cells as well as CD4 ISP-like and DP-like T cell precursors, however from weeks 4-6 was progressively confined to the DP and CD8 SP populations. This was consistent with a bypass of β-selection at the DN stage in the presence of a functional TCR, followed by relatively preserved differentiation and appropriate MHC class I restricted positive selection. In contrast, mock-transduced cells from control ATOs demonstrated normal expression of CD3 and TCRαβ at the DP stage, which was followed by positive selection of both CD8+ and CD4+ T cells. These observations were consistent with allelic exclusion of endogenous TCR α and β loci by the transgenic TCR. Indeed, >95% of tetramer+ CD3+ CD8 SP cells expressed the transduced Vβ13.1 segment to the exclusion of alternative segments.

We next confirmed that ATO-derived antigen-specific T cells were functionally mature. Like CD8 SP T cells from mock-transduced ATOs, tetramer+ CD8 SP cells exhibited maturation to the mature, naïve CD45RA+ CD45RO− CD1a$^{low}$ CD27+ CCR7+ phenotype. As in control ATOs, residual CD45RO+ cells were CD1a+, consistent with recent emergence from the DP pool as opposed to an activated/memory phenotype. Tetramer+ CD8 SP T cells (or equivalent TCRαβ+CD8 SP cells from mock-transduced ATOs) were sorted and exposed to K562-based artificial antigen presenting cells (aAPCs) that co-express HLA-A*0201, beta-2-microglobulin, CD80, and either NY-ESO-1$_{157-165}$ (ESO+) or an irrelevant control peptide from MART-1 (MART1+). As expected, antigen-specific T cells produced interferon gamma and degranulated (as marked by membrane trafficking of LAMP1/CD107a) in response to ESO+ but not MART1+ aAPCs. T cells from mock-transduced ATOs did not undergo significant activation in response to either aAPC. Antigen-specific T cells also underwent proliferation in response to ESO+ aAPC. Sustained in vitro expansion mediated by aAPCs could be maintained beyond 14 days. Finally, aAPC-primed antigen-specific T cells demonstrated antigen-specific tumor cell killing when challenged with HLA-A*0201+ K562 target cells pulsed with NY-ESO-1 but not MART1 peptides. Taken together, ATOs offer a robust system for the de novo generation and manipulation of functional, antigen-specific T cells.

It was demonstrated that ATOs can be manipulated to specifically study and enhance the process of positive selection. Positive selection in the thymus occurs through the interaction of developing thymocytes with cortical epithelial cells (cTEC). In ATOs, which lack cTECs, it was hypothesized that positive selection is mediated by interactions with self-MHC on autologous hematopoietic cells. To test this, CB HSPCs from HLA-A*0201-positive and negative donors were transduced with the HLA-A*0201/NY-ESO-$1_{157-165}$ specific TCR, as above, and differentiated into T cells in ATOs. Using this model, we found that donor HLA-A*0201 improved the percentage of CD8SP cells, in addition to inducing qualitative changes associated with enhanced positive selection, as upregulation of CCR7. Interestingly, ectopic expression of HLA-A*02:01 in MS5-hDLL1 stromal cells in ATOs modestly enhanced CD8SP percentage in HLA-A*02:01 negative donor ATOs, and greatly enhanced it in ATOs with HLA-A*02:01+ donor HSPCs. This demonstrated that ATOs can be manipulated by transduction with human HLA to enhance the generation of positively selected antigen-specific T cells, and that ATOs used in combination with an allogeneic TCR and MHC-transduced stroma provide a precisely defined system for mechanistic studies of positive selection in human T cells.

Example 2—Artificial Thymic Organoids Induce Positive Selection and Allelic Exclusion of TCR-Engineered T Cells from Human Hematopoietic Stem Cells Engineered T cell therapies offer unprecedented opportunities for the treatment of cancer and chronic viral infections. The ability to generate engineered T cells directly from hematopoietic stem and progenitor cells (HSPC) has the potential to overcome key therapeutic limitations associated with the use of peripheral blood T cells, including alloreactivity. Described here is a clinically relevant artificial thymic organoid (ATO) system that supports highly efficient in vitro differentiation and positive selection of native and TCR-engineered human T cells from cord blood, bone marrow, and peripheral blood HSPCs. ATO-derived T cells exhibited a naïve phenotype, diverse TCR repertoire, and TCR-dependent activation and proliferation. ATO-derived TCR-engineered T cells also matured to a naïve phenotype and furthermore showed near complete lack of endogenous TCR expression, consistent with induction of allelic exclusion. ATOs thus present a simple and direct method for the generation of naïve, non-alloreactive engineered T cells for adoptive cell therapy.

Adoptive cell therapy using T cells engineered to express antigen-specific T cell receptors (TCR) offers a targeted and potentially curative treatment for malignancies and chronic viral infections. Current strategies rely on the genetic modification and ex vivo expansion of mature circulating T cells. These approaches pose key therapeutic limitations including limited in vivo activity after re-infusion and mispairing between transduced and endogenous TCR chains, with the potential for reduced antigen-specific reactivity or induction of autoimmunity. Furthermore, alloreactivity imparted by endogenous TCR expression has restricted most approaches to the use of autologous T cells, which may ultimately limit access to therapy through increased cost, limited production capacity, and patient ineligibility in the setting of lymphopenia. In vitro generation of engineered T cells from hematopoietic stem and progenitor cells (HSPC) has the potential to solve these problems by simultaneously permitting the de novo generation of naïve antigen specific T cells and the suppression of endogenous TCR expression through allelic exclusion.

Owing to the spatiotemporal complexity of T cell development in the thymus, methods of in vitro T cell differentiation have thus far been unable to fully recapitulate human T cell development. A major advance in such methods was the discovery that murine stromal cell lines transduced with a Notch ligand could support in vitro T cell differentiation from murine or human HSPCs, as demonstrated in the classic OP9-DL1 co-culture system. In this and similar monolayer systems, human HSPCs undergo T lineage commitment and early T cell differentiation. However, positive selection of T cell precursors with productively rearranged TCRs is impaired, and minimal maturation to CD8+ or CD4+ single positive (SP) T cells is seen. The inventors and others have shown that three-dimensional (3D) organoid systems using murine or human thymic tissue supports improved positive selection and maturation of human T cells in vitro. However these systems are not suitable for the generation of T cells for therapeutic applications due to low cell output, high experimental variability, and dependence on primary thymic tissue. The inventors therefore pursued the development of an artificial organoid system able to support the differentiation and positive selection of human T cells from HSPC while retaining key translational properties such as standardized components, reproducibility, and scalability.

Described in this example is the development of an artificial thymic organoid (ATO) system based on a DLL1-transduced stromal cell line and serum-free, off-the-shelf components. In contrast to monolayer systems, ATOs supported robust in vitro differentiation, positive selection, and maturation of human CD3+TCRαβ+CD8SP and CD4SP T cells from human cord blood, bone marrow, and peripheral blood CD34+ HSPCs. ATO-derived mature T cells exhibited an antigen naïve phenotype, diverse TCR repertoire, and activation/proliferation in response to antigenic stimuli. ATOs also supported highly efficient differentiation of antigen-specific TCR-engineered T cells from HSPCs transduced with a HLA-A*02:01-restricted TCR specific for the tumor-associated antigen NY-ESO-1. ATO-derived engineered T cells exhibited a naïve phenotype and underwent antigen specific activation and cytotoxic priming. Positive selection of TCR-engineered T cells was further enhanced by the expression of cognate major histocompatibility complex (MHC) in ATO stromal cells. Finally, TCR-engineered T cells generated in ATOs exhibited a near complete lack of endogenous TCR expression, consistent with the induction of allelic exclusion during development, and suggesting a direct and efficient approach to generating non-alloreactive engineered T cells for adoptive cell therapy.

A. Results

Figure 3A:
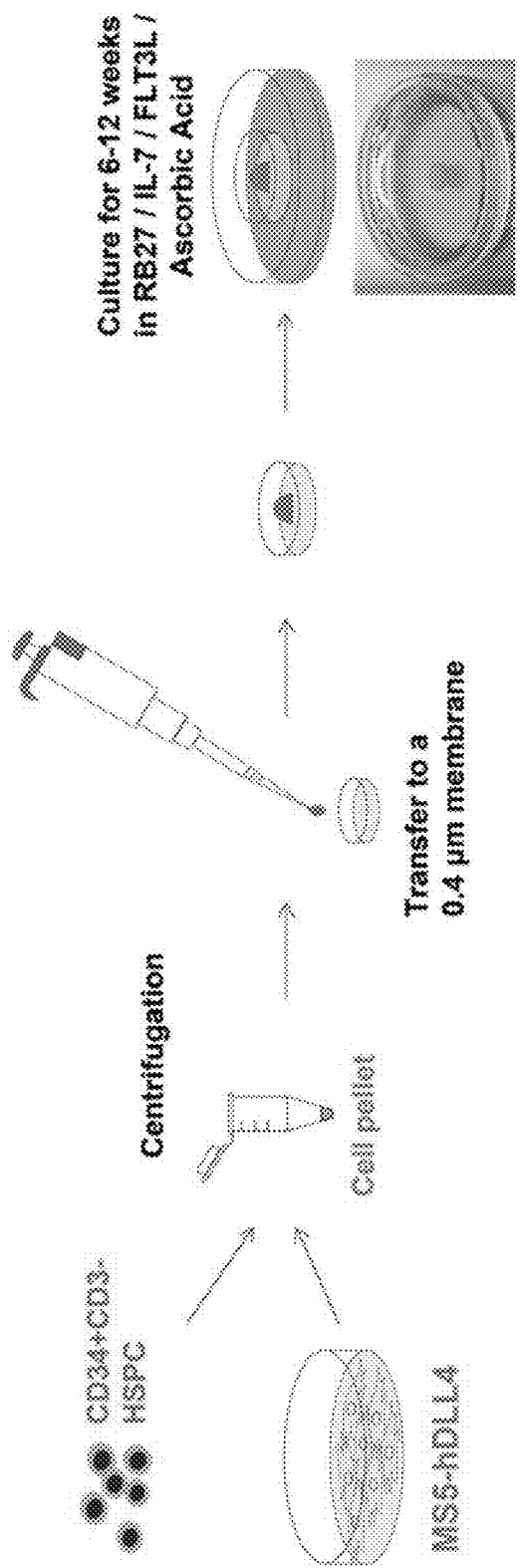
FIG. 3A-G: Efficiency and reproducibility of human T cell development in the ATO system. (a) Schematic of the ATO model. (b) Kinetics of T cell differentiation from CB CD34+CD3− HSPCs at the indicated weeks (gated on CD14−CD56− cells to exclude myeloid and NK cells respectively). (c) Maintenance of early CD34+ thymic T cell progenitor phenotypes in ATOs based on two classification schemes (gated on CD34+ cells as shown in (b)). (d) Immunofluorescence staining for CD3 in week 4 organoids generated with CB HSPCs and MS-5 cells (left) or MS5-hDLL1 cells (i.e. ATO) (right). (e) Total cell expansion in biological replicate CB ATOs (n=18) initiated with 2-5×10$^4$ HSPCs in a 1:10 to 1:30 HSPC to stromal cell ratio. (f) Monocyte (CD14+), NK cell (CD56+), or T lineage cell (CD7+CD5+) frequencies (gated on total cells); and (g) T cell and precursor frequencies (gated on CD14−CD56− cells) in week 6 biological replicate ATOs (n=18).

1. Development of an Optimized Artificial Thymic Organoid System for in Vitro Human T Cell Differentiation One goal was to develop a clinically translatable organoid system that could support in vitro positive selection and maturation of human T cells from HSPCs. To avoid the use of primary thymic tissue, DLL1-transduced stromal cell lines were tested for the ability to support human T cell development in 3D organoid cultures. As the inventors and others have observed that T cell differentiation in the OP9-DL1 system is highly variable, depending on specific lots of fetal calf serum and frequent changes of stromal cells, the inventors also sought to identify serum-free conditions capable of consistently supporting T cell differentiation in organoid cultures. To avoid the use of proprietary scaffold materials the inventors used a compaction reaggregation technique shown to be effective in thymic tissue-based organoids in which stromal cells are aggregated with HSPCs by centrifugation and deployed on cell culture inserts at an air-fluid interface (FIG. 3A). In these 3D cultures, the inventors identified the MS-5 murine bone marrow stromal cell line transduced with human DLL1 (MS5-hDLL1, hereafter) as strongly supportive of human T cell differentiation from T cell depleted CD34+ cord blood (CB) HSPCs. Furthermore, the inventors identified RPMI supplemented with B27, a multi-component additive used in neuronal and embryonic stem cell cultures, and FLT3L, IL-7, and ascorbic acid ("RB27", hereafter) as a novel serum-free medium that consistently supported robust human T cell differentiation in MS5-hDLL1 organoid cultures.

Figure 3B:
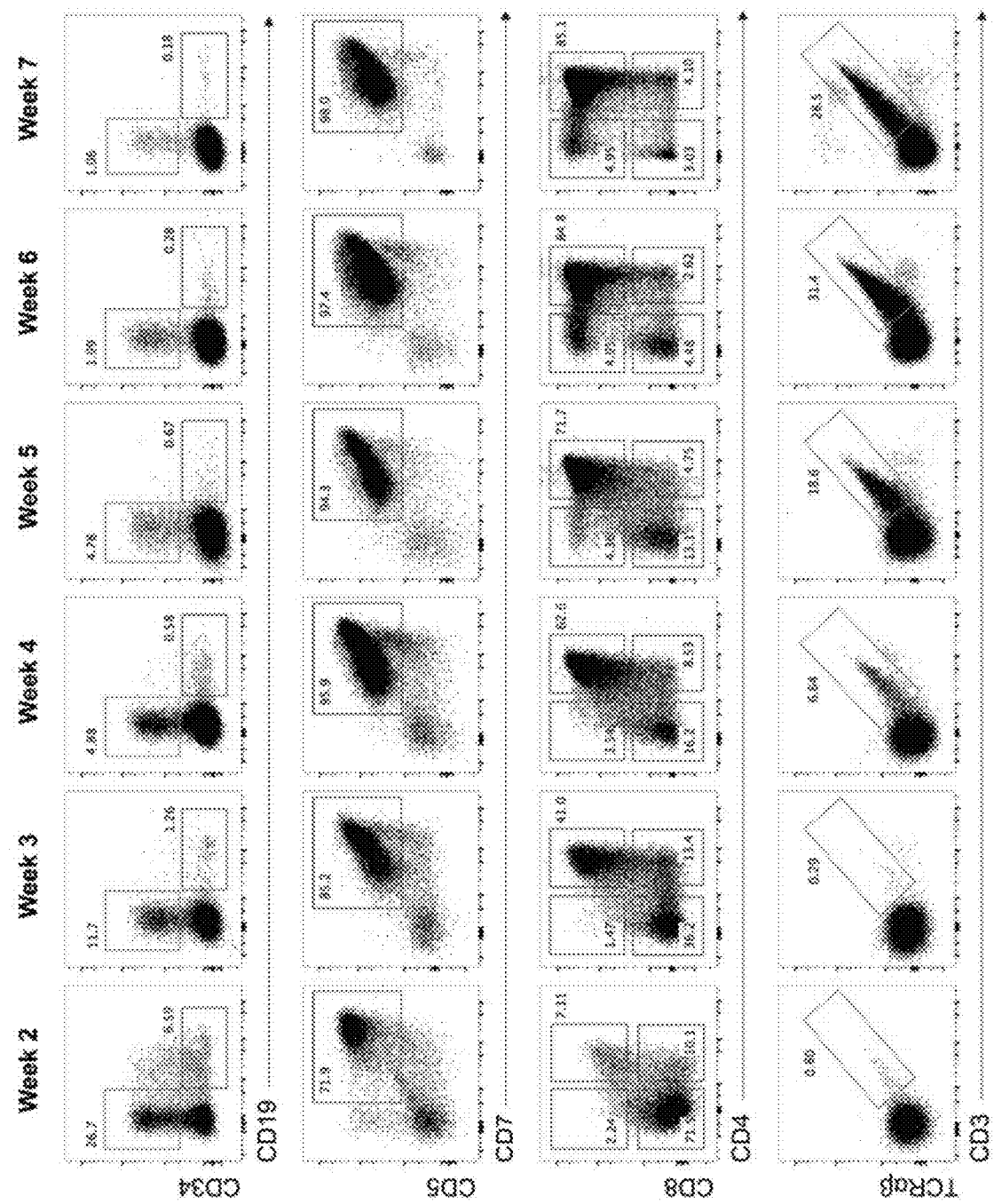

This optimized artificial thymic organoid (ATO) system induced rapid and robust T lineage commitment from CB CD34+CD3− HSPCs, as shown by a predominance of CD5+CD7+ cells and appearance of CD4 ISP and CD4+CD8+ (DP) cells by week 2 (FIG. 3B). Mature CD3+TCRαβ+ cells emerged as early as week 2, and increased over time, reaching an average of 25% at week 6 (FIGS. 3B and G). CD3+TCRαβ+ cells were predominantly DP at early timepoints but progressively matured to CD8SP and, to a lesser extent, CD4SP T cells, consistent with positive selection in ATOs.

Figure 3C:
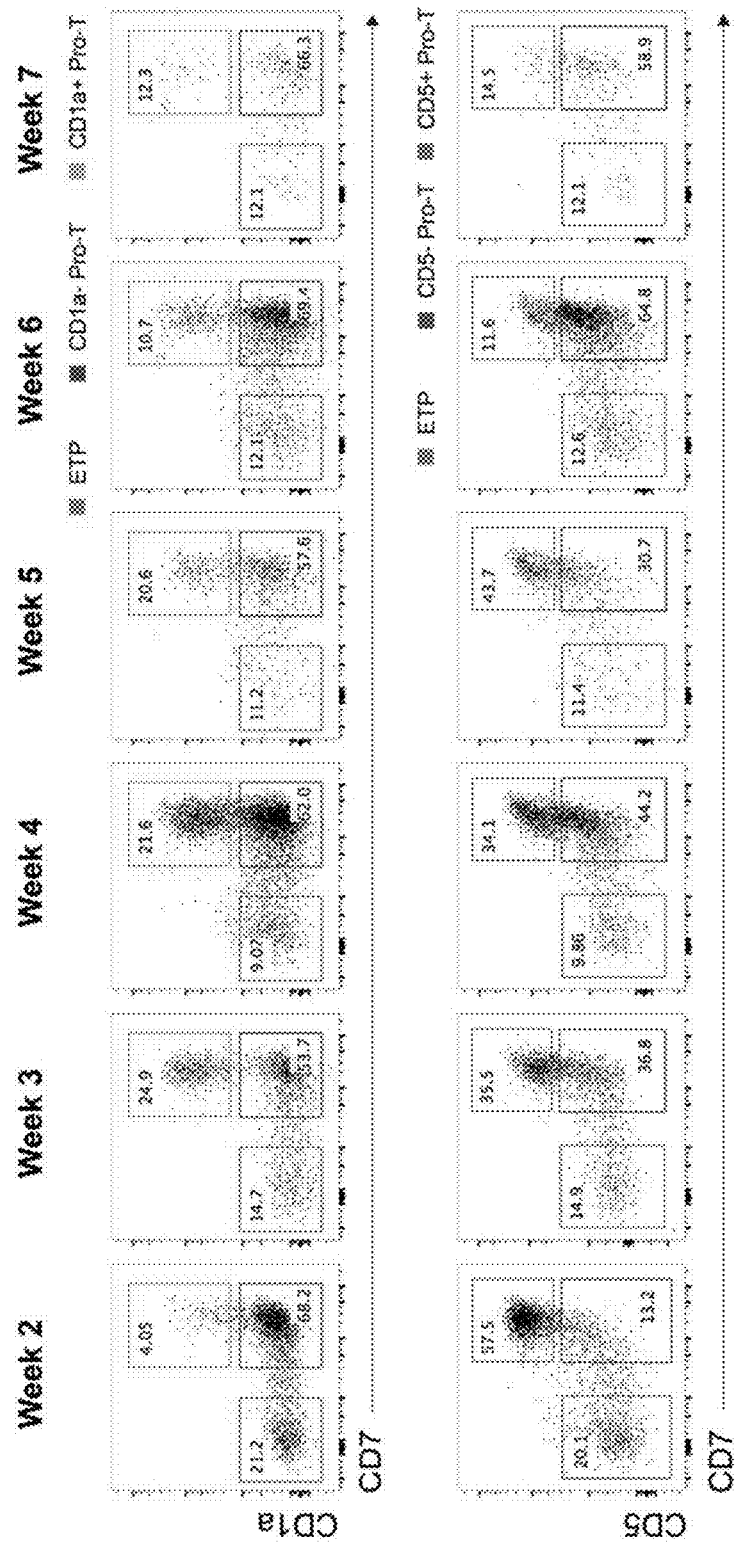
Figures 3D, 3E, 3F, 3G:
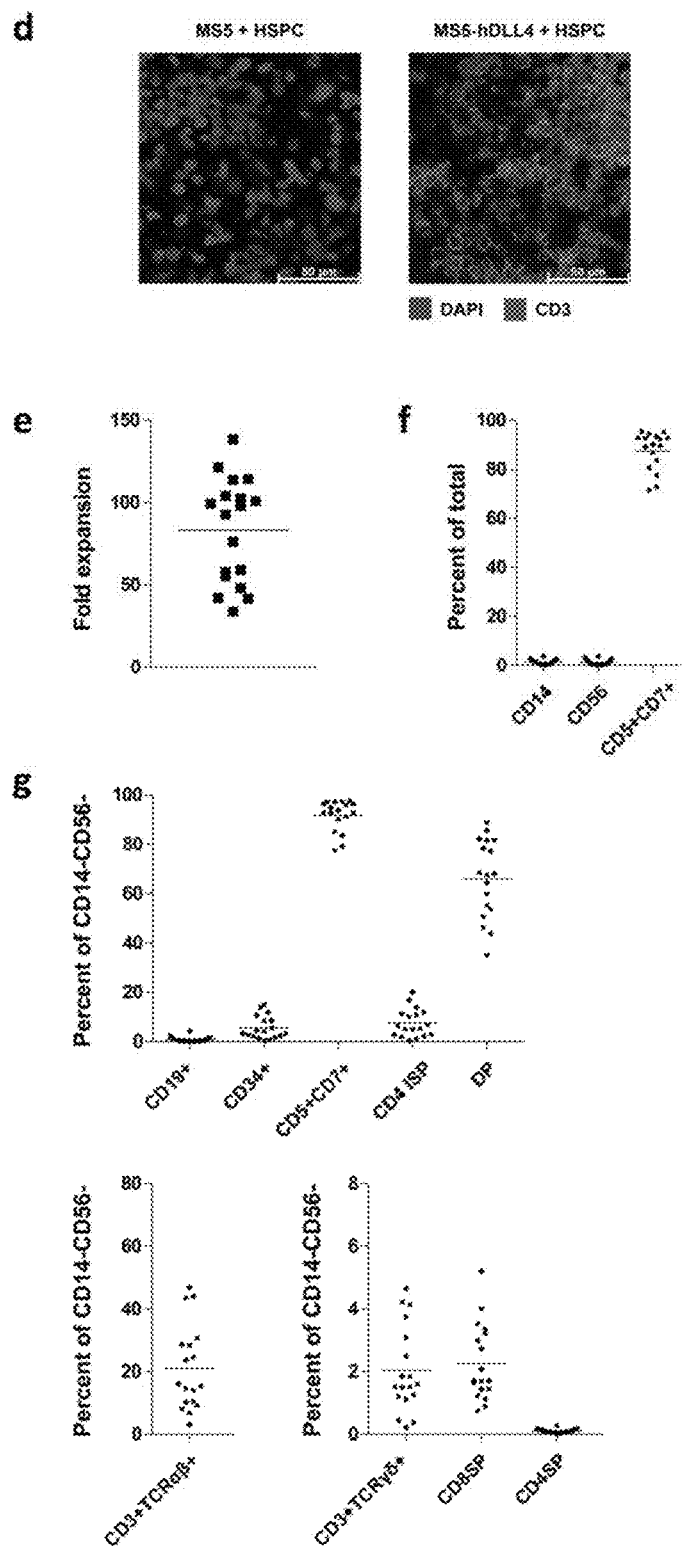
Figure 9A:
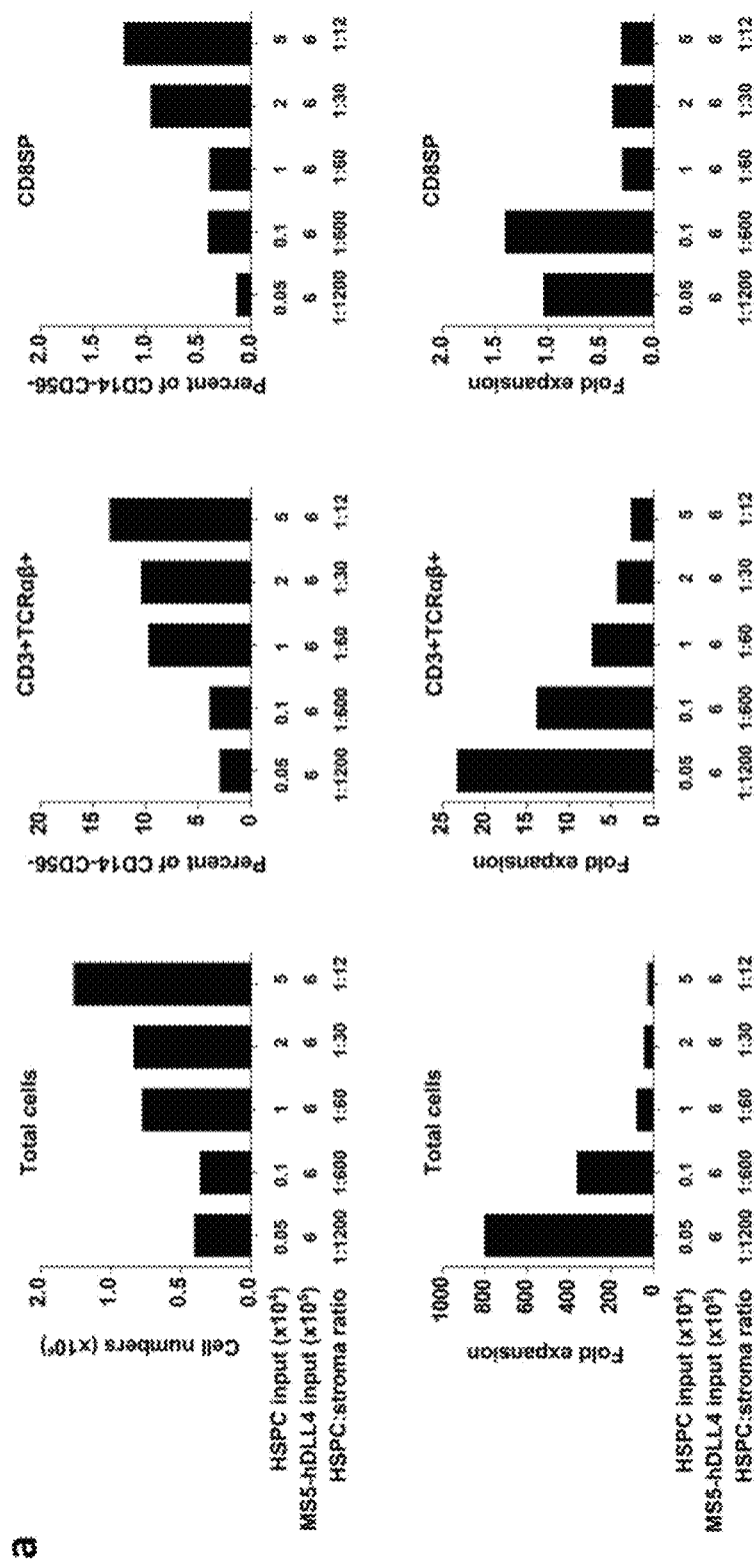
FIG. 9A-B: ATO cell expansion and T cell differentiation are related to input HSPC numbers and HSPC:stromal ratios. Cell expansion and T cell frequency data from week 6 ATOs generated with (a) varying numbers of CD34+CD3− CB HSPCs and constant stromal cell (MS5-hDLL1) numbers, or (b) varying numbers of HSPCs and stromal cells. Optimal total and mature T cell expansion was seen with lowest input HSPC numbers per ATO (7,500 cells) and a 1:20-1:40 HSPC to stromal cell ratio.
Figure 9B:
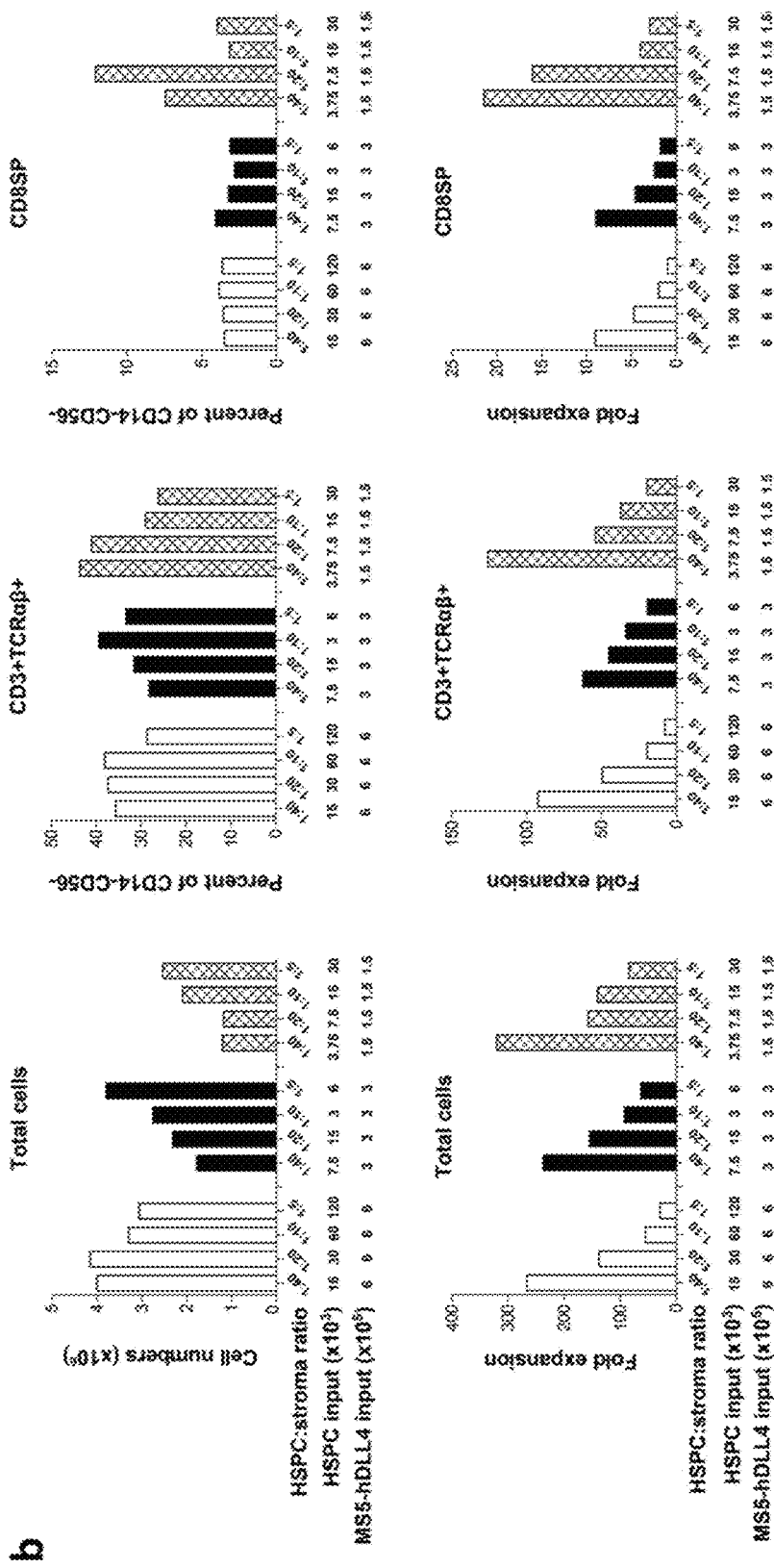
Figures 10A, 10B, 10C, 10D, 10E:
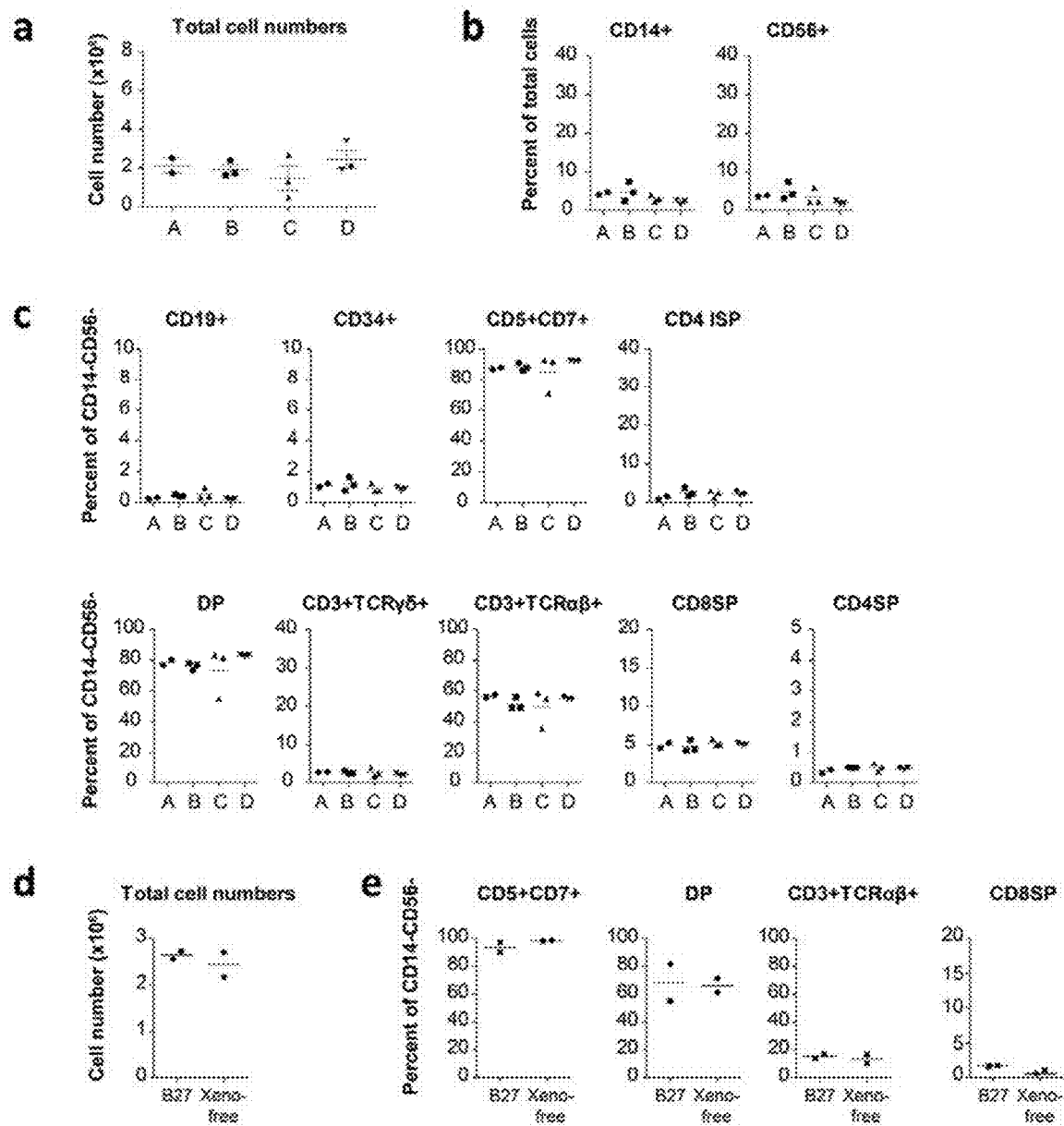
FIG. 10A-G: T cell differentiation in ATOs is highly reproducible and not affected by B27 lots, xeno-free B27, or stromal irradiation. No significant effect of B27 lot variation on (a) total ATO cell output, (b) myeloid (CD14+) or NK cell (CD56+) differentiation, or (c) B cell (CD19+) or T cell differentiation in week 6 ATOs generated from a single CB sample and cultured with 4 different lots of B27 supplement (labeled A-D). Technical ATO replicates (n=2-3) are shown for each B27 lot. All ATOs were set up with $3\times10^4$ HSPCs at a 1:20 HSPC to stromal cell ratio. (d) Substitution of B27 with xeno-free B27 had no impact on cell numbers or (e) T cell differentiation in week 6 ATOs. (f) ATOs generated with MS5-hDLL1 cells irradiated at the indicated doses showed comparable T cell differentiation (gated on total CD14−CD56− cells) or (g) gated on CD3+TCRαβ+ cells as shown in (f).
Figures 10F, 10G:
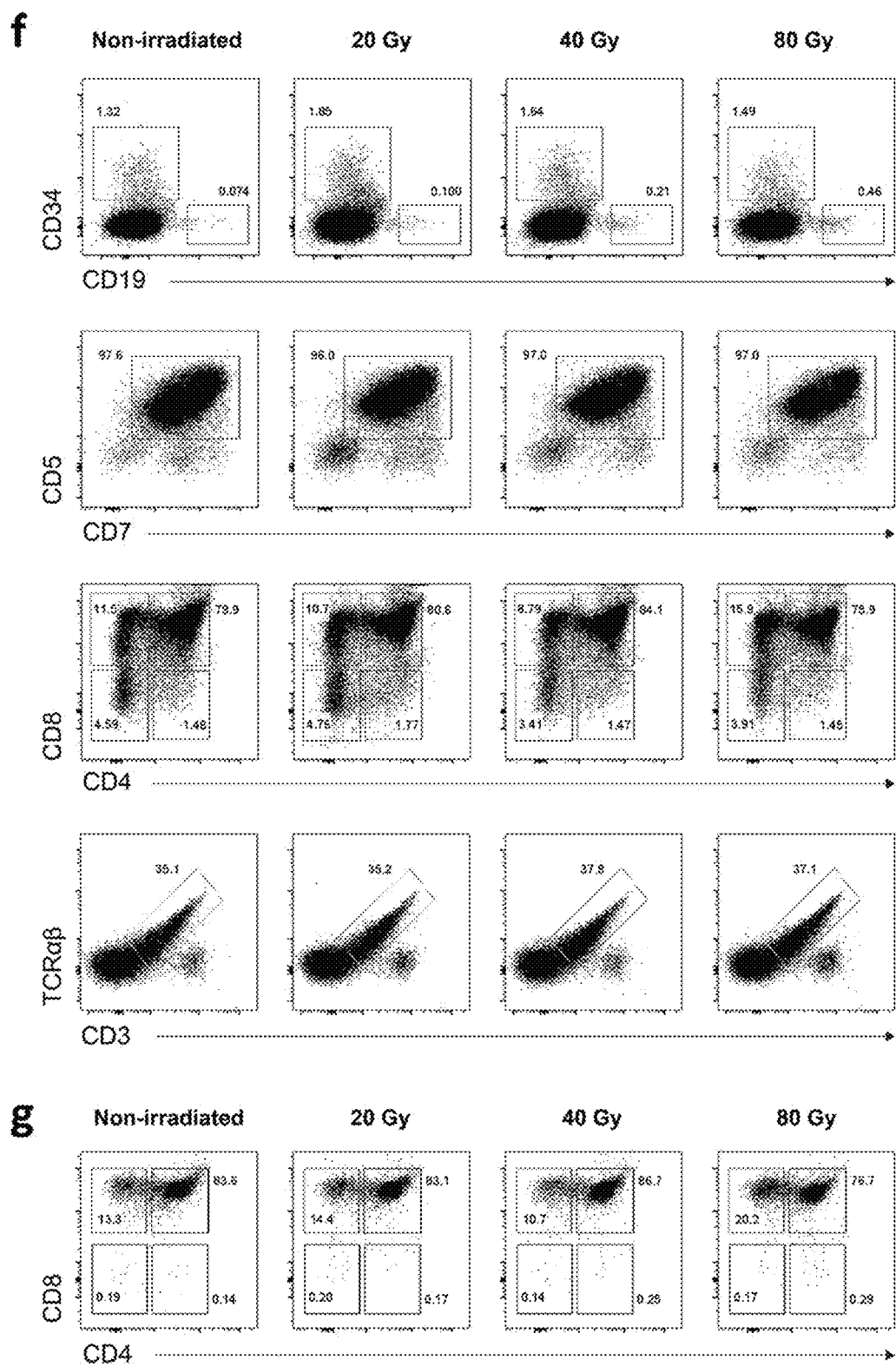

ATOs sustained ongoing T cell differentiation from primitive progenitor cells even in prolonged culture. At 6 weeks, all three phenotypic stages of thymic T cell progenitors were present, including multipotent CD34+CD7−CD1a− early thymic progenitors (ETP) and downstream CD34+CD7+CD1a− and CD34+CD7+CD1a+ T-lineage progenitors (FIG. 3C). Pro-T1 and pro-T2 progenitor phenotypes were also identified in the CD34+ fraction based on an alternative classification scheme (FIG. 3C). CD19+ B cell frequency decreased over time, and NK and myeloid frequencies were low throughout (FIG. 3B, F-G). Histological sections of ATOs demonstrated a dense, tissue-like architecture with abundant lymphoid cells (data not shown), clusters of which were positive for CD3 (FIG. 3D). Cell expansion in ATOs relative to input HSPC was on average 80-fold at week 6 (FIG. 3E), and while variation in expansion was seen between different biological CB units, precursor and mature T cells were consistently generated from all samples (n=18) (FIG. 3G). Total cell expansion was also inversely related to starting cell numbers and the ratio of HSPC to stromal cells, with up to 800-fold increase over input HSPC in some combinations (FIG. 9A, B). High reproducibility of both cell expansion and T cell differentiation was seen across technical replicates (n=11) and different lots of B27 (n=4) (FIG. 10A-C). Of significance to clinical translation, comparable T cell differentiation was seen in ATOs using medium supplemented with xeno-free B27 (containing human serum albumin) (FIG. 10D-E) or made with irradiated stromal cells (FIG. 10F-B).

Figure 11A:
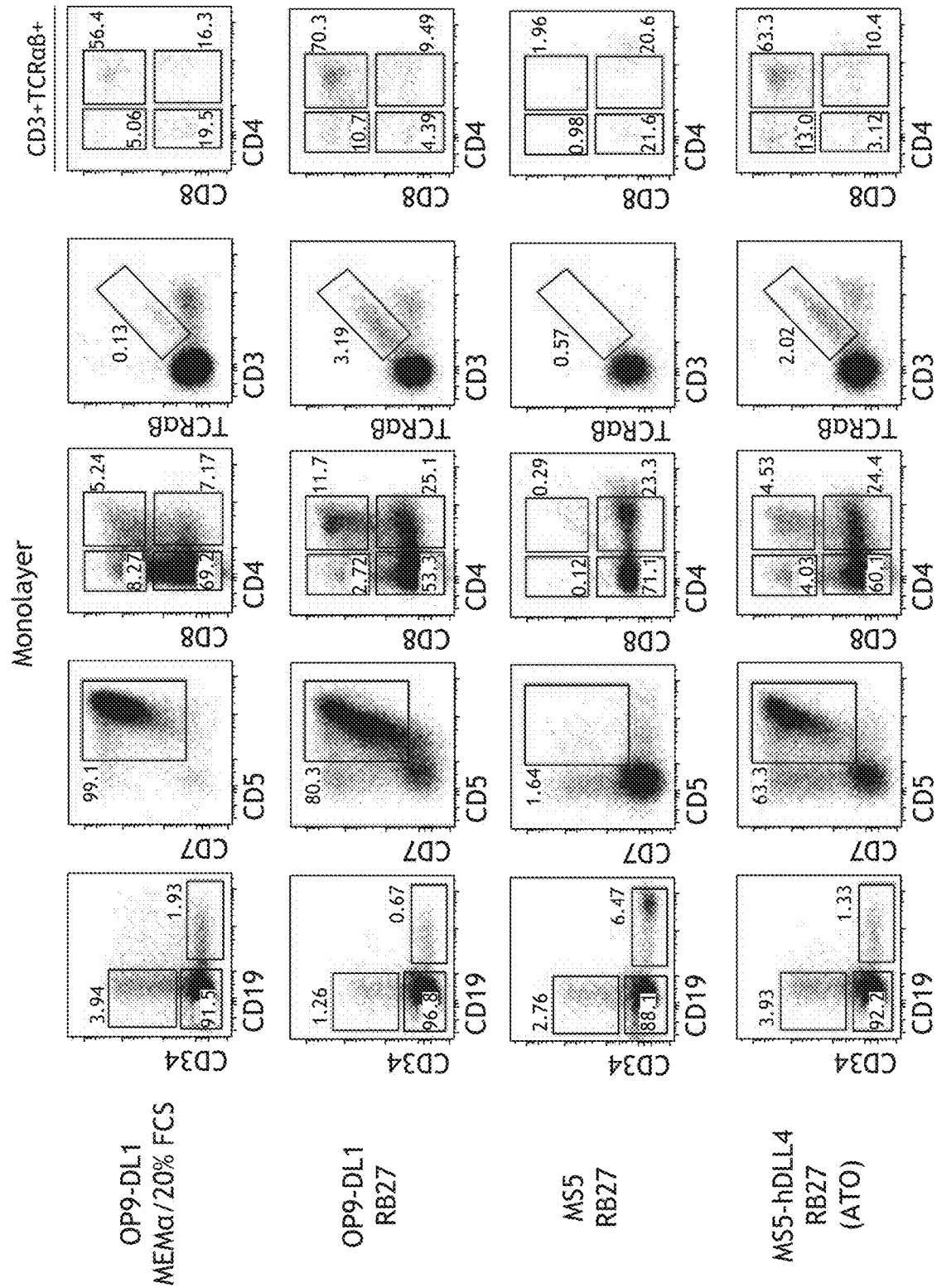
FIG. 11A-C: Enhanced positive selection in ATO versus monolayer systems. (a) Enhanced T cell positive selection and maturation in ATOs (i.e. MS5-hDLL1 in 3D culture with RB27) compared with monolayer co-cultures. Week 6 monolayer cultures (left) were compared with 3D organoid cultures (right) and included cross-over comparisons with OP9-DL1 as indicated. Standard medium for OP9-DL1 monolayer co-cultures was MEMα/20% FCS, and standard medium for ATOs was RB27, as described in Methods. Monolayer or organoid cultures using the parental MS-5 cell line (not transduced with DLL1) are also shown. All plots are gated on CD14−CD45− cells or CD3+TCRαβ+ subgates as indicated above plots. (b) Percent and (c) fold expansion of relevant cell populations in standard OP9-DL1 monolayer cultures versus ATOs at 6 weeks. Cultures were initiated in parallel using the same CB units. ATOs were set up with $3\times10^4$ HSPCs at a 1:20 HSPC to stromal cell ratio.
Figure 11A:
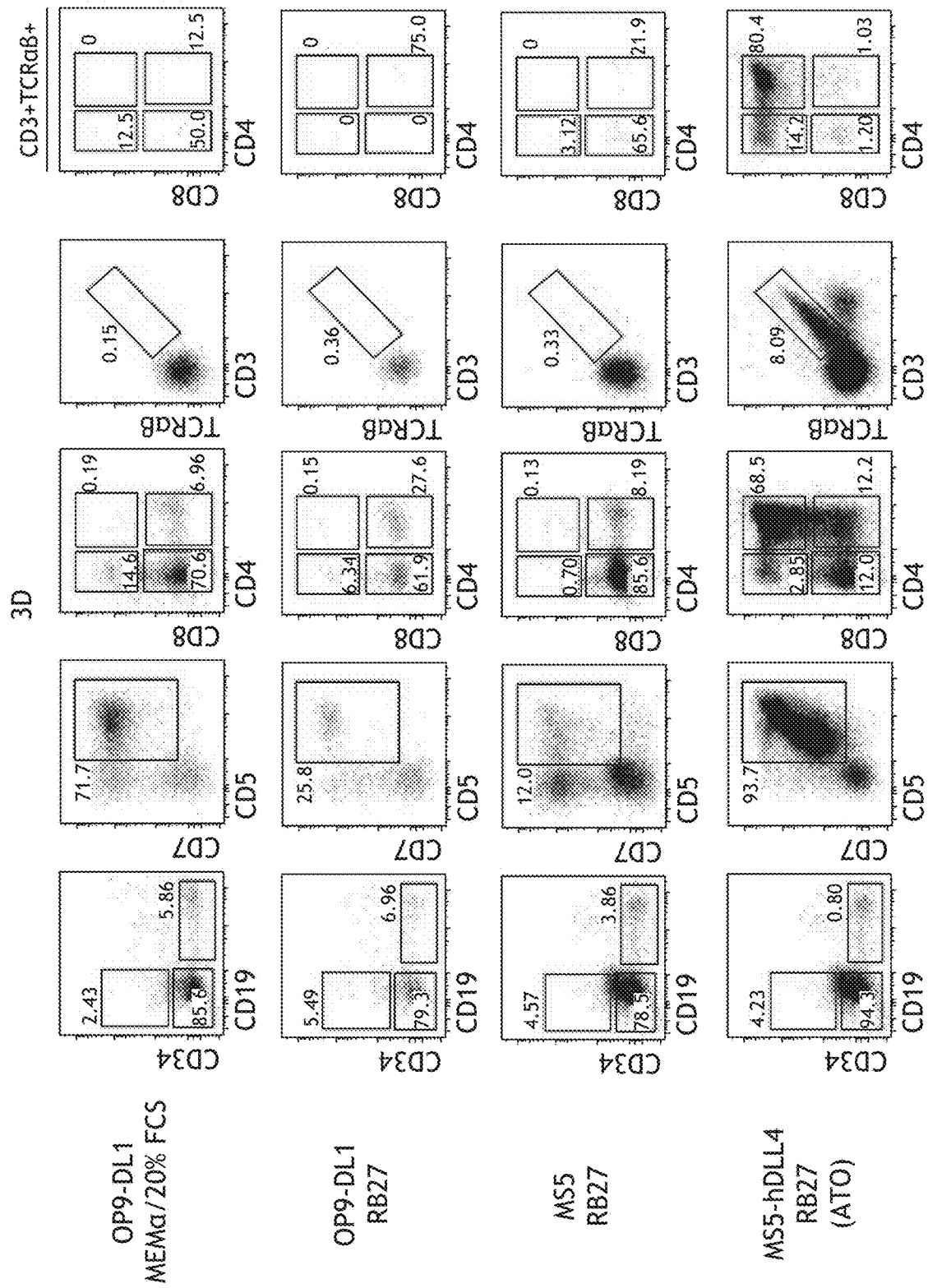
Figure 11B:
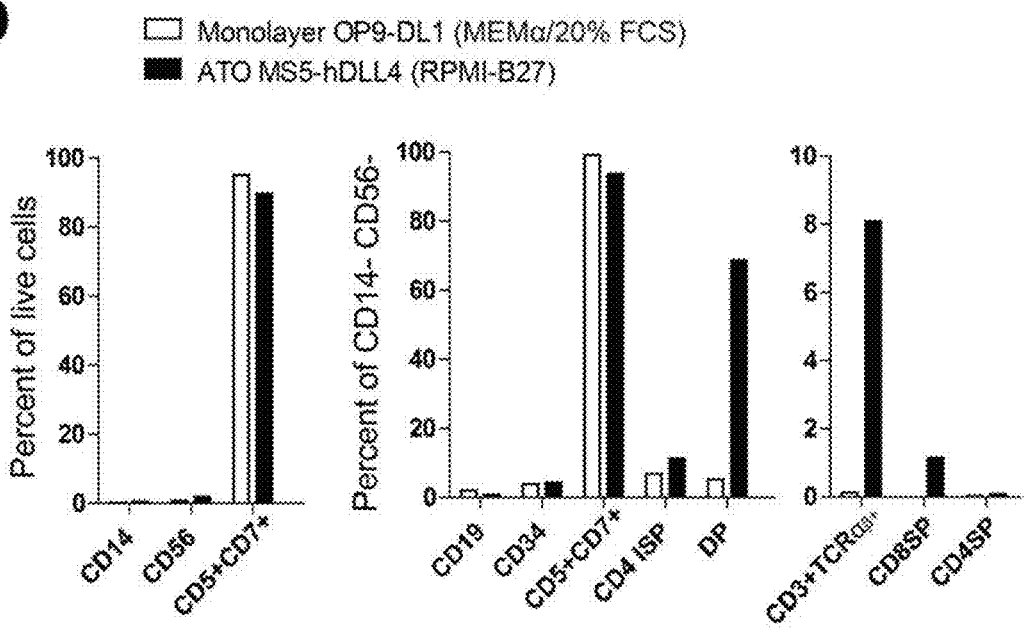
Figure 11C:
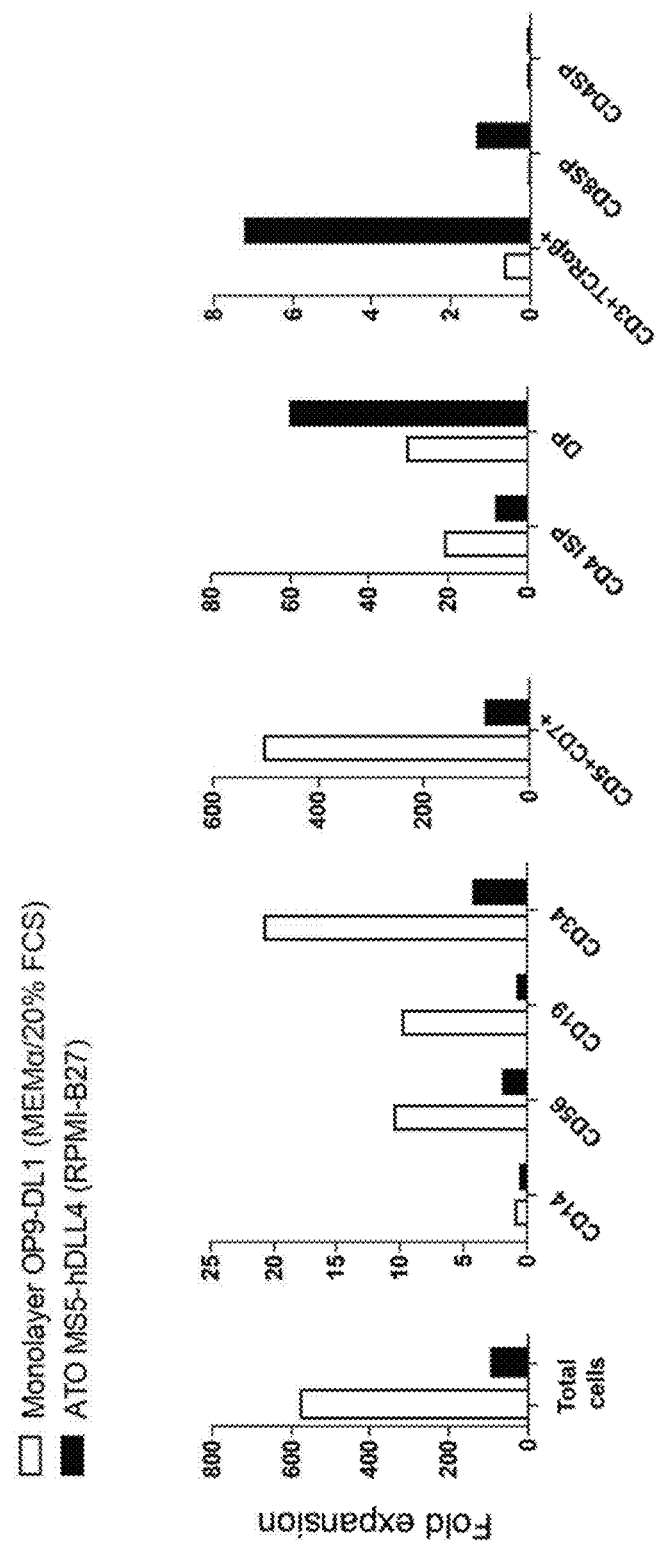

When compared with the OP9-DL1 monolayer culture system using same-donor CB HSPCs, ATOs revealed markedly superior generation of CD3+TCRαβ+ T cells (FIG. 11A-C). Consistent with previous reports, OP9-DL1 monolayers supported efficient T-lineage commitment (CD7+CD5+) and progression through the ETP, pro-T and CD4 ISP stages, but inefficient generation of DP, CD3+TCRαβ+, and mature SP cells, all of which readily developed in ATOs (FIG. 11B-C). Indeed, optimal positive selection and maturation required all three components of the ATO system: 3D structure, MS5-hDLL1 stromal cells, and RB27 medium (FIG. 11A). In contrast to MS5-hDLL1, OP9-DL1 survived poorly in RB27 and showed poor support of T cell differentiation in organoid cultures. The parental MS-5 cell line lacking DLL1 expression did not support T cell development in either monolayer or 3D cultures (FIG. 11A).

In summary, ATOs provide a standardized, serum-free organoid system that supports robust and reproducible T cell differentiation from CD34+ HSPCs, permitting positive selection and maturation of human TCRαβ+ and TCRγδ+ T cells.

2. Recapitulation of Thymic Naïve T Cell Development in ATOs

Figure 4A:
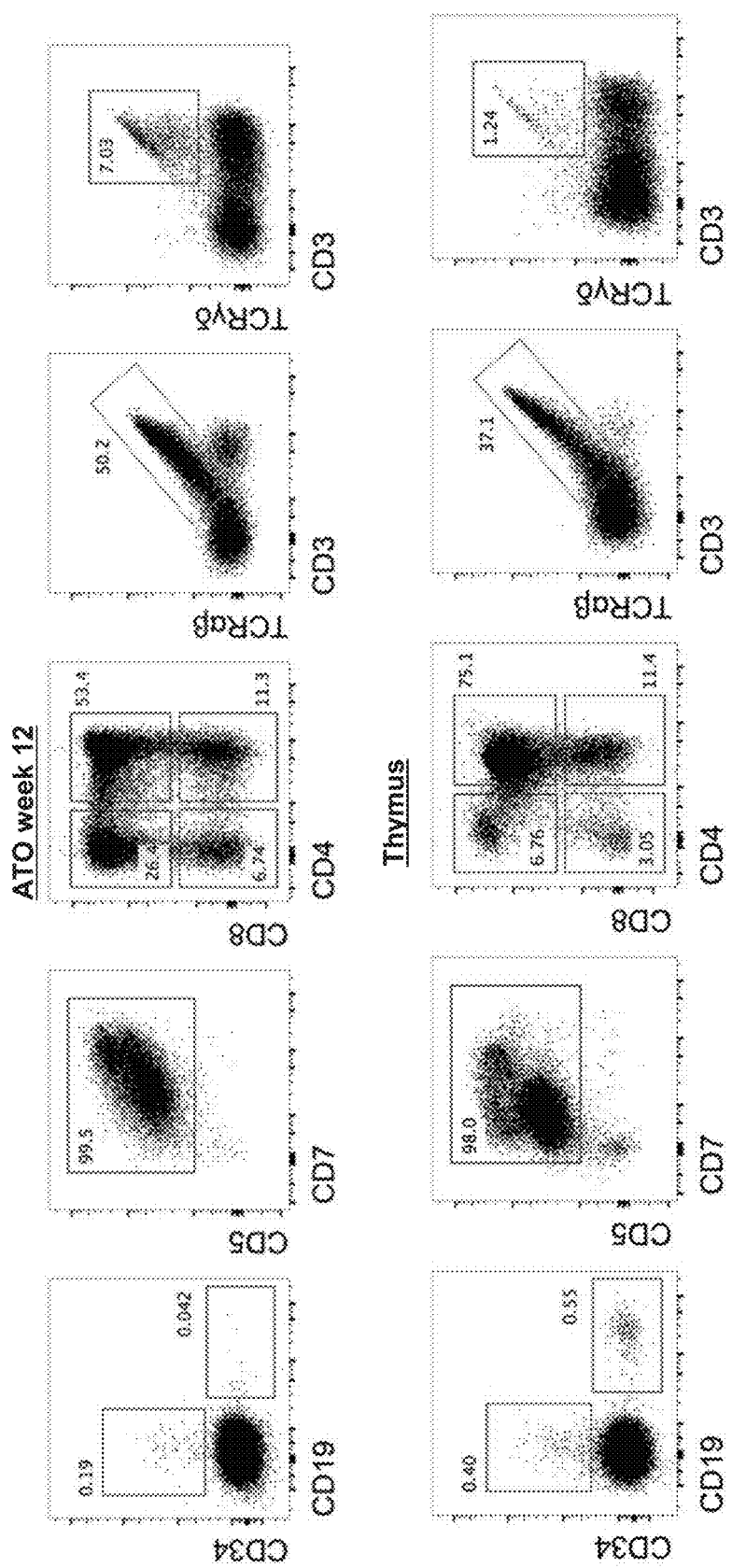
FIG. 4A-C: Recapitulation of thymopoiesis and naïve T cell development in ATOs. Comparison of T cell differentiation between week 12 CB ATOs and human postnatal thymocytes gated on (a) total CD14−CD56− and (b) CD3+ TCRαβ+ cells. (c) Generation of immature (CD45RA−CD45RO+) and mature (CD45RA+CD45RO−) naïve T cells in week 12 ATOs or thymus (gated on CD3+TCRαβ+ cells, with CD8SP or CD4SP subgates indicated).
Figure 4B:
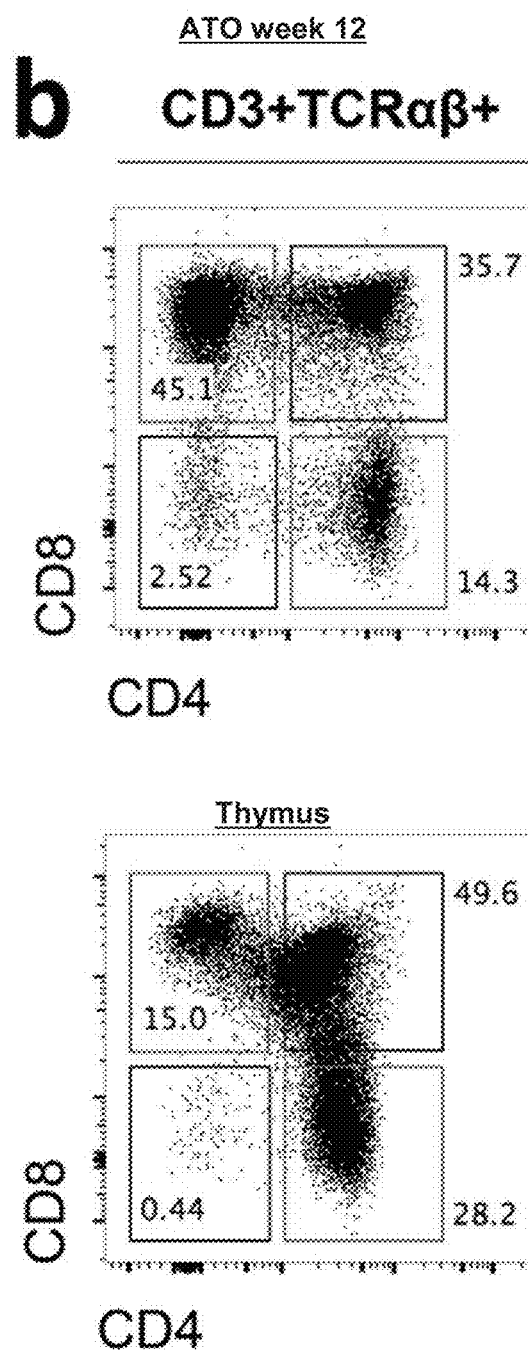
Figure 12A:
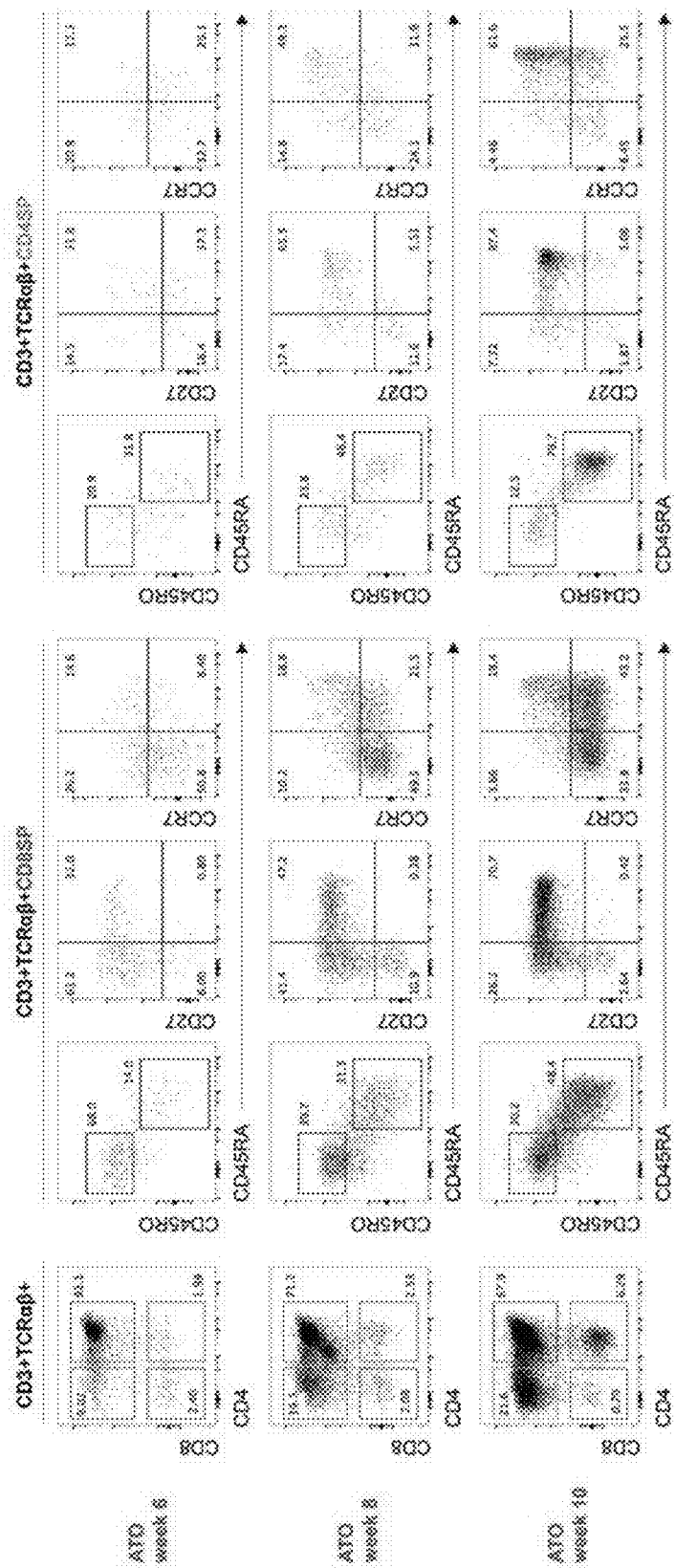
FIG. 12A-C: Recapitulation of thymopoiesis and naïve T cell phenotypes in ATOs. (a) Progressive differentiation of CD3+TCRαβ+CD8SP and CD4SP cells in ATOs between weeks 6-10. ATOs were cultured in parallel from same donor CB HSPCs and serially analyzed at the indicated weeks. Cells are gated on CD14−CD56-TCRαβ+CD3+ cells, and sequential sub-gates (CD8SP or CD4SP) are indicated above plots. (b,c) Additional markers characterizing week 12 ATO-derived naïve CD8SP and CD4SP T cells compared with corresponding populations in the human thymus. All cells are gated on CD14−CD56−CD3+TCRαβ+ and subgated on (b) CD8SP or (c) CD4SP cells.

T cell differentiation in long term ATOs was next compared to that in the postnatal human thymus. Week 12 CB ATOs showed a similar frequency of T-lineage committed (CD5+CD7+) and CD34+ T cell progenitors to the thymus (FIG. 4A), whereas DP and SP frequencies suggested more advanced T cell maturation in week 12 ATOs than in the thymus (FIG. 4A). As in the thymus, the majority of CD3+ cells in ATOs were TCRαβ+, with a smaller but consistent TCRγδ+ population (FIG. 4A). Among ATO-derived CD3+TCRαβ+ cells, generation of mature CD8SP and CD4SP T cells increased between weeks 6-12 (FIG. 4B and FIG. 12A). In contrast to the thymus, ATOs exhibited proportionately fewer CD4SP T cells relative to CD8SP T cells, possibly reflecting slower kinetics of CD4+ T cell development; CD4+ cells continued to increase in frequency until week 12, the furthest time point analyzed (FIG. 4B and FIG. 12A).

Figure 4C:
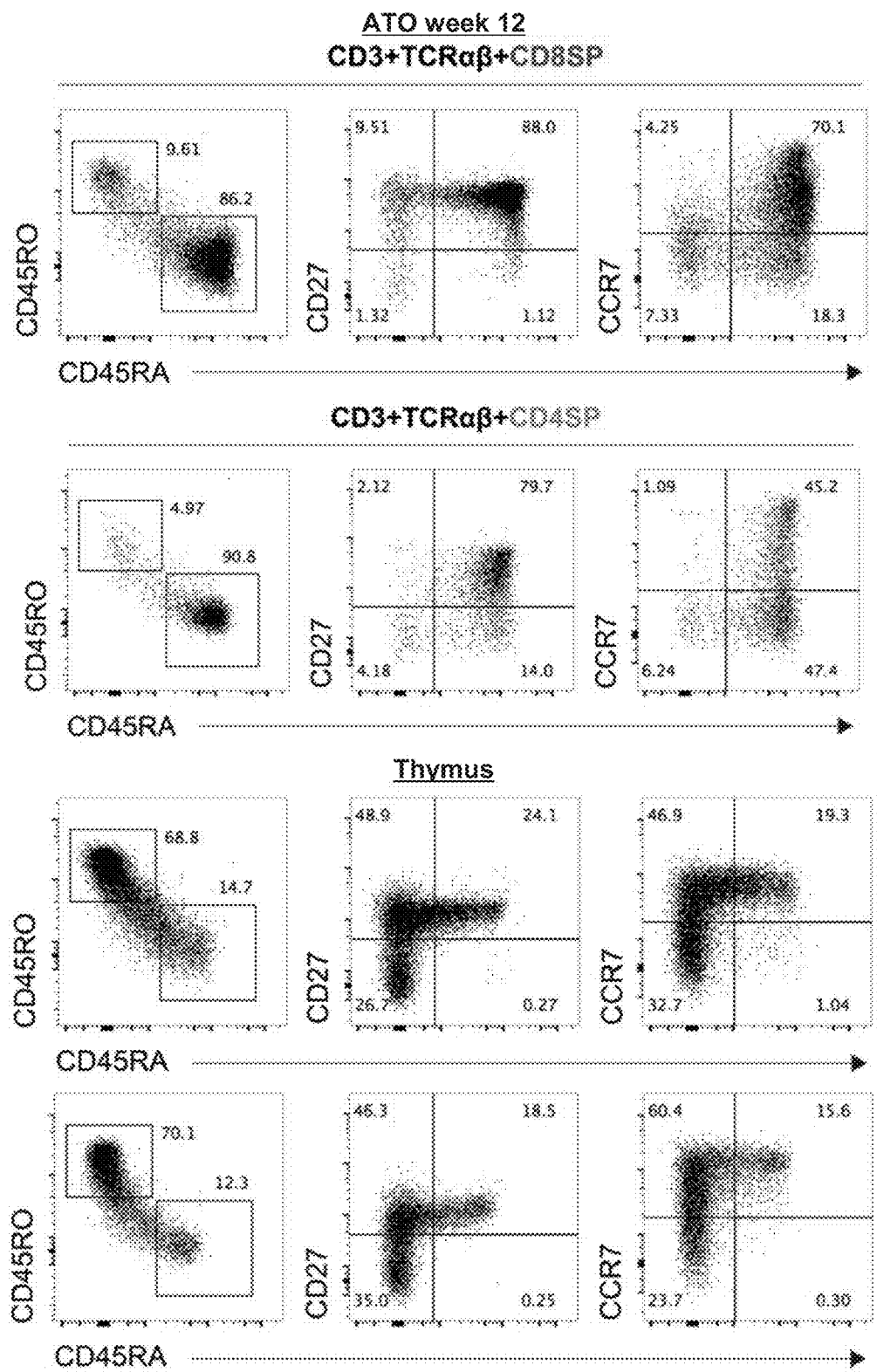
Figures 12B, 12C:
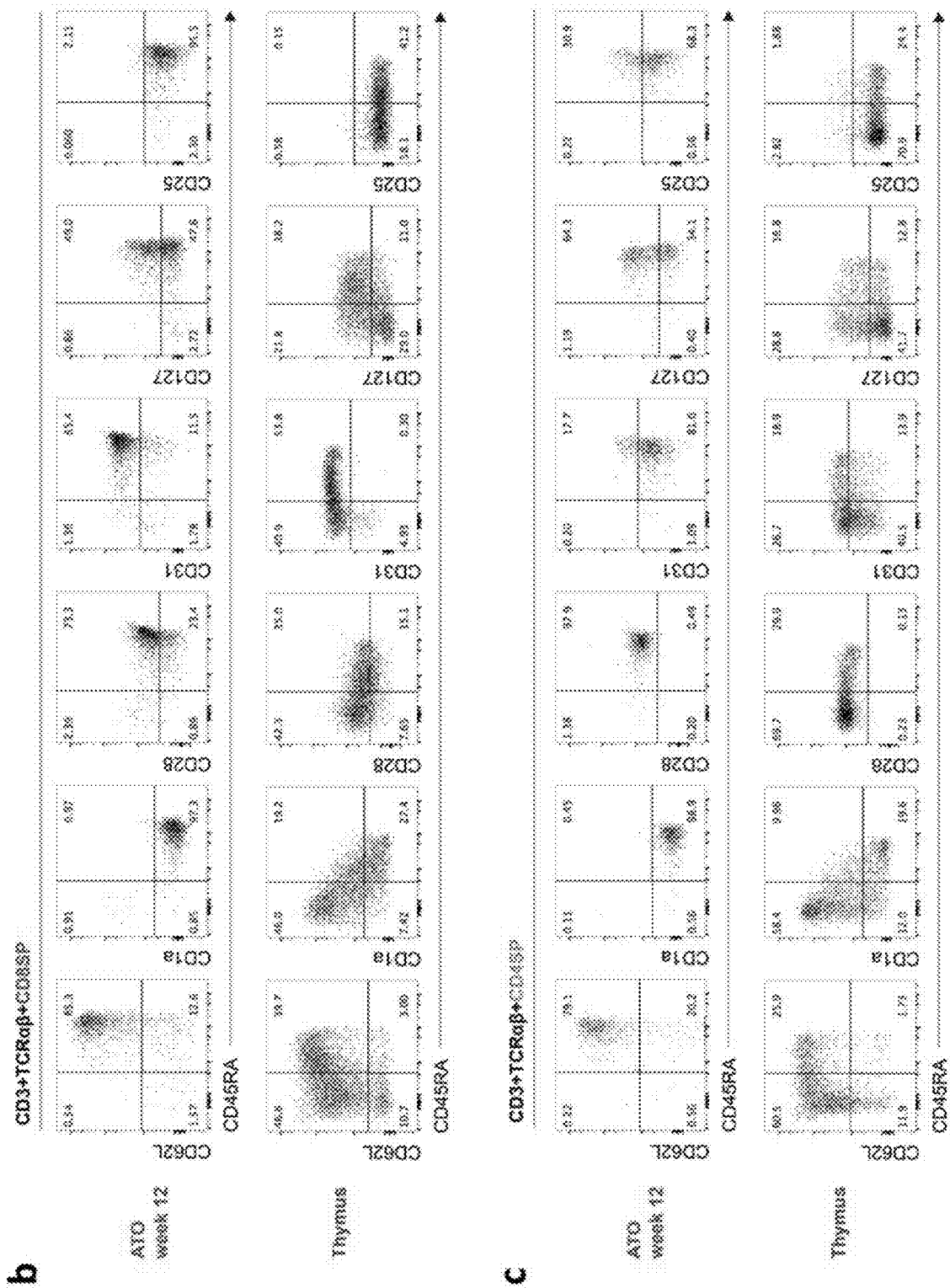

As in the thymus, ATO-derived CD3+TCRαβ+CD8SP and CD4SP T cells transited from an "immature naïve" (CD45RA−CD45RO+CD27+CCR7−CD1A$^{hi}$) to a "mature naïve" (CD45RA+CD45RO−CD27+CCR7+CD1a$_{lo}$) phenotype (FIG. 4C and FIG. 12A-C). In ATOs this occurred between weeks 6-12, and resulted in a higher frequency of mature naïve T cells in week 12 ATOs than in the thymus (FIG. 4C and FIG. 12B-C). Both immature and mature naïve subsets co-expressed CD62L and CD28, with subset co-expression of CD127 and CD31, the latter associated with recent thymic emigrant T cells in the blood (FIG. 12B-C). The activation marker CD25 was not expressed on ATO-derived CD8SP T cells, but was observed on a subset of CD4SP T cells (FIG. 12B-C). Taken together, these data show remarkable fidelity of T cell differentiation in ATOs compared to the human thymus, culminating in the emergence of bona fide naïve T cells similar to those found in the thymus and blood.

3. T Cell Differentiation from Multiple HSPC Sources and Subsets

Figures 5A, 5B:
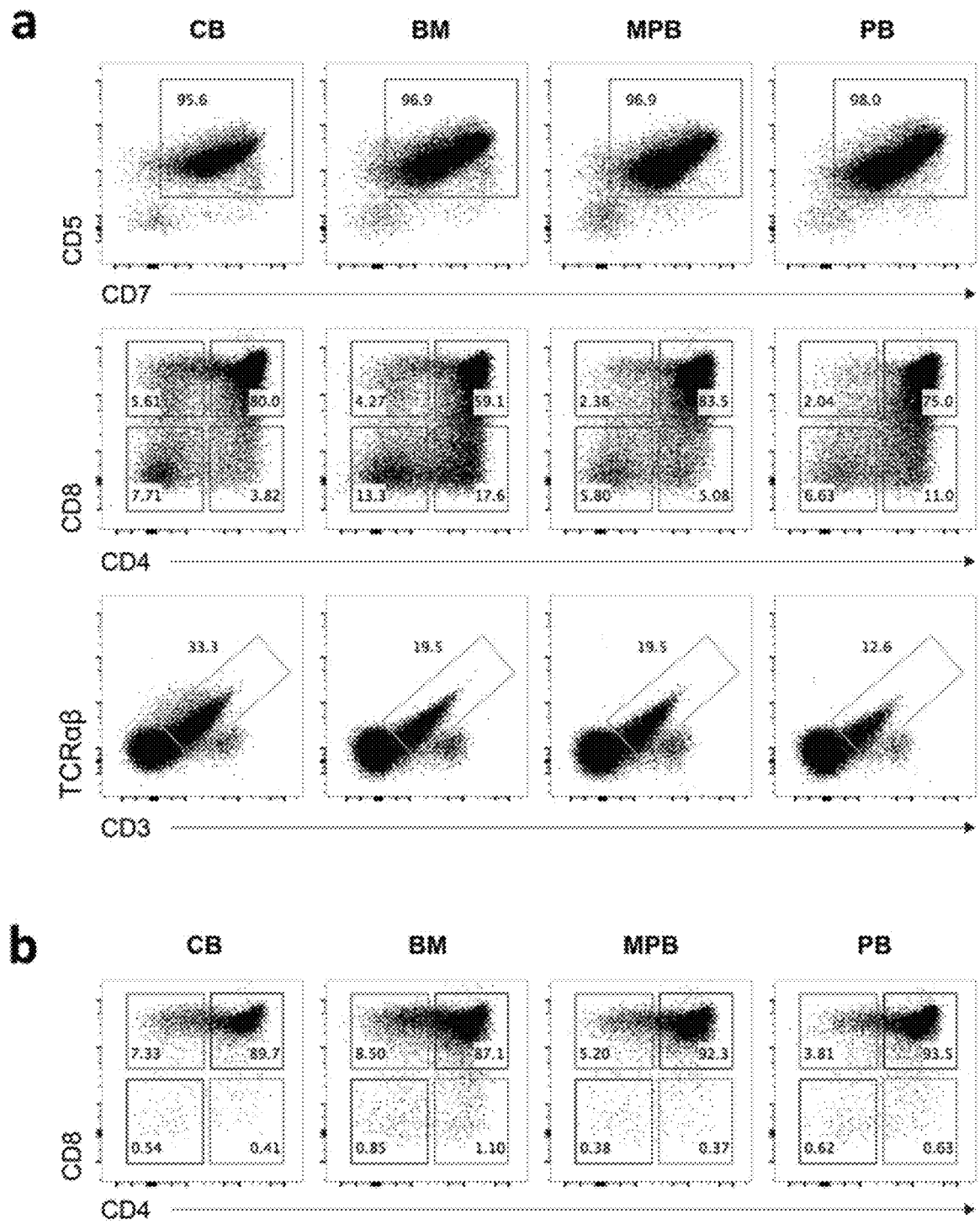
FIG. 5A-F: Generation of T cells from multiple HSPC sources and subsets. Efficient T cell development in week 6 ATOs initiated with CD34+CD3− HSPCs from human cord blood (CB), adult bone marrow (BM), G-CSF mobilized peripheral blood (MPB), or non-mobilized peripheral blood (PB). Gated on (a) total CD14−CD56− cells, and (b) CD14−CD56−CD3+TCRαβ+ T cells. (c) T cell differentiation from Lin−CD34+CD38− hematopoietic stem cell (HSC) enriched fractions from CB, BM, and MPB in week 6 ATOs, gated on CD14−CD56− or (d) CD14−CD56−CD3+TCRαβ+ T cells. (e) T cell differentiation in week 3 ATOs initiated with adult BM HSC and progenitor subsets, gated on CD14−CD56− cells and (f) CD34+ cells as shown in (e).
Figures 5C, 5D:
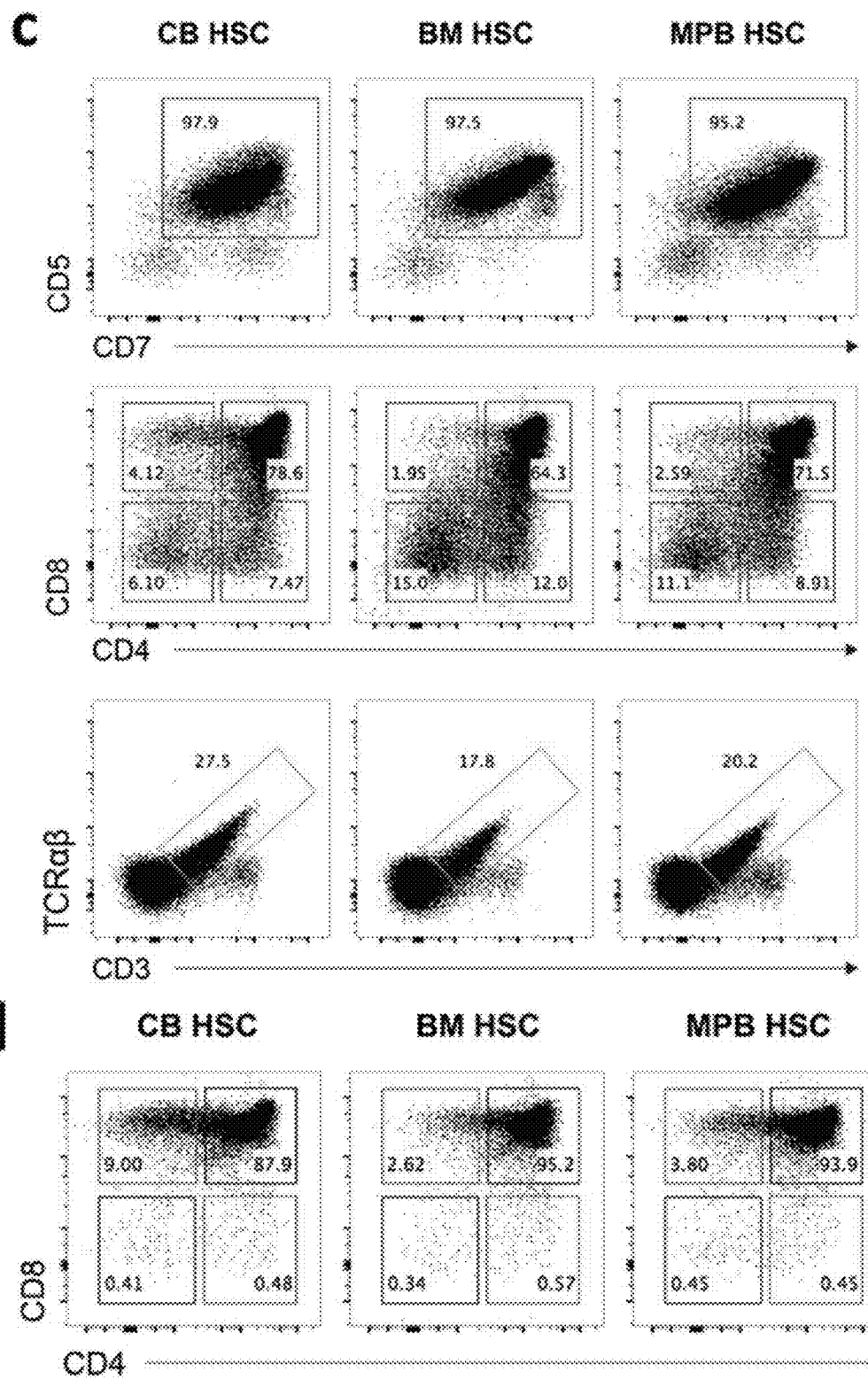
Figures 13A, 13B, 13C:
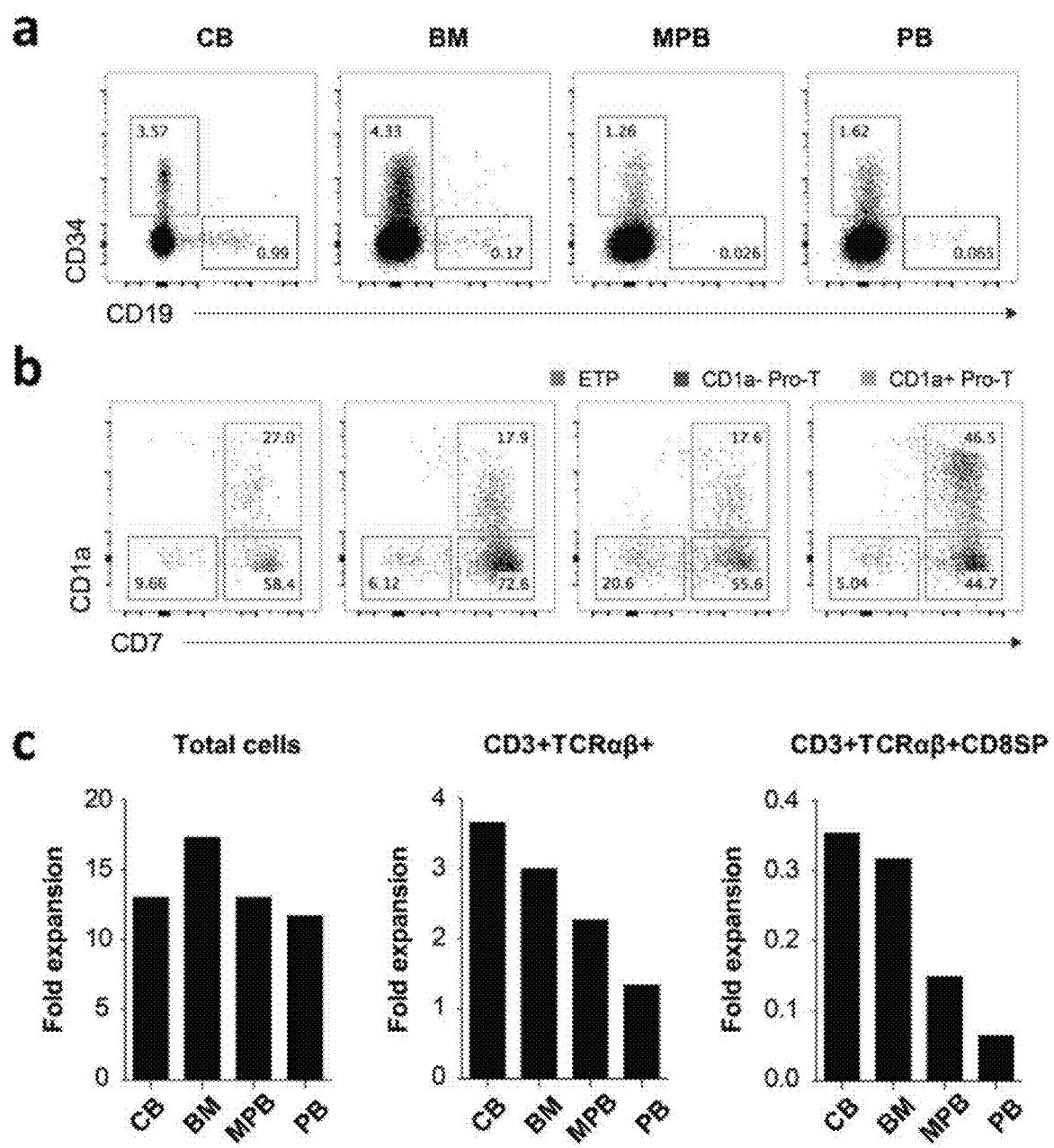
FIG. 13A-F: Generation of T cells from multiple HSPC sources and subsets. (a) Maintenance of CD34+ cells in week 6 ATOs from different human cord blood (CB), adult bone marrow (BM), G-CSF mobilized peripheral blood (MPB), or non-mobilized peripheral blood (PB) HSPCs. (b) phenotype of CD34+ T cell progenitor subsets, gated on CD34+ cells as shown in (a). (c) Fold expansion of total cells and relevant T cell subsets in week 6 ATOs using HSPC sources as shown in (a). Fold expansion is relative to starting number of HSPCs. ATOs were set up using $3\times10^4$ CD34+CD3− HSPCs per ATO at a 1:20 HSPC to stromal cell ratio. (d) Maintenance of CD34+ cells and (e) phenotype of CD34+ T cell progenitors in week 6 ATOs initiated from hematopoietic stem cell (HSC)-enriched (Lin-CD34+CD38−) fractions from different HSPC sources. (f) Fold expansion of total cells in week 3 ATOs initiated with purified BM hematopoietic stem and progenitor subsets. ATOs were initiated with $2-4\times10^4$ of each population per ATO at a 1:15-1:40 HSPC to stromal cell ratio. Data are relative to starting numbers of HSPCs.

Efficient T cell differentiation with similar frequencies of precursor and CD3+TCRαβ+ T cells was seen from all clinically relevant HSPC sources, i.e. adult bone marrow (BM), G-CSF mobilized peripheral blood (MPB), and non-mobilized peripheral blood (PB) (FIG. 5A-B and FIG. 13A, B). Total cell expansion was also comparable across HSPC sources (FIG. 13C). Highly enriched hematopoietic stem cell (HSC) fractions (Lin−CD34+CD38−) from CB, BM, or MPB demonstrated similarly robust T cell differentiation (FIG. 5C-D and FIG. 13D-E), suggesting that T cell potential from these sources is independent of pre-existing lymphoid-committed progenitors.

Figure 5E:
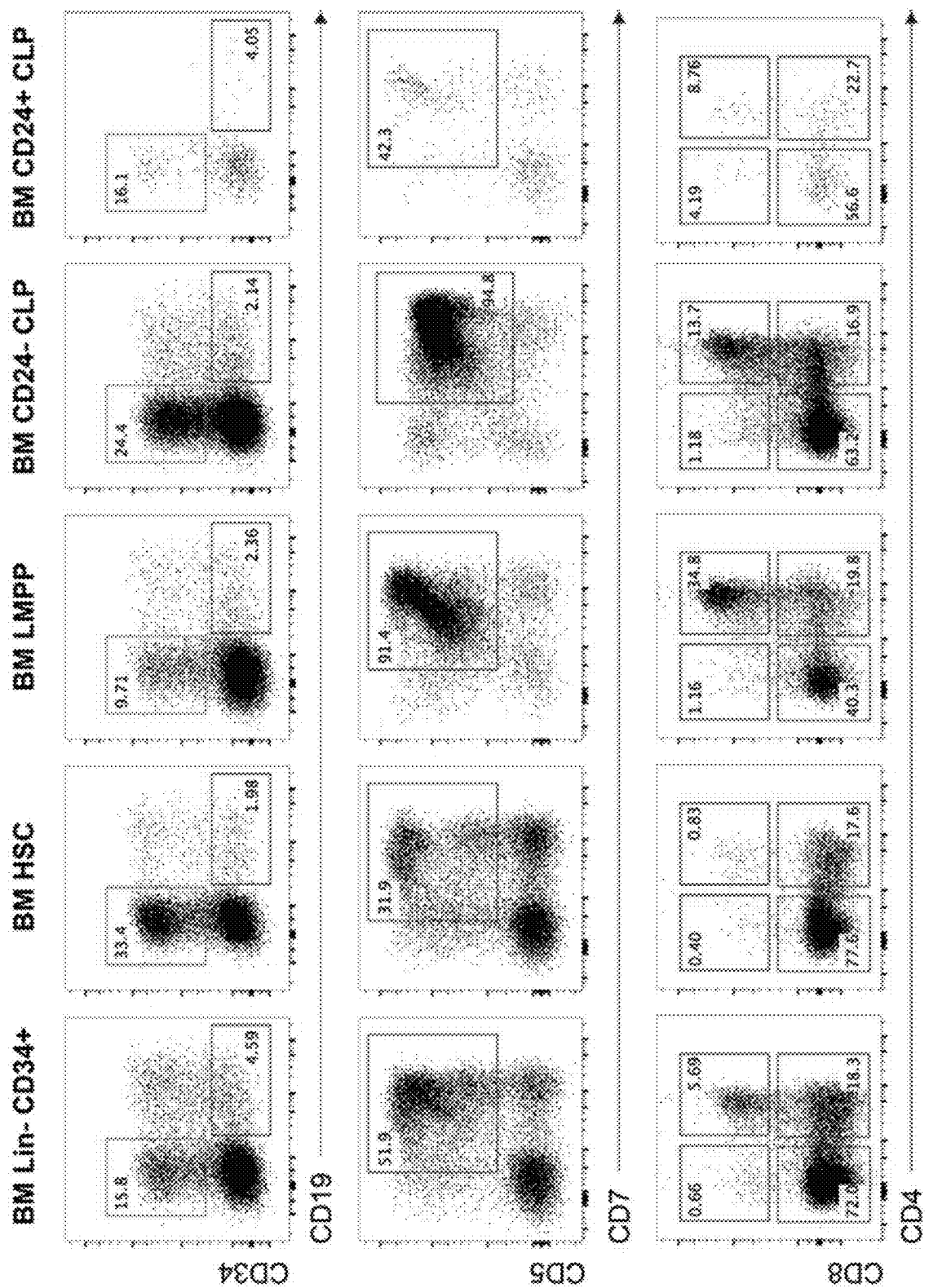
Figure 5F:
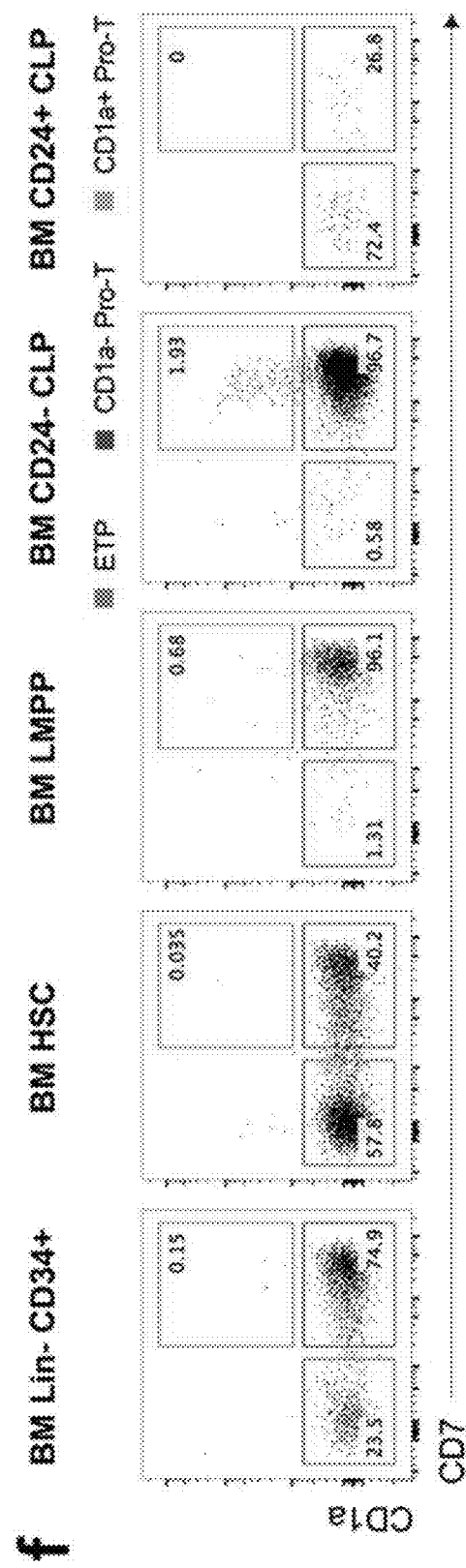
Figures 13D, 13E, 13F:
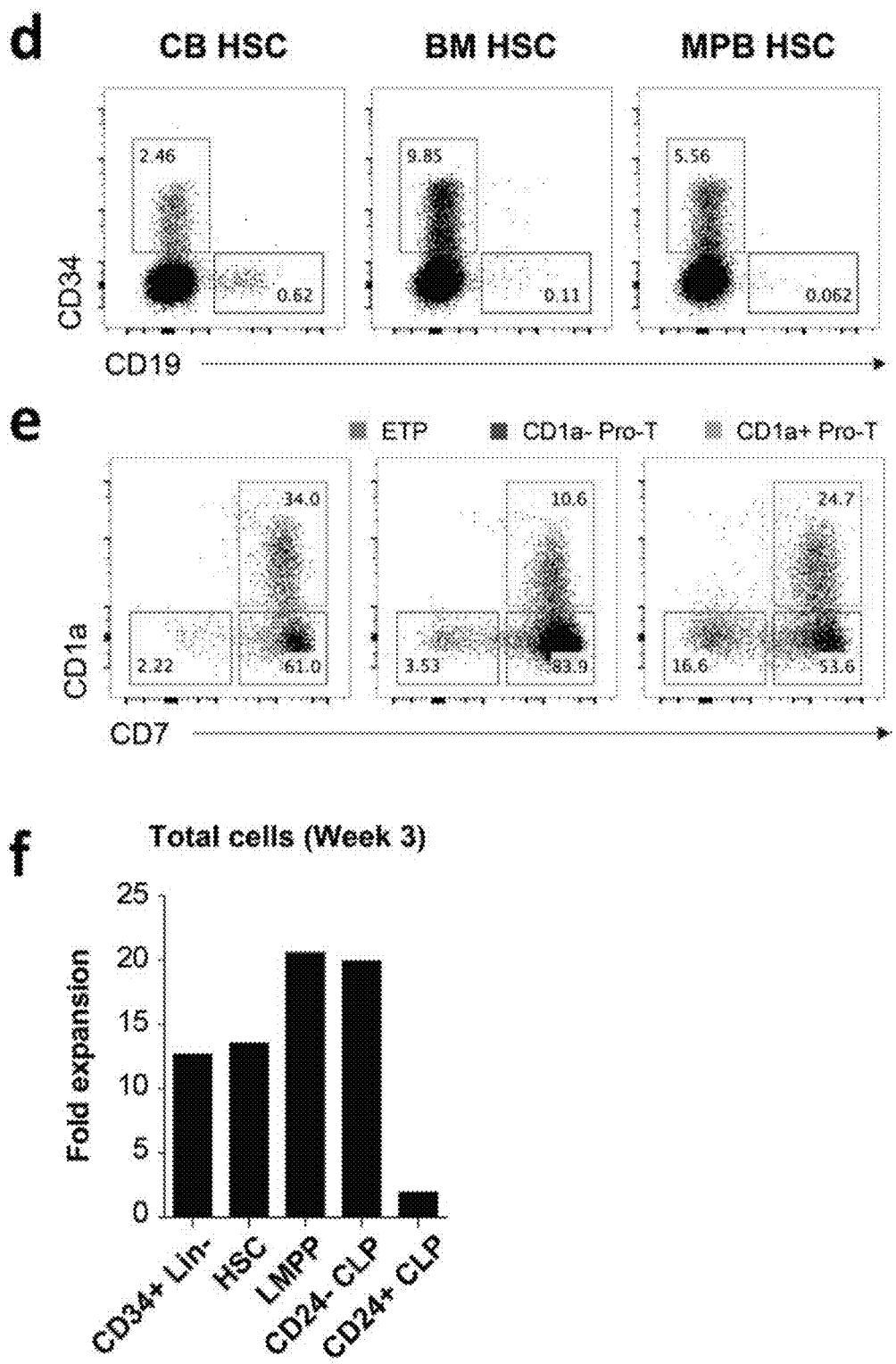

T cell differentiation in ATOs was also initiated from purified lymphoid progenitors. At three weeks, adult BM lymphoid-primed multipotent progenitors (LMPP) and CD24− common lymphoid progenitors (CLP) differentiated through CD4 ISP and DP stages more rapidly and efficiently than either HSC or unfractionated CD34+ HSPCs (FIG. 5E-F). In contrast, CD24+ CLPs, which possess primarily B and NK cell potential, grew poorly in ATOs with low cell output (FIG. 13F). Thus ATOs can serve as a tool for evaluating T lineage potential from human stem and progenitor cell populations.

4. TCR Diversity and Function of ATO-Derived T Cells

Figures 6A, 6B:
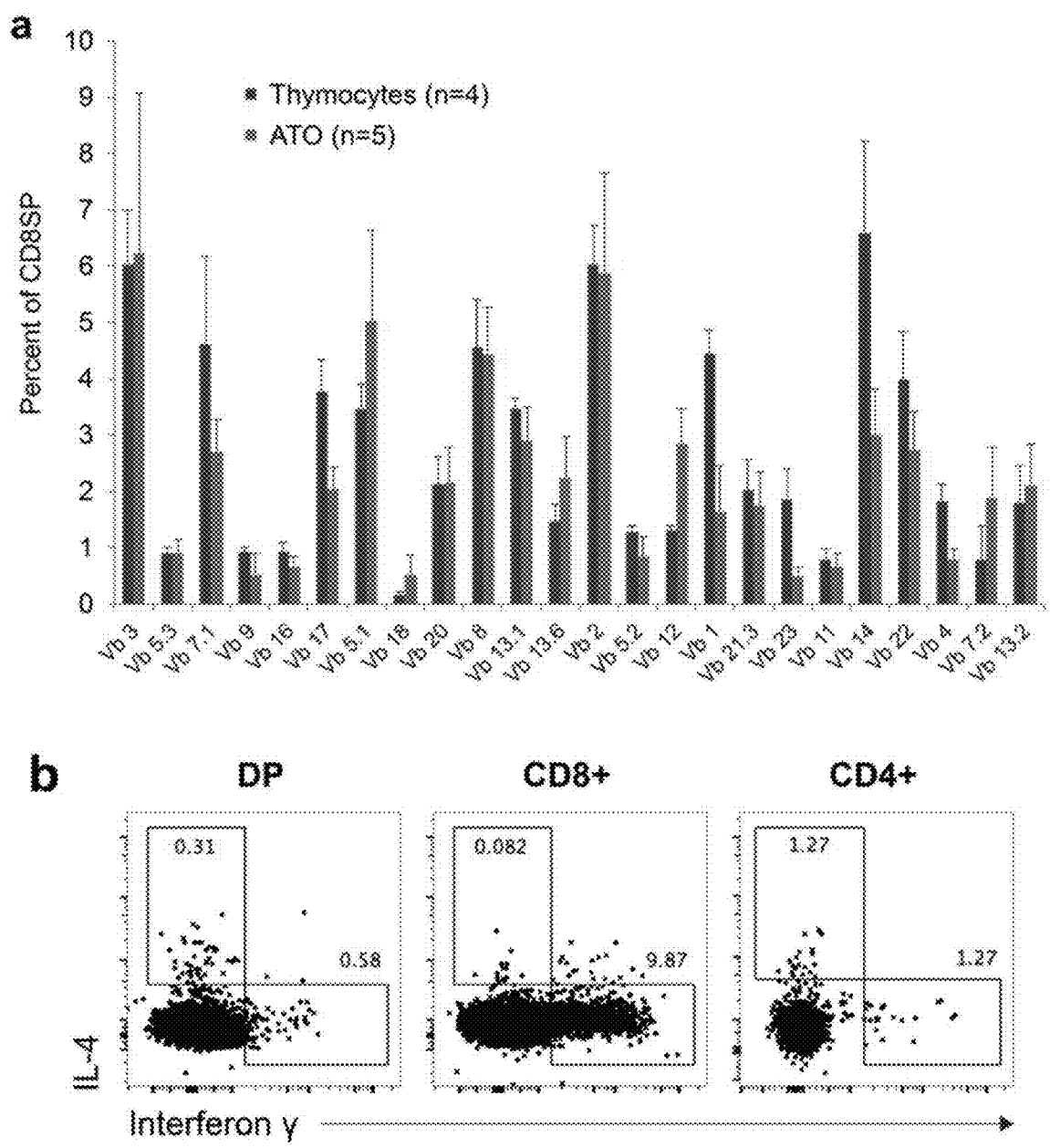
FIG. 6A-E: TCR diversity and function of ATO-derived T cells. (a) Generation of physiological TCR diversity in CD8SP T cells from week 7 ATOs (n=5) or human thymi (n=4), as shown by flow cytometric analysis of TCR Vβ usage. (b) Intracellular staining for interferon γ and IL-4 production in sorted ATO-derived DP, CD8SP and CD4SP cells treated with PMA/ionomycin for 12 h. (c) Proliferation (CFSE dilution) and activation (upregulation of CD25) of ATO-derived CD8SP cells in response to anti-CD3/CD28 and IL-2. (d) Comparable responses of CD8SP cells isolated from ATOs initiated with HSPCs from cord blood (CB), bone marrow (BM), or mobilized peripheral blood (MPB), as shown by Interferon γ production in response to PMA/ionomycin (shown versus an empty analysis channel), and (e) comparable in vitro expansion relative to input cell number in response to anti-CD3/CD28 and IL-2.

The inventors next characterized the TCR diversity and function of mature T cells generated in ATOs. Flow cytometry of ATO-derived CD3+TCRαβ+CD8SP T cells for common TCR Vβ segments revealed a strikingly similar diversity to that of corresponding CD8SP T cells from human thymi (FIG. 6A). Importantly, neither skewed Vβ usage nor clonal selection was observed, arguing against the predominance in ATOs of unconventional T cell subsets or clonally expanded mature T cells, respectively.

Figures 6C, 6D:
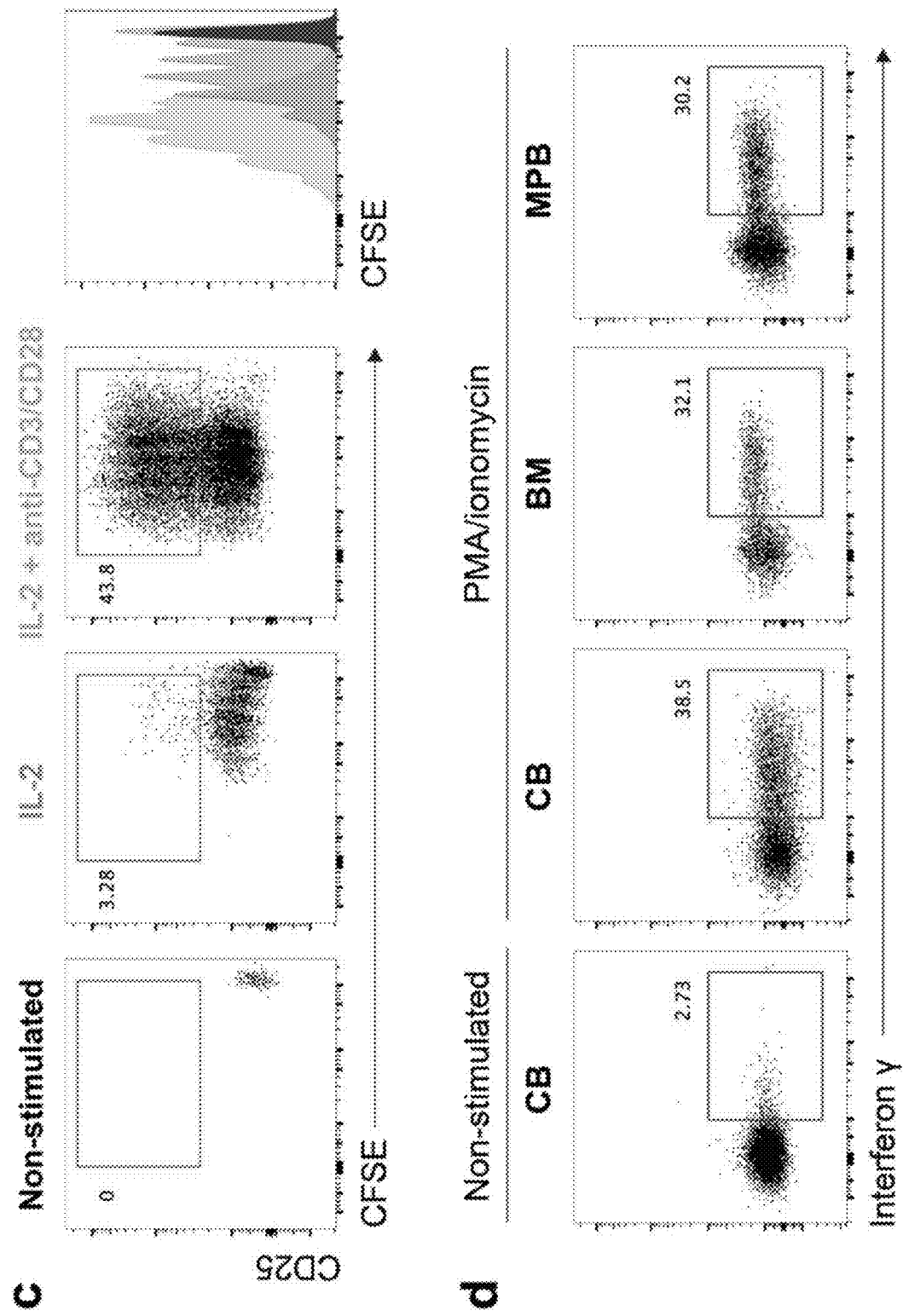
Figure 6E:
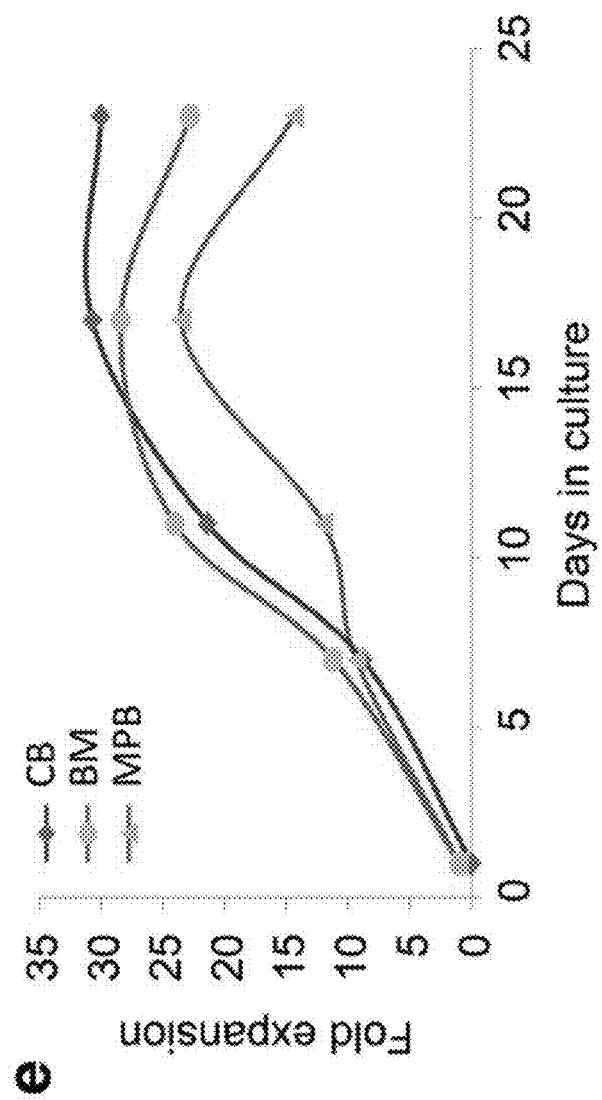

ATO-derived CD8SP T cells exhibited strong IFNγ and low IL-4 production in response to PMA/ionomycin, consistent with a cytotoxic phenotype (FIG. 6B). CD4SP cells produced both IFNγ+ and IL-4+ cells, consistent with Th1 and Th2 polarization, respectively; and few DP cells responded to stimulation, consistent with their immature state (FIG. 6B). ATO-derived CD8SP cells also underwent proliferation and upregulation of CD25 in response to anti-CD3/CD28 antibodies and IL-2 (FIG. 6C). Furthermore, CD8SP cells generated from CB, BM, or MPB ATOs exhibited similar production of IFNγ in response to PMA/ionomycin (FIG. 6D), and in vitro expansion with anti-CD3/CD28 and IL-2 (FIG. 6E). In summary, mature T cells generated in ATOs exhibited physiological TCR diversity and functional responses to antigenic stimuli.

5. Generation of Naïve TCR-Engineered T Cells in ATOs

Figure 7A:
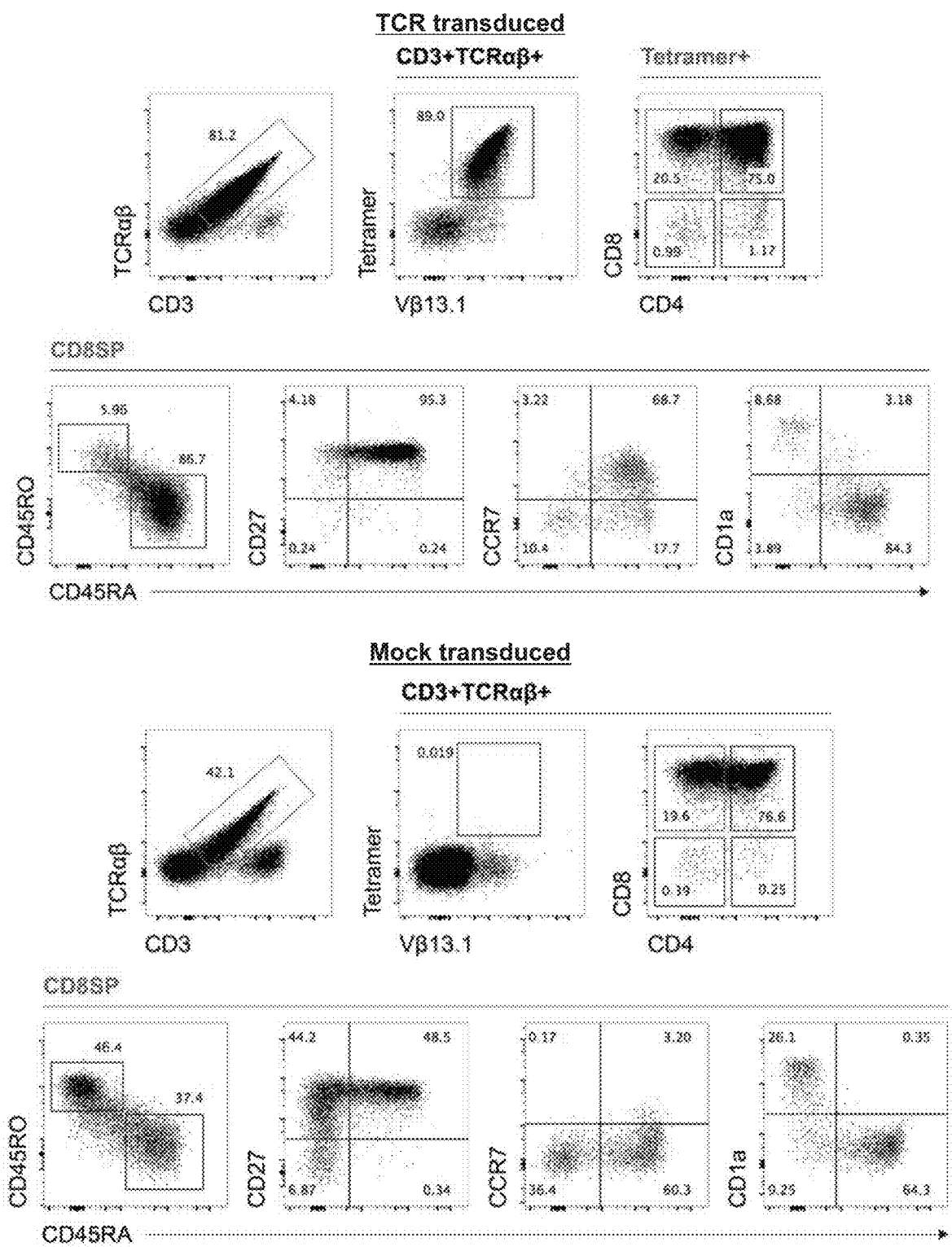
FIG. 7A-G: Differentiation and allelic exclusion of TCR-engineered T cells in ATOs. (a) Efficient generation of HLA-A*0201/NY-ESO-1$_{157-165}$ specific TCR-engineered T cells in week 7 ATOs initiated with TCR-transduced (top row) or mock transduced (bottom row) CB HSPCs. Plots are gated on CD14−CD56− cells with sequential sub-gates indicated above each plot. (b) Enhanced total cell expansion in week 6 TCR-transduced versus mock-transduced ATO generated with $3\times10^4$ CB HSPCs at a 1:20 HSPC to stromal cell ratio. (c) Enhancement of cell expansion in week 5 TCR-transduced ATOs by decreasing numbers of both HSPC and stroma. ATOs were generated with either $3\times10^4$ or $7.5\times10^3$ TCR-transduced CB HSPCs at a 1:20 HSPC to stromal cell ratio. (d) Cytotoxic priming of ATO-derived TCR-transduced CD8SP T cells. Interferon γ production and CD107a membrane mobilization following co-culture with K562 cells or K562 artificial APCs expressing CD80 and cognate peptide-MHC (T cells gated on CD3+tetramer+CD8SP). (e) Cell expansion of CD8SP T cells from TCR-transduced or mock-transduced ATOs in response to anti-CD3/CD28 and IL-2. (f) TCR Vβ diversity of CD8SP cells from TCR-transduced (n=3) or non-transduced (n=5) ATOs. Vβ frequency determined by flow cytometry, gated on tetramer+CD3+CD8SP cells from TCR-transduced ATOs (n=3) or CD3+CD8SP cells from non-transduced ATOs (n=5). (g) Representative flow cytometry plots from (f) showing enrichment for the transduced Vβ13.1 chain in tetramer+CD3+CD8SP cells from TCR-transduced ATOs. CD3+CD8SP T cells from a non-transduced ATO or human thymus are shown for comparison.

The inventors next adapted ATOs for the in vitro generation of TCR-engineered T cells from HSPCs. CB CD34+CD3− HSPCs were transduced with a lentiviral vector encoding the α and β chains of a HLA-A*02:01-restricted TCR specific for NY-ESO-1$_{157-165}$. At six weeks, TCR-transduced ATOs showed similar frequencies of CD5+CD7+ T-committed cells as mock-transduced controls, but markedly increased CD3+TCRαβ+ T cells, the majority of which expressed the transduced TCR, as seen by staining with a tetramer or antibody against the transduced Vβ13.1 chain (FIG. 7A). The frequency of CD8SP cells was similar between tetramer+ cells and CD3+TCRαβ+ cells from mock-transduced controls, however tetramer+CD8SP cells displayed accelerated maturation to a mature naïve phenotype (i.e. CD45RA+CD45RO−CD27+CCR7+CD1a$^{lo}$) (FIG. 7A). As with non-transduced ATOs, differentiation to effector/memory phenotypes was not observed (FIG. 7A).

Figure 7B:
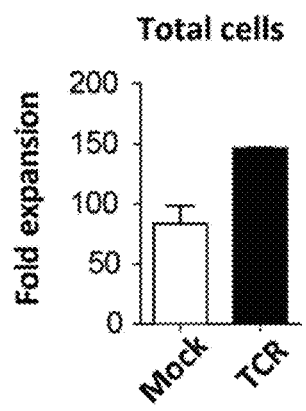
Figure 7C:
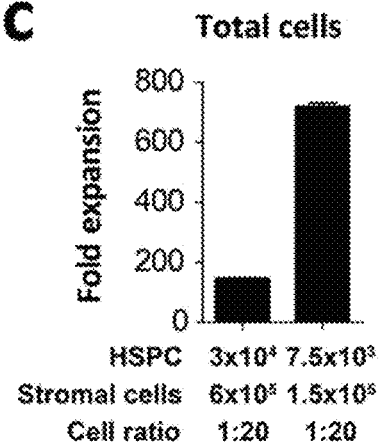

TCR transduction also resulted in enhanced total cell expansion in ATOs (FIG. 7B), the majority of which were tetramer+CD3+ T cells. Total cell expansion relative to input HSPCs was typically 150 fold in TCR-transduced ATOs (FIG. 7A), but could be further increased to over 700-fold by limiting the starting HSPC and stromal cell numbers per ATO (FIG. 7C). Thus, a single ATO initiated with 7,500 TCR-transduced HSPCs could generate approximately $5 \times 10^6$ cells, of which approximately $7.5 \times 10^5$ (15%) were tetramer+CD3+CD8SP mature naïve T cells (FIG. 7A-C).

Figure 7D:
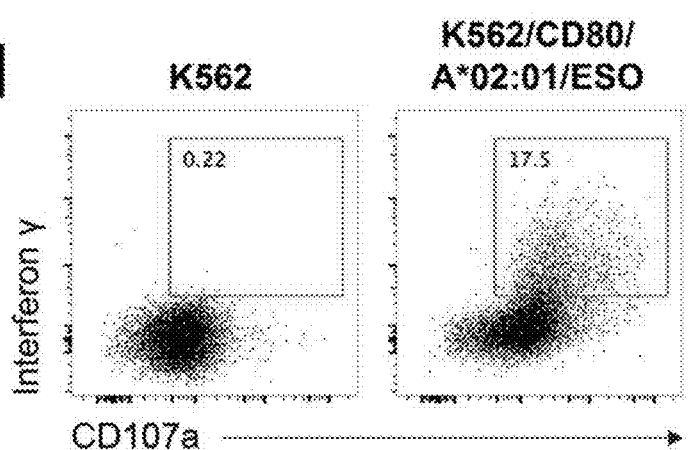
Figure 7E:
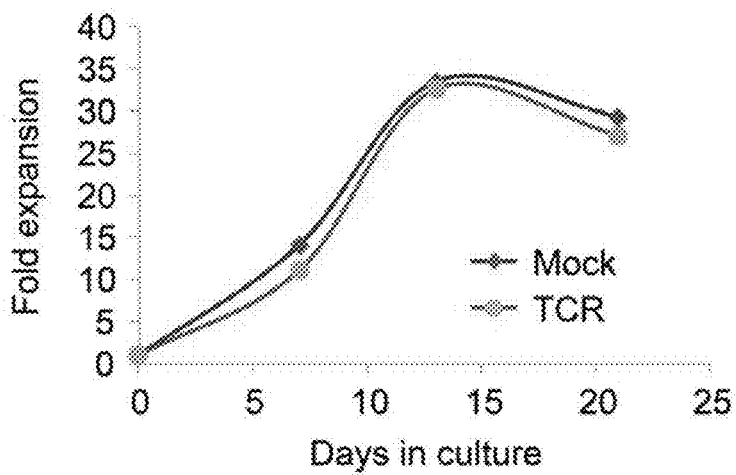

ATO-derived CD8SP cells from TCR-transduced ATOs underwent antigen-specific activation and degranulation, as measured by IFNγ production and CD107a membrane mobilization, respectively, in response to artificial antigen presenting cells expressing cognate peptide-MHC and CD80, but not to parental K562 cells (FIG. 7D). Furthermore, CD8SP T cells from TCR-transduced ATOs underwent equivalent in vitro expansion in response to anti-CD3/CD28 and IL-2 as those from mock-transduced ATOs (FIG. 7E).

Figure 7F:
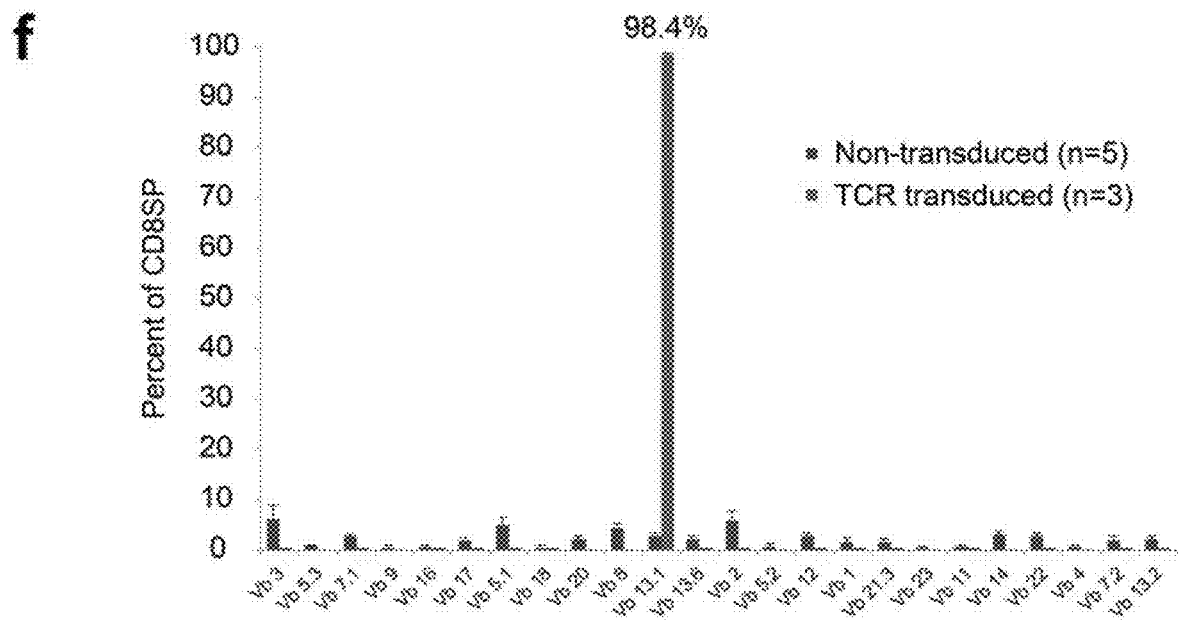
Figure 7G:
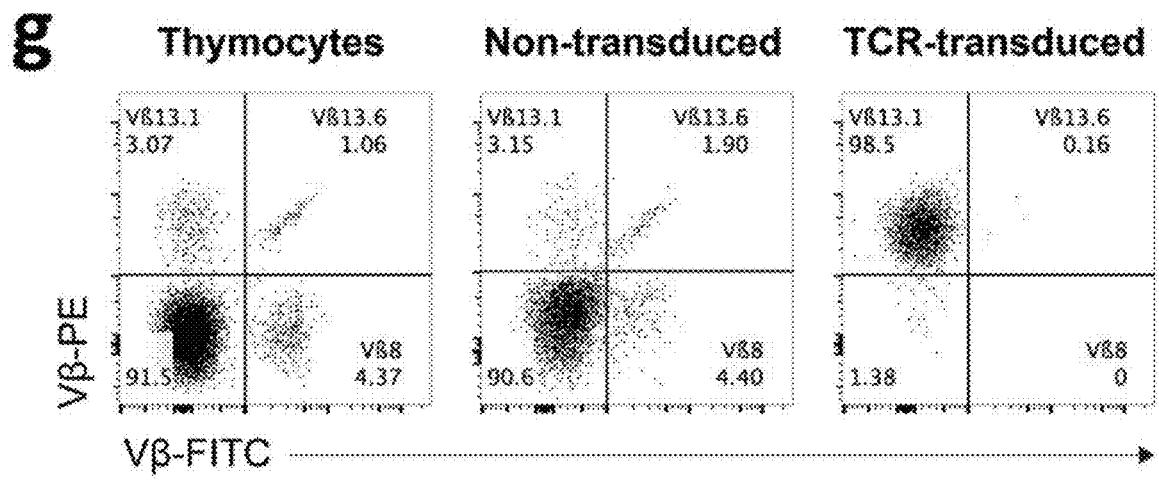

Analysis of Vβ diversity in ATO-derived TCR-engineered T cells revealed over 98% of tetramer+CD8SP T cells expressed only the transduced Vβ13.1 segment (FIG. 7F-G), consistent with near complete allelic exclusion of endogenous TCR expression during differentiation of TCR-engineered T cells. Thus ATOs supported robust differentiation of functional, TCR-engineered T cells from HSPCs, and introduction of a TCR enhanced cell expansion and promoted the differentiation of mature naïve T cells that lack endogenous TCR expression.

6. Enhanced Positive Selection of TCR-Engineered T Cells in MHC-Modified ATOs

Figure 8A:
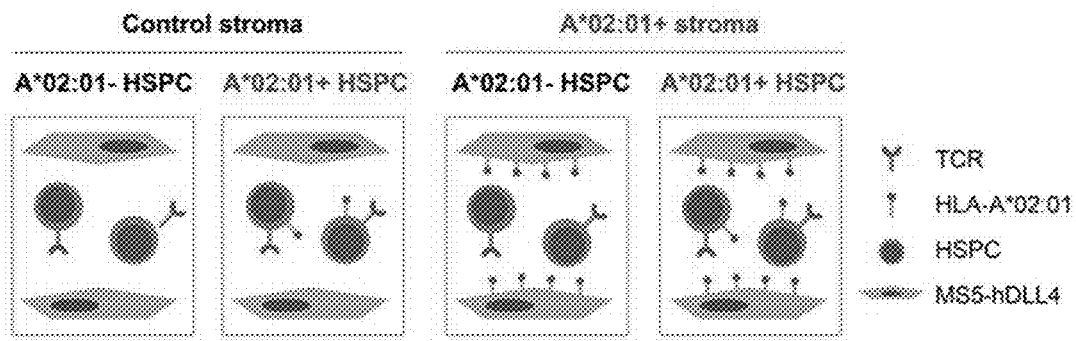
FIG. 8A-C: Enhanced positive selection of TCR-engineered T cells in MHC-modified ATOs. (a) Schematic of approach to modeling hematopoietic and/or stromal "self" MHC expression in ATOs. Hematopoietic HLA-A*02:01 expression was achieved by using HLA-typed donor CB units, and stromal expression was achieved by transduction of MS4-hDLL1 cells with a lentivirus expressing HLA-A*02:01. All HSPCs were transduced with a HLA-A*02:01-restricted NY-ESO-1-specific TCR. (b) Synergistic effects of stromal and hematopoietic "self" MHC expression on the positive selection of tetramer+CD8SP T cells in ATOs. Cells are gated on CD14−CD56−, and sequential subgates are indicated above plots. (c) Enhanced maturation of TCR-engineered T cells to a mature naïve T cell phenotype in ATOs with stromal HLA-A*02:01 expression, as shown by upregulation of CD45RA, CD27, and CCR7, and downregulation of CD45RO and CD1a. All plots are gated on tetramer+CD3+CD8SP T cells.
Figure 8B:
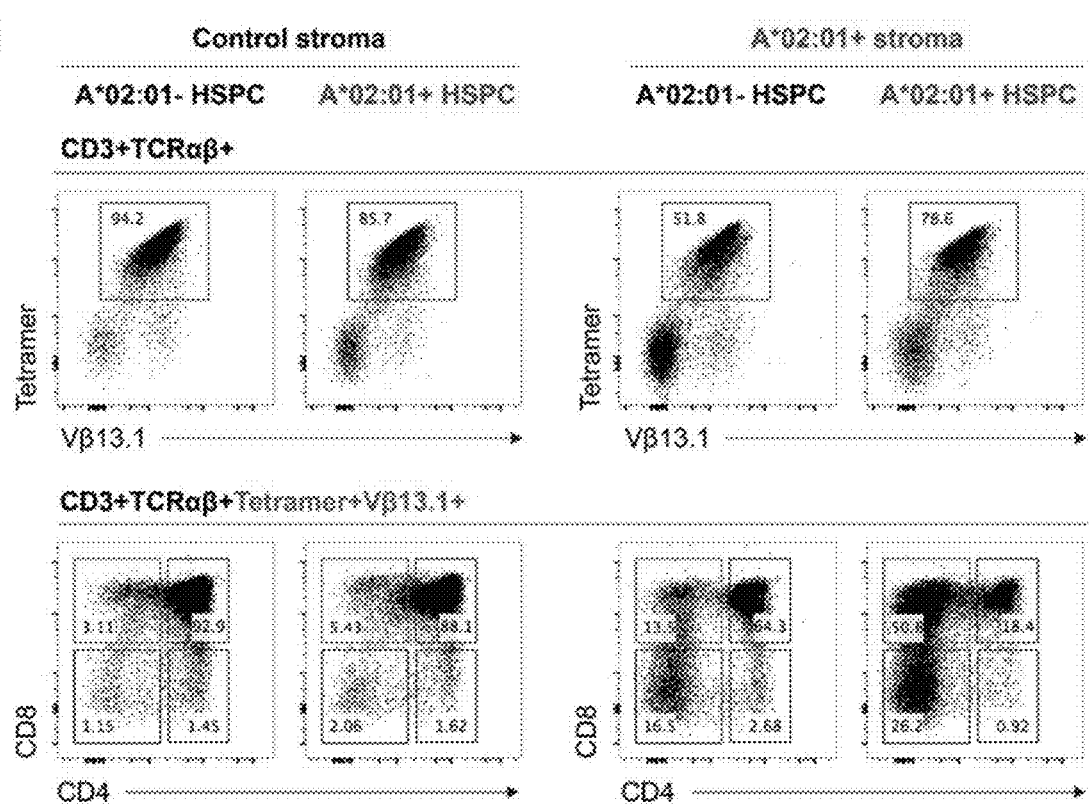
Figure 8C:
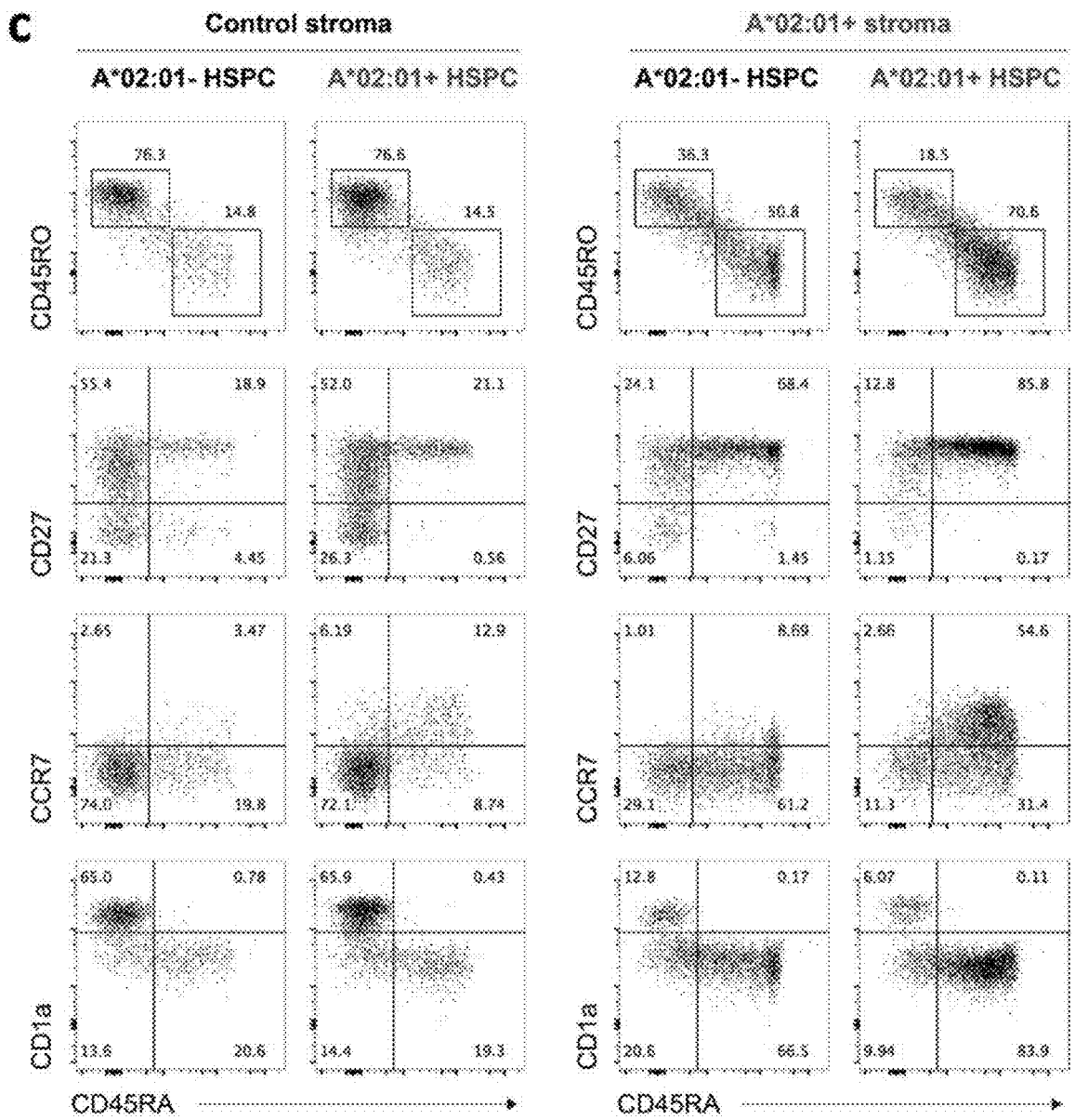

Positive selection in the thymus is mediated by interactions between TCRs on T cell precursors and self-MHC on thymic stroma and hematopoietic cells. Thus, it was investigated whether hematopoietic or stromal expression of "self" MHC in ATOs could enhance positive selection of TCR-engineered T cells. HLA-A*02:01 positive or negative donors were used to test the effect of hematopoietic expression of self MHC on positive selection within ATOs, and stromal cell MHC expression was tested by generating ATOs using MS5-hDLL1 cells transduced with HLA-A*02:01 (FIG. 8A). In all cases, HSPCs were transduced with the HLA-A*02:01-restricted NY-ESO-1-specific TCR, and frequency of tetramer+CD3+CD8SP T cells was used as a readout of positive selection. Hematopoietic expression of HLA-A*02:01 exerted only a modest effect on the positive selection of tetramer+CD8SP T cells (FIG. 8B). In contrast, expression of HLA-A*02:01 in ATO stromal cells markedly enhanced positive selection of tetramer+CD8SP T cells, and was synergistic with donor hematopoietic HLA-02:01 expression (FIG. 8B). TCR-engineered T cells in MHC-modified ATOs also exhibited greater maturation to a mature naïve phenotype, including upregulation of CCR7 (FIG. 8C), consistent with enhanced positive selection. In summary, ATOs comprising TCR-transduced HSPCs and MHC-transduced stromal cells are a versatile system for modeling positive selection of human T cells in vitro, as well as a simple method for enhancing positive selection and maturation of in vitro-derived TCR-engineered T cells for adoptive cell therapy.

B. Comments

The ability to faithfully recapitulate thymopoiesis in vitro creates a unique opportunity for the production of engineered T cells with desirable therapeutic traits, including an antigen naïve state and lack of endogenous TCR expression. As demonstrated here using standardized, off-the-shelf components, the ATO system faithfully recapitulates thymopoiesis from HSPCs, culminating in the production of mature CD3+TCRαβ+CD8SP and CD4SP T cells closely resembling naïve T cells from the thymus or peripheral blood.

ATOs offer distinct biological and translational advantages compared to existing methods of in vitro T cell differentiation, such as the OP9-DL1 system. First, ATOs support positive selection and maturation of human T cells, both of which are impaired in monolayer systems. Enhanced positive selection in ATOs is dependent on 3D structure, as monolayer cultures set up with identical ATO components resulted in inefficient T cell differentiation. This is consistent with support of positive selection, albeit with low efficiency, in FTOCs or reaggregated 3D cultures using thymic components. It is possible that 3D interactions support T cell development by increasing the valence and/or duration of contact between T cell precursors and developmental ligands, such as DLL1, or selective ligands such as self MHC. Alternatively, 3D configuration may facilitate cross-talk between stromal and hematopoietic cells or exert developmental signals on T cell precursors through mechanical forces and/or metabolic changes not otherwise possible in 2D.

Another major advance of the ATO system over existing methods is highly efficient T cell differentiation from clinically relevant adult sources of HSPCs, including bone marrow and resting or mobilized peripheral blood. Studies using the OP9-DL1 system show inefficient development of TCRαβ+ T cells from CB, BM, or MPB16-19, and data for resting peripheral blood HSPCs are not reported. Improved T cell development on OP9-DL1 has been reported with postnatal thymus-derived CD34+ cells, consistent with priming of these progenitor populations by the thymic microenvironment, however human thymi remain an impractical source of HSPCs for therapeutic translation.

The ATO system also offers technical simplicity, reproducibility, and potential scalability. The use of serum-free medium avoids the marked variability observed with fetal calf serum in monolayer systems, and the ability to maintain ATOs intact for the duration of culture (up to 12 weeks) with simple media changes avoids the frequent transfer of cells onto fresh stromal cells, as is required with monolayer systems. The use of off-the-shelf components and specifically the avoidance of primary stromal cells or proprietary scaffold materials, together with the ability to combine ATO production with xeno-free reagents and stromal cell irradiation should facilitate translation of ATOs to a clinical grade platform for generating T cells for adoptive therapy. The simplicity of the system also permits straightforward adoption of the method in laboratories interested in modeling human T cell development and positive selection.

As demonstrated here, the ATO system is a highly efficient method for the in vitro generation of TCR-engineered naïve T cells from HSPCs. Differentiation of TCR-engineered T cells from human HSPCs has been demonstrated in the OP9-DL1 system, however in these cases maturation to CD8SP cells was impaired (typically representing only 0-2% of cultures), with the highest efficiencies achieved using thymus-derived CD34+ cells. In contrast, ATOs supported robust positive selection of TCR-engineered T cells from CB HSPCs, with similar results observed using MPB HSPCs (not shown). The mature naïve T cell phenotype achieved in ATOs may be a distinct advantage of ATO-derived engineered cells over modified peripheral blood T cells, based on studies showing that improved in vivo survival and activity of adoptively transferred T cells is correlated with less activated phenotypes. Enhanced positive selection of engineered T cells in ATOs by expression of cognate MHC in stromal cells provides a further avenue for increasing the quality and yield of ATO-derived engineered T cells.

The presence in ATOs of a transduced TCR throughout T cell differentiation mediated near-complete allelic exclusion of endogenous TCR loci, consistent with in vivo studies with transplanted murine and human HSPCs. The expression of potentially alloreactive endogenous TCRs on engineered peripheral blood T cells is a major barrier to the development of scalable, off-the-shelf adoptive T cell therapies, currently necessitating labor-intensive, individualized production of autologous engineered T cells. Strategies to develop allogeneic engineered T cell therapies include disruption of endogenous TCR/CD3 expression using gene editing tools, or TCR-transduction of virus-specific T cells; however both such approaches require extensive manipulation and expansion of gene-modified T cells, potentially compromising in vivo function. The use of ATOs for the de novo generation of naïve, allelically-excluded engineered T cells thus presents a highly efficient alternative strategy for producing non-alloreactive T cells for adoptive cell therapy.

C. Methods

1. Isolation of Human CD34+CD3− HSPCs

Neonatal cord blood was obtained from discarded placentae from normal deliveries at UCLA. Bone marrow (BM) was obtained from healthy adult donors through discarded material from allogeneic BM donor harvests at UCLA or purchased from AllCells Inc. (Alameda, CA). G-CSF mobilized peripheral blood was obtained from consenting healthy adult donors undergoing apheresis for allogeneic stem cell transplant donation at UCLA. Non-mobilized peripheral blood was obtained from healthy adult donors through the UCLA CFAR Virology Core. All tissue samples were obtained under UCLA IRB-approved protocols or exemptions. All samples were enriched for mononuclear cells by Ficoll-Paque (GE Healthcare Life Sciences, Pittsburgh, PA) gradient centrifugation followed by positive selection of CD34+ cells by magnetic cell sorting (MACS) using the CD34 MicroBead Kit UltraPure (Miltenyi, Auburn CA). CD34+ cell enriched fractions were cryopreserved after MACS, unless otherwise noted. Prior to use, cells were thawed and residual T cells excluded by FACS by sorting CD34+CD3− cells, which were immediately seeded into ATOs or transduced as described below. In some experiments, HSCs were enriched by FACS sorting for Lin-CD34+CD38− cells prior to seeding in ATOs. HLA-typing of HSPCs was performed by the UCLA Immunogenetics Center using high resolution sequence-specific oligonucleotide (SSO) beads.

2. Isolation of Human Bone Marrow Progenitor Subsets

CD34+ HSPCs were enriched from fresh BM aspirates, as above, and immediately sorted by FACS for stem/progenitor populations based on positive expression of CD45 and absent expression of lineage markers (CD3, CD14, CD19, CD56, and CD235a; "Lin-") combined with the following markers: total HSPCs (CD34+), HSC (CD34+CD38−CD45RA), LMPP (CD34+CD38+CD45RA+CD10−CD62Lhi), CD24− CLP (CD34+CD38+CD45RA+CD10+CD24−), and CD24+ CLP (CD34+CD38+CD45RA+CD10 CD24+).

3. Isolation of Human Thymocytes

Postnatal human thymi were obtained under IRB exemption as discarded waste from patients undergoing cardiac surgery at Children's Hospital Los Angeles (CHLA). Thymic fragments were finely minced in RPMI and disrupted by pipetting to release thymocytes into suspension, followed by passage through a 70 μm nylon strainer. Cells were analyzed fresh on the same or following day. Flow cytometry analysis of thymic and ATO-derived T cell progenitors used the following surface phenotypes: Early thymic progenitor (ETP; CD34+CD7−CD1a−), CD1a− pro-T (CD34+CD7+CD1a−), and CD1a+ pro-T (CD34+CD7+CD1a+); or CD5− pro-T (pro-T1; CD34+CD7+CD5−) and CD5+ pro-T (pro-T2; CD34+CD7+CD5+). Thymic and ATO-derived T cells and precursors were defined as CD14−CD56− in combination with the following phenotypes: total T lineage cells (CD7+CD5+), double negative (DN; CD4−CD8−), CD4 immature single positive (CD4ISP; CD5+CD4+CD3), double positive (DP; CD4+CD8+), CD8SP (CD3+TCRαβ+CD8+CD4−), CD4SP (CD3+TCRαβ+CD8−CD4+), immature naïve (CD45RA−CD45RO+ that were CD8SP or CD4SP), mature naïve (CD45RA+CD45RO− that were CD8SP or CD4SP). Immature and mature naïve phenotypes were confirmed by co-staining for CD1a, CD27, CD28, and CCR7.

4. Cell Lines

The MS-5 murine stromal cell line was obtained as a gift. To generate MS5-hDLL1, MS-5 cells were transduced with a lentiviral vector encoding human DLL1 and GFP. The highest 5% GFP-expressing cells were sorted by FACS and passaged in DMEM/10% FCS. Stable expression was confirmed by flow cytometry for GFP expression after several weeks of culture. MS5-hDLL1-A2.1 cells were created by transducing MS5-hDLL1 cells with a human HLA-A*02:01 lentiviral vector (gift from Dr. David Baltimore, Caltech), followed by FACS sorting of transduced cells using an antibody recognizing human HLA-A2 (BB7.2) (Biolegend, San Diego, CA). The OP9-DL1 cell line was a gift from Dr. Juan Carlos Zúñiga-Pflücker (University of Toronto) and was passaged in MEMα (ThermoFisher Scientific, Grand Island, NY)/20% FBS in 0.1% gelatin-coated flasks. The K562 cell line was obtained from ATCC. The K562-CD80/HLA-A*02:01/NY-ESO-1 aAPC cell line was a gift from Dr. Antoni Ribas (UCLA).

5. Artificial Thymic Organoid (ATO) Cultures

MS5-hDLL1 (or MS-5 or OP9-DL1, as noted) cells were harvested by trypsinization and resuspended in serum free ATO culture medium ("RB27") composed of RPMI 1640 (Corning, Manassas, VA), 4% B27 supplement (ThermoFisher Scientific, Grand Island, NY), 30 mM L-ascorbic acid 2-phosphate sesquimagnesium salt hydrate (Sigma-Aldrich, St. Louis, MO) reconstituted in PBS, 1% penicillin/streptomycin (Gemini Bio-Products, West Sacramento, CA), 1% Glutamax (ThermoFisher Scientific, Grand Island, NY), 5 ng/ml rhFLT3L and 5 ng/ml rhIL-7 (Peprotech, Rocky Hill, NJ). RB27 was made fresh weekly. 4% XenoFree B27 was substituted for B27 in the indicated experiments. Depending on the experiment, $1.5-6 \times 10^5$ MS5-hDLL1 cells were combined with $5 \times 10^2 - 1 \times 10^5$ purified CD34+CD3− cells (or other HSPC populations, as indicated) per ATO in 1.5 ml Eppendorf tubes and centrifuged at 300 g for 5 min. at 4° C. in a swinging bucket centrifuge. Supernatants were carefully removed and the cell pellet was resuspended by brief vortexing. For each ATO, a 0.4 μm Millicell transwell insert (EMD Millipore, Billerica, MA; Cat. PICMORG50) was placed in a 6-well plate containing 1 ml RB27 per well. To plate ATOs, inserts were taken out and rested on the edge of plate to drain excess medium. The cell slurry was adjusted to 5-8 μl per ATO, drawn up in with a 20 μl pipet tip and plated by forming a drop at the end of the pipet tip which was gently deposited onto the cell insert. The cell insert was placed back in the well containing 1 mL RB27. Medium was changed completely every 3-4 days by aspiration from around the cell insert followed by replacement with 1 ml with fresh RB27/cytokines. ATOs were cultured in this fashion for up to 12 weeks. At the indicated times, ATO cells were harvested by adding FACS buffer (PBS/0.5% bovine serum album/2 mM EDTA) to each well and briefly disaggregating the ATO by pipetting with a 1 ml "P1000" pipet, followed by passage through a 70 μm nylon strainer. In some experiments, single cell suspensions of MS5-hDLL1 cells were 7-irradiated at the indicated doses prior to use in ATOs.

6. T Cell Monolayer Co-Cultures

OP9-DL1 monolayer cultures were set up as previously described in the art. Briefly, OP9-DL1 were seeded into 0.1% gelatin-coated 12 well plates 1-2 days prior to use to achieve 70-80% confluence. Medium was aspirated from monolayers and $1 \times 10^4 - 1.5 \times 10^4$ purified CD34+CD3− HSPCs were plated on the stromal monolayers in 2 ml of medium composed of MEMα, 20% FBS, 30 mM L-Ascorbic acid, 5 ng/ml rhFLT3L and 5 ng/ml rhIL-7. In some experiments, MS-5 or MS5-hDLL1 were substituted for OP9-DL1, and RB27 was substituted as the culture medium. Cells were transferred to new stromal cell monolayers every 4-5 days by harvesting cells, filtering through a 70 μm nylon strainer, and replating in fresh medium. When confluent, cells were split into multiple wells containing fresh stromal layers. Cultures were maintained for up to 10 weeks.

7. Lentiviral Vectors and Transduction

The full-length coding sequence of human DLL1 was cloned by RT-PCR from a human universal reference RNA set (Agilent Technologies, Santa Clara, CA) into the third generation lentiviral vector pCCL-c-MNDU3-X-IRES-eGFP (gift from Dr. Donald Kohn, UCLA). The HLA-A*02:01 lentiviral vector pHAGE6-HGHSS-HLAA2.1-IRES-Zs-Green was a gift from Dr. David Baltimore (Caltech). The third generation lentiviral vector encoding the α and β chains of a codon-optimized TCR specific for HLA-A*02:01/NY-ESO-1$_{157-165}$ is previously described, and was a gift from Dr. Antoni Ribas (UCLA). Packaging and concentration of lentiviral particles was performed as previously described. Briefly, 293T cells (ATCC) were co-transfected with a lentiviral vector plasmid, pCMV-AR8.9, and pCAGGS-VSVG using TransIT 293T (Mirus Bio, Madison, WI) for 17 hours followed by treatment with 20 mM sodium butyrate for 8 hours, followed by generation of cell supernatants in serum-free UltraCulture for 48 hours. Supernatants were concentrated by tangential flow filtration using Amicon Ultra-15 100K filters (EMD Millipore, Billerica, MA) per the manufacturer's protocol, and stored at −80 C. For HSPC transduction, $1 \times 10^5 - 1 \times 10^6$ FACS-sorted CD34+CD3− HSPCs were plated in 6-well non-treated plates coated with 20 μg/ml Retronectin (Clontech, Mountain View, CA) in 1 ml X-VIVO-15 (Lonza, Basel, Switzerland) supplemented with 50 ng/ml of recombinant human SCF, FLT3L, and TPO, and 10 ng/ml IL-3 (Peprotech, Rocky Hill, NJ) for 12-18 h, after which concentrated lentiviral supernatant was added at a multiplicity of infection (MOI) of 100. Mock transduced cells were cultured in identical conditions but without addition of vector. Cells were harvested 24 hours post-transduction, washed, and seeded into ATOs. TCR-transduced HSPCs were from HLA-A*02:01+ CB units unless indicated.

8. Immunohistochemistry

For hematoxylin and eosin (H&E) images, ATOs were embedded in Histogel (ThermoFisher Scientific, Grand Island, NY) and fixed overnight in 10% neutral-buffered formalin (ThermoFisher Scientific, Grand Island, NY). 5 μm sections and H&E staining were performed by the UCLA Translational Pathology Core Laboratory (TPCL). For immunofluorescence imaging, ATOs were isolated by cutting the culture insert around each ATO with a scalpel, followed by embedding the membrane and ATO in Tissue-Tek OCT (VWR Radnor, PA) and freezing on dry ice. 5 μm frozen sections were fixed in 10% neutral-buffered formalin and stained with anti-CD3 (clone UCHT1; Biolegend, San Diego, CA) at a 1:50 dilution overnight at 4° C. followed by incubation with AlexaFluor 594-conjugated anti-mouse IgG (H+L) (Jackson ImmunoResearch, West Grove, PA) at room temperature. H&E and immunofluorescence images were acquired on a Zeiss AzioImager M2 with AxioCam MRM and AxioVision software (Zeiss, Jena, Germany).

9. Intracellular Cytokine Staining

CD8SP, CD4SP, or DP cells from ATOs were sorted by FACS using anti-CD8 and anti-CD4 antibodies and plated in 96-well U-bottom plates in 200 μl AIM V (ThermoFisher Scientific, Grand Island, NY) with 5% heat-inactivated human AB serum (Gemini Bio-Products, West Sacramento, CA). PMA/ionomycin/protein transport inhibitor cocktail or control protein transport inhibitor cocktail (both from eBioscience, San Diego, CA) were added to each well and incubated for overnight. Cells were stained for CD3, CD4, and CD8 (Biolegend, San Diego, CA) and UV455 fixable viability dye (eBioscience, San Diego, CA) prior to fixation and permeabilization with an intracellular staining buffer kit (eBioscience, San Diego, CA) and cytokine staining with antibodies against IFNγ and IL-4 (Biolegend, San Diego, CA).

10. T Cell Activation and Proliferation Assays

For CFSE proliferation assays, ATO-derived CD8SP T cells were sorted by FACS and labeled with 5 μM CFSE (Biolegend, San Diego, CA) per the manufacturer's protocol. Labeled cells were incubated with anti-CD3/CD28 beads (ThermoFisher Scientific, Grand Island, NY) in AIM V supplemented with 5% AB serum and 20 ng/ml rhIL-2 (Peprotech, Rocky Hill, NJ) or IL-2 alone, costained for CD25 (Biolegend, San Diego, CA) and analyzed by flow cytometry on day 5. For in vitro cell expansion assays, $1 \times 10^4$ FACS sorted, ATO-derived CD8SP T cells were plated in 96-well U-bottom plates in 200 μl Immunocult XF medium (Stem Cell Technologies, Vancouver, BC, Canada) supplemented with 20 ng/ml rhIL-2 and 1× anti-CD3/CD28 tetrameric antibody complex (Stem Cell Technologies, Vancouver, BC, Canada). Fresh medium and cytokines were added every 2-3 days with replating into larger wells as needed. Fresh anti-CD3/CD28 was added on day 7 and 14. Cells were counted weekly with a hemacytometer.

11. Artificial APC (aAPC) CTL Priming Assay $5 \times 10^4$ total ATO-derived CD8SP T cells were sorted from week 6 TCR-transduced ATOs and co-cultured with K562-based aAPCs expressing CD80 and a HLA-A*02:01/B2M/NY-ESO-$1_{157-165}$ single chain trimer (gift from Dr. Antoni Ribas, UCLA) or parental K562 cells in 96-well U-bottom plates in 200 μl AIM V/5% human AB serum at a 5:1 T cell:K562 ratio overnight. CD170a-APC antibody (Biolegend, San Diego, CA) was added to wells at a 1:50 final dilution together with a protein transport inhibitor cocktail (eBioscience, San Diego, CA) for the final 4 hours of culture, followed by fixation, permeabilization, and intracellular cytokine staining as described above.

12. TCR Vβ Analysis

Total cells from week 7 ATOs or postnatal thymi were stained for CD3, CD4, CD8, and TCRγδ, in conjunction with the IOTest Beta Mark TCR V Kit (Beckman Coulter, Indianapolis, IN). CD3+TCRgd–CD8+CD4– cells were gated for Vβ analysis. For TCR-transduced ATOs, week 6 total ATO cells were also labeled with an APC-conjugated HLA-A*02:01/NY-ESO-$1_{157-165}$ tetramer (MBL International, Woburn, MA), and gated on CD3+TCRγδ-tetramer+ CD8+CD4– for Vβ analysis.

13. Flow Cytometry and Antibodies

All flow cytometry stains were performed in PBS/0.5% BSA/2 mM EDTA for 30 min on ice. FcX (Biolegend, San Diego, CA) was added to all samples for 5 min prior to antibody staining. For tetramer co-staining, PE or APC-conjugated tetramers (MBL International, Woburn, MA) were added to cells at a 1:50 final dilution at room temperature for 10 minutes prior to addition of antibodies for an additional 20 minutes on ice. DAPI was added to all samples prior to analysis. Analysis was performed on an LSRII Fortessa, and FACS on an ARIA or ARIA-H instrument (BD Biosciences, San Jose, CA) at the UCLA Broad Stem Cell Research Center Flow Cytometry Core. For all analyses DAPI+ cells were gated out, and single cells were gated based on FSC-H vs. FSC—W and SSC-H vs. SSC-W profiles. Antibody clones used for surface and intracellular staining were obtained from Biolegend (San Diego, CA): CD1a (H1149), CD3 (UCHT1), CD4 (RPA-T4), CD5 (UCHT2), CD8 (RPA-T8), CD10 (6H6), CD14 (M5E2), CD19 (HIB19), CD24 (ML5), CD25 (BC96), CD27 (0323), CD28 (CD28.2), CD31 (WM59), CD34 (581), CD38 (HIT2), CD45 (H1I30), CD45RA (HI100), CD45RO (UCHL1), CD56 (HCD56), CD107a (H4A3), CD127 (A019D5), CD235a (H1I264), CCR7 (G043H7), HLA-A2 (BB7.2), interferon γ (4S.B3), IL-4 (MP4-25D2), TCRαβ (IP26), TCRγδ (B1), Vβ13.1 (H131), human lineage cocktail (CD3, CD14, CD19, CD20, CD56); or BD Biosciences (San Jose, CA): CD7 (M-T701), and CD62L (DREG-56).

Example 3: Artificial Thymic Organoids Induce Positive Selection and Allelic Exclusion of TCR-Engineered T Cells from Human Hematopoietic Stem Cells Engineered T cell therapies offer unprecedented opportunities for the treatment of cancer and chronic viral infections. The ability to generate engineered T cells directly from hematopoietic stem and progenitor cells (HSPC) has the potential to overcome key therapeutic limitations associated with the use of peripheral blood T cells, including alloreactivity. This example describes a clinically relevant artificial thymic organoid (ATO) system that supports highly efficient in vitro differentiation and positive selection of native and TCR-engineered human T cells from cord blood, bone marrow, and peripheral blood HSPCs. ATO-derived T cells exhibited a naïve phenotype, diverse TCR repertoire, and TCR-dependent activation and proliferation. ATO-derived TCR-engineered T cells also matured to a naïve phenotype and furthermore showed antigen specific tumor killing in vitro and in vivo, and near complete lack of endogenous TCR Vβ expression, consistent with induction of allelic exclusion. ATOs thus present an efficient method for the generation of naïve and potentially non-alloreactive engineered T cells for adoptive cell therapy.

Adoptive cell therapy using T cells engineered to express antigen-specific T cell receptors (TCR) offers a targeted and potentially curative treatment for malignancies and chronic viral infections. Current strategies rely on the genetic modification and ex vivo expansion of mature circulating T cells. These approaches pose several therapeutic limitations including limited in vivo activity after re-infusion; and mispairing between transduced and endogenous TCR chains, with the potential for reduced antigen-specific reactivity or induction of autoimmunity. Furthermore, alloreactivity imparted by endogenous TCR expression has restricted most approaches to the use of autologous T cells, which may ultimately limit access to therapy through increased cost, limited production capacity, and patient ineligibility in the setting of lymphopenia. In vitro generation of engineered T cells from hematopoietic stem and progenitor cells (HSPC) has the potential to solve these problems by simultaneously permitting the de novo generation of naïve antigen specific T cells and the suppression of endogenous TCR expression through allelic exclusion.

Owing to the spatiotemporal complexity of T cell development in the thymus, methods of in vitro T cell differentiation have thus far been unable to fully recapitulate human T cell development. A major advance in such methods was the discovery that murine stromal cell lines transduced with a Notch ligand could support in vitro T cell differentiation from murine or human HSPCs, as demonstrated in the classic OP9-DL1 co-culture system. In this and similar monolayer systems, human HSPCs undergo T lineage commitment and early T cell differentiation. However, positive selection of T cell precursors with productively rearranged TCRs is impaired, and minimal maturation to CD8+ or CD4+ single positive (SP) T cells is seen. The inventors have shown that three-dimensional (3D) organoid systems using murine or human thymic tissue supports improved positive selection and maturation of human T cells in vitro. However these systems are not suitable for the generation of T cells for therapeutic applications due to low cell output, high experimental variability, and dependence on primary thymic tissue. The inventors therefore pursued the development of an artificial organoid system able to support the differentiation and positive selection of human T cells from HSPC while retaining key translational properties such as standardized components, reproducibility, and scalability.

This example shows the development of an artificial thymic organoid (ATO) system based on a DLL1-transduced stromal cell line and serum-free, off-the-shelf components. In contrast to monolayer systems, ATOs supported robust in vitro differentiation, positive selection, and maturation of human CD3+TCRαβ+CD8SP and CD4SP T cells from human cord blood, bone marrow, and peripheral blood CD34+ HSPCs. ATO-derived mature T cells exhibited an antigen naïve phenotype, diverse TCR repertoire, and activation/proliferation in response to antigenic stimuli. ATOs also supported highly efficient differentiation of TCR-engineered antigen-specific T cells from HSPCs transduced with a HLA-A*02:01-restricted TCR specific for the tumor-associated antigen NY-ESO-1. Positive selection of TCR-engineered T cells was further enhanced by the expression of cognate major histocompatibility complex (MHC) in ATO stromal cells. ATO-derived TCR-engineered T cells exhibited a naïve phenotype and underwent antigen specific activation with robust tumor-killing in vitro and in vivo. Finally, TCR-engineered T cells generated in ATOs exhibited a near complete lack of endogenous Vβ TCR expression, consistent with the induction of allelic exclusion during development, and suggesting a direct and efficient approach to generating non-alloreactive engineered T cells for adoptive cell therapy.

I. Results

A. Development of an Optimized Artificial Thymic Organoid System for In Vitro Human T Cell Differentiation A goal was to develop a clinically translatable organoid system that could support in vitro positive selection and maturation of human T cells from HSPCs. To avoid the use of primary thymic tissue, the inventors tested DLL1-transduced stromal cell lines for the ability to support human T cell development in 3D organoid cultures. It was observed that T cell differentiation in the OP9-DL1 system is highly variable, depending on specific lots of fetal calf serum, and the inventors sought to identify serum-free conditions capable of consistently supporting T cell differentiation in organoid cultures. To avoid the use of proprietary scaffold materials, a compaction reaggregation technique shown to be effective in thymic tissue-based organoids was used, in which stromal cells are aggregated with HSPCs by centrifugation and deployed on cell culture inserts at an air-fluid interface (FIG. 3A). In these 3D cultures, the inventors identified the MS-5 murine bone marrow stromal cell line transduced with human DLL1 (MS5-hDLL1, hereafter) as strongly supportive of human T cell differentiation from T cell depleted CD34+ cord blood (CB) HSPCs. Furthermore, the inventors identified RPMI supplemented with B27, a multi-component additive used in neuronal and embryonic stem cell cultures, and FLT3L, IL-7, and ascorbic acid ("RB27", hereafter) as a novel serum-free medium that consistently supported robust human T cell differentiation in MS5-hDLL1 organoid cultures.

Figure 14A:
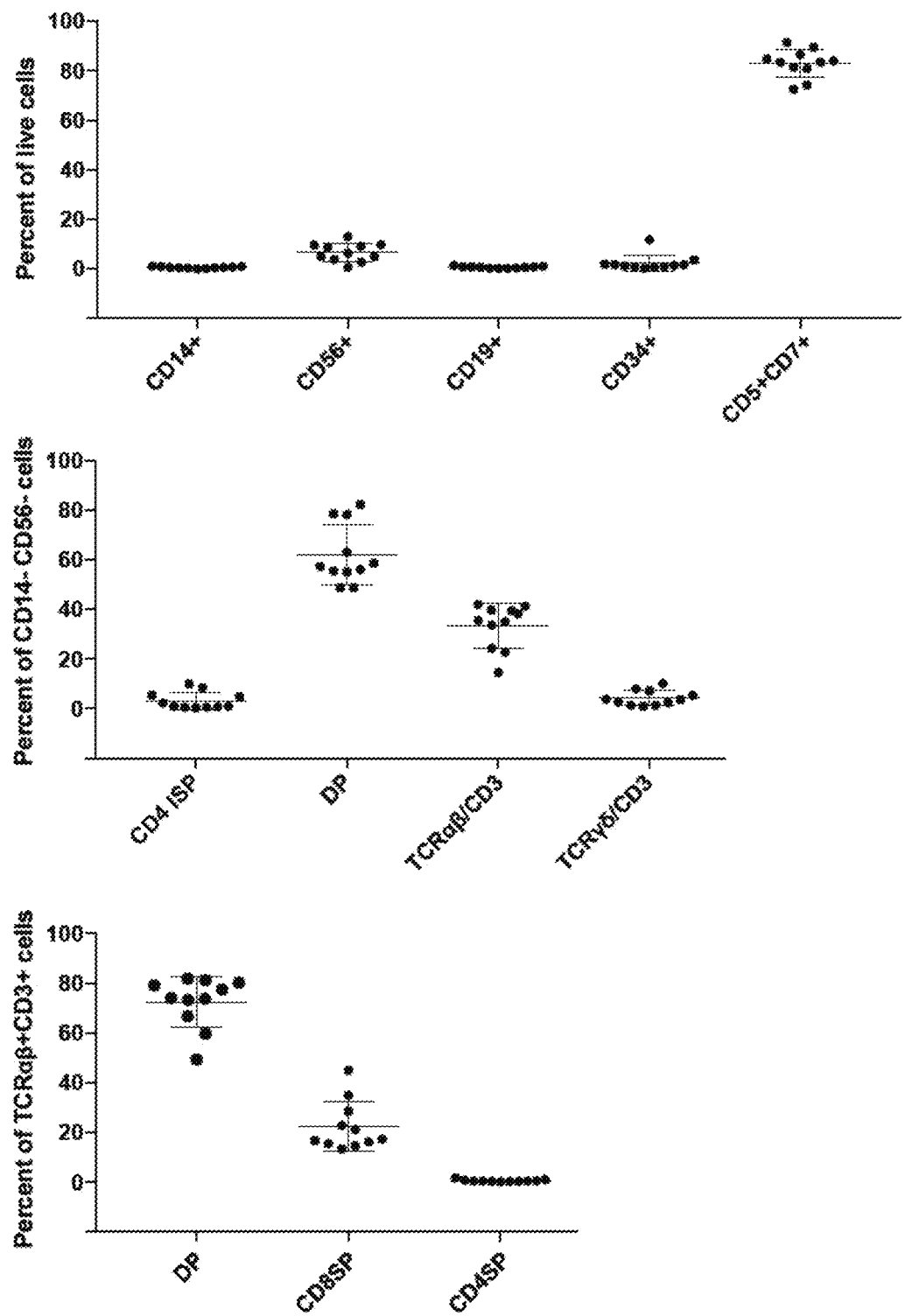
FIG. 14A-B: Efficiency and reproducibility of human T cell development in the ATO System. (a) Frequencies of cell types in ATOs at 6 weeks. Top panel: frequencies of monocytes (CD14+), NK cells (CD56+), B cells (CD19+), HSPCs (CD34+), or T lineage cell (CD7+CD5+) (gated on total live cells). Middle panel: T cell precursor and TCR+ T cell frequencies (gated on CD14−CD56− cells). Bottom panel: frequency of DP and mature CD8 and CD4 single positive (SP) T cells (gated on CD3+TCRαβ+ cells). (b) Total cell numbers and CD3+TCRαβ+CD8SP T cells generated per ATO at week 6 from 7.5-22.5×10³ CB HSPCs per ATO. Data are shown for 11 biological replicates (error bars indicate standard deviation).

This optimized artificial thymic organoid (ATO) system induced rapid and robust T lineage commitment from CB CD34+CD3− HSPCs, as shown by a predominance of CD5+CD7+ cells and appearance of CD4+CD3− immature single positive (ISP) cells and CD4+CD8+ (DP) cells by week 2 (FIG. 3B). More mature CD3+TCRαβ+ cells emerged as early as week 4, and increased over time, reaching an average of ~30% of cells at week 6 (FIG. 3B, 14A). A smaller fraction of CD3+TCRγδ+ T cells was also generated (FIG. 14A). CD3+TCRαβ+ cells were predominantly DP at early timepoints (FIG. 14A) but progressively matured to CD8SP and, to a lesser extent, CD4SP T cells, consistent with positive selection in ATOs.

CD34+ progenitor cells remained detectable in ATOs at all time points studied, and at 6 weeks still included all three phenotypic stages of thymic T cell progenitors: multipotent CD34+CD7−CD1a− early thymic progenitors (ETP) and developmentally downstream CD34+CD7+CD1a− and CD34+CD7+CD1a+ T-lineage progenitors (FIG. 3C). Pro-T1 and pro-T2 progenitor phenotypes were also identified within the CD34+ fraction based on an alternative classification scheme (FIG. 3C). CD19+ B cell frequency decreased over time, and NK and myeloid frequencies were low throughout (FIG. 3B, 14A). Histological sections of ATOs demonstrated a dense, tissue-like architecture with abundant lymphoid cells (FIG. 19), clusters of which were positive for CD3 (FIG. 3D).

Figure 14B:
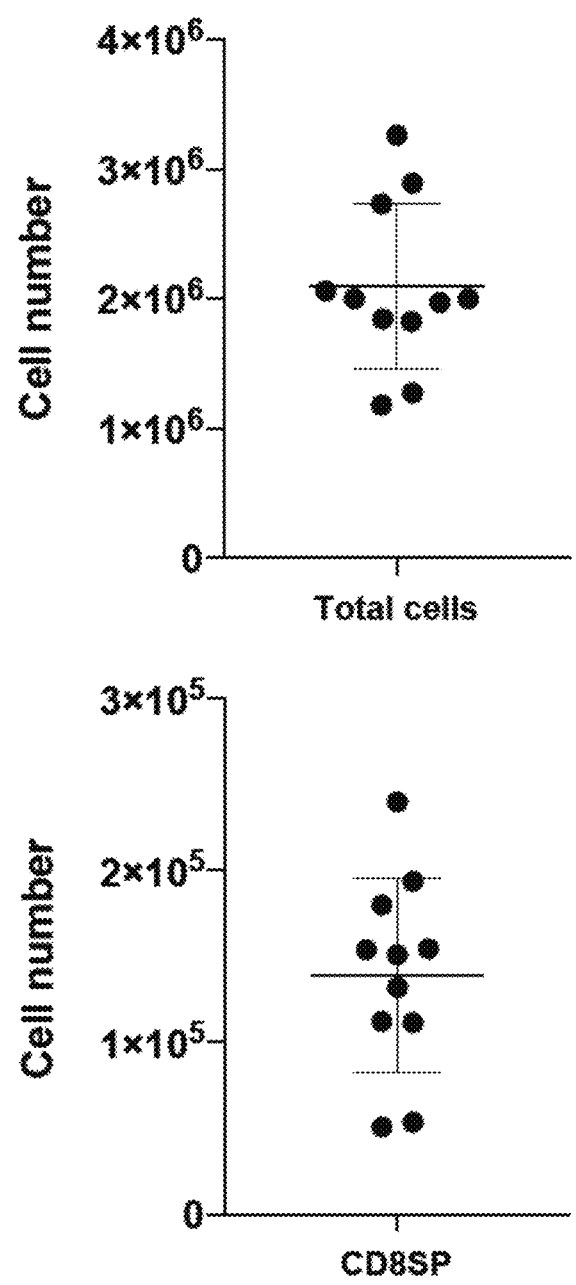
Figure 20A:
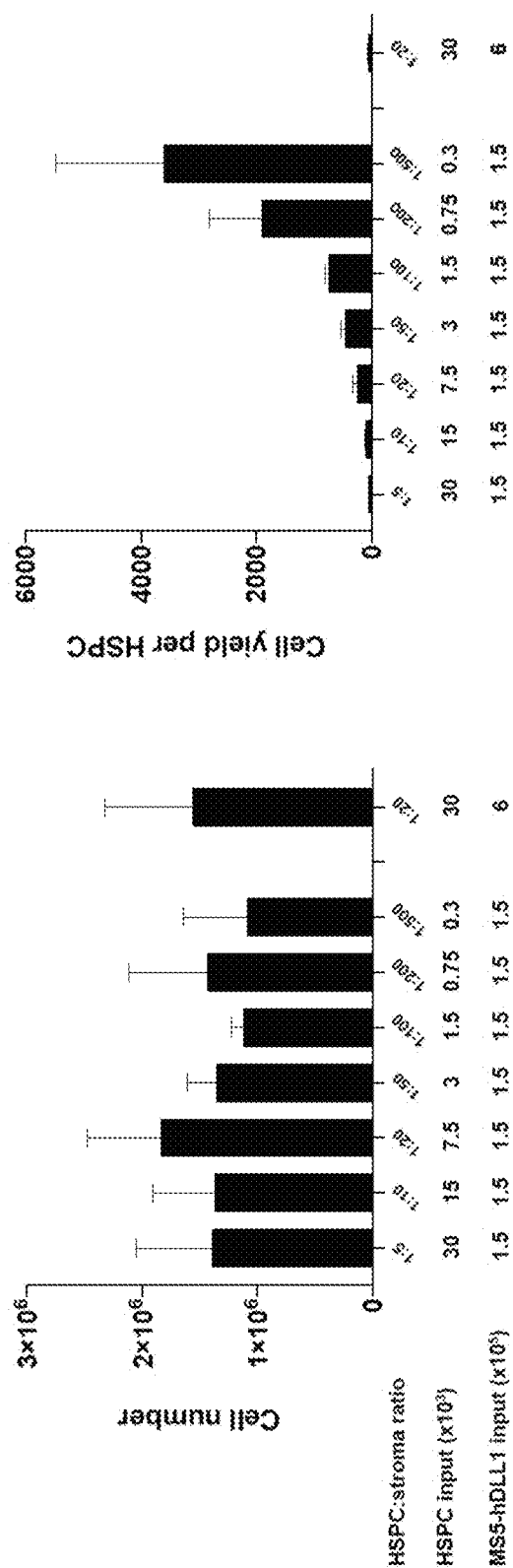
FIG. 20A-B: The starting number of HSPCs per ATO affects cell yield per HSPC, but not total cell output or T cell differentiation. (a) Total cell number and yield per input HSPC in week 6 ATOs generated with varying numbers of CD34+CD3− CB HSPCs (0.3-30×10³ per ATO) and a constant number of MS5-hDLL1 stromal cells (1.5×10⁵ per ATO). Comparison is shown at right with larger ATOs (using 30×10³ HSPC and 6×10⁵ stromal cells, at a ratio of 1:20). (b) T cell precursor and mature T cell frequencies in ATOs as described in (a). Mean and SD of triplicate ATOs are shown. Data are representative of two biological replicates.
Figure 20B:
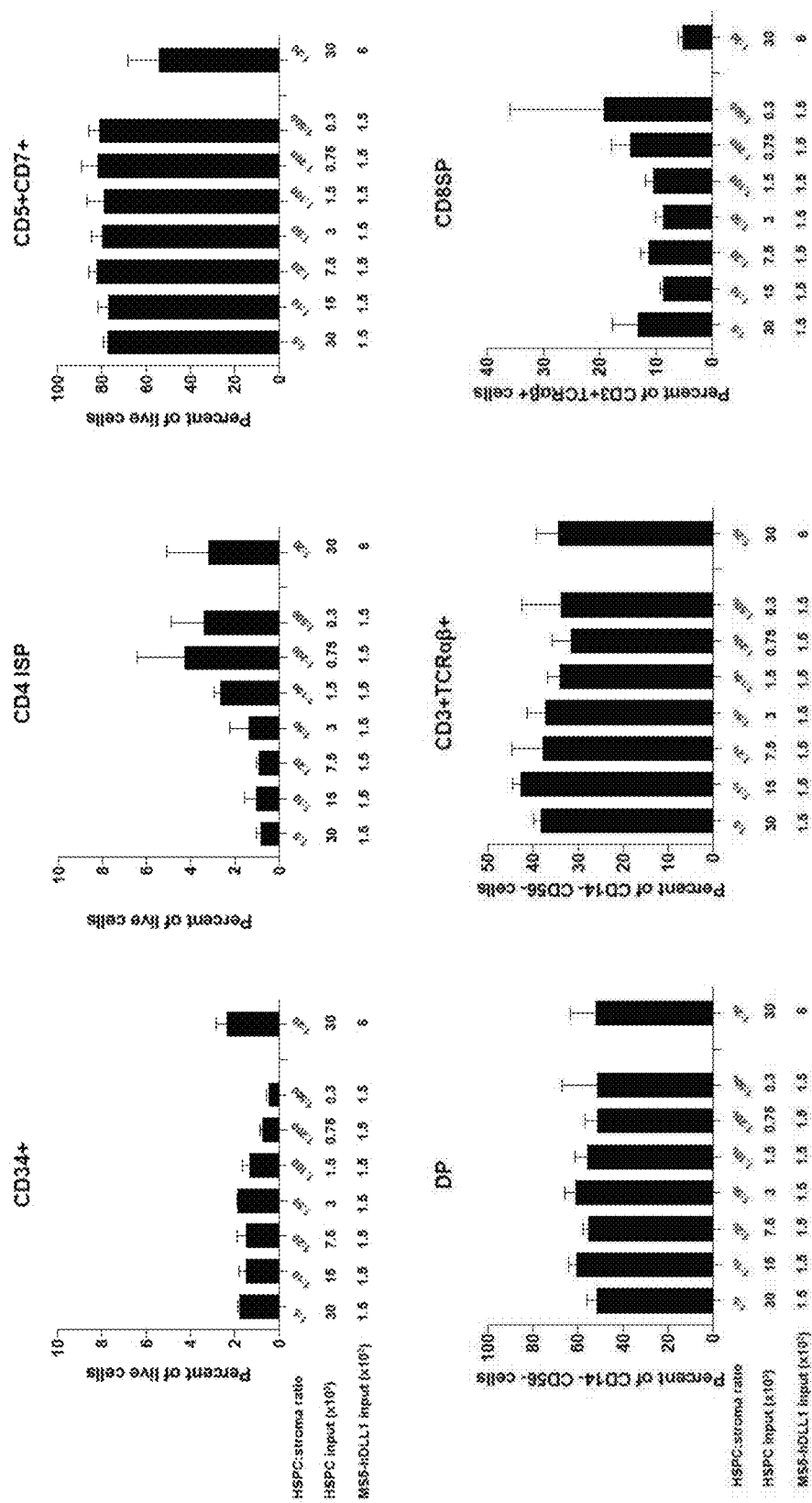
Figure 21F:
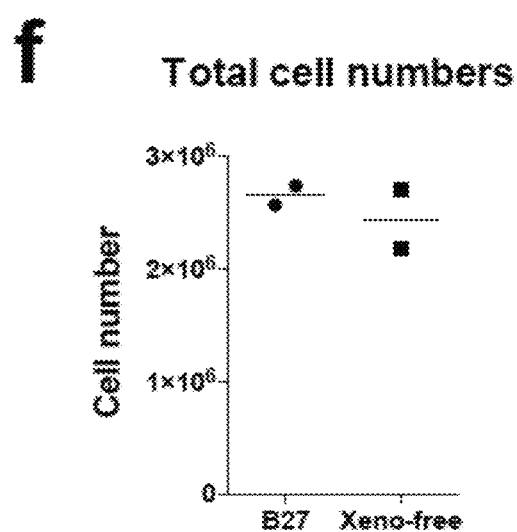
Figure 21G:
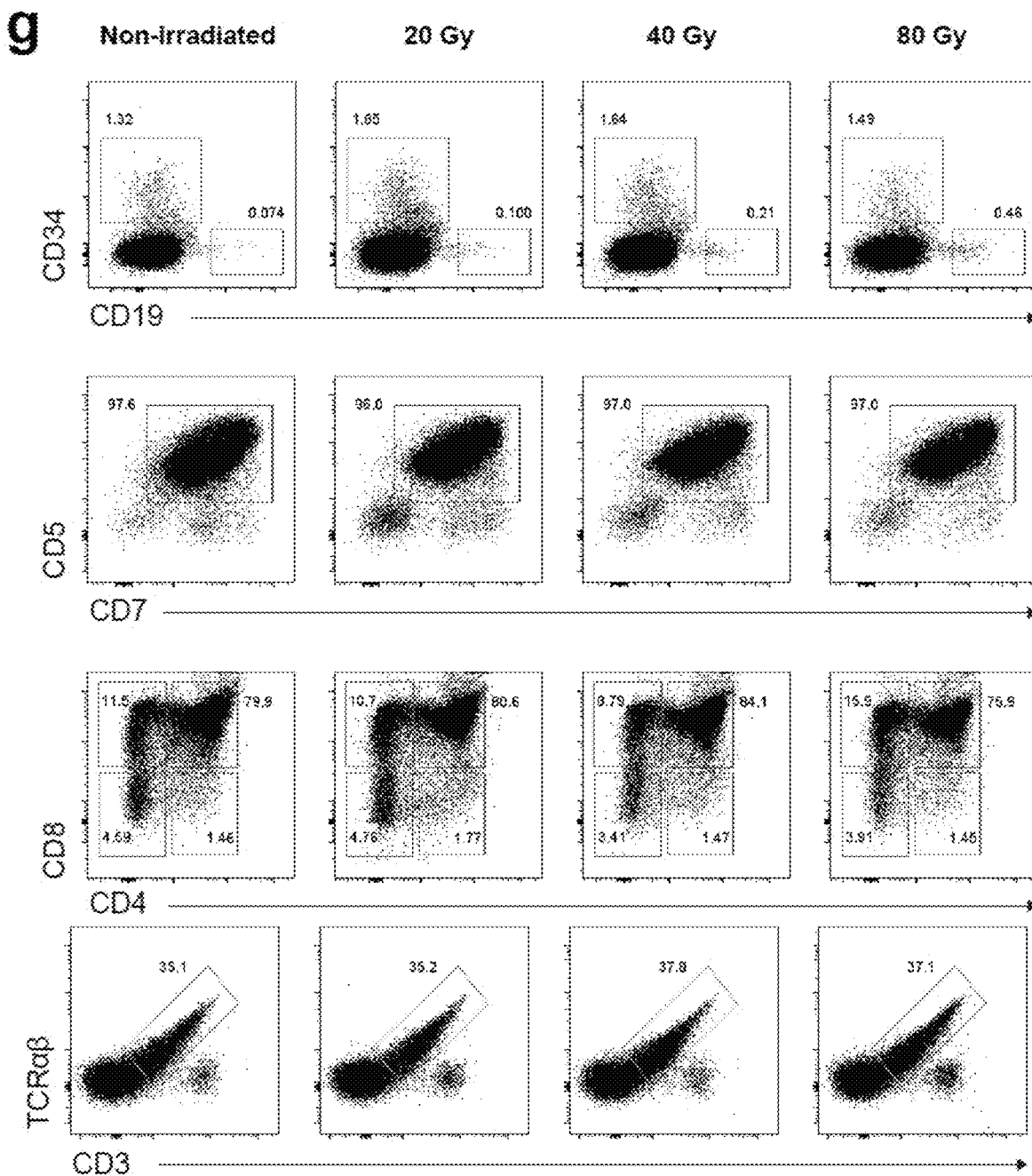
Figure 21H:
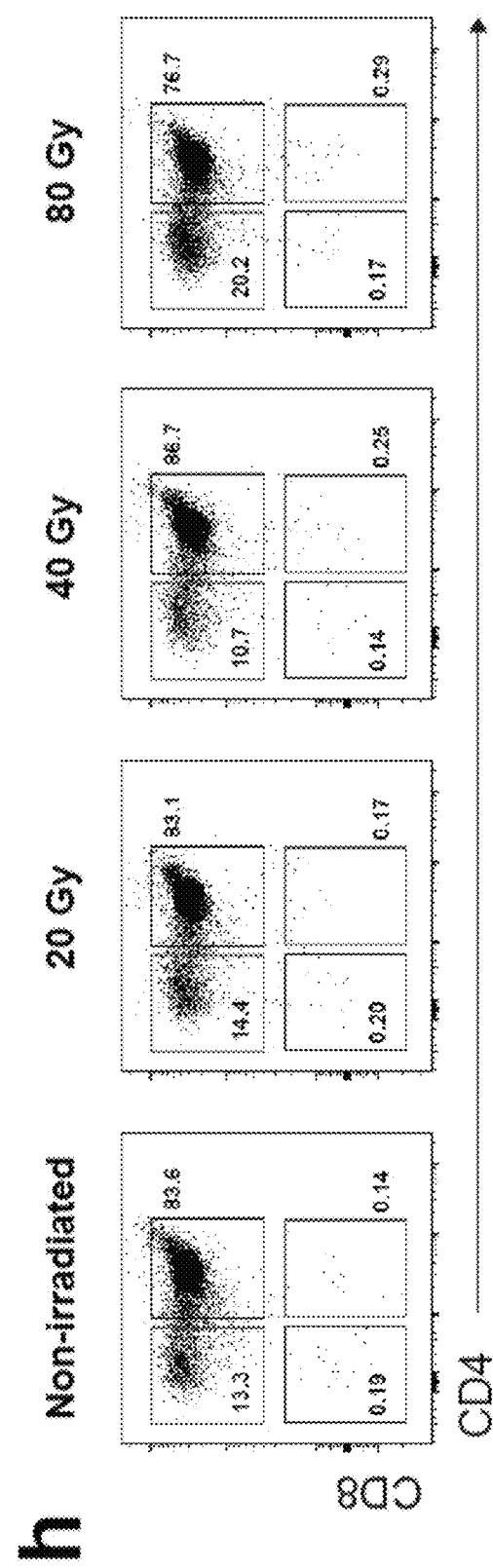
Figure 21I:
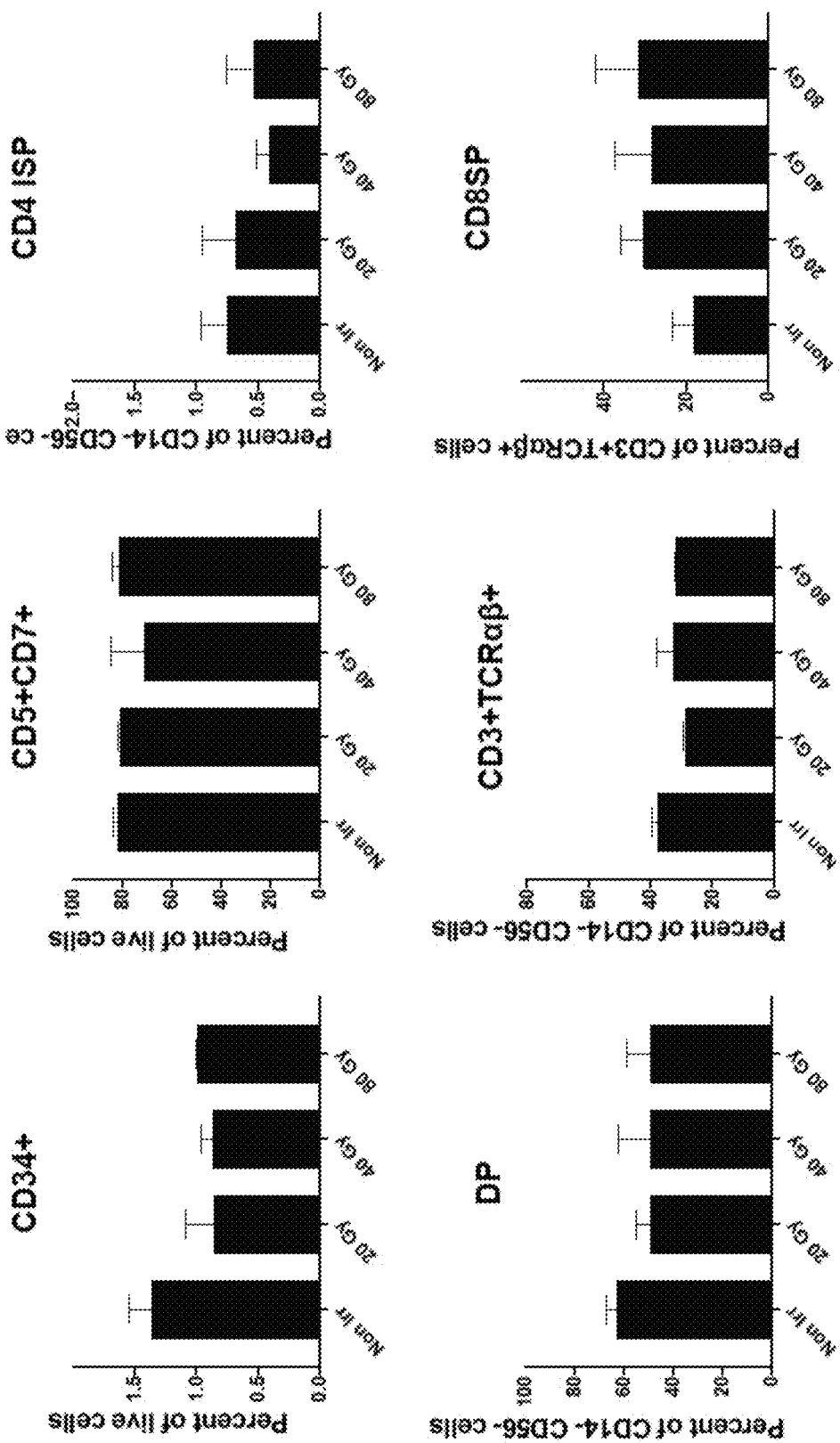

Each ATO typically generated ~2×10$^6$ total cells at 6 weeks (FIG. 14B); however ATO cell yield per HSPC was inversely related to the number of HSPCs seeded and the ratio of HSPCs to stromal cells, with a yield of 4-5,000 cells per HSPC generated at the lowest ratios (FIG. 20A). Frequencies of precursor and mature T cells in ATOs was similar across initial HSPC numbers and ratios (FIG. 20B), with the exception of ATOs generated with large numbers of stromal cells (6×10$^5$ per ATO), which showed impaired mature T cell development. Thus, smaller ATOs with an optimal HSPC to stromal cell ratio of 1:20 (typically 7500 HSPCs:6×10$^5$ stromal cells per ATO) were used for further experiments. High reproducibility of both cell output and T cell differentiation was observed across technical replicates (n=11) and four different lots of B27 (FIG. 21A-D). Of translational relevance, comparable T cell differentiation and cell output was also seen in ATOs using medium supplemented with xeno-free B27 (containing human serum albumin) (FIG. 21E-F) or containing irradiated stromal cells (FIG. 21G-J). Recovery of hematopoietic cells generated in ATOs was achieved by simple mechanical disruption and collection of cells suspension, which resulted in >99% CD45+ hematopoietic cells and <0.5% stromal cells (FIG. 21K).

Figure 22:
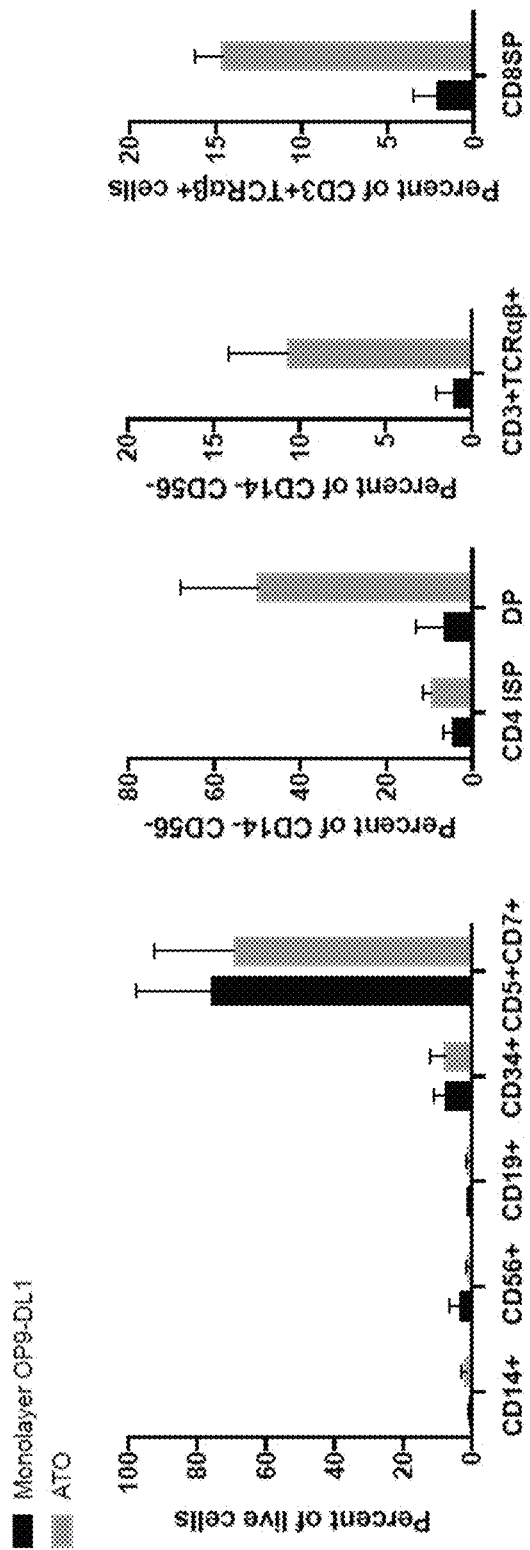
FIG. 22: Enhanced positive selection in ATO versus monolayer culture systems. Frequencies of monocytes (CD14+), NK cells (CD56+), B cells (CD19+), HSPCs (CD34+), or T lineage cell (CD7+CD5+), and T cell precursor and T frequencies cell types in OP9-DL1 monolayer cultures versus ATOs at 6 weeks (sequential gates are indicated on each graph). Cultures were initiated using the same CB unit for monolayer and ATO cultures. Data are representative of three biological replicates.

When compared with the OP9-DL1 monolayer culture system using same-donor CB HSPCs, ATOs revealed markedly superior generation of CD3+TCRαβ+ T cells (FIG. 11A, 22). Consistent with previous reports, OP9-DL1 monolayers supported efficient T-lineage commitment (CD7+ CD5+) and progression through the ETP, pro-T and CD4 ISP stages, but inefficient generation of DP, CD3+TCRαβ+, and mature SP cells, all of which readily developed in ATOs (FIG. 11A, 22). Indeed, optimal positive selection and maturation required all three components of the ATO system: 3D structure, MS5-hDLL1 stromal cells, and RB27 medium (FIG. 11A), as OP9-DL1 survived poorly in RB27 and showed poor support of T cell differentiation in 3D cultures. The parental MS-5 cell line lacking DLL1 expression did not support T cell development in either monolayer or 3D cultures (FIG. 11A).

In summary, ATOs provide a standardized, serum-free 3D system that supports robust and reproducible T cell differentiation from CD34+ HSPCs, permitting positive selection and maturation of human TCRαβ+ T cells.

B. Recapitulation of Thymic Naïve T Cell Development in ATOs

T cell differentiation in ATOs was next compared to that in the postnatal human thymus. Week 12 CB ATOs showed a similar frequency of T-lineage committed (CD5+CD7+) and CD34+ progenitors to the thymus (FIG. 4A). As in the thymus, the majority of CD3+ T cells in ATOs were TCRαβ+, but a readily detectable TCRγδ+ population was also consistently seen (FIG. 4A). Among ATO-derived CD3+TCRαβ+ cells, generation of mature CD8SP and CD4SP T cells increased between weeks 6-12 (FIG. 4B, and FIG. 12A-C). In contrast to the thymus, ATOs exhibited proportionately fewer CD4SP T cells relative to CD8SP T cells.

As in the thymus, ATO-derived CD3+TCRαβ+CD8SP and CD3+TCRαβ+CD4SP T cells transited from an "immature naïve" (CD45RA−CD45RO+CD27+CCR7−CD1Ahi) to a "mature naïve" (CD45RA+CD45RO−CD27+CCR7+CD1alo) phenotype (FIG. 4C, 12A-C). In ATOs this occurred between weeks 6-12, and resulted in a higher frequency of mature naïve T cells by week 12 ATOs than in the thymus (FIG. 4C, 12B-C). Both immature and mature naïve subsets co-expressed CD62L and CD28, with subset co-expression of CD127 and CD31, the latter marker associated with recent thymic emigrant T cells in the blood (FIG. 12B-C). The activation marker CD25 was not expressed on ATO-derived CD8SP T cells, but was observed on a subset of CD4SP T cells (FIG. 12B-C). Taken together, these data show remarkable fidelity of T cell differentiation in ATOs compared to the human thymus, culminating in the emergence of bona fide naïve T cells similar to those found in the thymus and blood.

Figure 23A:
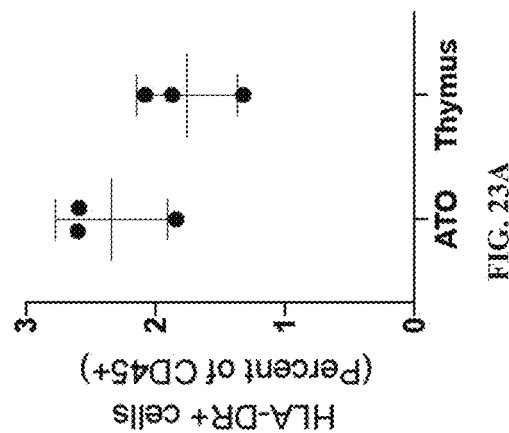
FIG. 23A-B: Recapitulation of thymopoiesis and naïve T cell phenotype in ATOs. (a) Frequency of HLA-DR+ cells in CB ATOs compared with postnatal thymi (gated on CD45+ cells). (b) Multiple HLA-DR+ antigen presenting cell (APC) populations are present in week 6 ATOs. Sequential gates are shown above each plot. HLA-DR+ populations include monocytes (CD14+), granulocytes (CD66b+), B cells (CD19+), HSPCs (CD34+), plasmacytoid DC (CD303+CD123+), CLEC9A+DC (CD141+CLEC9A+), and CD1c+ DC (CD1c+CLEC9A−). Paired analysis from a postnatal thymus is shown for comparison. Data in (a) and (b) are representative of three biological replicates.
Figure 23B:
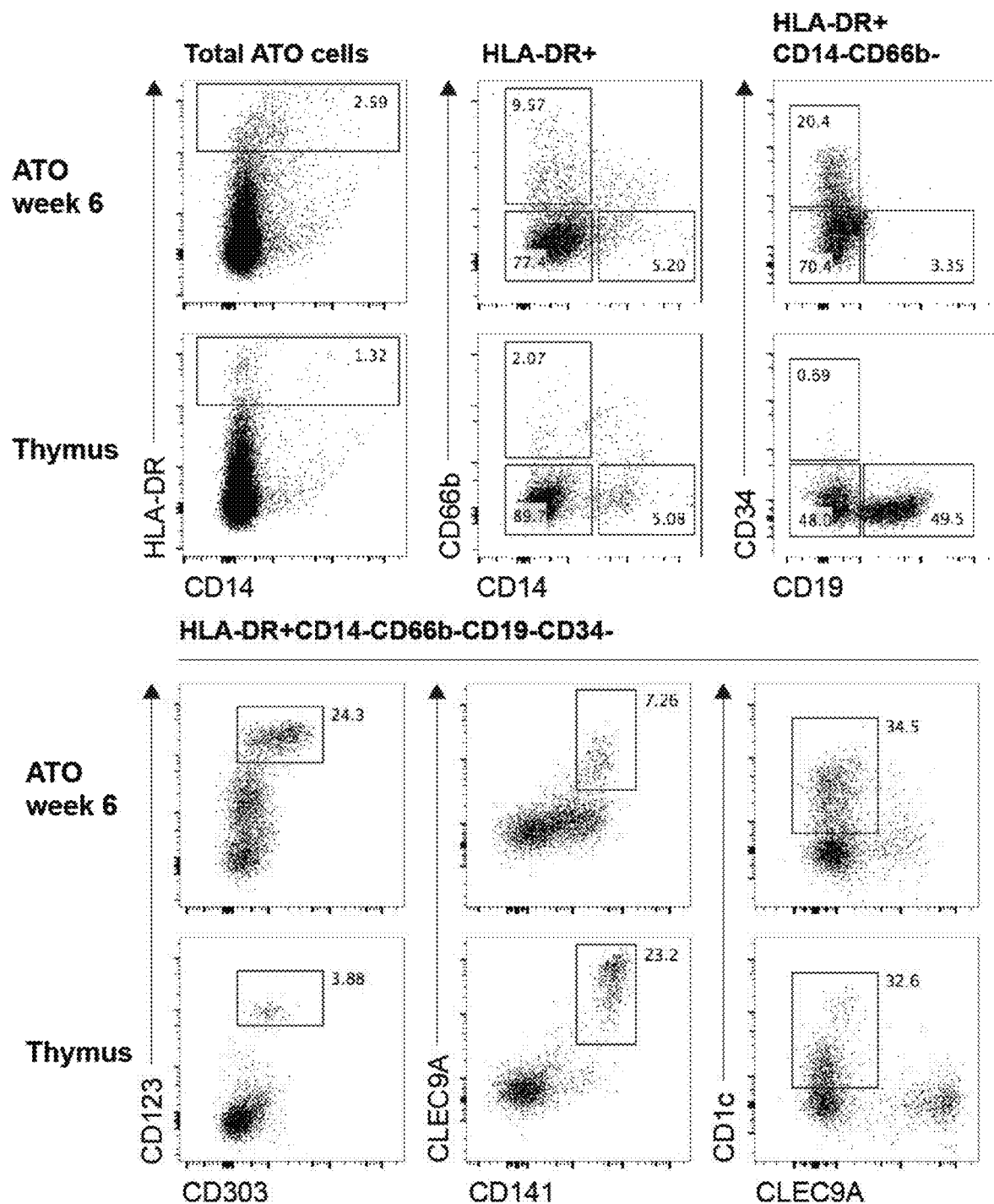

Given the late emergence of mature CD4SP T cells in ATOs, it was postulated that dendritic cells might also develop in ATOs and mediate positive selection through MHC class II expression. Indeed, rare HLA-DR+ cells were present in ATOs at a frequency similar to that in the thymus (FIG. 23A). Further analysis of this population revealed antigen presenting cells including monocytes, B cells, and plasmacytoid, CLEC9A+, and CD1c+ dendritic cells, all of which are also present in the thymus (FIG. 23B).

C. T Cell Differentiation from Multiple HSPC Sources and Subsets

Efficient T cell differentiation in ATOs, with similar frequencies of precursor and CD3+TCRαβ+ T cells, was seen from all clinically relevant HSPC sources, i.e. adult bone marrow (BM), G-CSF mobilized peripheral blood (MPB), and non-mobilized peripheral blood (PB) (FIG. 3A-B, 15A-B, 13A-B). HSPCs from these sources and also from thymus, displayed different kinetics of T cell differentiation (FIG. 15A), however T cell output was comparable across HSPC sources (FIG. 3d). Highly enriched hematopoietic stem cell (HSC) fractions (lin-CD34+CD38−) from CB, BM, or MPB demonstrated similarly robust T cell differentiation (FIG. 5C-D, 13D-E).

Figure 15A:
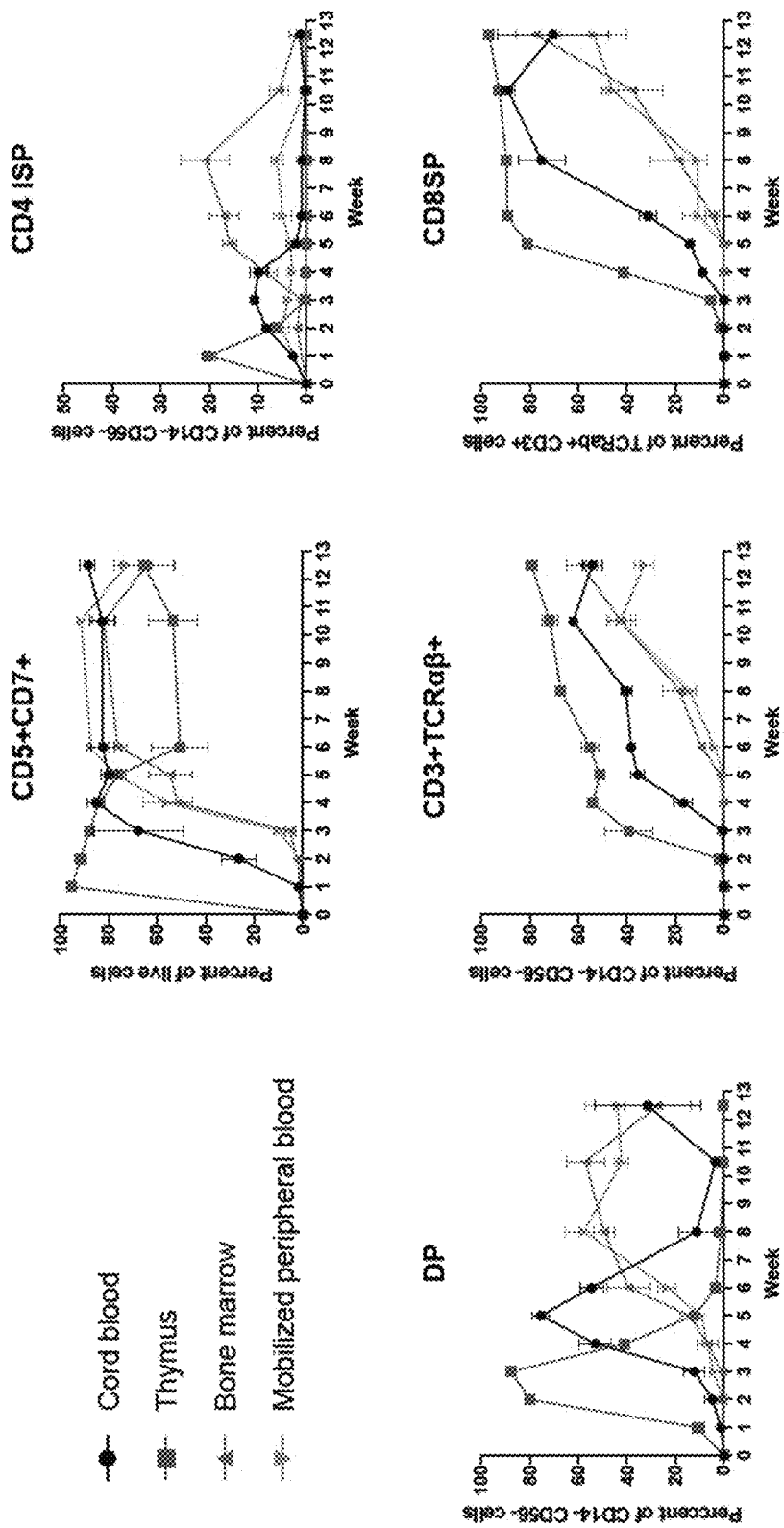
FIG. 15A-D: Generation of T cells from multiple HSPC sources and subsets. (a) T cell differentiation kinetics over 12 weeks in ATOs generated from 7500 CD34+CD3− cells isolated from CB, neonatal thymi, BM, or MPB. Mean and SD of frequencies of T cell precursors and mature T cells are shown from three technical replicates per tissue and data are representative of two different experiments. (b) Numbers of total cells and CD3+TCRαβ+CD8SP T cells from ATOs shown in (a). (c) T cell differentiation potential of adult BM HSPC (CD34+lin−) and progenitor (LMPP and CLP) subsets in ATOs at week 6 (gates indicated). (d) Numbers of total cells and CD3+TCRαβ+CD8SP T cells from ATOs shown in (c). Mean and SD of technical triplicates are shown, and data are representative of three biological replicates.
Figure 15B:
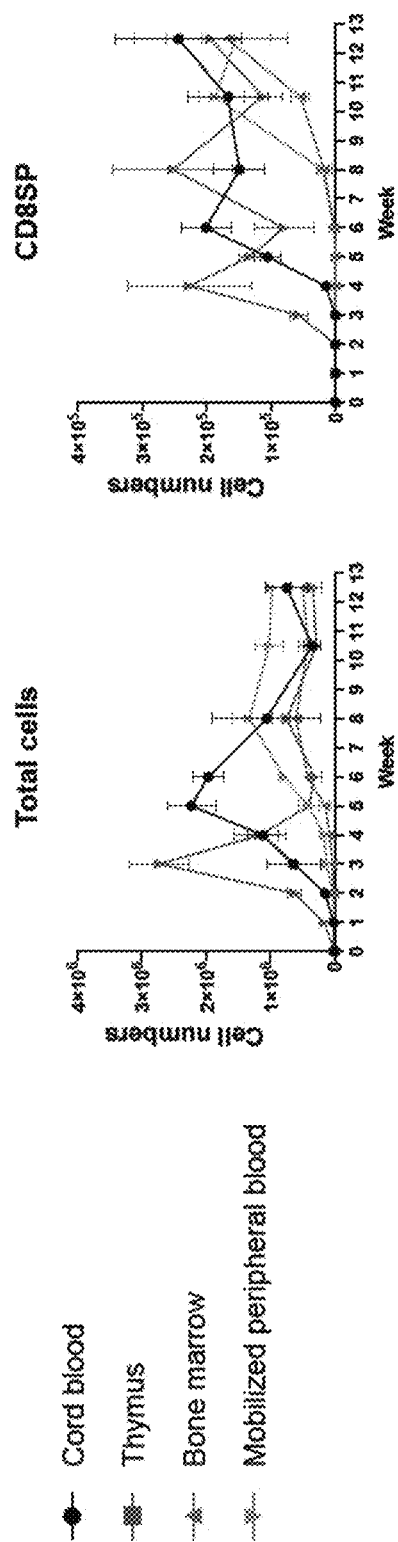
Figure 15C:
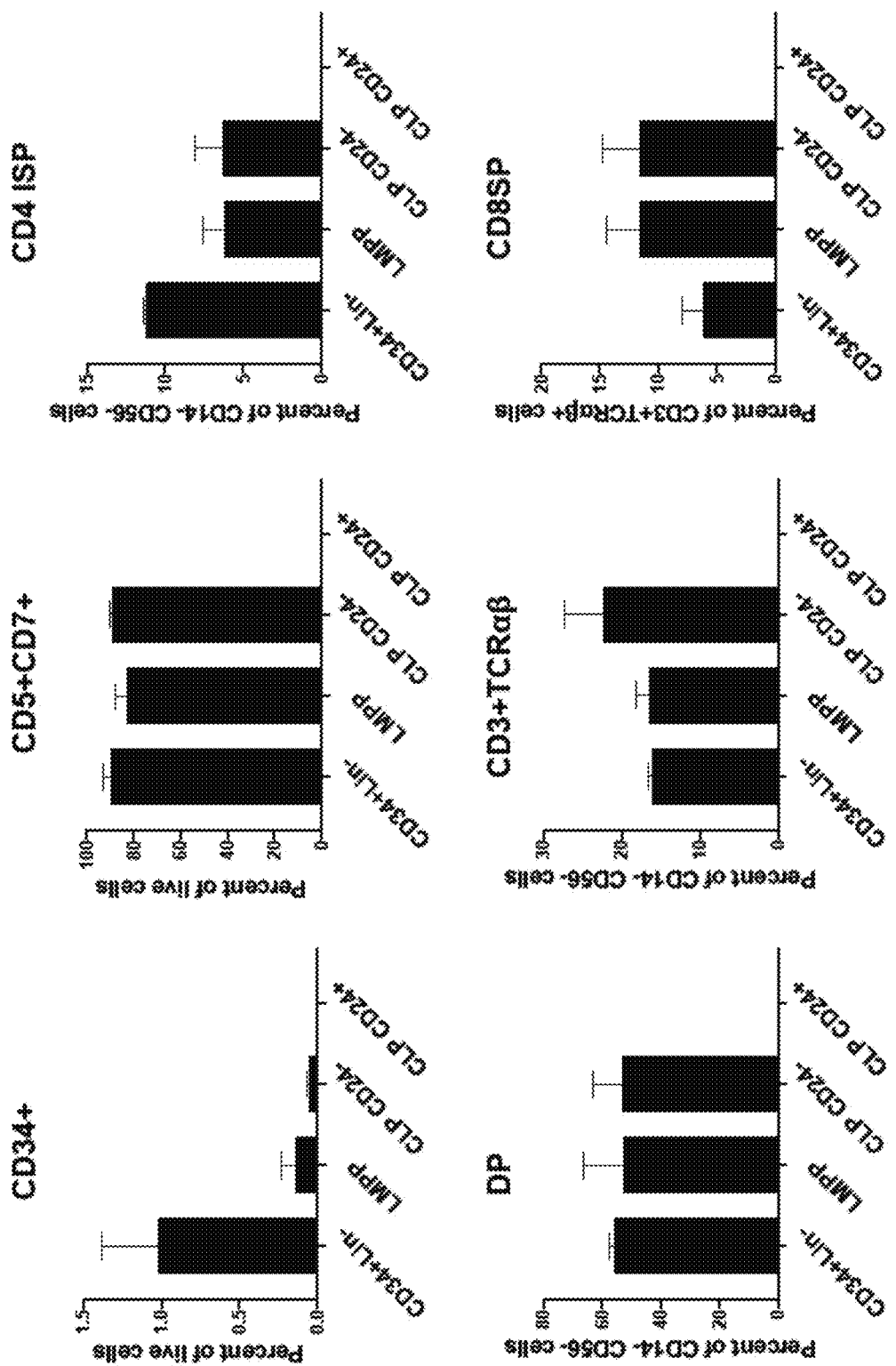
Figure 15D:
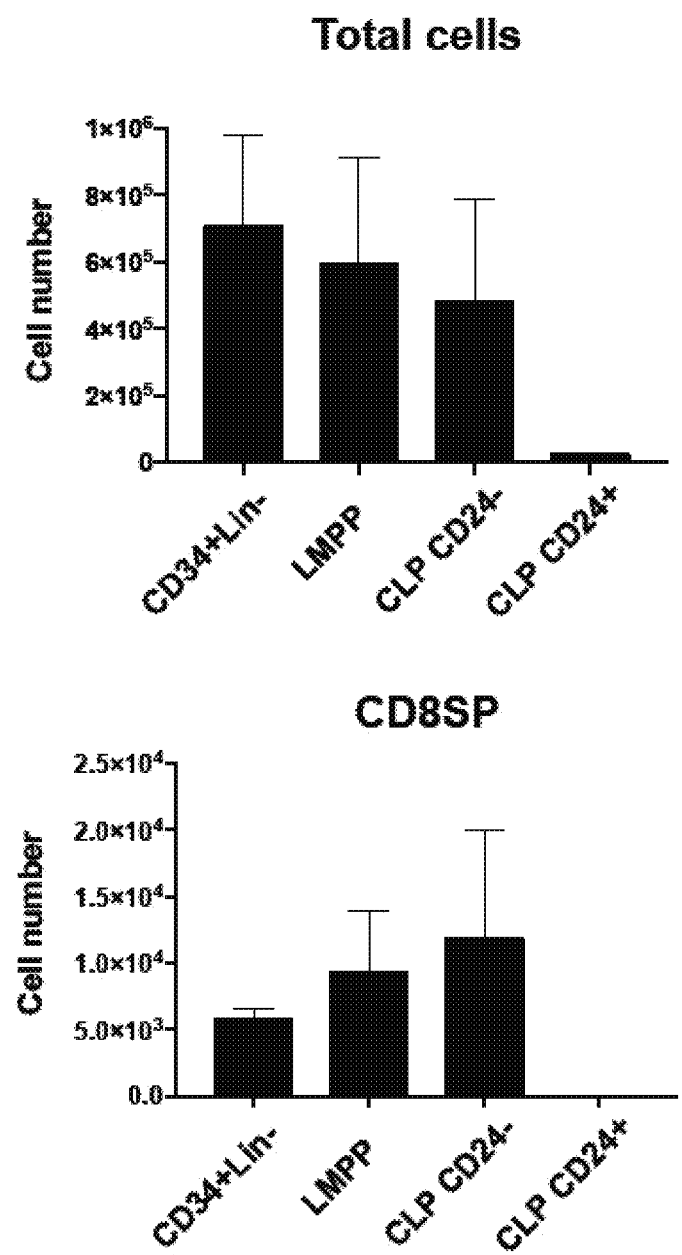

ATOs also induced T cell differentiation from purified lymphoid progenitors isolated from BM (FIG. 15C-D). Lymphoid-primed multipotent progenitors (LMPP) and CD24-common lymphoid progenitors (CLP) differentiated more rapidly than either HSC (not shown) or unfractionated CD34+lin− HSPCs (FIG. 24A-B). In contrast, CD24+ CLPs, which possess primarily B and NK cell potential, resulted in poor T cell differentiation and cell output in ATOs (FIG. 15C-D, 24A). Thus ATOs can serve as a tool for evaluating T lineage potential from human stem and progenitor cell populations.

D. TCR Diversity and Function of ATO-Derived T Cells

Figure 16A:
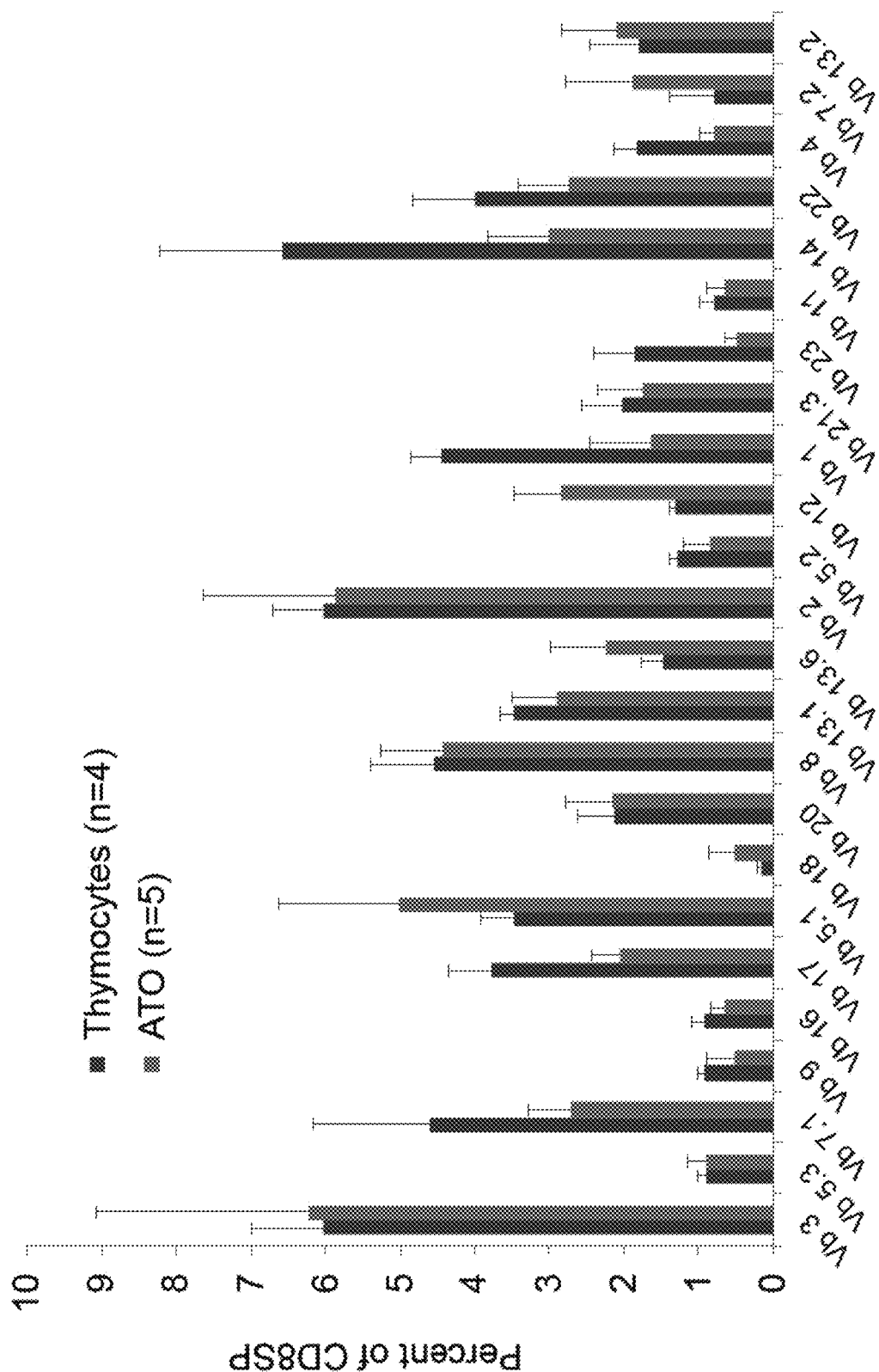
Figure 16B:
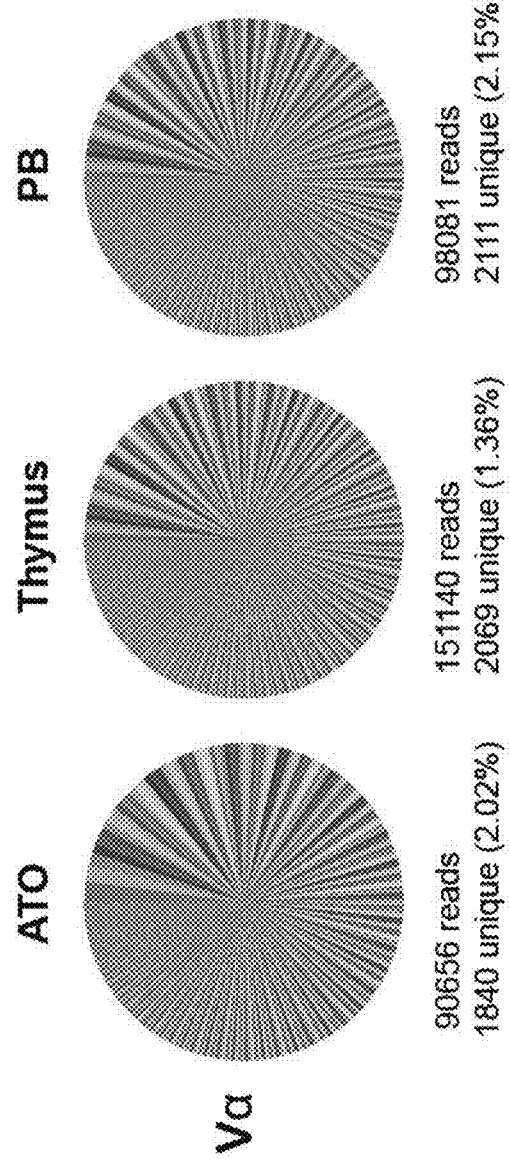
Figure 16C:
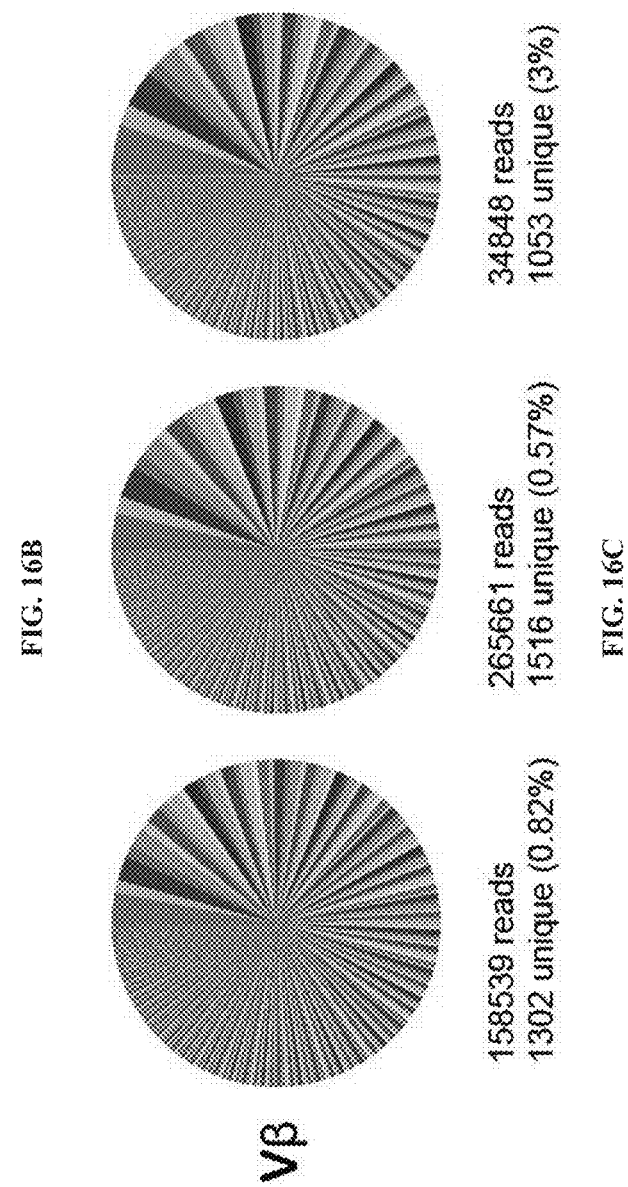
Figure 25A:
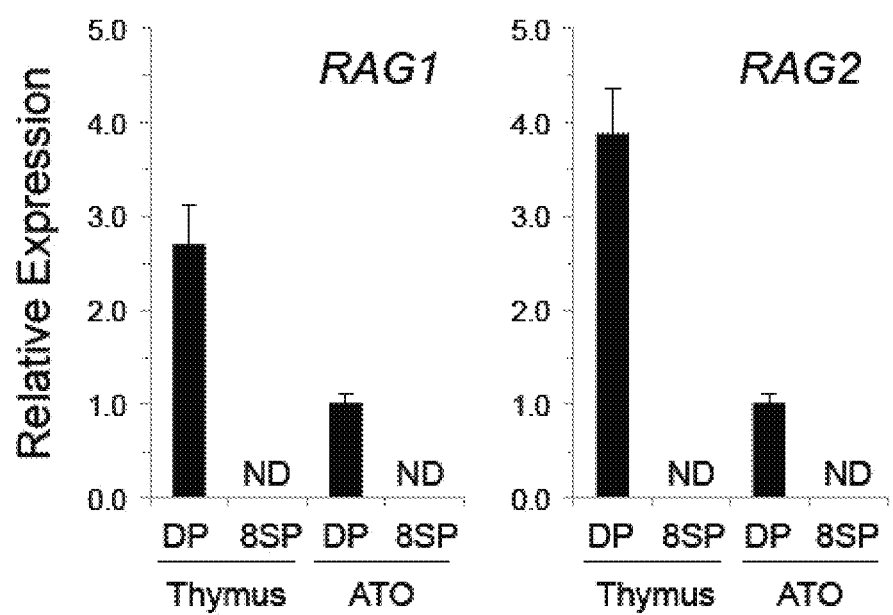
Figure 25B:
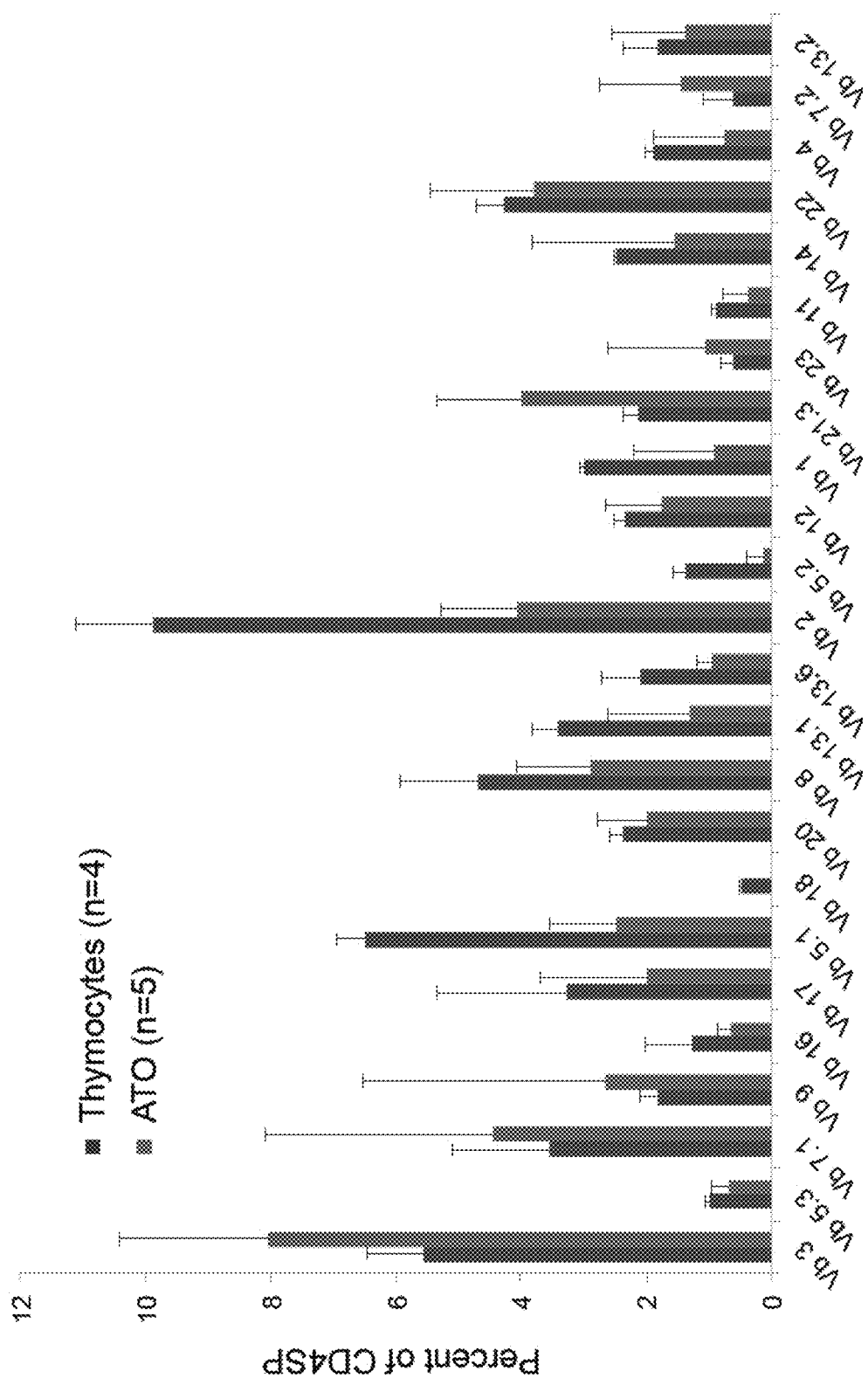

Similar to thymus, RAG1 and RAG2 were expressed in ATO-derived DPs (FIG. 25A). Flow cytometry analysis of TCR Vβ family usage in ATO-derived CD3+TCRαβ+CD8SP (FIG. 16A) and CD3+TCRαβ+CD4SP (FIG. 25B) T cells revealed a strikingly similar diversity to that of corresponding T cells from human thymi. In addition, a highly diverse TCR repertoire in CD3+TCRαβ+CD8SP was seen by deep sequencing of TCR Vα and Vβ CDR3 regions, comparable to that in thymic CD8SP cells and PB naïve CD8+ T cells (FIG. 16B-C). Importantly, skewed Vα or Vβ usage was not observed, arguing against the predominance in ATOs of unconventional T cell subsets or clonally expanded mature T cells.

Figure 16F:
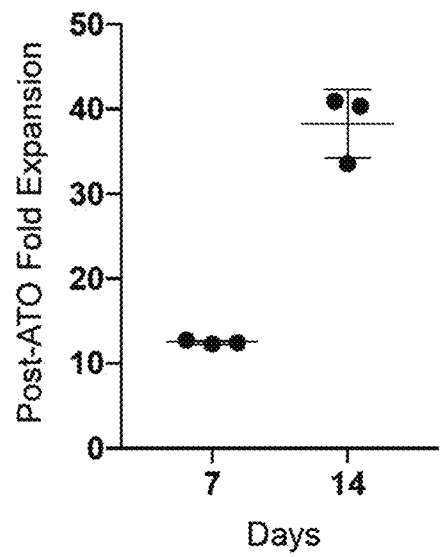
Figure 25E:
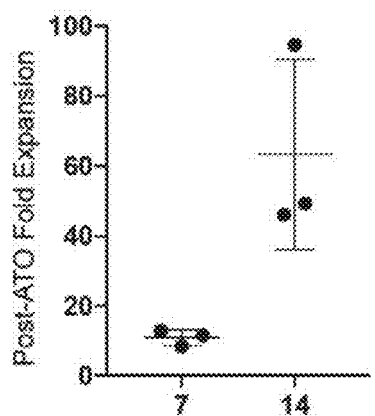

ATO-derived CD8SP T cells exhibited polyfunctional IFNγ, TNFα, and IL-2 production in response to PMA/ionomycin, consistent with a cytotoxic phenotype (FIG. 16D), as well as robust proliferation and upregulation of CD25 and 4-1BB in response to anti-CD3/CD28 and IL-2 stimulation (FIG. 16E). ATO-derived CD4SP cells produced IFNγ and IL-2 and proliferated in response to anti-CD3/CD28 and IL-2 (FIG. 25C-D). Numbers of CD8SP (FIG. 16F) and CD4SP (FIG. 25E) isolated from ATOs expanded ~60 fold and ~40 fold respectively over 14 days with anti-CD3/CD28 and IL-2. In summary, mature T cells generated in ATOs exhibited physiological TCR diversity and functional responses to antigenic stimuli.

E. Generation of Naïve TCR-Engineered T Cells in ATOs

Figure 17A:
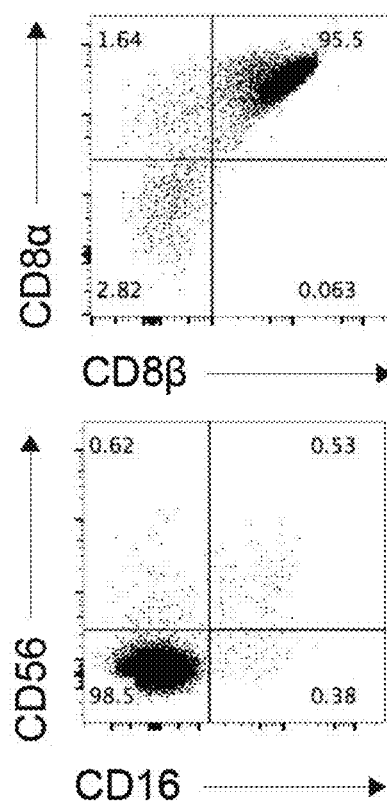
FIG. 17A-F: Differentiation and allelic exclusion of TCR-engineered T cells in ATOs. (a) Co-expression of CD8a and CD80 and lack of CD56 and CD16 expression on CD3+TCRαβ+tetramer+ T cells from TCR-transduced CB ATOs, indicating conventional T cell development. Data are representative of 3 biological replicates. (b) Enhanced total cell output and cell yield relative to starting number of HSPCs in TCR-transduced versus mock-transduced ATO at 6 or 7 weeks, generated with 7.5-18×10³ starting CB HSPCs. Mean and SD of biological replicate experiments are shown (mock n=3, TCR n=8, **p=0.002). (c) Cytotoxic priming of ATO-derived TCR engineered T cells by artificial antigen presenting cells (aAPCs). Cytokine production and CD107a membrane mobilization of CD3+tetramer+CD8SP T cells in response to K562 cells or K562 aAPCs that express CD80 and HLA-A*02:01 single chain trimers presenting an irrelevant (MART1$_{26-35}$) or cognate (NY-ESO1$_{156-165}$) peptide. Data are representative of three biological replicates. (d) Proliferation (CFSE dilution) and activation (CD25 upregulation) of ATO-derived CD3+tetramer+CD8SP T cells in response to irrelevant (MART1) or cognate (NY-ESO-1) aAPCs for 72 h. Data are representative of two biological replicates. (e) Post-ATO expansion of ATO-derived CD3+TCRαβ+CD8SP T cells from TCR transduced ATOs relative to starting cell number in response to anti-CD3/CD28 and IL-2 or IL-7/IL-15 after 7 and 14 days. Mean and SD of technical triplicates are shown, and data are representative of three biological replicates. (f) Allelic exclusion of endogenous TCR Vβ in CD3+TCRαβ+tetramer+CD8SP cells from TCR-transduced (n=3) compared with non-transduced (n=5) ATOs as shown by flow cytometric analysis. Error bars represent SD.

The inventors next adapted ATOs for the in vitro generation of TCR-engineered T cells from HSPCs. CB CD34+CD3−HSPCs were transduced with a lentiviral vector encoding codon optimized α and β chains of a HLA-A*02:01-restricted TCR specific for the NY-ESO-1$_{157-165}$ peptide. At 7 weeks, TCR-transduced ATOs showed similar frequencies of CD5+CD7+ T-lineage cells as mock-transduced controls, but markedly increased CD3+TCRαβ+ T cells, the majority of which expressed the transduced TCR, as seen by staining with a tetramer or antibody against the transduced Vβ13.1 chain (FIG. 7A). The frequency of CD8SP cells was similar between CD3+TCRαβ+tetramer+ cells and CD3+TCRαβ+ cells from mock-transduced controls, however tetramer+CD8SP cells displayed accelerated maturation to a mature naïve phenotype (i.e. CD45RA+CD45RO−CD27+CCR7+CD1a$^{lo}$) (FIG. 7A). Of note, tetramer+CD8SP cells displayed a conventional CD8αβ T cell phenotype without expression of CD16 or CD56, markers associated with NK cells and intraepithelial lymphocytes (FIG. 17A).

Figure 17B:
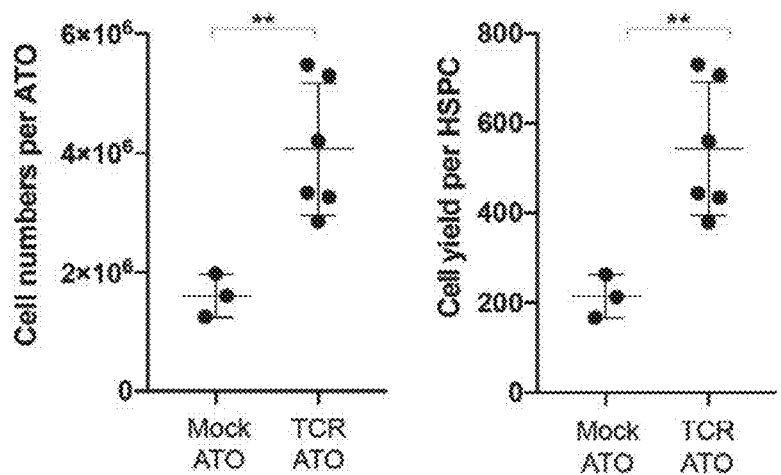

TCR transduction also resulted in significantly enhanced cell yield from ATOs (average ~450 cells per HSPC) (FIG. 17B), the majority of which were CD3+tetramer+ T cells. Thus, a single ATO initiated with 7,500 TCR-transduced HSPCs typically generated ~4×10$^6$ cells, of which approximately 15% (6×10$^5$) were CD3+tetramer+ CD8SPCD45RA+ mature naïve T cells by 7 weeks (FIG. 7A, 17B).

Figure 17C:
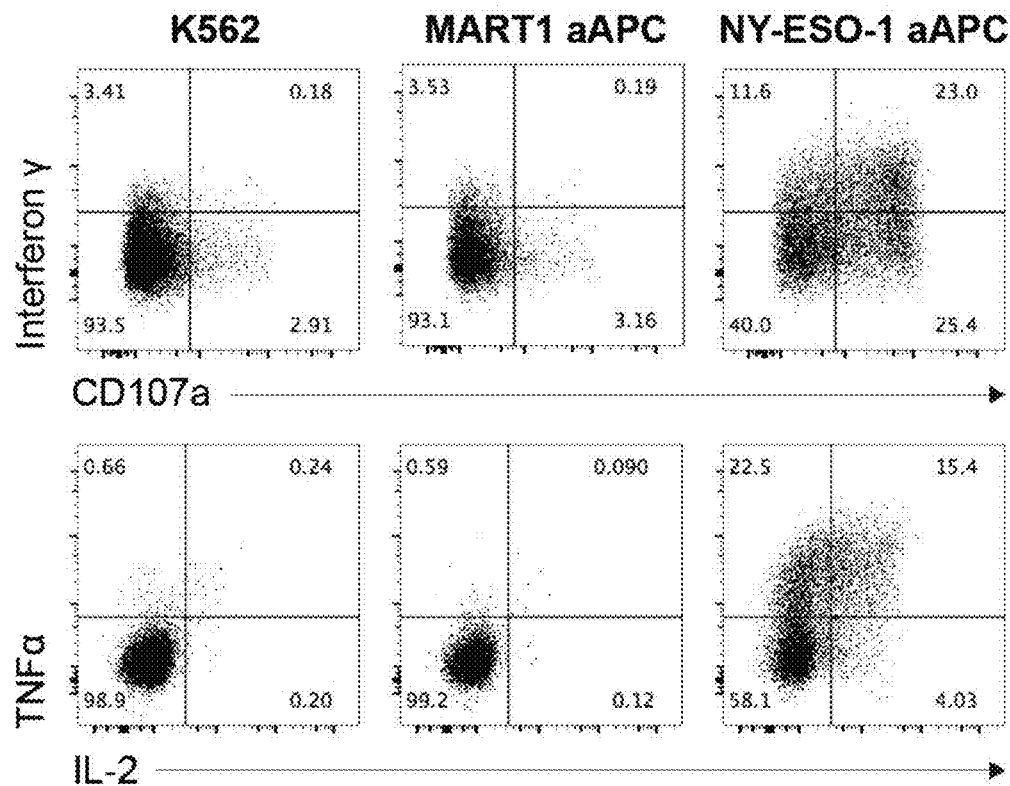
Figure 17D:
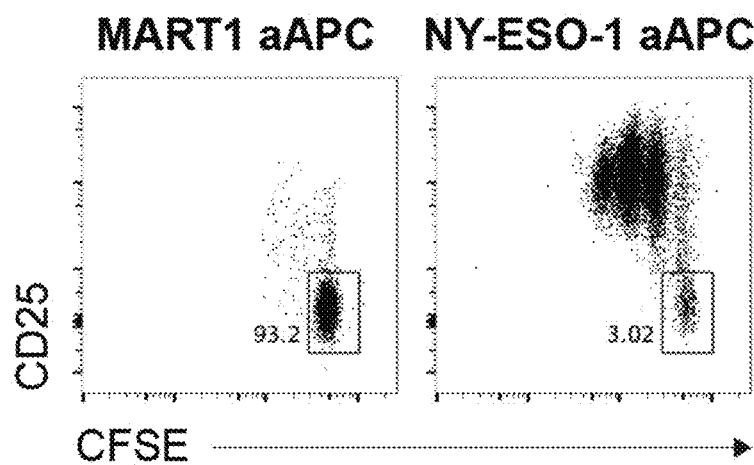
Figure 17E:
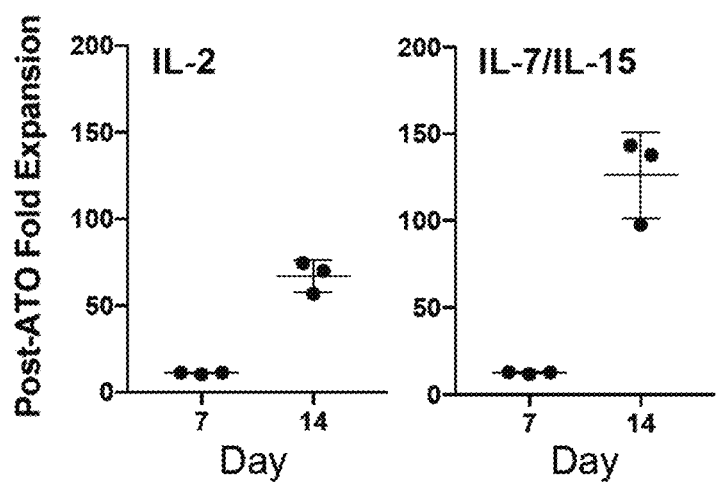
Figure 17F:
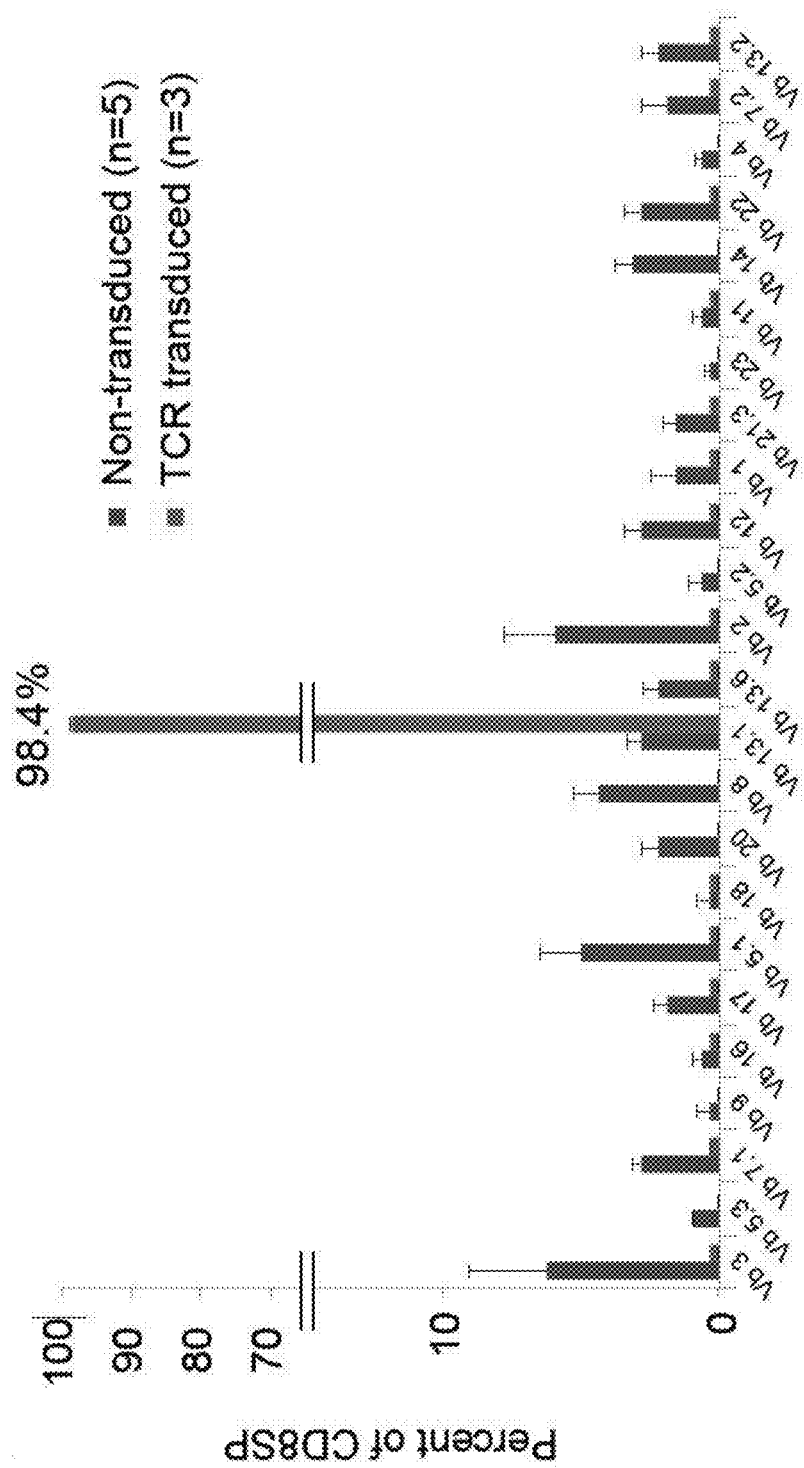
Figure 26A:
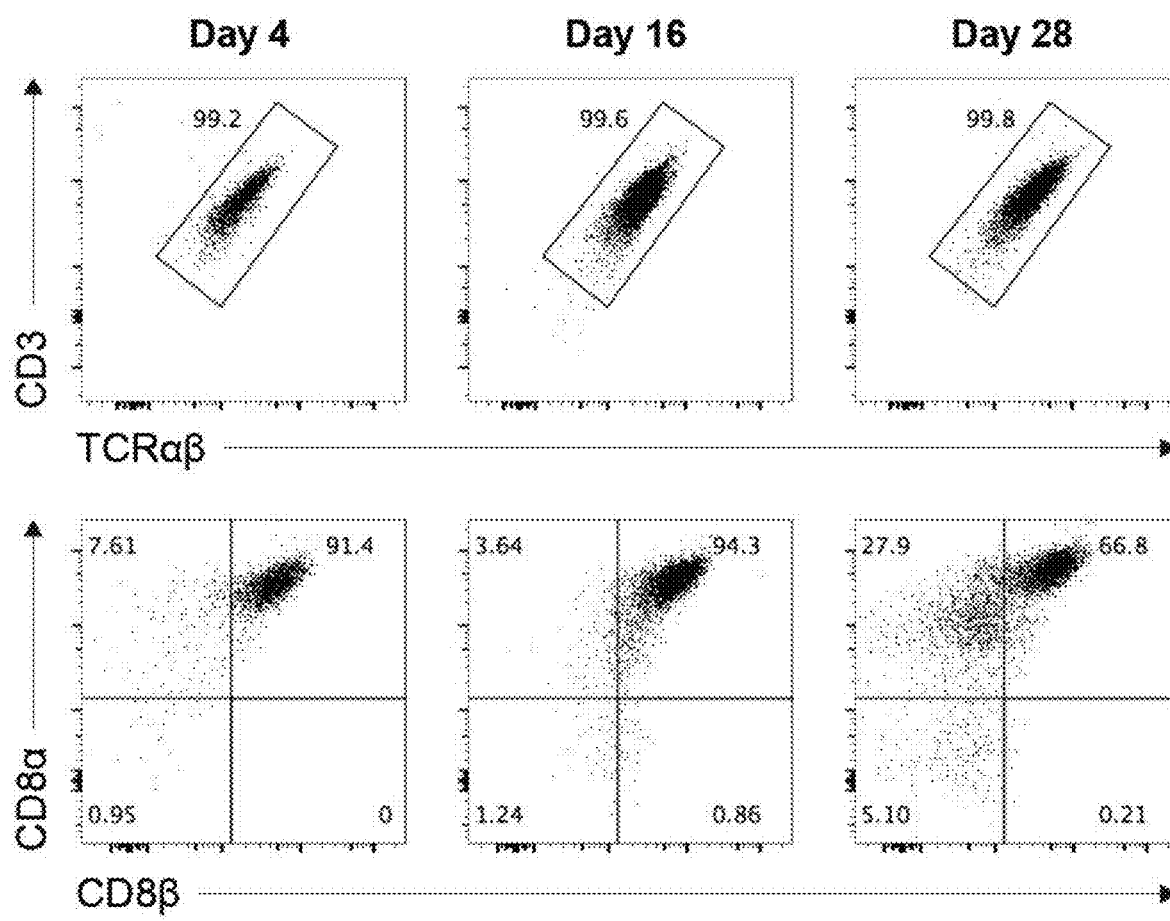
FIG. 26A-D: Differentiation and allelic exclusion of TCR-engineered T cells in ATOs. (a) ATO-derived TCR-engineered T cells retain a conventional T cell phenotype despite expansion and re-stimulation. CD8SP T cells from ATOs generated from CB HSPCs transduced with a HLA-A*0201/NY-ESO-1$_{157\text{-}165}$ specific TCR were activated with anti-CD3/28 beads+IL-2, expanded in IL-2, and re-stimulated with anti-CD3/28 beads on day 14. Preserved surface co-expression of CD8a and CD80 was confirmed by flow cytometry. Data are representative of two biological replicates. (b) Flow cytometric Vβ analysis of CD3+TCRαβ+tetramer+CD8SP T cells from TCR-transduced CB ATOs. Data are representative of 5 biological replicates. (c) Generation of TCR-engineered T cells from TCR-transduced CB HSPCs in ATOs using an HLA-A*02:01/MART1$_{26\text{-}35}$ specific TCR. Differentiation at week 6 is shown (gated on total CD14−CD56− ATO cells, with sequential gates shown above each plot). Data are representative of two biological replicates. (d) Antigen-specific priming of MART1-specific and NY-ESO-1-specific ATO-derived TCR-engineered T cells by artificial antigen presenting cells (aAPCs) that express CD80 and a HLA-A*02:01 single chain trimer presenting either MART1$_{26\text{-}35}$ or NY-ESO1$_{155\text{-}165}$ peptide. CD107a membrane mobilization and intracellular IFNγ staining at 6 h is shown.

ATO-derived CD8SP cells from TCR-transduced ATOs underwent antigen-specific activation (IFNγ, TNFα and IL-2 production), degranulation (CD107a membrane mobilization) (FIG. 17C), and proliferation (FIG. 17ED) in response to artificial antigen presenting cells (aAPC) expressing CD80 and a cognate HLA-A*02:01/NY-ESO-1 peptide-MHC single chain trimer, but not to irrelevant HLA-A*02:01/MART-1 aAPC or parental K562 cells. Furthermore, CD8SP T cells isolated from TCR-transduced ATOs showed robust expansion in response to anti-CD3/CD28 and either IL-2 or IL-7/IL-15 (FIG. 17E). Tetramer+ cells furthermore maintained a conventional CD8αβ phenotype even following prolonged expansion and reactivation (FIG. 26A).

Figure 26B:
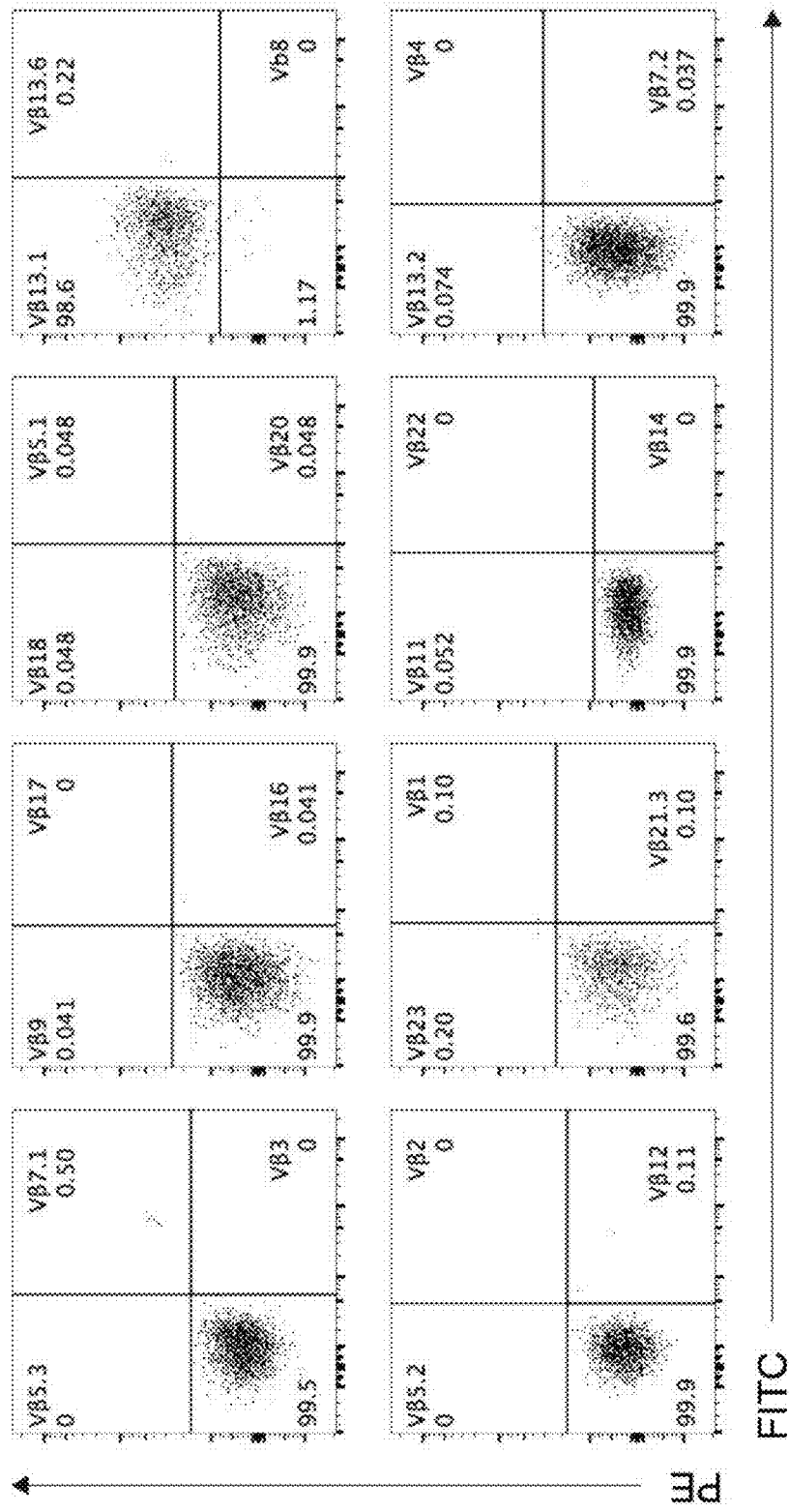

Flow cytometry analysis of Vβ diversity in ATO-derived TCR-engineered T cells revealed over 98% of tetramer+ CD8SP T cells expressed only the transduced Vβ13.1 segment (FIG. 7F, 26B), consistent with near complete allelic exclusion of endogenous Vβ expression during differentiation of TCR-engineered T cells in ATOs. Thus ATOs supported robust differentiation of functional, TCR-engineered T cells from HSPCs, and introduction of a TCR enhanced cell expansion and promoted the differentiation of mature naïve T cells that lacked endogenous TCR Vβ expression.

Figure 26C:
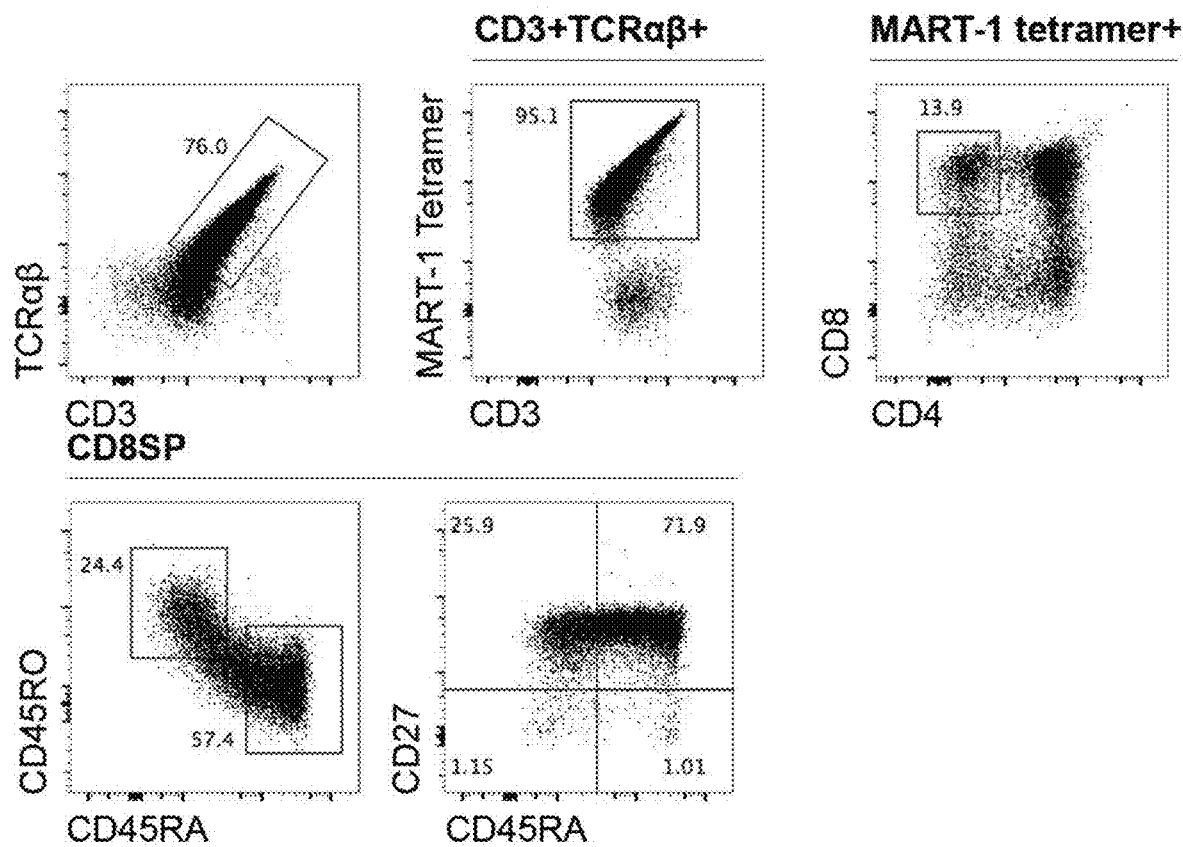
Figure 26D:
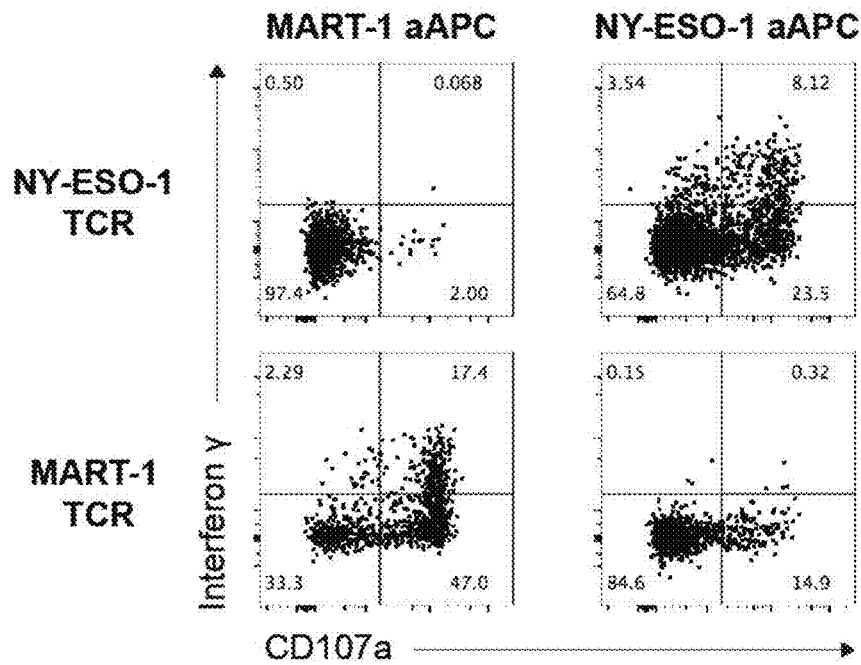

To test if the findings above could be extended beyond the NY-ESO-1 TCR, ATOs were generated using a codon-optimized HLA-A*02:01-restricted MART-1-specific TCR. CD3+tetramer+CD8SP isolated from these ATOs demonstrated a naïve T cell phenotype (FIG. 26C), and upregulated IFNγ and CD107a surface expression in response to MART-1 aAPC but not NY-ESO-1 aAPC (FIG. 26D).

F. Enhanced Positive Selection of TCR-Engineered T Cells in MHC-Modified ATOs

Figure 27A:
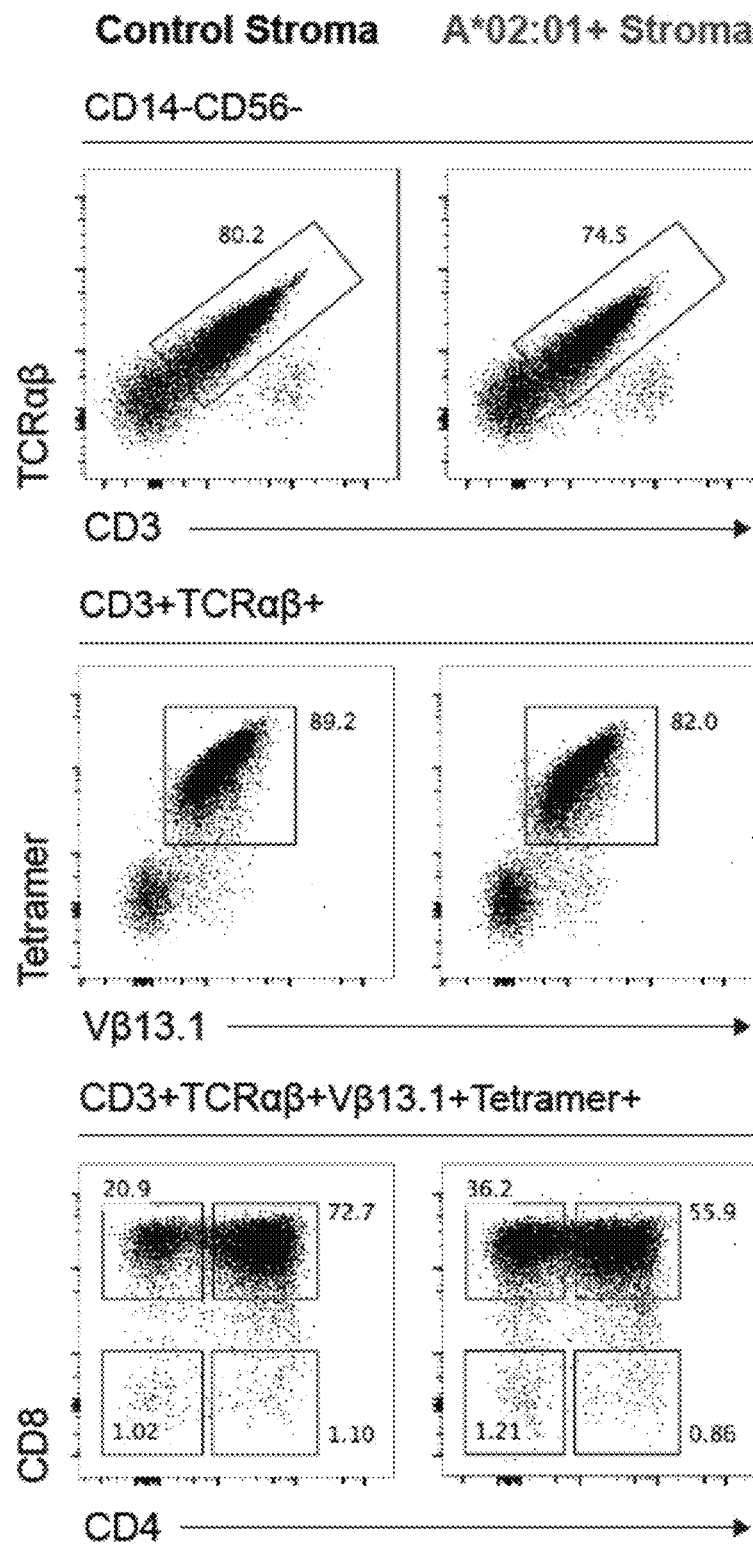
FIG. 27A-B: Enhanced positive selection of TCR-engineered T cells in MHC-modified ATOs. (a) Enhanced production of TCR-engineered CD3+TCRαβ+tetramer+CD8SP T cells in week 6 ATOs generated with TCR-transduced CB HSPCs from a single donor and either standard or HLA-A*02:01-transduced MS5-hDLL1 stromal cells. Sequential gates are shown above each plot. (b) Normal maturation of TCR-engineered T cells to a mature naïve T cell phenotype in MHC-modified ATOs, as shown in (a). Cells are gated on CD3+Vβ13.1+tetramer+CD8SP T cells. Data are representative of three biological replicates.
Figure 27B:
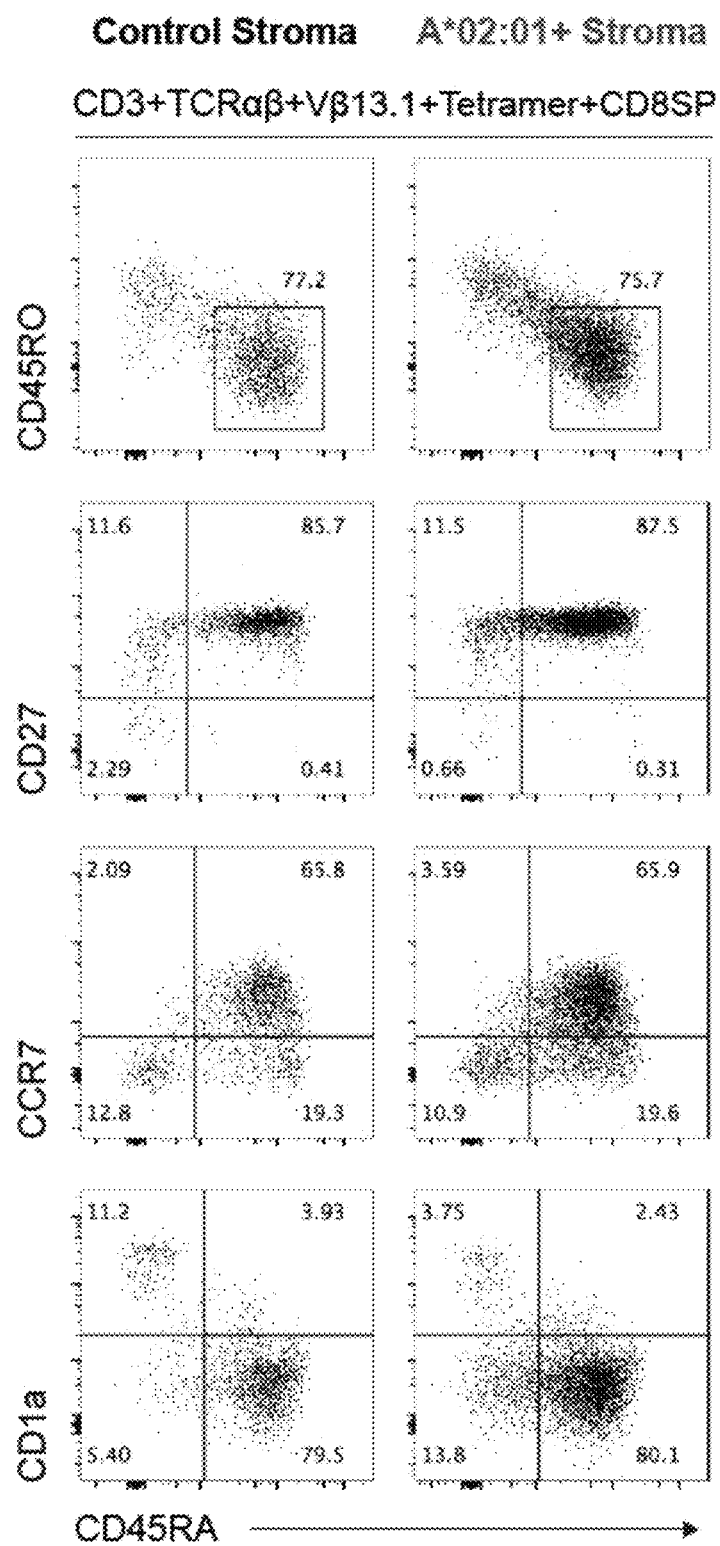

Positive selection in the thymus is mediated by interactions between TCRs on T cell precursors and self-MHC on thymic stroma and hematopoietic cells. It was thus investigated whether increased stromal expression of "self" MHC in ATOs could enhance positive selection of TCR-engineered T cells. HLA-A*02:01 positive HPSCs were transduced with the HLA-A*02:01-restricted NY-ESO-1-specific TCR, and combined with control MS5-hDLL1 stroma or MS5-hDLL1 transduced with HLA-A*02:01 (FIG. 27A). Expression of HLA-A*02:01 in ATO stromal cells enhanced positive selection of tetramer+CD3+CD8SP T cells (FIG. 27A) while maintaining normal differentiation to a mature naïve phenotype (FIG. 27B).

G. Antigen-Specific Tumor Killing by ATO-Derived TCR Engineered T Cells

Figure 18A:
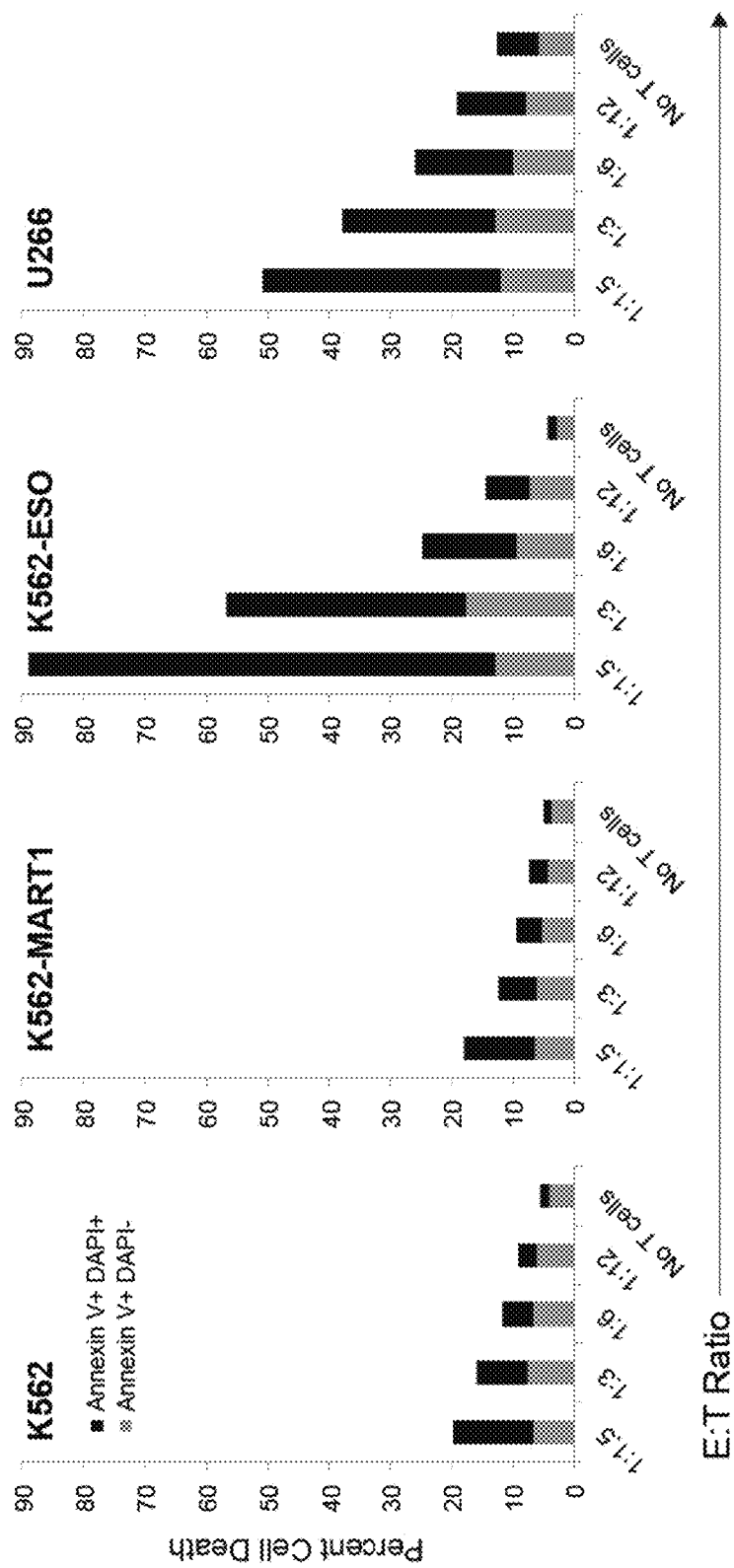

The inventors next tested antigen-specific cytotoxicity of ATO-derived TCR-engineered T cells. Purified CD8SP T cells, isolated from NY-ESO-1-specific TCR-transduced ATOs and activated in vitro for 36 hours, potently induced apoptosis in NY-ESO-1 expressing cell lines (K562 cells transduced with an HLA-A*02:01/NY-ESO-1 pMHC complex; and the HLA-A*02:01+ U266 multiple myeloma cell line in which NY-ESO-1 antigen is endogenously expressed), but showed little activity against parental K562 cells or K562 cells expressing the irrelevant HLA-A*02:01/MART-1 pMHC (FIG. 18A-B). Furthermore, antigen-specific cytotoxicity was preserved following prolonged (14 day) in vitro expansion, consistent with retention of a conventional T cell phenotype (FIG. 18C); cytotoxicity was similar to that of TCR-transduced PB CD8+ T cells expanded for the same period (FIG. 18C). Consistent with these results, expanded ATO-derived TCR-engineered T cells were able to significantly control disease burden in NSG mice subcutaneously engrafted with K562 tumors expressing cognate (K562-ESO) but not irrelevant (K562-MART1) pMHC antigens (FIG. 18D-F).

II. Comments

The ability to faithfully recapitulate thymopoiesis in vitro creates a unique opportunity for the production of engineered T cells with desirable therapeutic traits, including an antigen naïve state and lack of endogenous TCR expression. As demonstrated here using standardized, off-the-shelf components, the ATO system efficiently initiates and maintains the normal stages of T cell commitment and differentiation from HSPCs, culminating in the production of mature CD3+ TCRαβ+CD8SP and CD3+TCRαβ+CD4SP T cells closely resembling naïve conventional T cells from the thymus and peripheral blood.

ATOs offer distinct biological and translational advantages compared to existing methods of in vitro T cell differentiation. First, ATOs support positive selection and maturation of human T cells, both of which are impaired in monolayer systems. Enhanced positive selection in ATOs is dependent on 3D structure, as monolayer cultures set up with identical components resulted in inefficient T cell differentiation. This is consistent with observed positive selection, albeit with lower efficiency, in FTOCs or re-aggregated 3D cultures using thymic components. It is possible that 3D interactions support improved T cell development by increasing the valence and/or duration of contact between T cell precursors and developmental ligands, such as DLL1, or selective ligands such as self MHC. Alternatively, 3D configuration may facilitate crosstalk between stromal and hematopoietic cells or exert developmental signals on T cell precursors through mechanical forces and/or metabolic changes not otherwise possible in 2D.

Another major advance of the ATO system over existing methods is highly efficient T cell differentiation from clinically relevant adult sources of HSPCs, including cord blood, bone marrow, and resting or mobilized peripheral blood. Current monolayer systems allow only inefficient development of TCRαβ+ T cells from CB, BM, or MPB; data for resting peripheral blood HSPCs are not reported.

As demonstrated here, the ATO system can also generate TCR-engineered naïve T cells from HSPCs. Differentiation of TCR-engineered T cells from human HSPCs has been demonstrated in the OP9-DL1 system, however in these reports maturation to CD3+CD8SP cells was impaired (typically representing only 0-2% of cultures), with the highest efficiencies achieved using thymus-derived CD34+ cells. In contrast, ATOs supported robust positive selection of TCR-engineered T cells from CB HSPCs, with similar results observed using MPB HSPCs (not shown). The mature naïve T cell phenotype achieved in ATOs may also offer be a distinct advantage of ATO-derived engineered cells over modified peripheral blood T cells, based on studies showing that improved in vivo survival and activity of adoptively transferred T cells is correlated with less differentiated activated phenotypes. Enhanced positive selection of TCR-engineered naïve T cells by expression of cognate MHC in ATO stromal cells provides a further avenue for increasing the yield of mature ATO-derived antigen-specific T cells.

The presence in ATOs of a transduced TCR throughout T cell differentiation mediated near-complete allelic exclusion of endogenous Vβ TCR loci, consistent with in vivo studies of transplanted murine and human HSPCs. The expression of potentially alloreactive endogenous TCRs on engineered peripheral blood T cells is a major barrier to the development of scalable, off-the-shelf adoptive T cell therapies, necessitating labor-intensive, individualized production of autologous engineered T cells. Strategies to develop allogeneic engineered T cell therapies include disruption of endogenous TCR/CD3 expression by gene editing, or TCR-transduction of virus-specific T cells; however both such approaches require extensive manipulation and expansion of gene-modified T cells, potentially compromising subsequent in vivo function. The use of ATOs for the de novo generation of naïve, allelically-excluded engineered T cells thus presents a highly efficient alternative strategy for producing non-alloreactive T cells for adoptive cell therapy.

The ATO system also offers technical simplicity, reproducibility, and potential scalability. The use of serum-free medium avoids the marked variability observed with fetal calf serum in monolayer systems, and the ability to maintain ATOs intact for the duration of culture (up to 20 weeks) with simple media changes avoids the frequent transfer of cells onto fresh stromal cells, as is required with monolayer systems. Highly pure populations of T cells are readily collected from ATOs by mechanical dissociation and can be further purified by standard methods to remove the <0.5% of contaminating stromal cells. The use of off-the-shelf components and specifically the avoidance of primary stromal cells or proprietary scaffold materials, together with the ability to combine ATO production with xeno-free reagents and stromal cell irradiation will simplify translation of ATOs to a clinical grade platform for generating T cells for adoptive therapy. The simplicity of the system furthermore permits straightforward adoption of the method in laboratories interested in modeling human T cell development and positive selection.

III. Methods

A. Isolation of Human CD34+CD3− HSPCs

Neonatal umbilical cord blood was obtained from discarded cord and placental units from deliveries at UCLA. Bone marrow (BM) was obtained from healthy adult donors through discarded material from allogeneic BM donor harvests at UCLA or purchased from AllCells Inc. (Alameda, CA). G-CSF mobilized peripheral blood was obtained from consenting healthy adult donors undergoing apheresis for allogeneic stem cell transplant donation at UCLA. Non-mobilized peripheral blood was obtained from healthy adult donors through the UCLA CFAR Virology Core. All tissue samples were obtained under UCLA IRB-approved protocols or exemptions. All samples were enriched for mononuclear cells by Ficoll-Paque (GE Healthcare Life Sciences, Pittsburgh, PA) gradient centrifugation followed by positive selection of CD34+ cells by magnetic cell sorting (MACS) using the CD34 MicroBead Kit UltraPure (Miltenyi, Auburn CA). CD34+ cell enriched fractions were cryopreserved after MACS, unless otherwise noted. Prior to use, cells were thawed and residual T cells depleted by FACS by sorting CD34+CD3− cells, which were immediately seeded into ATOs or transduced as described below. In some experiments, HSCs were enriched by FACS for Lin-CD34+CD38− cells prior to seeding in ATOs. HSPCs used in TCR transduction experiments were from HLA-A*02:01+CB units. High-resolution HLA-A2 typing was performed by the UCLA Immunogenetics Center using sequence-specific oligonucleotide (SSO) beads.

B. Isolation of Human Bone Marrow Progenitor Subsets

CD34+ HSPCs were enriched from fresh BM aspirates, as above, and immediately sorted by FACS for stem/progenitor populations based on positive expression of CD45 and absent expression of lineage markers (CD3, CD14, CD19, CD56, and CD235a; "Lin−") combined with the following markers: total HSPCs (CD34+), HSC (CD34+CD38−CD45RA-LMPP (CD34+CD38+CD45RA+CD10−CD62L$^{hi}$), CD24− CLP (CD34+CD38+CD45RA+CD10+CD24−), and CD24+ CLP (CD34+CD38+CD45RA+CD10CD24+).

C. Isolation of Human Thymocytes

Postnatal human thymi were obtained under IRB exemption as discarded waste from patients undergoing cardiac surgery at Children's Hospital Los Angeles (CHLA). Thymic fragments were finely dissected in RPMI and disrupted by pipetting to release thymocytes into suspension, followed by passage through a 70 μm nylon strainer. Cells were analyzed fresh on the same or following day. Flow cytometry analysis of thymic and ATO-derived T cell progenitors used the following surface phenotypes: Early thymic progenitor (ETP; CD34+CD7−CD1a−), CD1a− pro-T (CD34+CD7+CD1a−), and CD1a+ pro-T (CD34+CD7+CD1a+); or CD5− pro-T (pro-T1; CD34+CD7+CD5−) and CD5+ pro-T (pro-T2; CD34+CD7+CD5+). Thymic and ATO-derived T cells and precursors were defined as CD14−CD56− in combination with the following phenotypes: total T lineage cells (CD7+CD5+), double negative (DN; CD4−CD8−), CD4 immature single positive (CD4 ISP; CD5+CD4+CD3−), double positive (DP; CD4+CD8+), CD8SP (CD3+TCRαβ+CD8+CD4−), CD4SP (CD3+TCRαβ+CD8−CD4+), immature naïve (CD45RA−CD45RO+ that were CD8SP or CD4SP), mature naïve (CD45RA+CD45RO− that were CD8SP or CD4SP). Immature and mature naïve phenotypes were confirmed by co-staining for CD1a, CD27, CD28, and CCR7.

D. Isolation of Primary Human T Cells

Thymic T cells were isolated from thymocytes preparations as described above, and peripheral blood and cord blood CD8+ T cells were isolated from mononuclear cell fractions as described above. CD8+ T cell isolation from all sources was by magnetic bead enrichment for CD8SP T cells using the CD8+ T cell Isolation Kit (Miltenyi). In some experiments, thymic T cells were further purified by FACS to deplete CD4 ISP or DP precursors, and PB T cells to isolate naïve T cells (CD45RO−CCR7+).

E. Cell Lines

The MS-5 murine stromal cell line was obtained as a gift. To generate MS5-hDLL1, MS-5 cells were transduced with a lentiviral vector encoding human DLL1 and GFP. The highest 5% GFP-expressing cells were sorted by FACS and passaged in DMEM/10% FCS. Stable expression was confirmed by flow cytometry for GFP expression after several weeks of culture, and DLL1 expression confirmed by qRT-PCR and DNA sequencing. MS5-hDLL1-A2.1 cells were created by transducing MS5-hDLL1 cells with a human HLA-A*02:01 lentiviral vector (gift from Dr. David Baltimore, Caltech), followed by FACS sorting of transduced cells using an antibody recognizing human HLA-A2 (BB7.2) (Biolegend, San Diego, CA). The OP9-DL1 cell line (expressing murine Dll1) was a gift from Dr. Juan Carlos Zúñiga-Pflücker (University of Toronto) and was passaged in MEMα (ThermoFisher Scientific, Grand Island, NY)/20% FBS in 0.1% gelatin-coated flasks. The K562 cell line was obtained from ATCC and maintained in RPMI/10% FCS. K562 aAPCs were generated by co-transduction of K562 cells with lentiviral vectors encoding full-length human CD80 and HLA-A*02:01/B2M/NY-ESO-1$_{157-165}$ or MART-1$_{26-35}$ single chain trimers (SCTs; gifts from Dr. David Baltimore, Caltech. K562 target cells were created by transduction with either SCT alone. K562 in vivo target cells were created by sequential transduction with a firefly luciferase lentiviral vector (a gift from Dr. Donald Kohn, UCLA) followed by either SCT. K562 transductants were FACS sorted prior to use. The U266 multiple myeloma cell line was a gift from Dr. John Chute (UCLA) and maintained in RPMI/10% FCS.

F. Artificial Thymic Organoid (ATO) Cultures

MS5-hDLL1 (or MS-5 or OP9-DL1, as noted) cells were harvested by trypsinization and resuspended in serum free ATO culture medium ("RB27") composed of RPMI 1640 (Corning, Manassas, VA), 4% B27 supplement (ThermoFisher Scientific, Grand Island, NY), 30 µM L-ascorbic acid 2-phosphate sesquimagnesium salt hydrate (Sigma-Aldrich, St. Louis, MO) reconstituted in PBS, 1% penicillin/streptomycin (Gemini Bio-Products, West Sacramento, CA), 1% Glutamax (ThermoFisher Scientific, Grand Island, NY), 5 ng/ml rhFLT3L and 5 ng/ml rhIL-7 (Peprotech, Rocky Hill, NJ). RB27 was made fresh weekly. 4% XenoFree B27 was substituted for B27 in the indicated experiments. Depending on the experiment, $1.5-6\times10^5$ MS5-hDLL1 cells were combined with $3\times10^2-1\times10^5$ purified CD34+CD3− cells (or other HSPC populations, as indicated) per ATO in 1.5 ml Eppendorf tubes and centrifuged at 300 g for 5 min. at 4° C. in a swinging bucket centrifuge. Supernatants were carefully removed and the cell pellet was resuspended by brief vortexing. For each ATO, a 0.4 µm Millicell transwell insert (EMD Millipore, Billerica, MA; Cat. PICMORG50) was placed in a 6-well plate containing 1 ml RB27 per well. To plate ATOs, inserts were taken out and rested on the edge of plate to drain excess medium. The cell slurry was adjusted to 5-8 µl per ATO, drawn up in with a 20 µl pipet tip and plated by forming a drop at the end of the pipet tip which was gently deposited onto the cell insert. The cell insert was placed back in the well containing 1 mL RB27. Medium was changed completely every 3-4 days by aspiration from around the cell insert followed by replacement with 1 ml with fresh RB27/cytokines. ATOs were cultured in this fashion for up to 20 weeks. At the indicated times, ATO cells were harvested by adding FACS buffer (PBS/0.5% bovine serum album/2 mM EDTA) to each well and briefly disaggregating the ATO by pipetting with a 1 ml "P1000" pipet, followed by passage through a 70 µm nylon strainer. In some experiments, single cell suspensions of MS5-hDLL1 cells were 7-irradiated at the indicated doses prior to use in ATOs.

G. T Cell Monolayer Co-Cultures

OP9-DL1 monolayer cultures were set up as previously described. Briefly, OP9-DL1 cells were seeded into 0.1% gelatin-coated 12 well plates 1-2 days prior to use to achieve 70-80% confluence. Medium was aspirated from monolayers and $1\times10^4-1.5\times10^4$ purified CD34+CD3− HSPCs were plated on the stromal monolayers in 2 ml of medium composed of MEMα, 20% FBS, 30 µM L-Ascorbic acid, 5 ng/ml rhFLT3L and 5 ng/ml rhIL-7. In some experiments, MS-5 or MS5-hDLL1 were substituted for OP9-DL1, and RB27 was substituted as the culture medium. Cells were transferred to new stromal cell monolayers every 4-5 days by harvesting cells, filtering through a 70 µm nylon strainer, and replating in fresh medium. When confluent, cells were split into multiple wells containing fresh stromal layers. Cultures were maintained for up to 10 weeks.

H. Lentiviral Vectors and Transduction

The full-length coding sequence of human DLL1 was cloned by RT-PCR from a human universal reference RNA set (Agilent Technologies, Santa Clara, CA) into the third generation lentiviral vector pCCL-c-MNDU3-X-IRES-eGFP (gift from Dr. Donald Kohn, UCLA). Human CD80 was similarly cloned into pCCL-c-MNDU3. The third generation lentiviral vector encoding the codon optimized α and β (Vb13.1) chains of a TCR specific for HLA-A*02:01/NY-ESO-1$_{157-165}$ (derived from the 1G4 TCR clone) is previously described, and was a gift from Dr. Antoni Ribas (UCLA). The codon-optimized HLA-A*02:01/MART-1$_{26-35}$ specific TCR (derived from the F5 TCR clone) was a gift from Dr. Donald Kohn (UCLA). Coding sequences for HLA-A*02:01 and HLA-A*02:01/B2M/NY− ESO-1$_{157-165}$ or HLA-A*02:01/B2M/MART-1$_{26-35}$ single chain trimers were a gift from Dr. David Baltimore (Caltech), and were sub-cloned into pCCL-c-MNDU3-X-IRES-mStrawberry. Packaging and concentration of lentiviral particles was performed as previously described. Briefly, 293T cells (ATCC) were co-transfected with a lentiviral vector plasmid, pCMV-AR8.9, and pCAGGS-VSVG using TransIT 293T (Mirus Bio, Madison, WI) for 17 hours followed by treatment with 20 mM sodium butyrate for 8 hours, followed by generation of cell supernatants in serum-free UltraCulture for 48 hours. Supernatants were concentrated by tangential flow filtration using Amicon Ultra-15 100K filters (EMD Millipore, Billerica, MA) at 4000×g for 40 minutes at 4° C. and stored as aliquots at −80 C. For HSPC transduction, $1\times10^5-1\times10^6$ FACS-sorted CD34+CD3− HSPCs were plated in 6-well non-treated plates coated with 20 µg/ml Retronectin (Clontech, Mountain View, CA) in 1 ml X-VIVO-15 (Lonza, Basel, Switzerland) supplemented with 50 ng/ml of recombinant human SCF, FLT3L, and TPO, and 10 ng/ml IL-3 (Peprotech, Rocky Hill, NJ) for 12-18 h, after which concentrated lentiviral supernatant was added at a multiplicity of infection (MOI) of 100. Mock-transduced cells were cultured in identical conditions without addition of vector. Cells were harvested 24 hours post-transduction, washed, and seeded into ATOs. For transduction of peripheral blood T cells, CD8+ T cells from healthy donors were isolated by magnetic negative selection using the CD8+ T cell Isolation Kit (Miltenyi) and activated/expanded in AIM V/5% human AB with anti-CD3/CD28 beads (ThermoFisher Scientific) and 20 ng/ml IL-2 for 4 days prior to transduction, as previously described. Transduced T cells were subsequently expanded in IL-2 (20 ng/ml) prior to use.

I. Immunohistochemistry

For hematoxylin and eosin (H&E) images, ATOs were embedded in Histogel (ThermoFisher Scientific, Grand Island, NY) and fixed overnight in 10% neutral-buffered formalin (ThermoFisher Scientific, Grand Island, NY). 5 µm sections and H&E staining were performed by the UCLA Translational Pathology Core Laboratory (TPCL). For immunofluorescence imaging, ATOs were isolated by cutting the culture insert around each ATO with a scalpel, followed by embedding the membrane and ATO in Tissue-Tek OCT (VWR Radnor, PA) and freezing on dry ice. 5 µm frozen sections were fixed in 10% neutral-buffered formalin and stained with anti-CD3 (clone UCHT1; Biolegend, San Diego, CA) at a 1:50 dilution overnight at 4° C. followed by incubation with AlexaFluor 594-conjugated anti-mouse IgG (H+L) (Jackson ImmunoResearch, West Grove, PA) at room temperature. H&E and immunofluorescence images were acquired on a Zeiss Aziolmager M2 with AxioCam MRM and AxioVision software (Zeiss, Jena, Germany).

J. T Cell Cytokine Assays

Mature CD8SP or CD4SP cells from ATOs were isolated by magnetic negative selection using the CD8+ or CD4+ Isolation Kits (Miltenyi) and sorted by FACS to further deplete CD45RO+ cells (containing immature naïve T cells and CD4ISP precursors). Purified T cell populations were plated in 96-well U-bottom plates in 200 μl AIM V (ThermoFisher Scientific, Grand Island, NY) with 5% human AB serum (Gemini Bio-Products, West Sacramento, CA). PMA/ionomycin/protein transport inhibitor cocktail or control protein transport inhibitor cocktail (eBioscience, San Diego, CA) were added to each well and incubated for 6 h. Cells were stained for CD3, CD4, and CD8 (Biolegend, San Diego, CA) and UV455 fixable viability dye (eBioscience, San Diego, CA) prior to fixation and permeabilization with an intracellular staining buffer kit (eBioscience, San Diego, CA) and intracellular staining with antibodies against IFNγ, TNFα, IL-2, IL-4, or IL-17A (Biolegend, San Diego, CA).

K. T Cell Activation and Proliferation Assays

For CFSE proliferation assays, ATO-derived CD8SP or CD4SP T cells were isolated by negative selection MACS as above (with further FACS purification of CD4SP T cells described above) and labeled with 5 μM CFSE (Biolegend, San Diego, CA) per the manufacturer's protocol. Labeled cells were incubated with anti-CD3/CD28 beads (ThermoFisher Scientific, Grand Island, NY) in AIM V supplemented with 5% AB serum and 20 ng/ml rhIL-2 (Peprotech, Rocky Hill, NJ), and costained for CD25 or 4-1BB (Biolegend, San Diego, CA) and analyzed by flow cytometry on day 5. In some experiments CFSE was substituted for CellTrace Violet (CTV; ThermoFisher) with labeling per the manufacturer's protocol. For in vitro cell expansion assays, $5 \times 10^3$-$1 \times 10^4$ ATO-derived CD8SP or CD4SP T cells isolated as above were plated in 96-well U-bottom plates in 200 μl, and activated/expanded with anti-CD3/28 beads and either 20 ng/mL IL-2 or 5 ng/mL IL-7 and 5 ng/mL IL-15 (Peprotech). Beads were removed on day 4, and fresh medium and cytokines were added every 2-3 days with replating into larger wells as needed. Cells were counted weekly with a hemacytometer. In some experiments, cells were restimulated with fresh anti-CD3/CD28 beads on day 14.

L. Artificial APC (aAPC) CTL Priming Assay $1 \times 10^5$ total ATO-derived CD8SP T cells were isolated from week 6 TCR-transduced ATOs by MACS, as above, and co-cultured with K562-derived aAPCs expressing CD80 and single chain trimers of either HLA-A*02:01/B2M/NY-ESO-$1_{157-165}$ or HLA-A*02:01/B2M/MART-$1_{26-35}$ or parental K562 cells in 96-well U-bottom plates in 200 μl AIM V/5% human AB serum at a 4:1 T cell:K562 ratio for 6 h. CD170a-APC antibody (Biolegend, San Diego, CA) was added to wells at a 1:50 final dilution together with a protein transport inhibitor cocktail (eBioscience, San Diego, CA) for the duration of culture. Cells were then stained for surface markers, fixed, permeabilized, and intracellularly stained for cytokines as described above.

M. TCR Vβ Phenotypic Analysis

Total cells from week 7 ATOs or postnatal thymi were stained for CD3, CD4, CD8, and TCRγδ, in conjunction with the IOTest Beta Mark TCR V Kit (Beckman Coulter, Indianapolis, IN). CD3+TCRγδ-CD8+CD4− cells were gated for Vβ analysis, and Vβ family usage was determined by percent FITC+, PE+, or FITC+PE+ cells, representing 3 different Vβ antibodies per tube. For Vβ analysis of TCR-transduced ATOs, total cells from week 6-7 ATOs were additionally labeled with an APC-conjugated HLA-A*02:01/NY-ESO-$1_{157-165}$ tetramer (MBL International, Woburn, MA) for 10 minutes prior to surface antibody staining, and cells were gated on CD3+TCRγδ-tetramer+CD8+CD4− for Vβ analysis.

N. TCR Repertoire Sequencing

Total RNA was purified from 40,000-200,000 ATO or thymic CD8SP, or PB CD45RO− CCR7+ naïve CD8+ T cells by FACS using the RNeasy Micro kit (Qiagen) according to manufacturer's instructions. RNA concentration and quality was determined using the Agilent RNA 6000 Nano chip. A targeted cDNA library comprising rearranged TCR variable genes was prepared by 5'-RACE using the SMARTer PCR cDNA Synthesis kit (Clontech) with modifications as follow. First strand cDNA was prepared from 3.5-500 ng total RNA using the manufacturer's protocol but substituting a poly-dT primer (5'-T30VN-3'). Double-stranded TCRα and TCRβ cDNA libraries were prepared separately by semi-nested PCR using the Advantage 2 PCR kit (Clontech). Initial amplification of TCRα cDNA used 0.5 μL first-strand reaction (=2.5 μL of 1:5 dilution in TE) with the manufacturer's forward Universal Primer Mix and a pair of reverse primers that bound TRAC (5'-GCCACAGCACTGTTGCTCTTGAAGTCC-3' (SEQ ID NO. 1)). Semi-nested amplification of TCRα cDNA was conducted with manufacturer's forward Primer IIA and barcoded reverse primers that bound TRAC (5'-X5GGCAGGGTCAGGGTTCTGGAT-3' (SEQ ID NO. 2), where X5 is a 5-nt sample-specific barcode enabling sample pooling prior to deep-sequencing). Amplification of TCRβ cDNA was similar but initial amplification was performed with a reverse primer that bound TRBC (5'-CCACCAGCTCAGCTCCACGTG-3' (SEQ ID NO. 3)) and semi-nested amplification was conducted with barcoded primers that bound TRBC (5'-X5GGGAACACSTTKTTCAGGTCCTC-3' (SEQ ID NO. 4)). TCRα and TCRβ cDNA preparations were cleaned up using the DNA Clean and Concentrator-5 kit (Zymo Research). TCRα and TCRβ cDNA preparations from up to ten samples were pooled prior to Illumina adaptor ligation and 2×150-bp paired-end sequencing on the MiSeq sequencer (Illumina). After de-multiplexing using sample-specific barcodes, reads were aligned to a custom reference database comprising all possible combinations of human TRAV, TRAJ, TRBV, TRBD, and TRBJ sequences downloaded from the IMGT database using BLAT. Best BLAT hits were identified with the pslCDnaFilter utility of the BLAT suite using '-maxAligns=1–ignoreIntrons' options and clonotype frequencies were calculated using custom Perl scripts.

O. In Vitro Cytotoxicity Assays

CD8SP T cells were isolated from ATOs by mechanical disruption and magnetic negative selection as described above. T cells were activated in 96 well round-bottom plated in AIM V/5% human AB serum with anti-CD3/CD28 beads (ThermoFisher Scientific) and 20 ng/ml IL-2 for 36 h. For extended expansions, cells were further cultured in IL-2 for up to 14 days. For cytotoxicity assays, 2-fold serial dilutions of T cells were plated per well in 96 well round bottom plates starting at $1 \times 10^5$ cells per well in AIM V/5% human AB serum. K562 target cells transduced with HLA-A*02:01/NY-ESO-$1_{157-165}$ or HLA−A*02:01/MART-$1_{26-35}$ single chain trimers, or HLA-A*02:01+ U266 that endogenously express NY-ESO-1 were plated at $5 \times 10^4$ cells per well. Apoptotic cell death of target cells was quantified by Annexin V/DAPI staining at 9 h. Percent antigen-specific T cells was determined by tetramer staining, and used to retrospectively calculate the effector:target (E:T) ratio of each well. T-cell specific cell death was calculated by subtracting percent Annexin V+ target cells in wells receiving no T cells from wells that received T cells.

In Vivo Tumor Assays

All animal experiments were conducted under a protocol approved by the UCLA Chancellor's Animal Research Committee. 4-6 week old NOD.Cg-Prkdcscid Il2rgtm1Wjl/SzJ (NSG) mice (Jackson Laboratory, Bar Harbor, Maine) were subcutaneously implanted with $2\times10^5$ K562 target cells transduced with HLA- A*02:01/NY-ESO-$1_{157-165}$ or MART-$1_{26-35}$ single chain trimers and firefly luciferase (as described in above). Mice were imaged for tumor bioluminescence on day 3 by intraperitoneal injection of luciferin. ATO-derived CD8SP T cells were isolated and activated/expanded as above for 14 days. $5.7\times10^6$ (containing $4.5\times10^6$ antigen-specific T cells as determined by tetramer staining on the day of injection) were injected via the retroorbital vein on day 3 following tumor implantation. Injection of PBS into control mice was also performed. Tumor bioluminescence was repeated every 3-4 days for at least 21 days, after which mice were sacrificed based on disease burden criteria.

P. Flow Cytometry and Antibodies

All flow cytometry stains were performed in PBS/0.5% BSA/2 mM EDTA for 30 min on ice. FcX (Biolegend, San Diego, CA) was added to all samples for 5 min prior to antibody staining. For tetramer co-staining, PE or APC-conjugated HLA-A*02:01/NY-ESO-$1_{157-165}$ or HLA-A*02:01/MART-$1_{26-35}$ tetramers (MBL International, Woburn, MA) were added to cells at a 1:50 final dilution at room temperature for 10 minutes prior to addition of antibodies for an additional 20 minutes on ice. DAPI was added to all samples prior to analysis. Analysis was performed on an LSRII Fortessa, and FACS on an ARIA or ARIA-H instrument (BD Biosciences, San Jose, CA) at the UCLA Broad Stem Cell Research Center Flow Cytometry Core. For all analyses DAPI+ cells were gated out, and single cells were gated based on FSC-H vs. FSC-W and SSC-H vs. SSC-W. Antibody clones used for surface and intracellular staining were obtained from Biolegend (San Diego, CA): CD1a (H1149), CD3 (UCHT1), CD4 (RPA-T4), CD5 (UCHT2), CD8 (SK1), CD10 (6H6), CD14 (M5E2), CD19 (HIB19), CD24 (ML5), CD25 (BC96), CD27 (0323), CD28 (CD28.2), CD31 (WM59), CD34 (581), CD38 (HIT2), CD45 (HI30), CD45RA (HI100), CD45RO (UCHL1), CD56 (HCD56), CD107a (H4A3), CD127 (A019D5), CD235a (H1264), CCR7 (G043H7), HLA-A2 (BB7.2), interferon γ (4S.B3), IL-2 (MQ1-17H12), IL-4 (MP4-25D2), IL-17A (BL168), TCRαβ (IP26), TCRγδ (B1), TNFα (Mab11), Vβ13.1 (H131), human lineage cocktail (CD3, CD14, CD19, CD20, CD56); and BD Biosciences (San Jose, CA): CD7 (M-T701), and CD62L (DREG-56).

Example 4: Different Stromal Cells can be Used in the ATO Model System

Figure 28A:
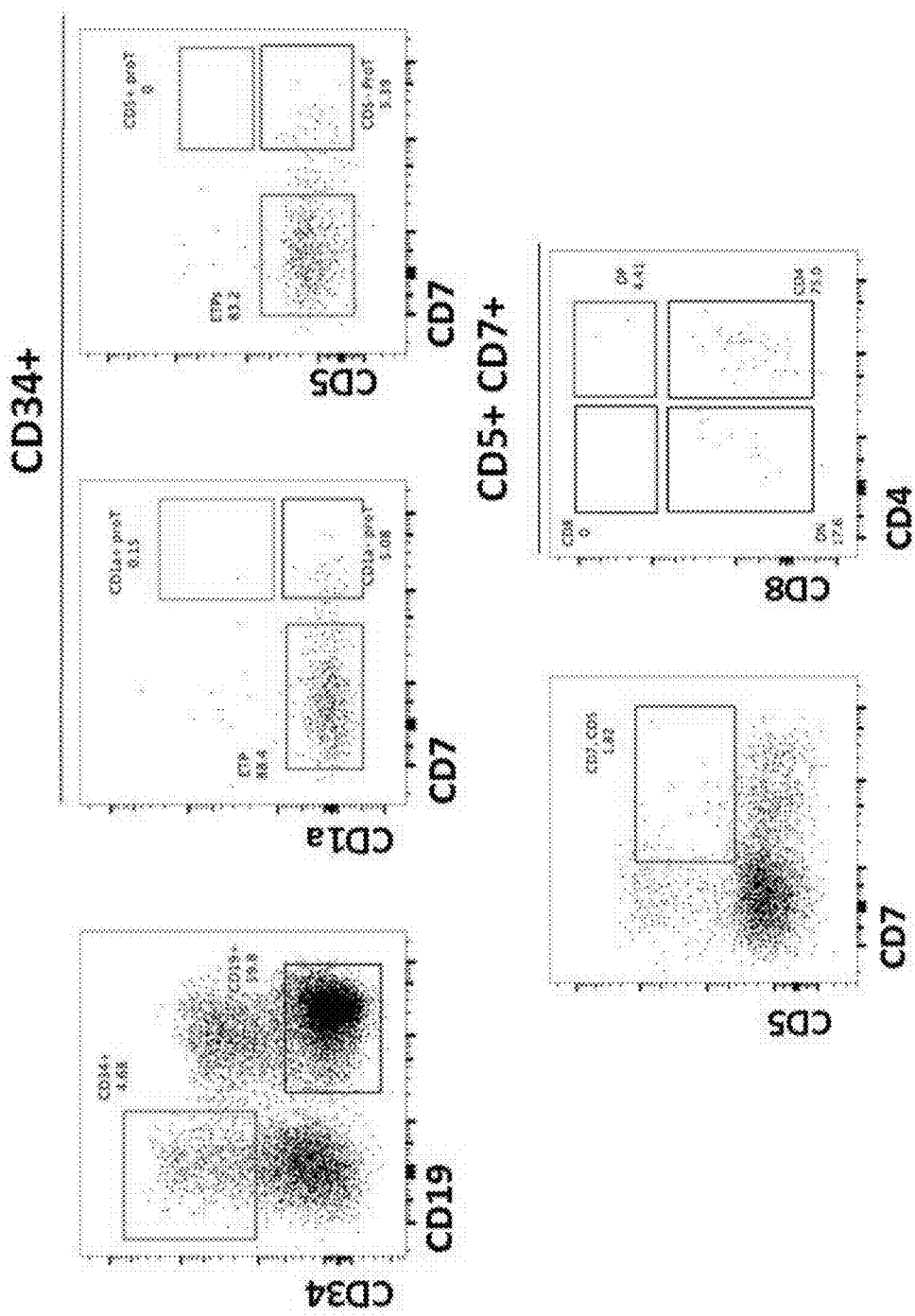
FIG. 28A-C: The unmodified human stromal line HS27a does not support T cell differentiation. A human stroma cell line (HS27a) was used in the ATO system without vector-mediated notch ligand expression. CD34+ HSPC from three different cord blood samples were tested: (a) E37, (b) E43, (c) E68. At week 4, none of the cord blood donors could generate CD5+CD7+ T cell committed cells in the absence of Notch signaling. Data shown are gated at CD45+CD56−CD14− unless otherwise shown.
Figure 28B:
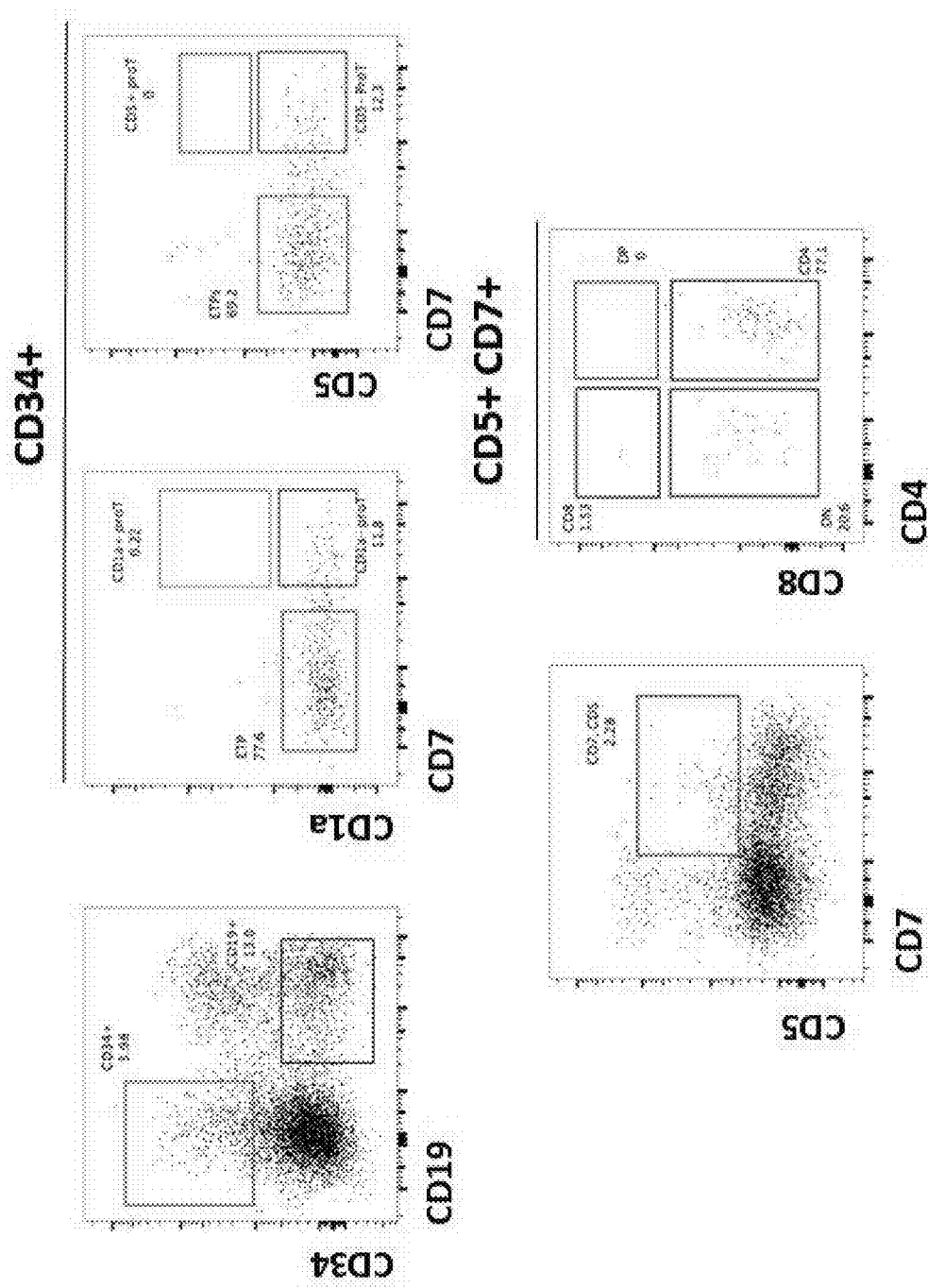
Figure 28C:
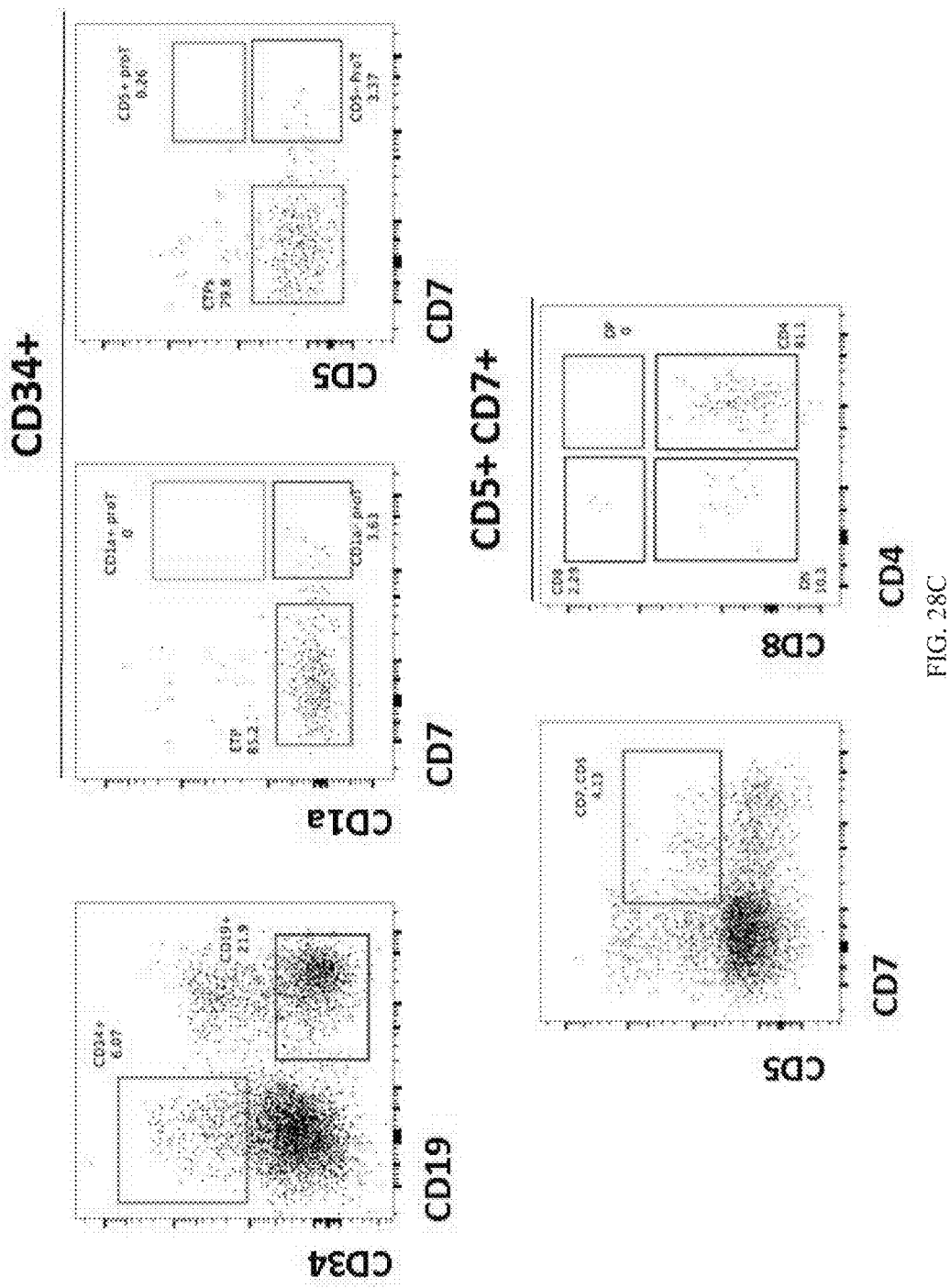
Figure 29A:
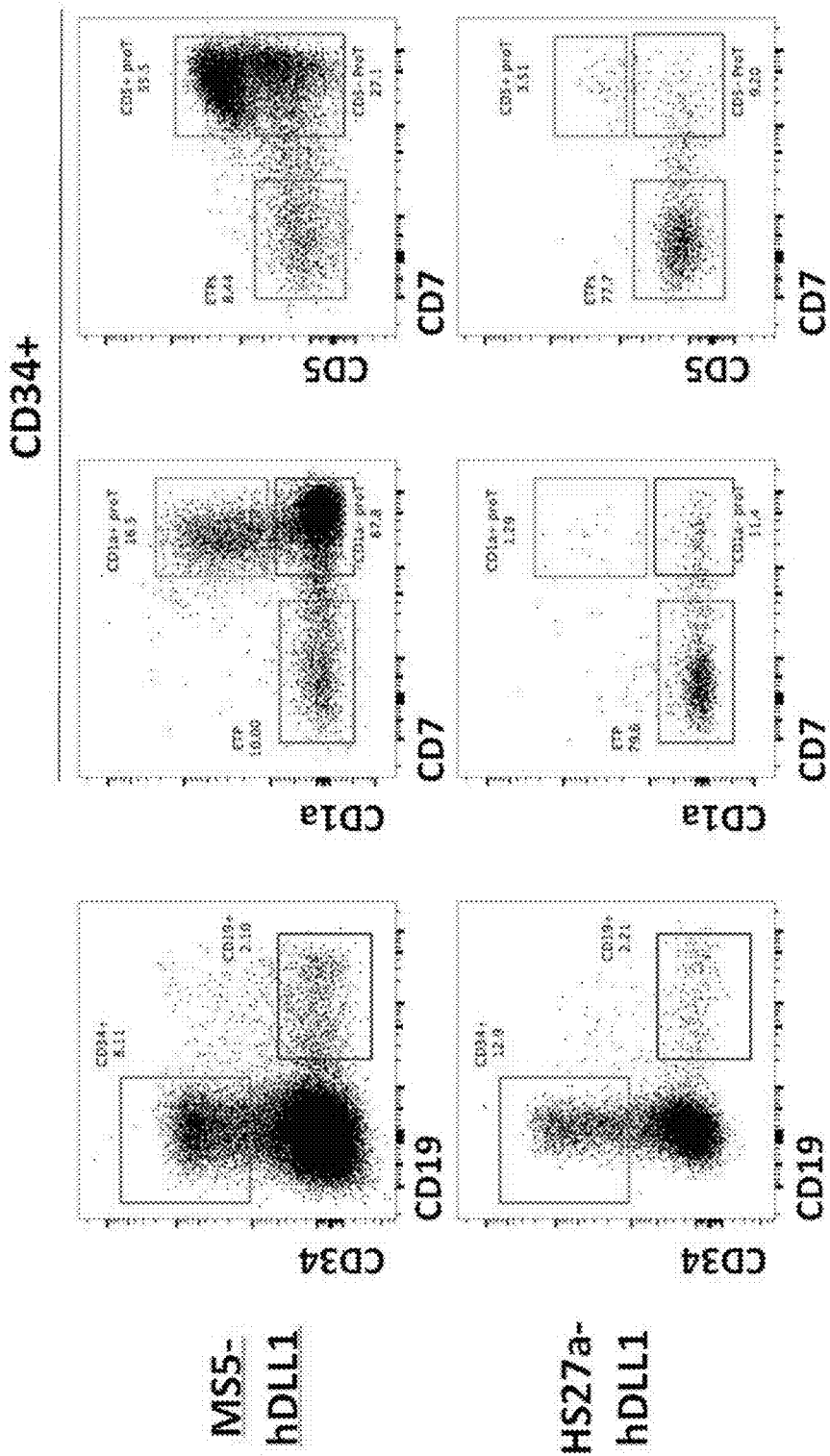
FIG. 29A-F: Notch ligand expression in the human stromal line HS27a can support T cell differentiation in ATOs. Shown is data from ATOs made with HS27a engineered via lentiviral transduction to express hDLL1. CD34+ HSPCs from the same three cord blood samples shown in FIG. 28: (a,b) E37, (c,d) E43, and (e,f) E68. Data using HS27a-hDLL1 ATOs are compared to data obtained using the MS5-hDLL1 stroma as a positive control. At week 4, all three of the cord blood donors generated CD5+CD7+ T cell committed cells in both HS27a-hDDL1 and MS5-hDLL1 ATOs. The data shown are gated at CD45+CD56−CD14− unless otherwise shown.
Figure 29B:
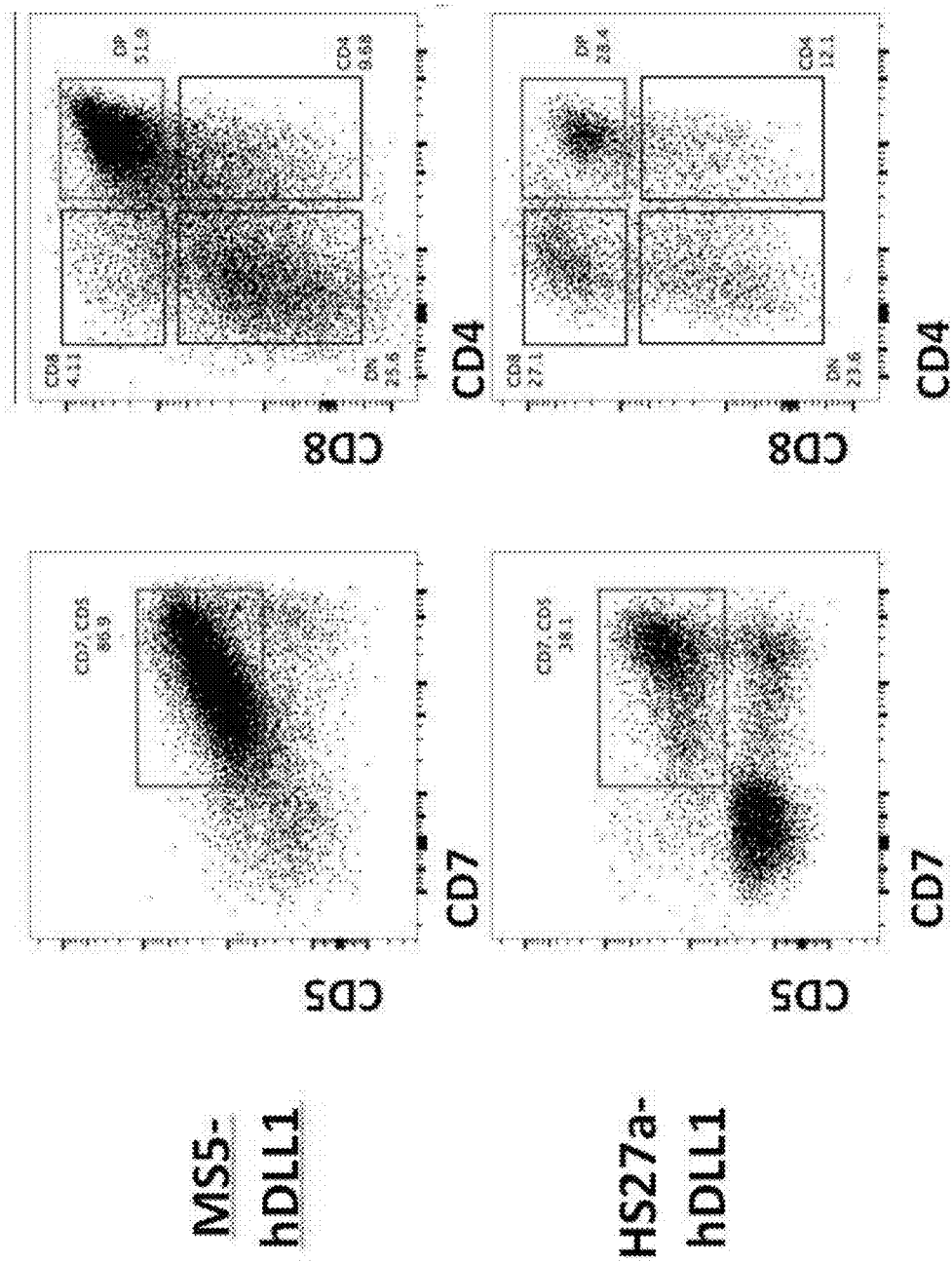
Figure 29C:
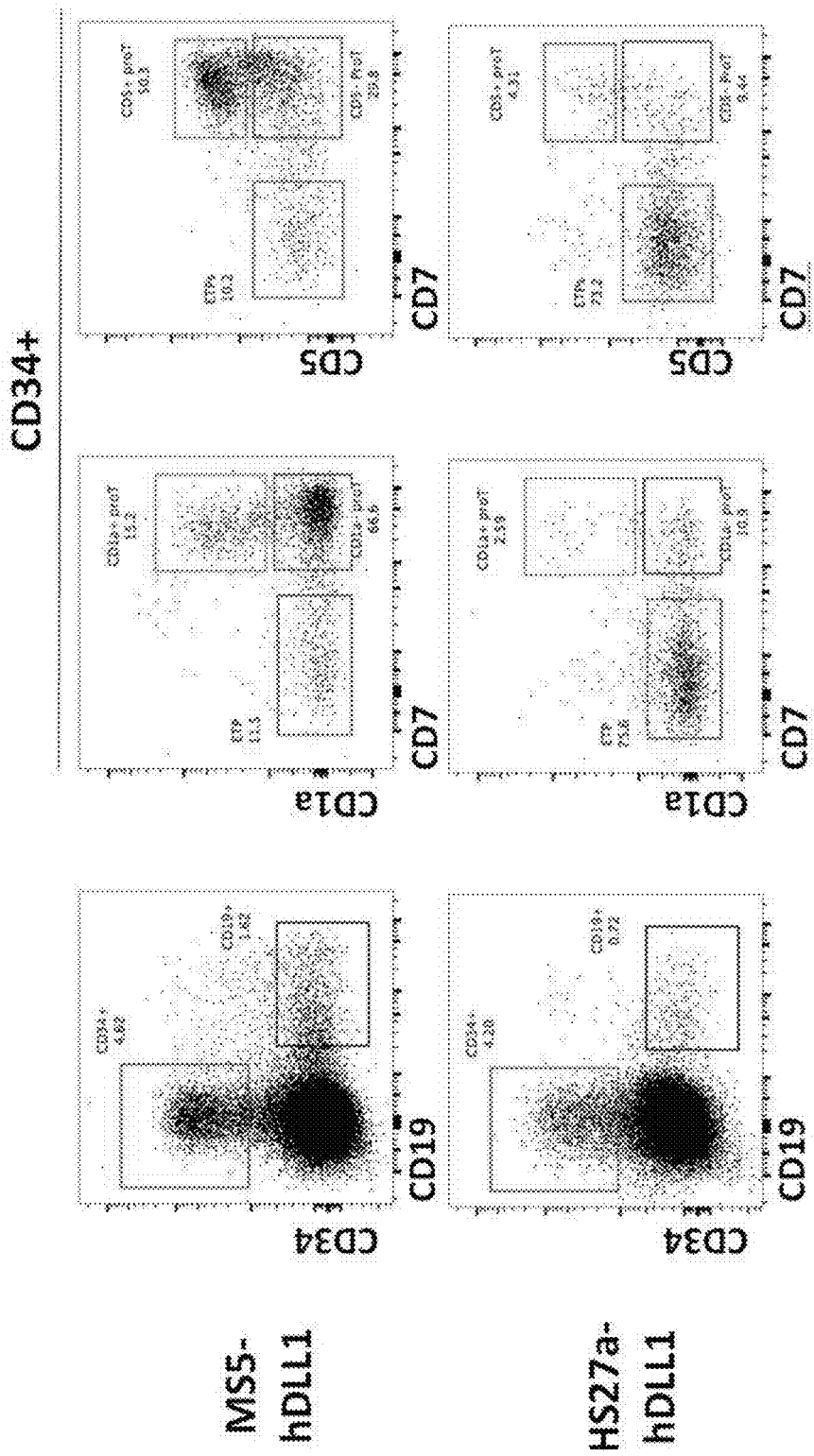
Figure 29D:
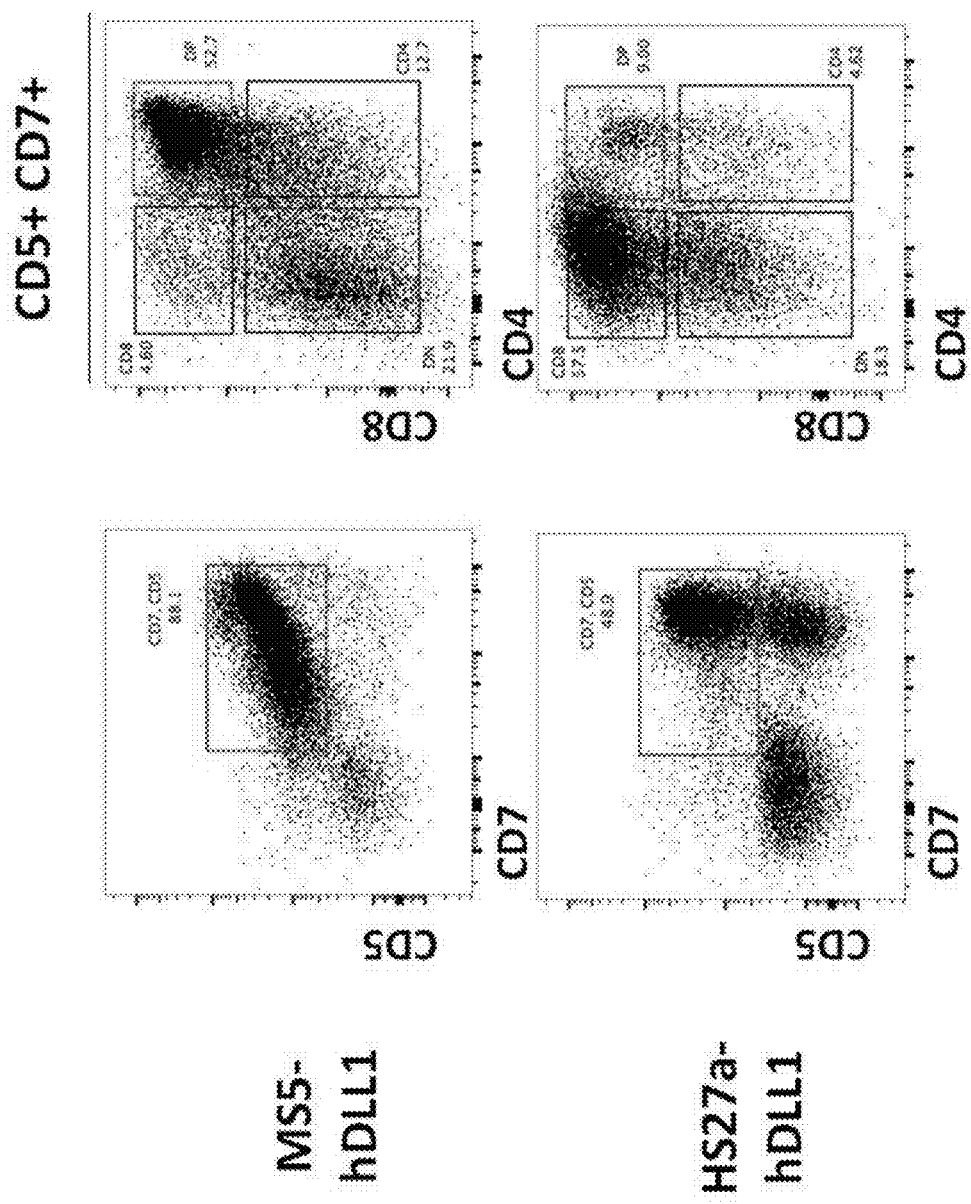
Figure 29E:
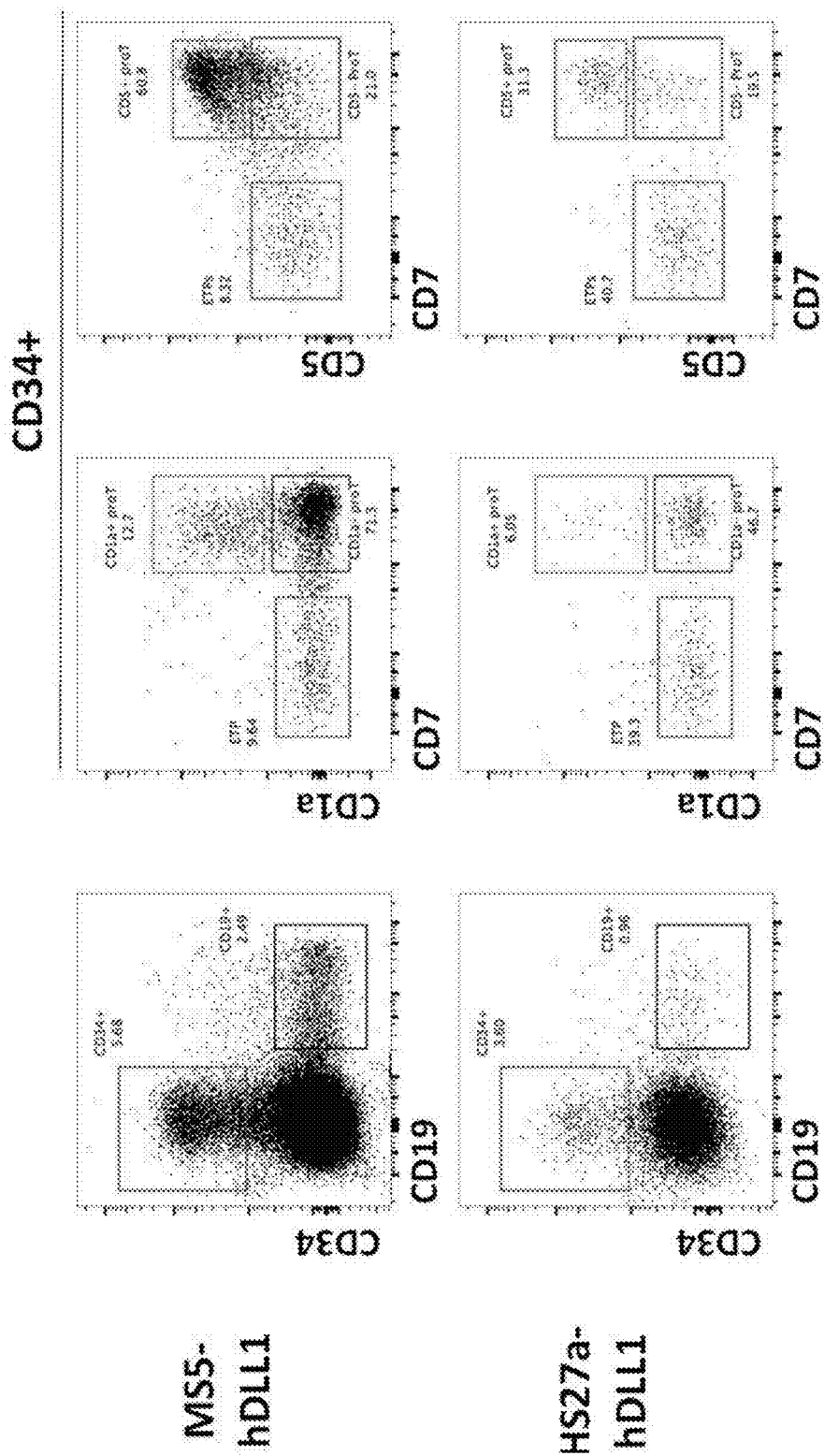
Figure 29F:
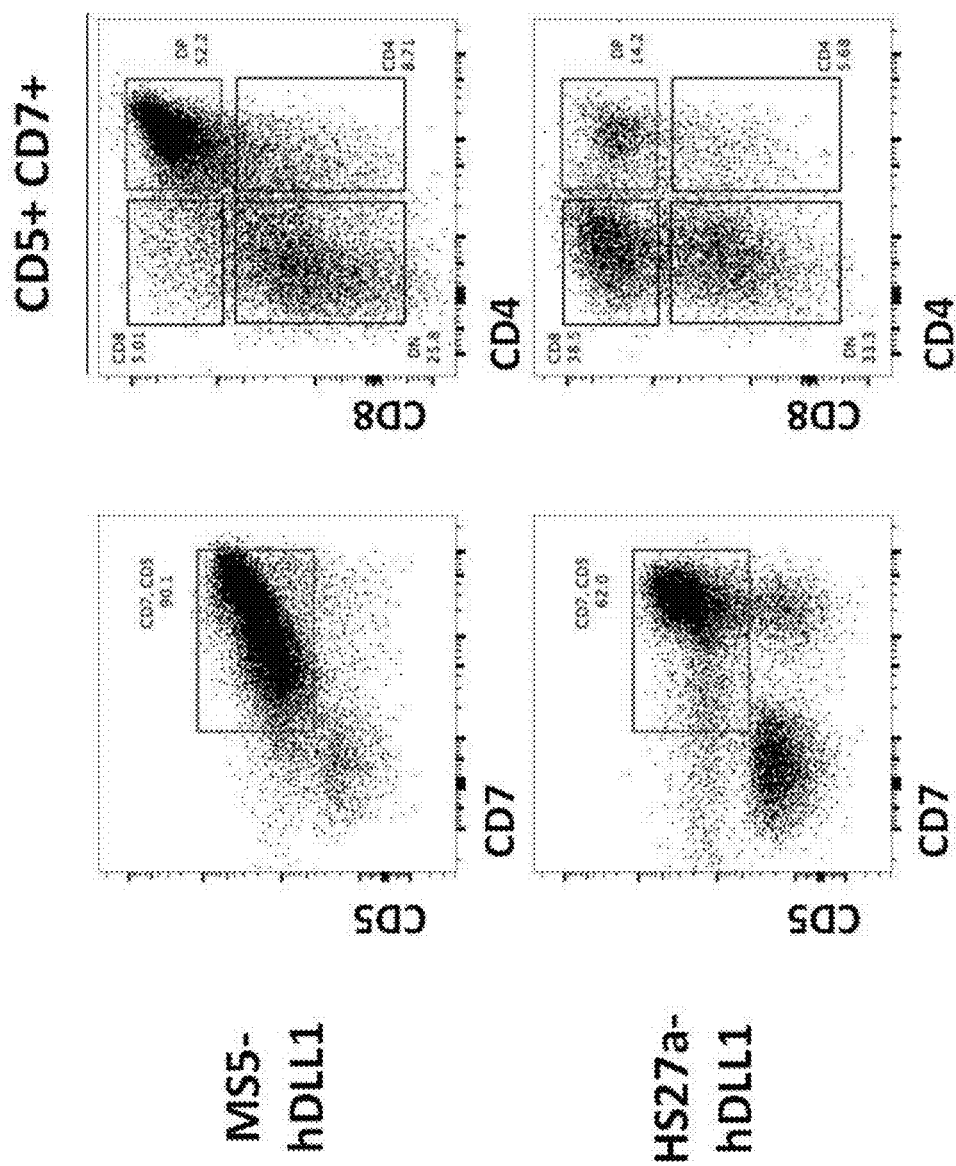
Figure 30:
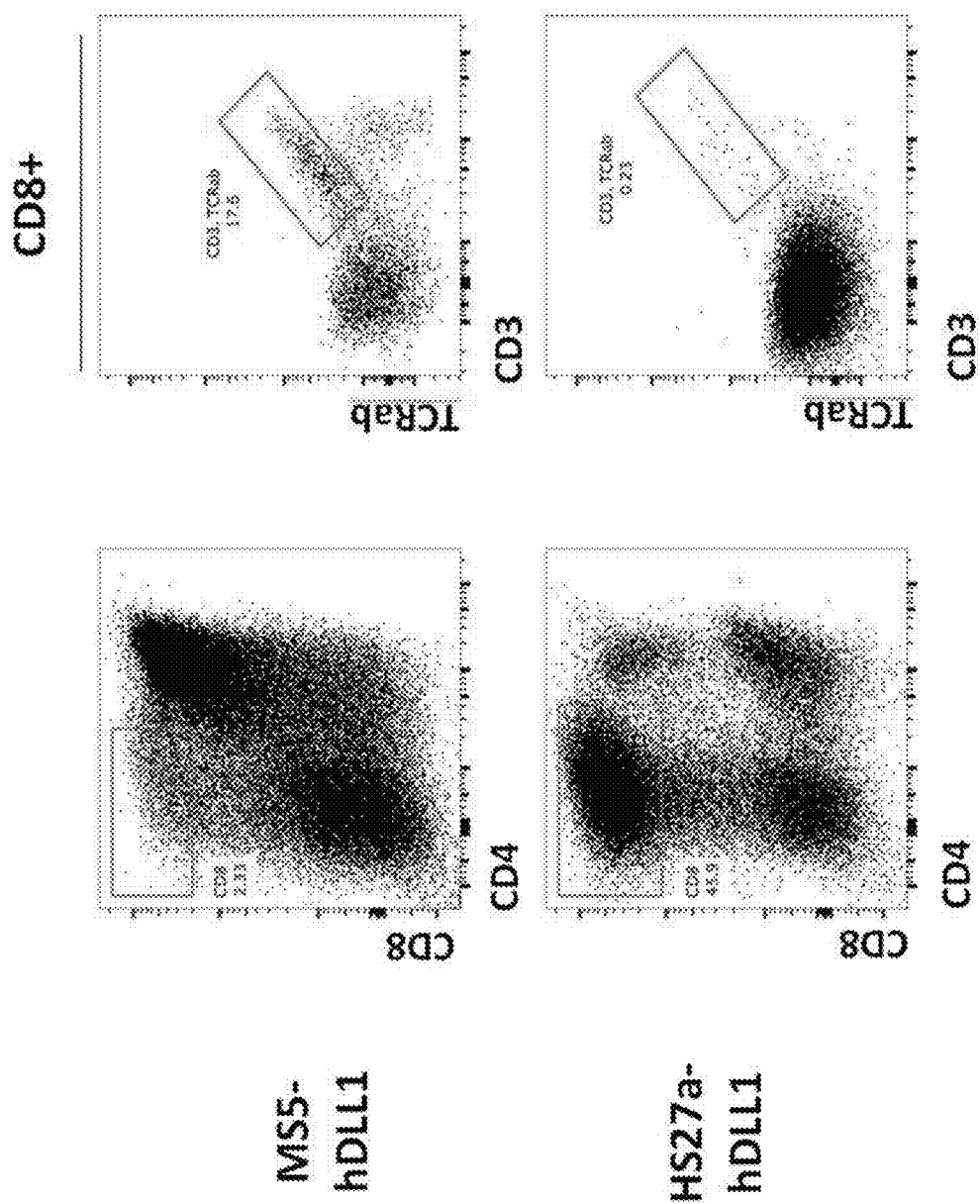
FIG. 30: The majority of the CD8+ cells generated in 4 week HS27a-DLL1 ATOs do not express CD3 or TCRab. Shown are data comparing from MS5-hDLL1 ATOs and HS27a-DLL1 ATOs.
Figure 31A:
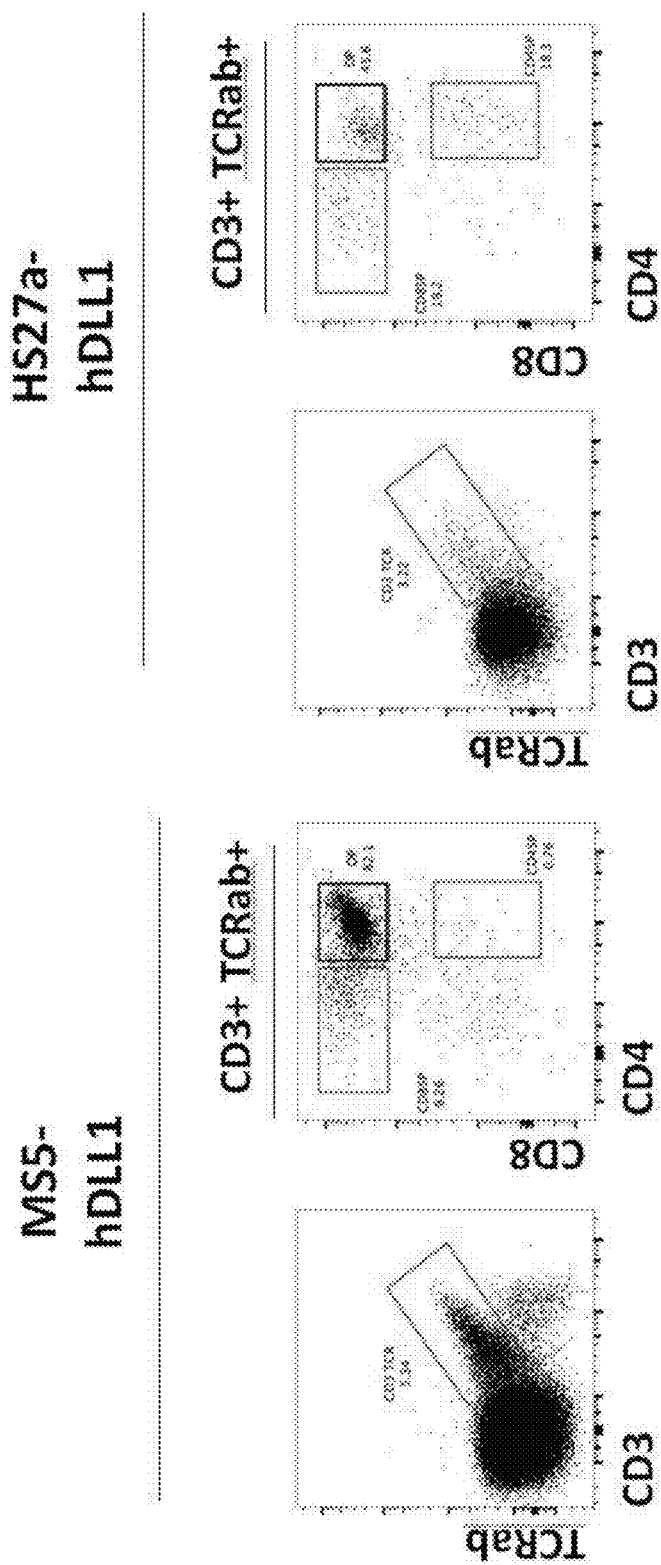
FIG. 31A-C: HS27a-hDLL1 ATOs can support the differentiation of mature T cells. T cell differentiation in MS5-hDLL1 ATOs and HS27a-hDLL1 ATOs (at four weeks) is shown using three different cord blood populations (a) E37, (b) E43, (c) E68. Data are gated at CD45+CD56−CD14− with additional CD3+TCRab gating in right panels.
Figure 31B:
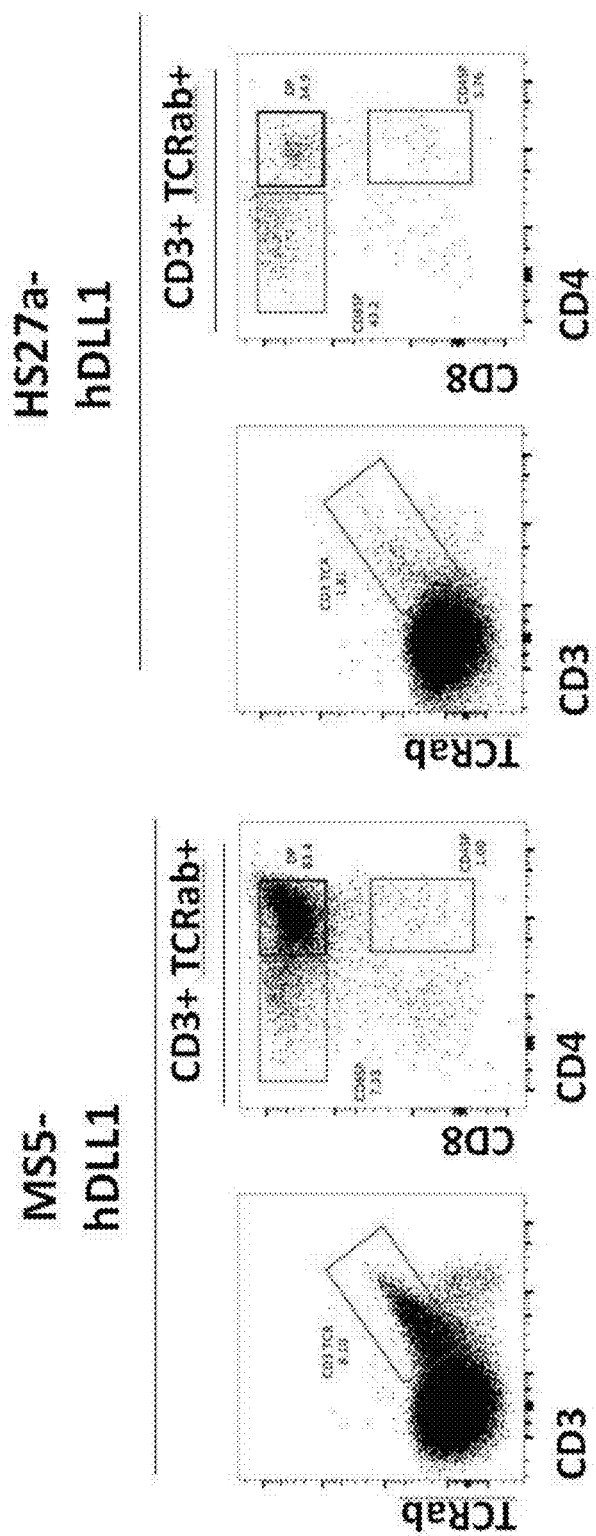
Figure 31C:
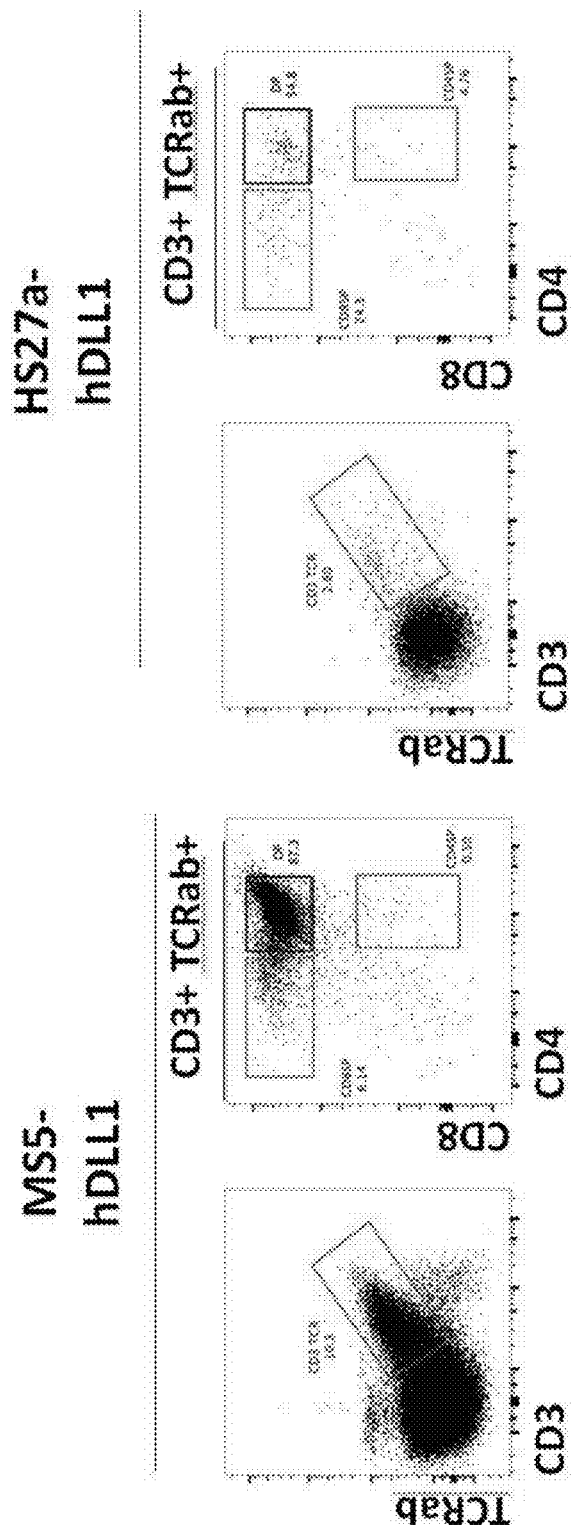

In order for the ATO system to be more translational, other stromal cell lines were tested for their ability to replace MS5-hDLL1 which are from murine origin. HS27a cells are a human bone marrow cell line and a great candidate since that secrete low levels of growth factors. A HS27a cell line expressing a Notch ligand (hDLL1) was generated by transducing the HS27a cells with hDLL1. Cells expressing high levels of hDLL1 were purified by FACS and expanded. In the absence of Notch signaling, the HS27a cells in the ATO system were unable to support T cell differentiation (FIG. 28A-C). It was found that HS27a, in addition to MS5 stroma cells were able to support T cell differentiation in the ATO system in three different cord blood sample preparations FIG. 29A-C. As shown in FIG. 30, the majority of the cell in the robust population of CD8+ cells seen in HS27a-DLL1 ATOs are not conventional CD8SP cells, since the do not express CD3 and TCRab. The use of maturation markers shows that HS27a-hDLL1 stromal cells can support the differentiation of mature T cells with the generation of TCRab+CD3+ CD8SP and CD4SP cells from three different cord blood preparations (FIG. 31A-C). The efficiency is however lower than in MS5-hDLL1 ATOs.

Figure 32A:
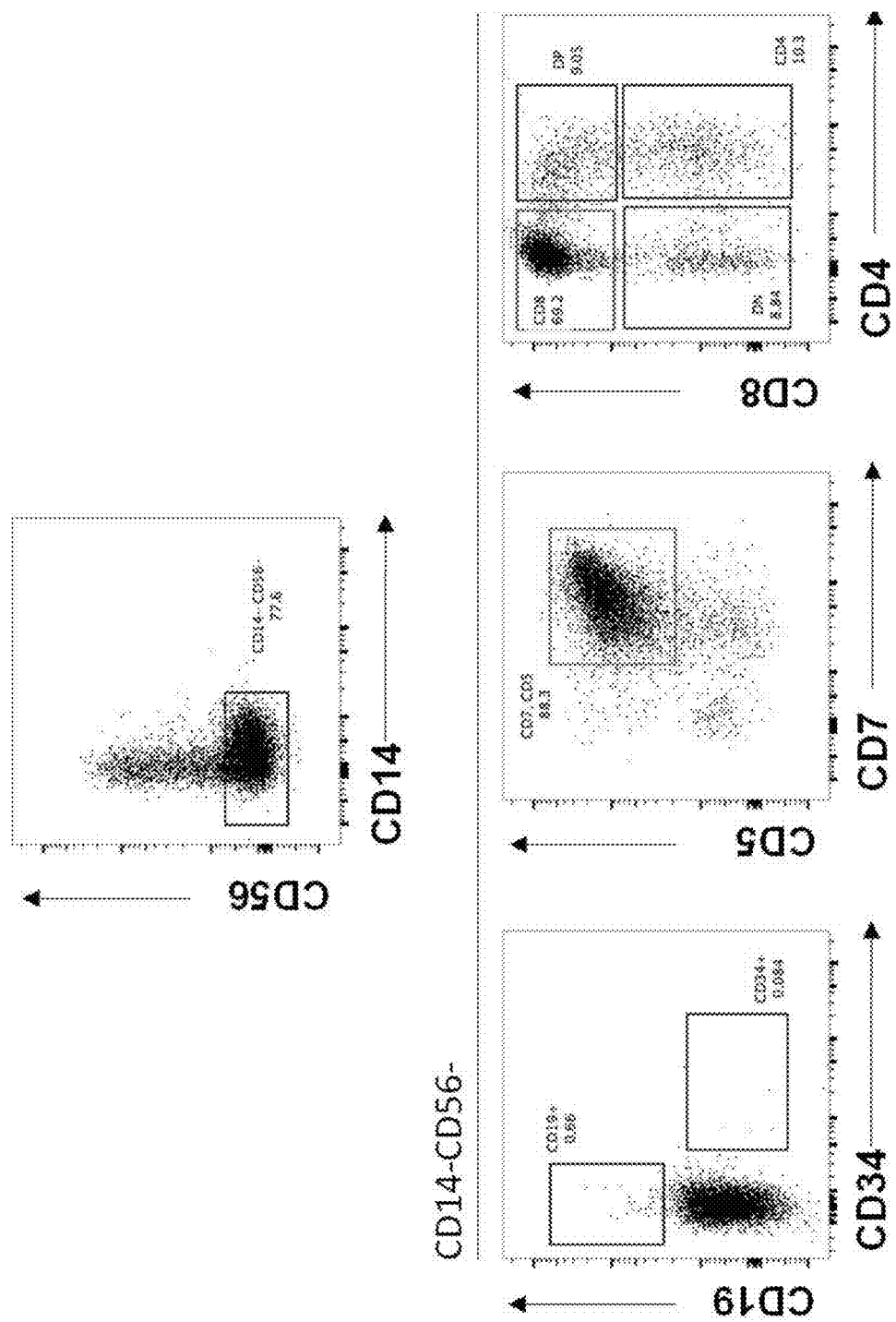
FIG. 32A-B: T-cell differentiation from human embryonic mesoderm progenitors (hEMP) cells (generated from hESC) in ATOs at week 5. Shown in (a) are CD56−CD14− gated T cell populations. Shown in (b) are CD56−CD14− gated cells with additional gating as shown (bottom row).
Figure 32B:
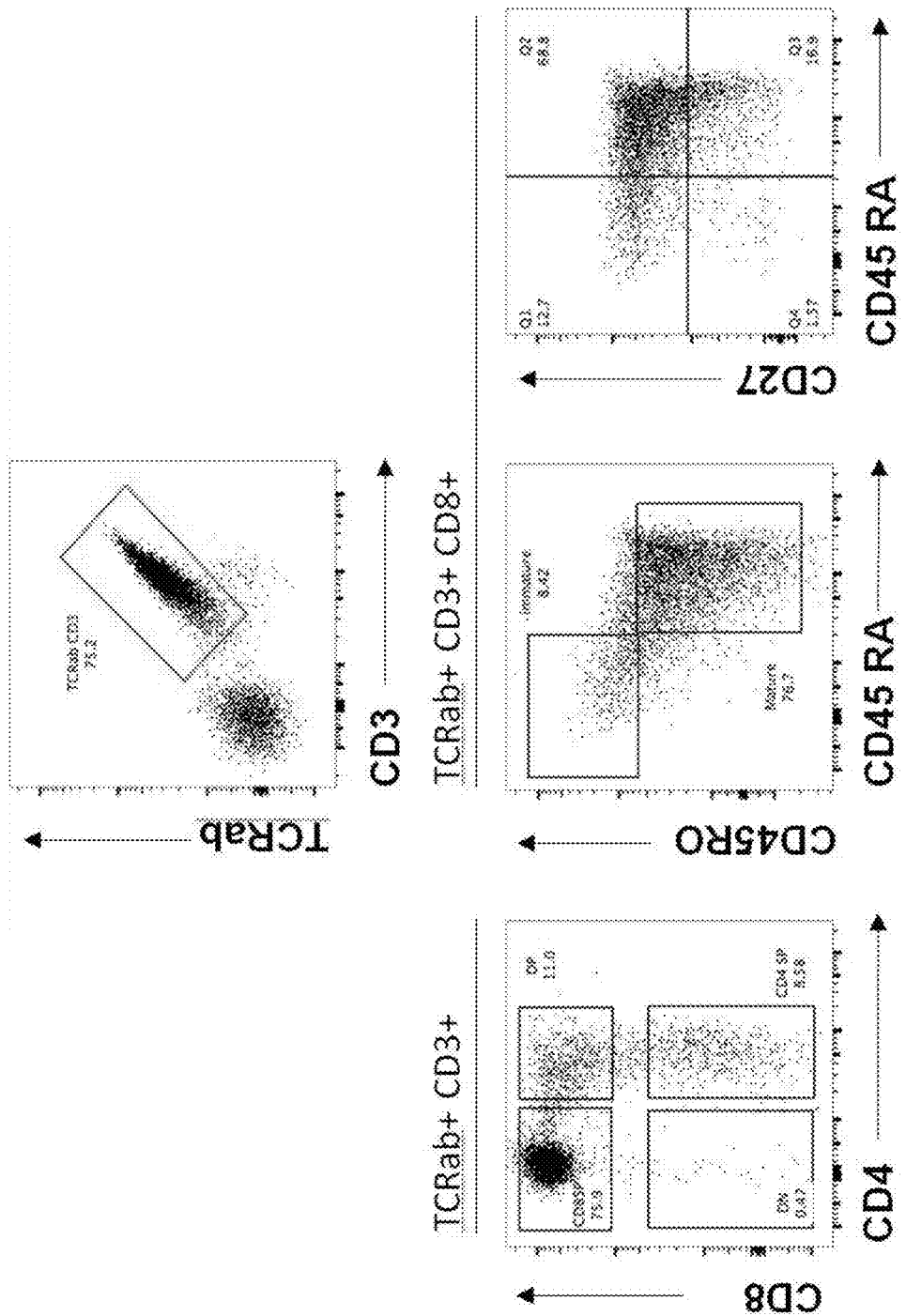
Figure 33A:
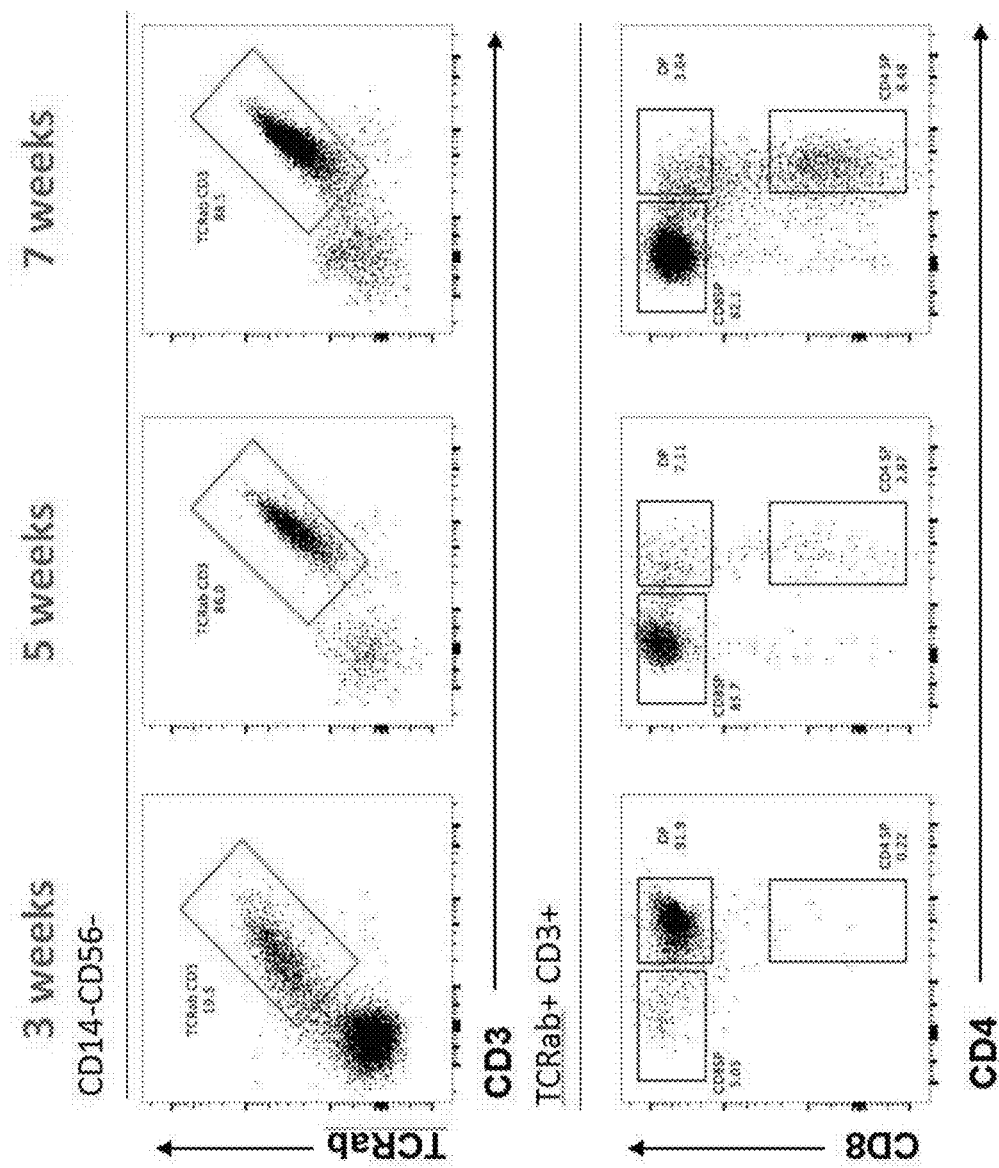
FIG. 33A-B: Kinetics of T-cell differentiation from hEMP in ATOs. Shown in (a) are populations gated as shown at 3, 5, and 7 weeks. Shown in (b) are further analyses of differentiation at 7 weeks showing that CD3+TCRab cells are CD8ab+.
Figure 33B:
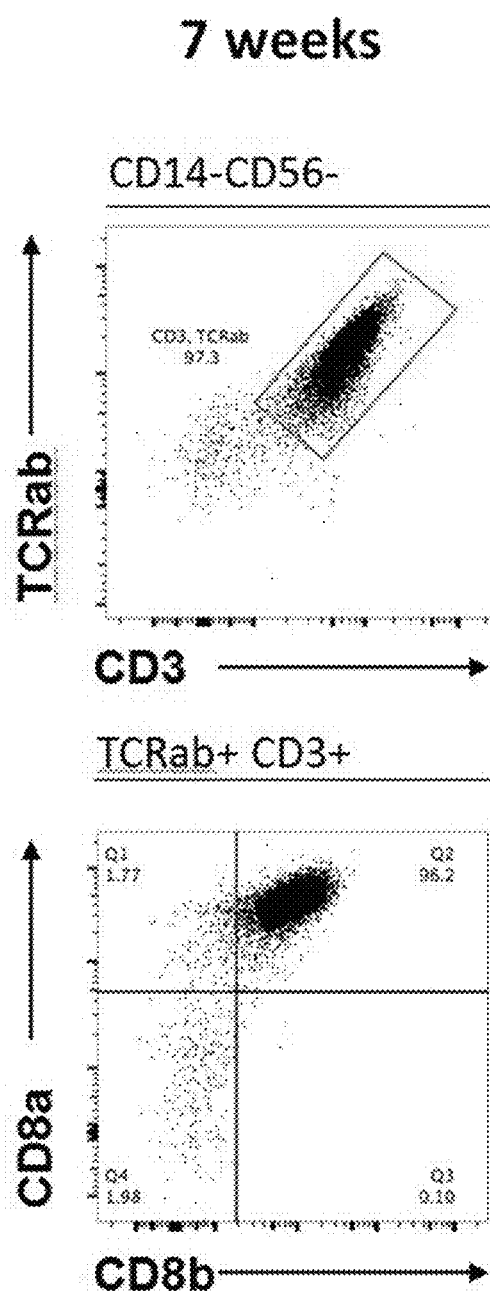
Figure 34A:
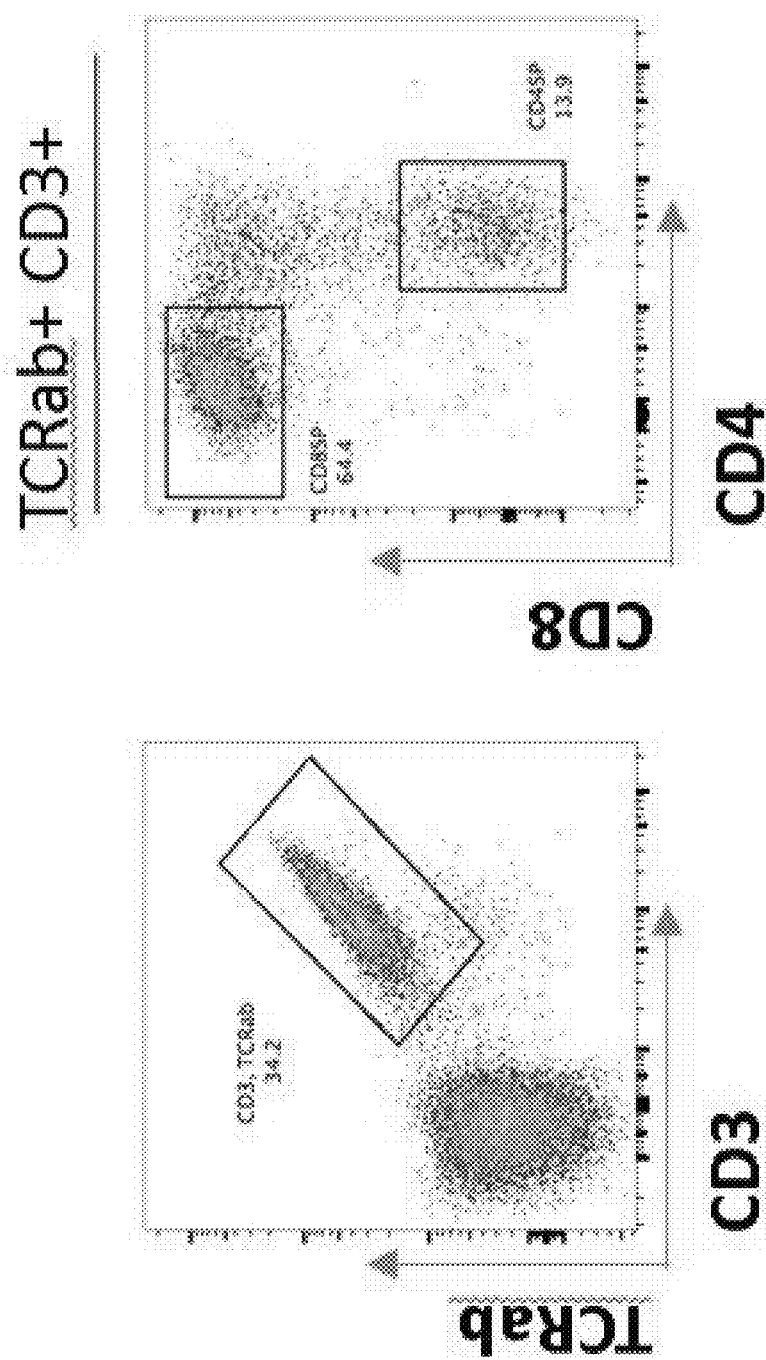
FIG. 34A-C: hES-derived hEMP produce T cells with a mature naïve phenotype. Shown are analyses at week 5 of ATOs (a) TCRab+CD3+.population is comprised of CD4+ and CD8+ cells and DP cells. Further analyses of (b) CDSP8 and (c) CDSP4 cells
Figure 34B:
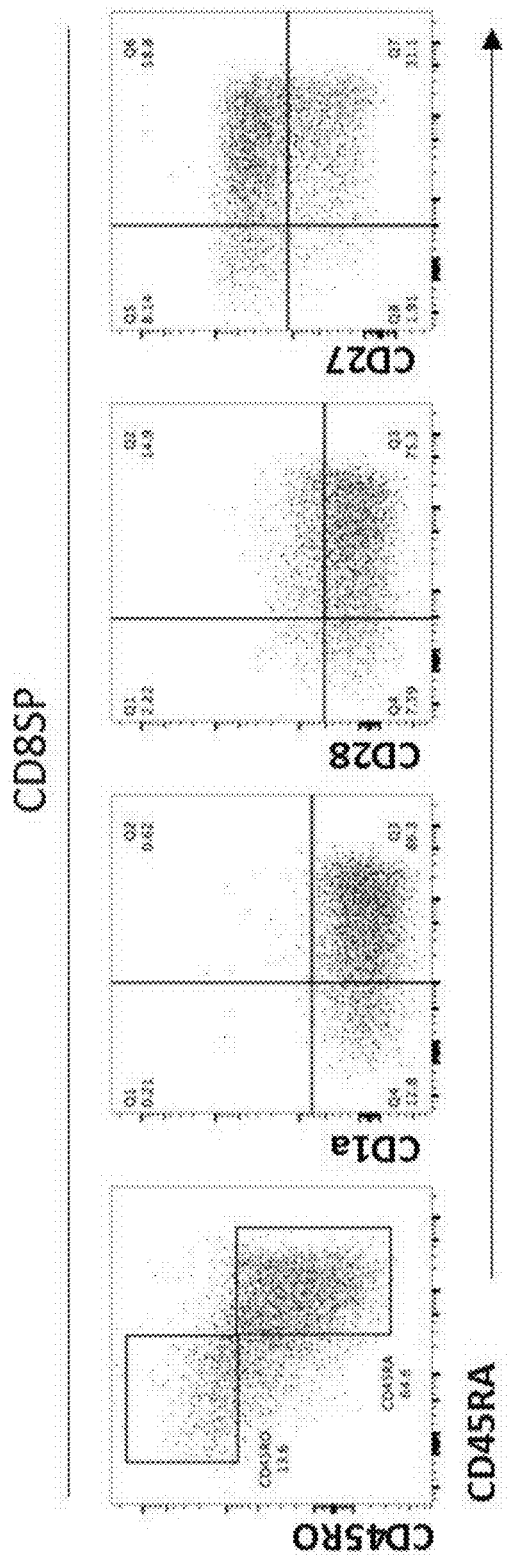
Figure 34C:
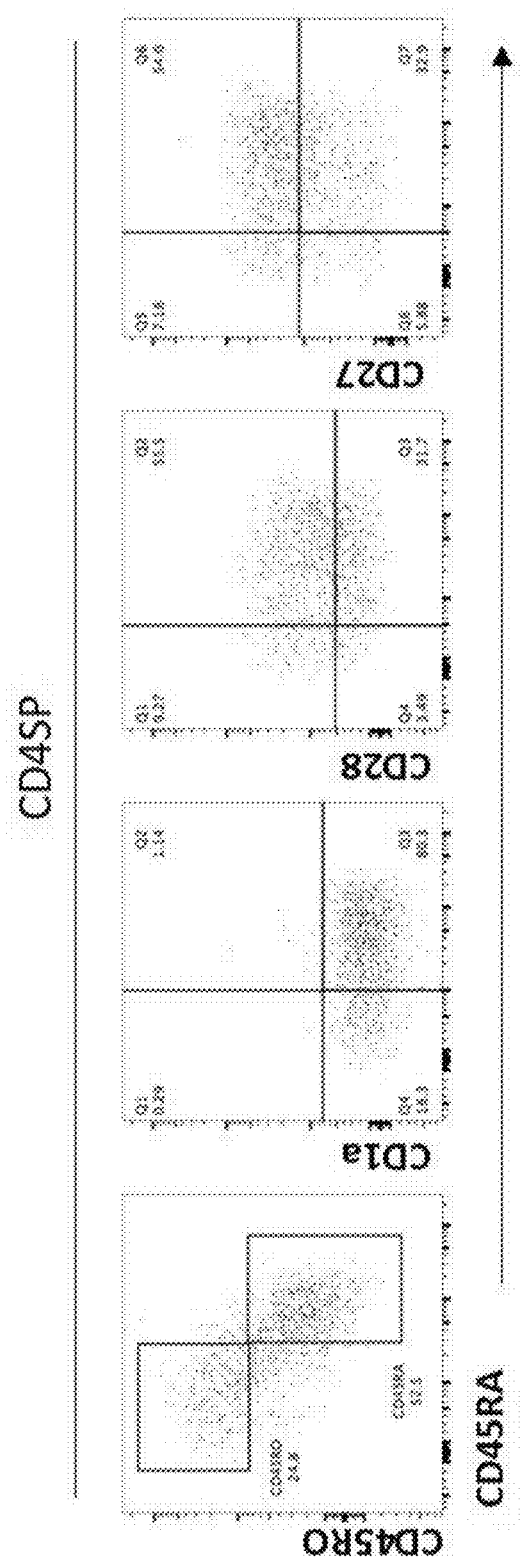
Figure 35A:
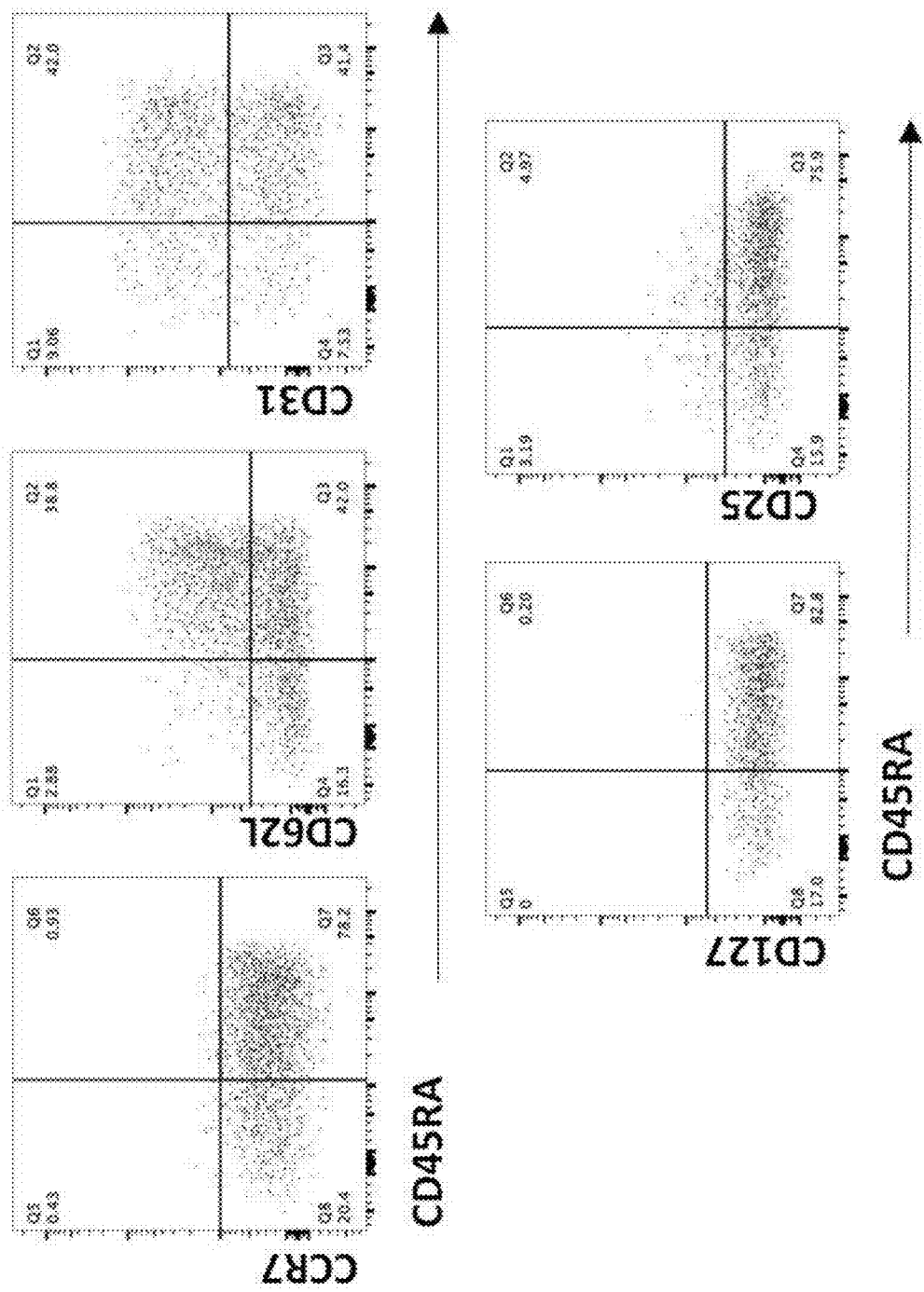
FIG. 35A-B: Expression of maturation markers in hEMP-derived T cells. Shown in (a) are analyses of CD8SP cells at week 5. Shown in (b) are analyses of CD4SP cells at week 5.
Figure 35B:
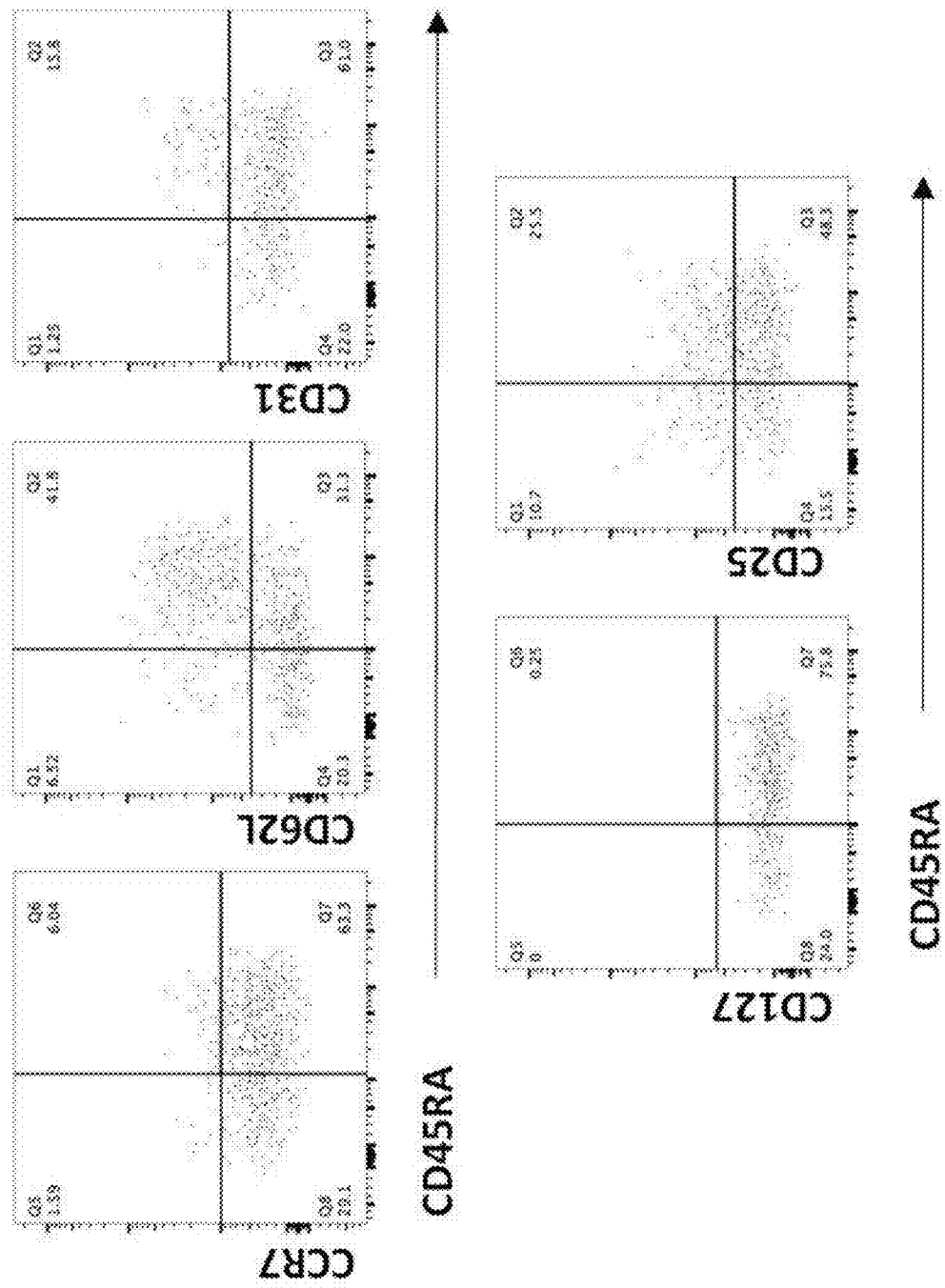
Figure 36:
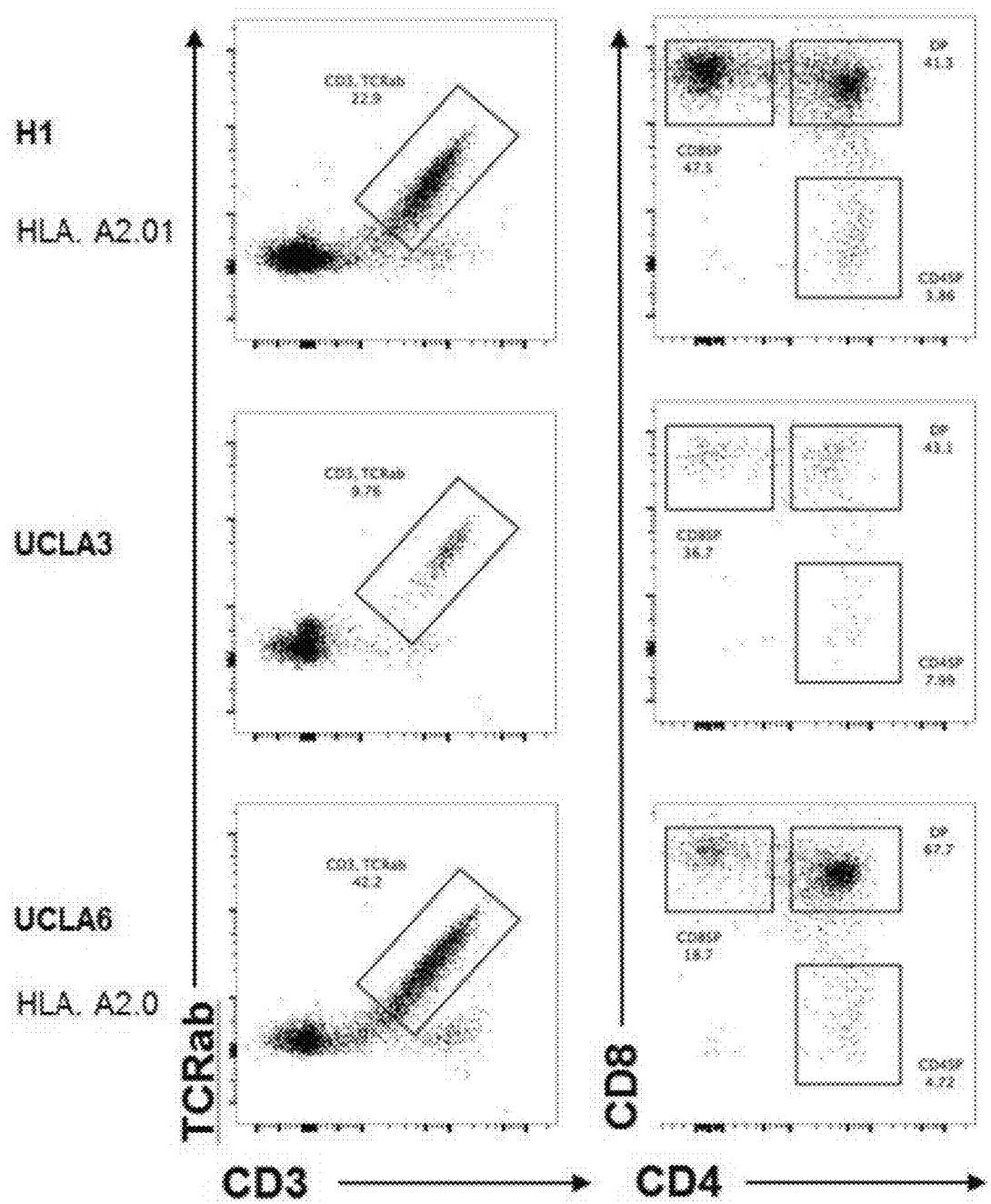
FIG. 36: T cell generation is reproducible across multiple hESC lines. hEMP generated from three different hESC lines generated T cells in the ATO system.
Figure 37:
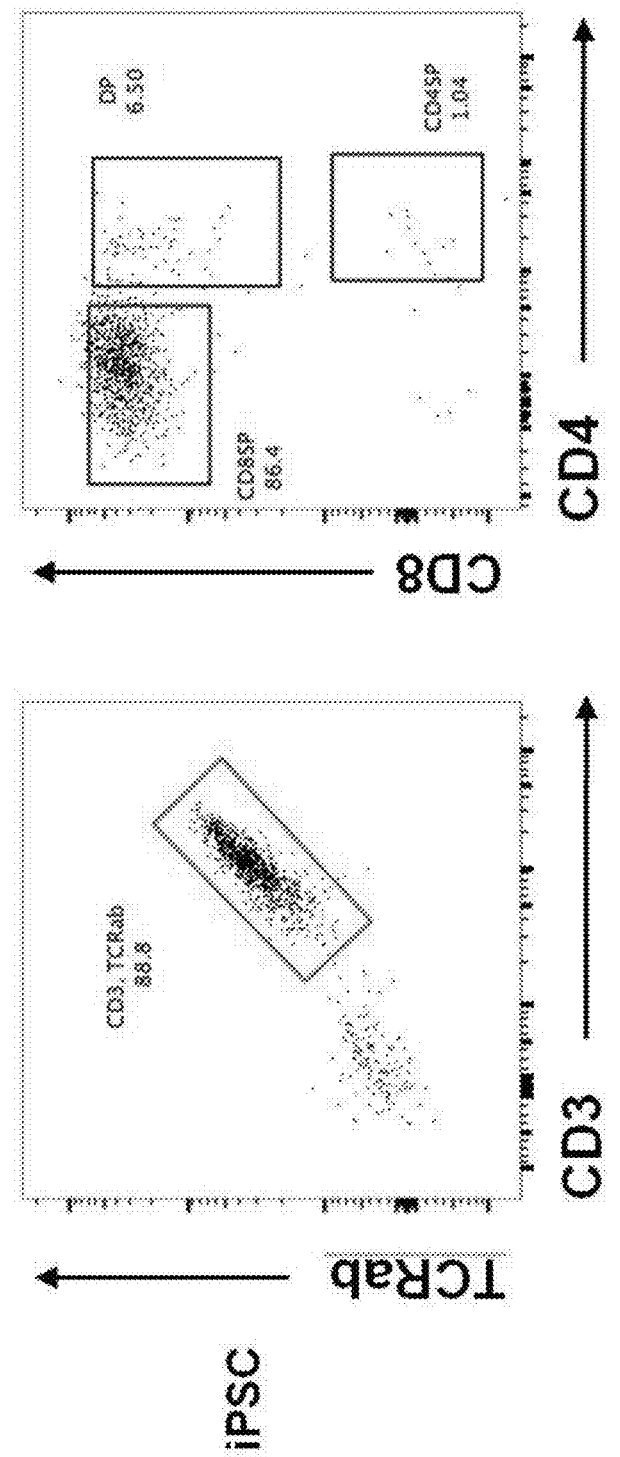
FIG. 37: T cell generation from iPSCs using the ATO system. This figure demonstrates that an iPSC line (HLA.A02.02, skin fibroblasts from healthy donor) generated T cells in the ATO system. The data is from week 6.
Figure 38A:
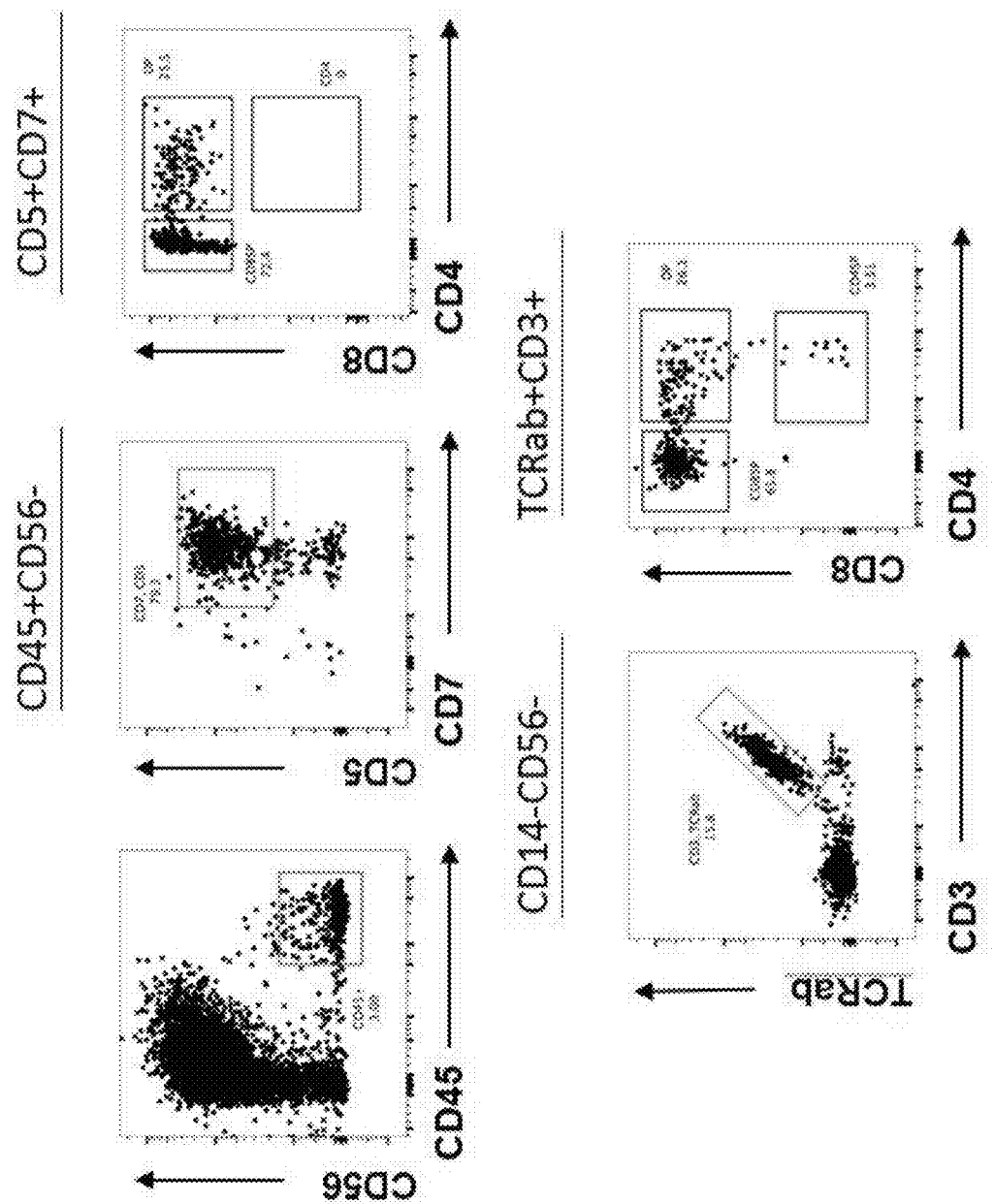
FIG. 38A-B: Undifferentiated hESC directly aggregated in ATOs can generat T-cells. Shown are T cell populations from week 5 (a) and week 7 (b) ATOs.
Figure 38B:
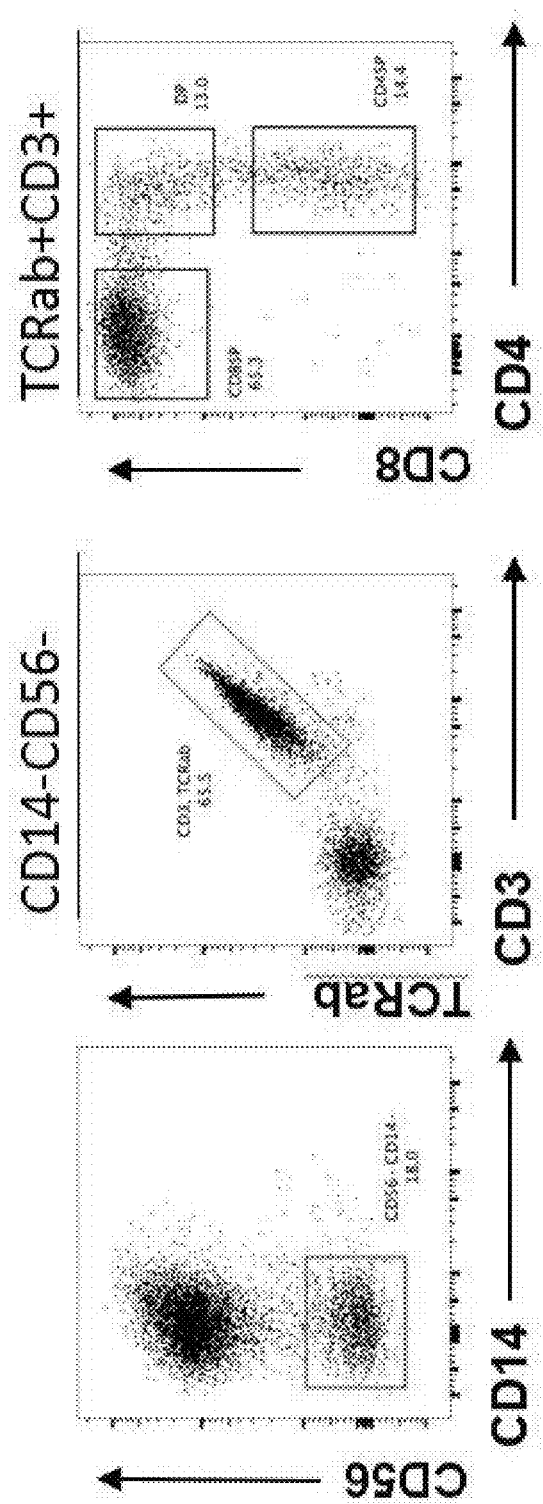
Figure 39:
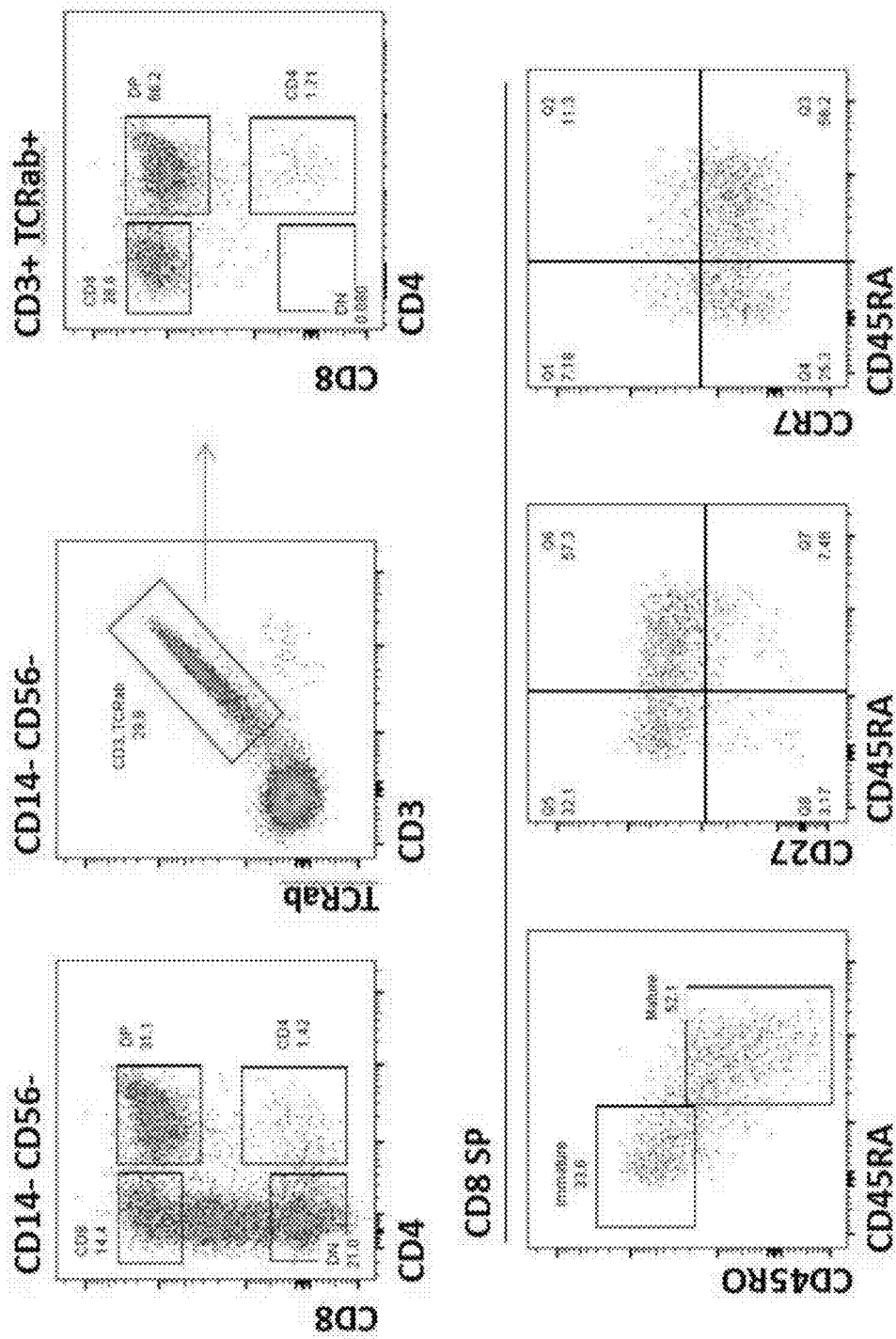
FIG. 39: The generation of mature T cells from hEMP in the ATO system using stromal cells expressing JAG1.
Figure 40:
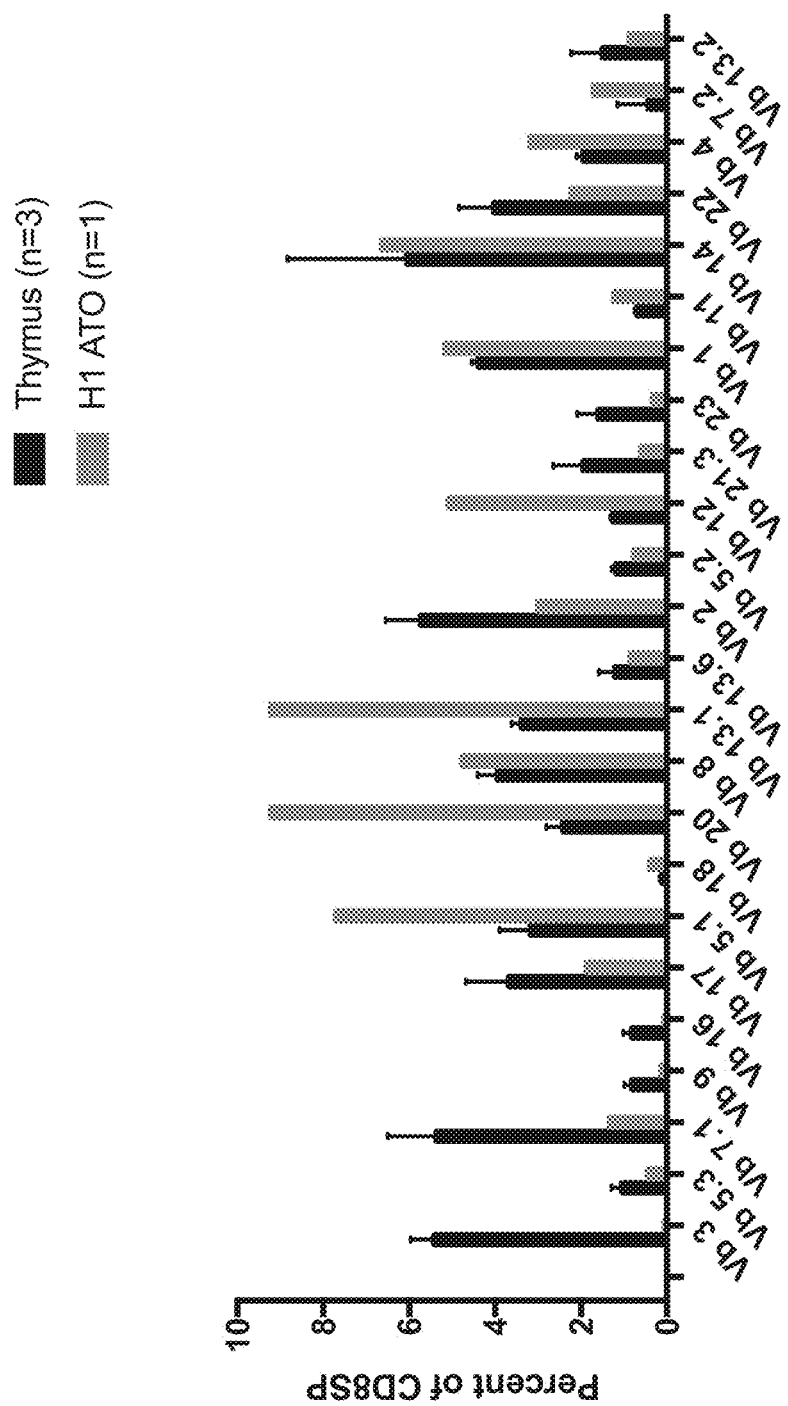
FIG. 40: T cells generated in the ATO system from hEMP show a diverse TCR Vb repertoire. Shown is a flow cytometry analysis of TCR Vb family usage of T cells generated in ATOs (CD8SP) from hEMP at week 5. Results were compared to TCR Vb family usage in thymocytes.
Figure 41A:
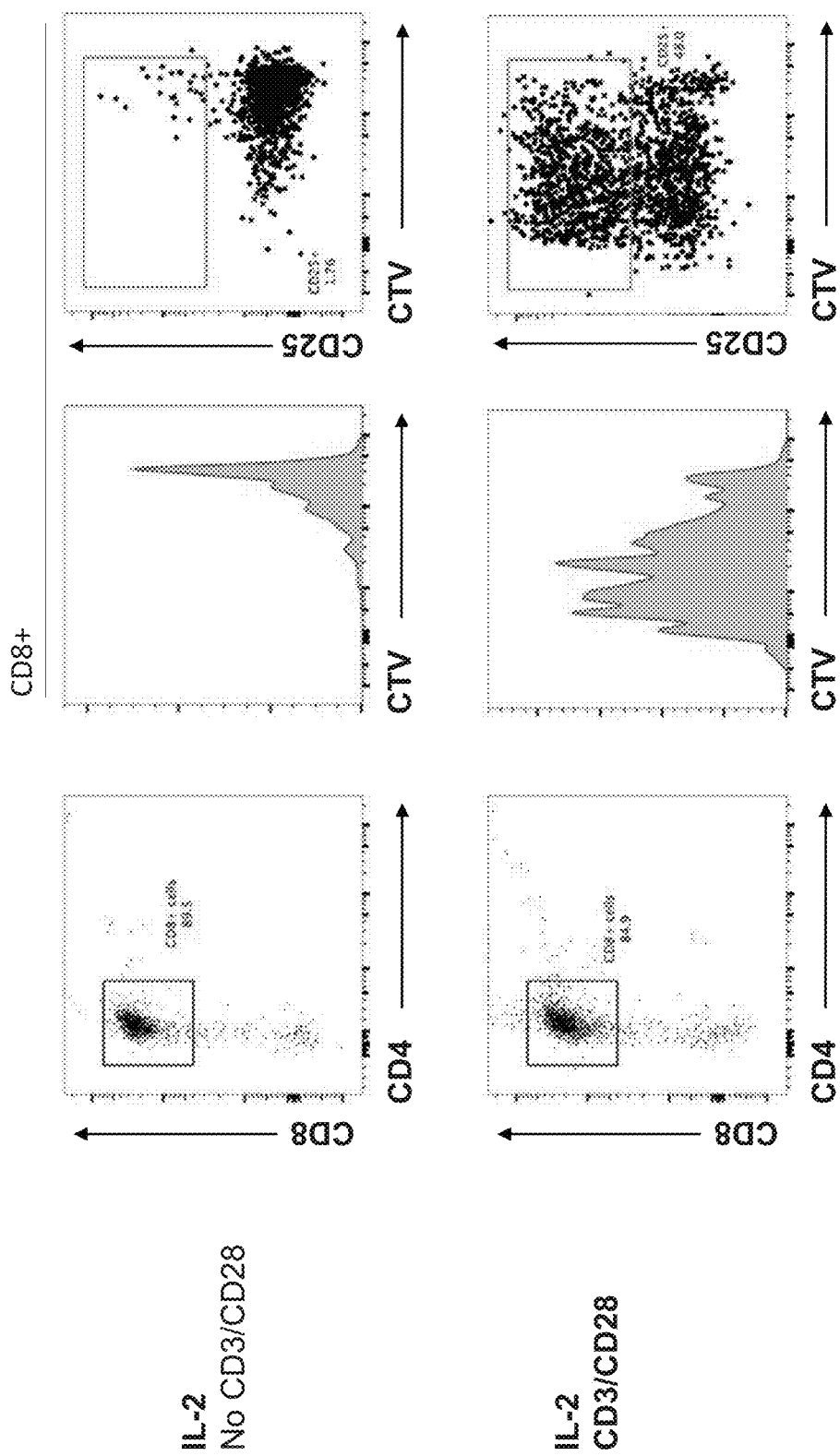
FIG. 41A-B: hESC-derived T cells exhibit proliferation and CD25 upregulation in response to anti-CD3/CD28 and IL2. CD8 SP T cells generated in ATOs from hESC (week 5) were tested functionally in vitro. (a) Isolated cells were stained with CTV (Cell tracker Violet) and incubated with CD3/CD28 activation beads for 5 days. Cell underwent multiple cell divisions as shown by the dilution of CTV and activation and the expression of CD25. (b) isolated cells were treated with PMA/Ionomycine for 6 hours and intracellular staining showed the production of cytotoxic cytokines (IFNg, IL2, TNFa).
Figure 41B:
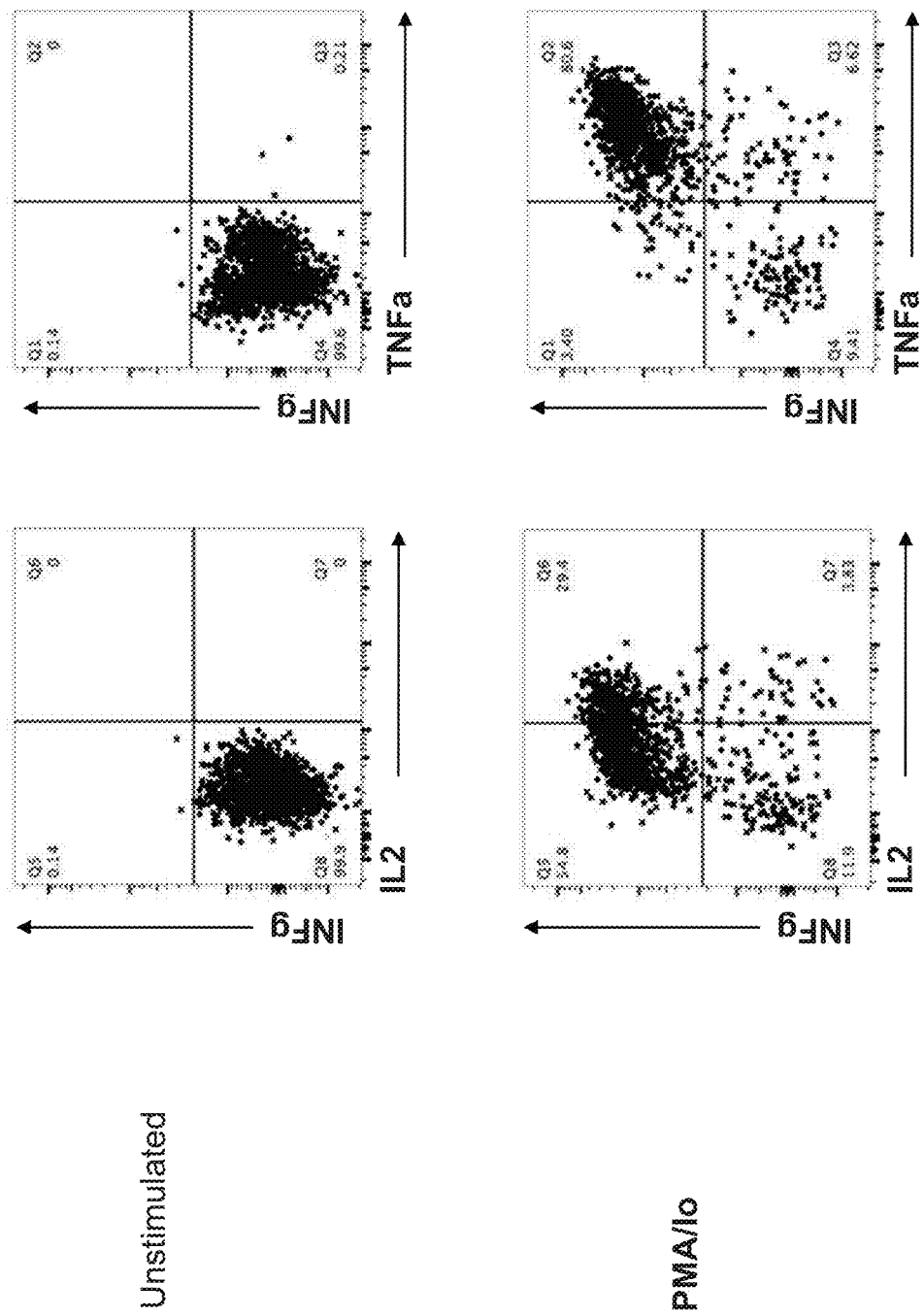

Example 5: Different Sources of Stem and Progenitor Cells can be Differentiated into T Cells Using the ATO System The ATO system described herein is an efficient and robust model to generate functional naïve T-cells in vitro from human hematopoietic stem cells (from different sources). This system has been adapted in order to generate mature functional naïve human T-cells from human Embryonic Stem Cells (hESC). The inventors have identified Embryonic Mesodermal Progenitor (hEMP) population that corresponds to the earliest mesoderm committed progenitors and that can give rise to all the mesodermal lineages (smooth muscle, cardiomyocytes, hematopoietic lineage, mesenchymal lineage). This hEMP population is defined by the loss of expression of Epcam marker (CD326) and the gain of expression of CD56 and can be easily isolated by FACS (See, for example, Evseenko et al., *Proc Natl Acad Sci USA.* 2010 Aug. 3; 107(31):13742-7). Briefly, hESCs cultured on MEFs (mouse embryonic fibroblasts) can be transferred to matrigel at 80-90% confluency. Once transferred (Day 0), the cells are cultured in media comprising Activin, BMP4, VEGF, bFGF. After 1-2 days, new media comprising BMP4, VEGF, and bFGF is added. On day 3-4, the cells can be sorted based on their loss of the EPCAM and gain of CD56. An ES-derived ATO system was created by isolating the hEMP population, and aggregating it with MS5-hDLL1 stromal cells. That protocols requires two weeks of hematopoietic induction, feeding the ATOs with EGM2 medium and hematopoietic cytokines (SB and SFT3) prior to the induction of T-cell differentiation by the use of RPMI-B27 medium (with additions of SCF/IL7/Flt3L). It was found that the 3D aggregation at the stage of hEMP supported the generation of T-cells. The generation of ATOs from isolated CD34+ differentiated from hEMPs on OP9 cells (no ATOs) did not support T cells differentiation (data not shown). Shown in FIG. 32 are T cell populations derived from ATOs with hESCs as the selected population of stem cells. Shown in FIG. 33 are the kinetics of differentiation of T cells in the ATO system from hESC, and the generation of CD8ab SP cells. As shown in FIGS. 34-35, T cells generated in the ATO system from hESC express the markers of a mature naïve phenotype, similar to what is observed using cord blood cells. As shown in FIG. 36, the use of hESCs is reproducible across multiple stem cell sources. FIG. 36 shows T cell differentiation from the ATO system (week 4) from three different hESC lines. The ATO system allowed the generation of mature T cells from an iPSC line (FIG. 37). Furthermore, 3D aggregation of undifferentiated hESC (instead of isolated hEMP) followed by the use of the different differentiation medium described previously allowed the generation of T cells as well (FIG. 38). Furthermore, multiple Notch ligands can be used in the ATO system. As shown in FIG. 39, the ATO system can also support T cells maturation from hESC when the stromal cell line expresses hJAG1 instead of hDLL1. It was also found that T cells generated in the ATO system from hESC showed a diverse TCR Vb repertoire (FIG. 40). As shown in FIG. 41, hESC-derived T cells exhibit proliferation and CD25 upregulation in response to anti-CD3/CD28 and IL2. Isolated cells were stained with CTV (Cell tracker Violet) and incubated with CD3/CD28 activation beads for 5 days. Cell underwent multiple cell divisions as shown by the dilution of CTV and activation as shown by the expression of CD25 (FIG. 41A). In a further experiment, isolated cells were treated with PMA/Ionomycine for 6 hours and intracellular staining showed the production of cytotoxic cytokines (IFNg, IL2, TNFa) in response to the stimulation (FIG. 41B).

Figure 42:
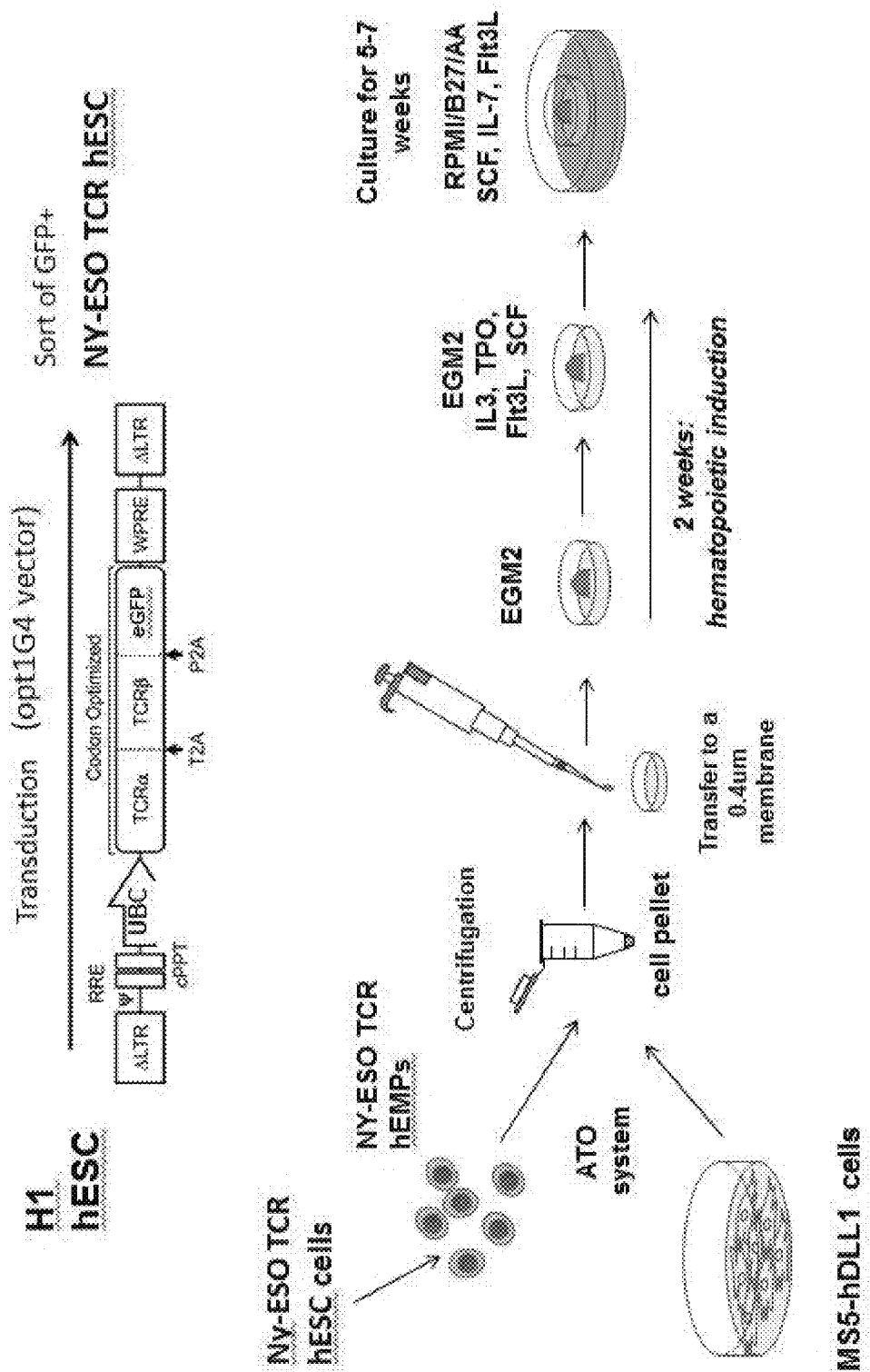
FIG. 42: Schema for generation of engineered-T cells from hESC in the ATO system. H1 hESC were transduced with the opt1G4 vector (NY-ESO TCR) expressing GFP. The H1 NY-ESO TCR hESC line was created by isolating the GFP+ cells and expanding them. Cells were then submitted to the same protocol as described above to induce T-cell differentiation.
Figure 43A:
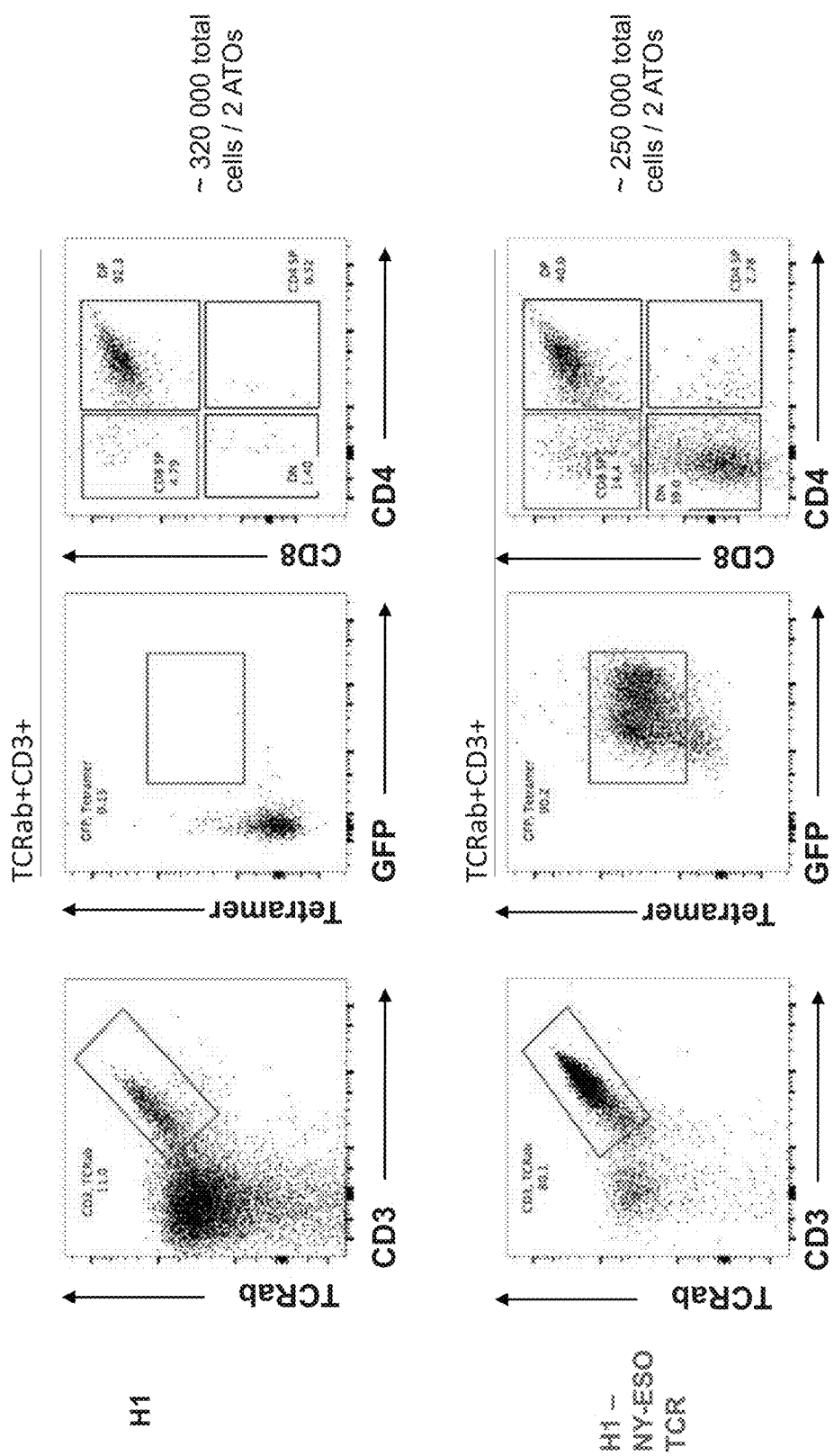
FIG. 43A-B: Characterization of NY-ESO TCR engineered T cells. Shown are FACS data from (a) week 3 and (b) week 5. Shown are data from non-transduced hESC (H1) and TCR-transduced hESC. Engineered T cells generated in ATOs from hESC, were identified by the expression of GFP and Tetramer and marker expression for T-cell differentiation (DP, CD3+/TCR+CD8SP).
Figure 43B:
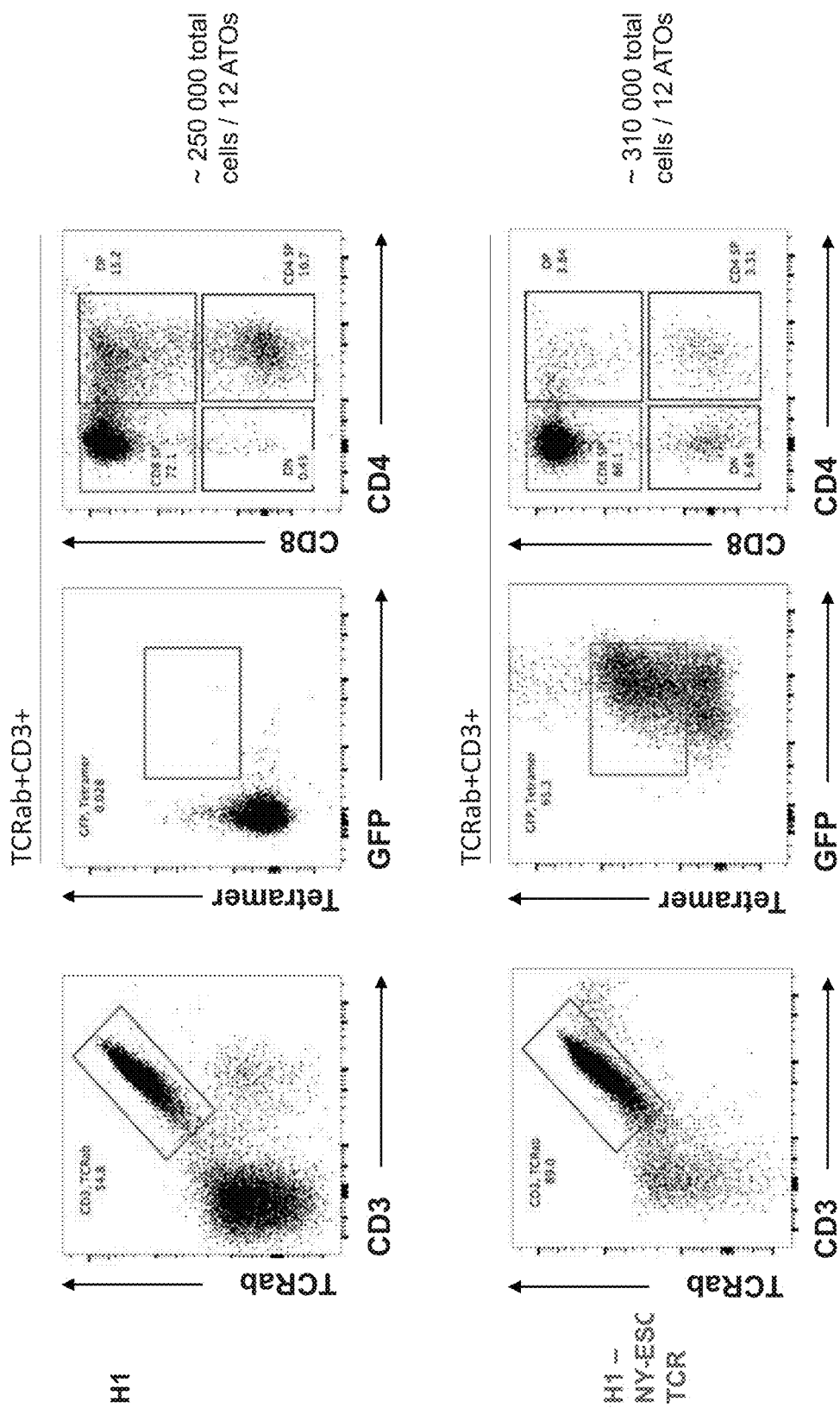
Figure 44A:
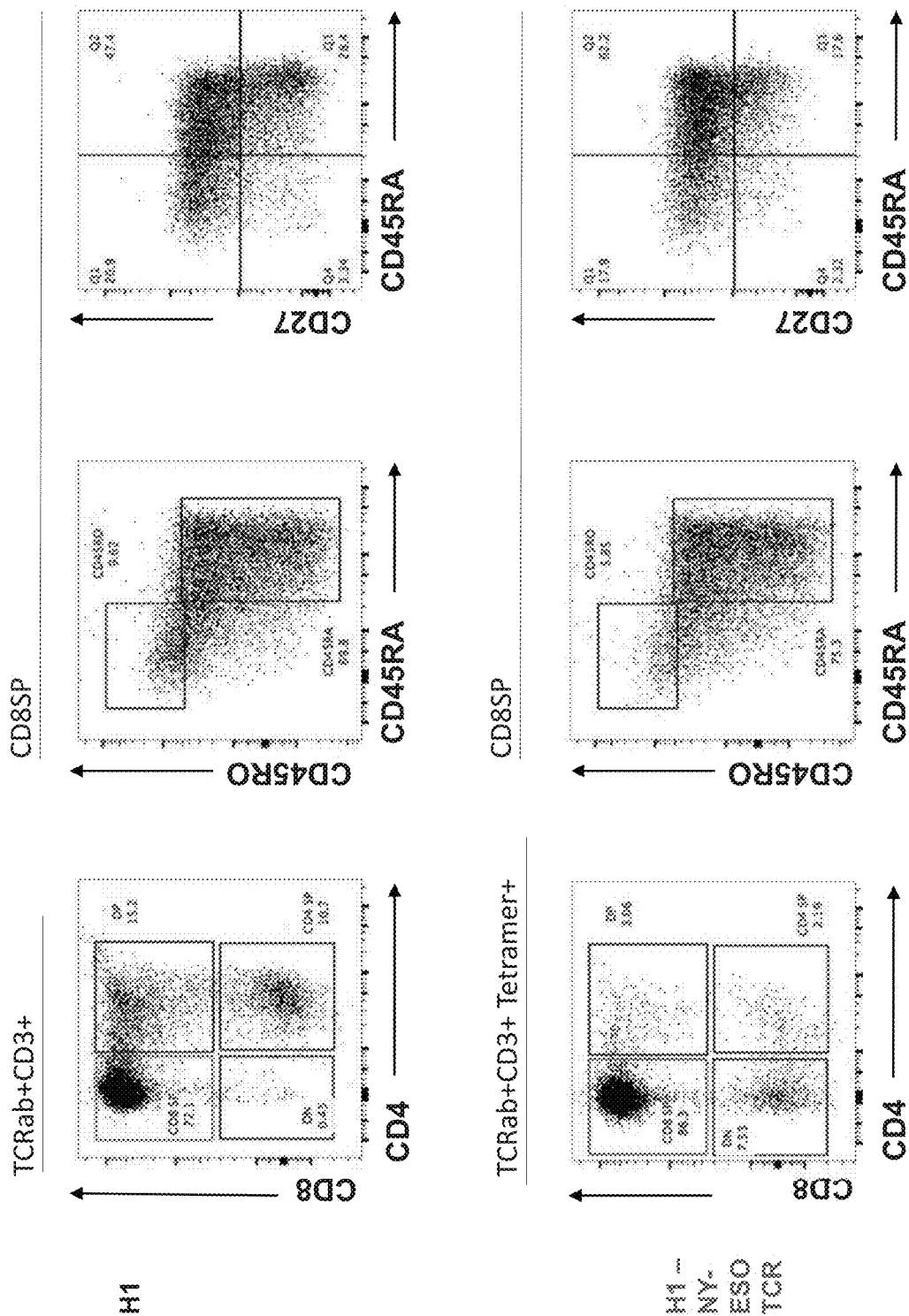
FIG. 44A-B: It was found that (a) engineered hESC-derived CD8SP T cells show a mature naïve phenotype and (b) that maturation markers were expressed in the engineered ES derived T cells.
Figure 44B:
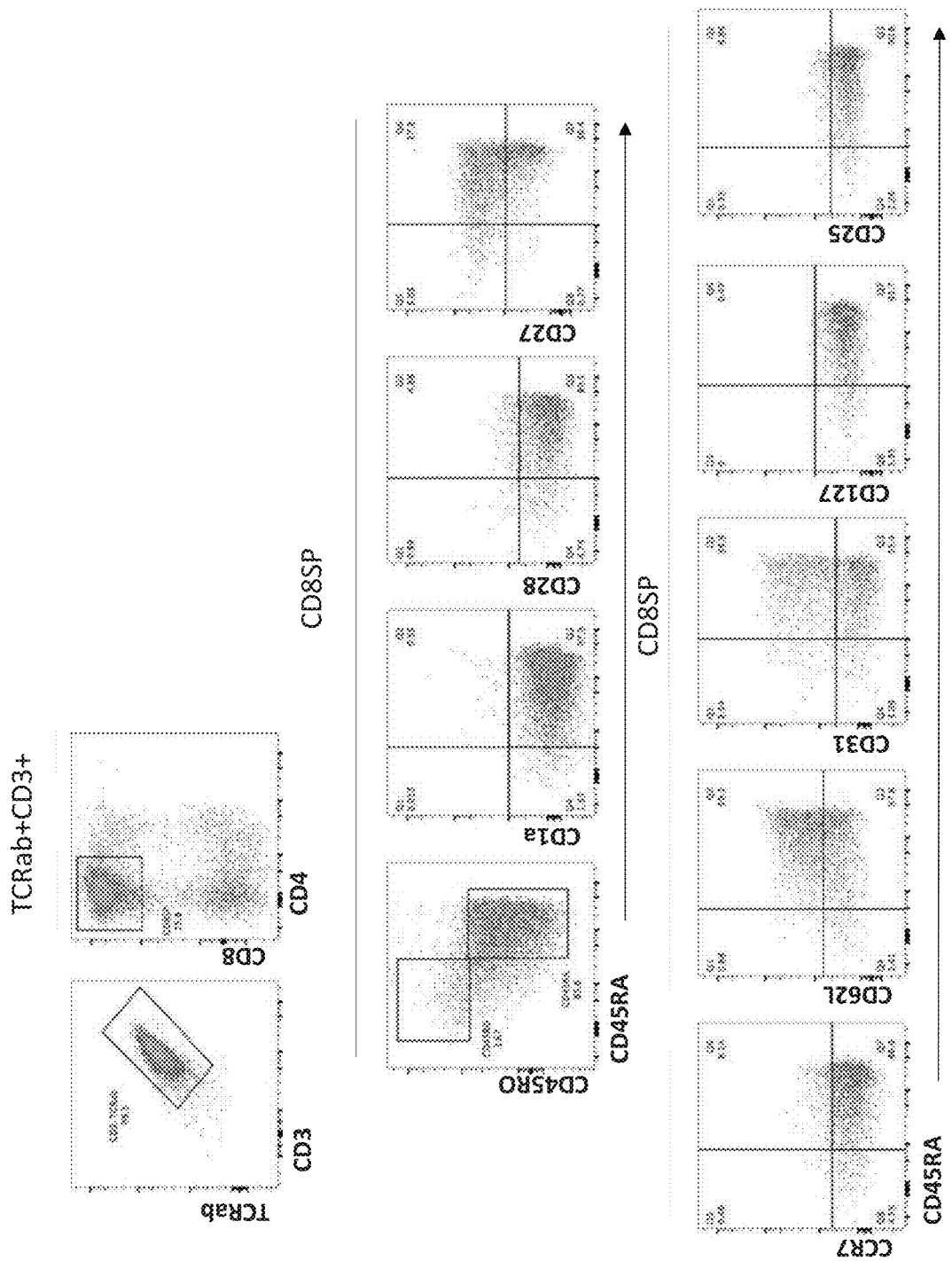
Figure 45:
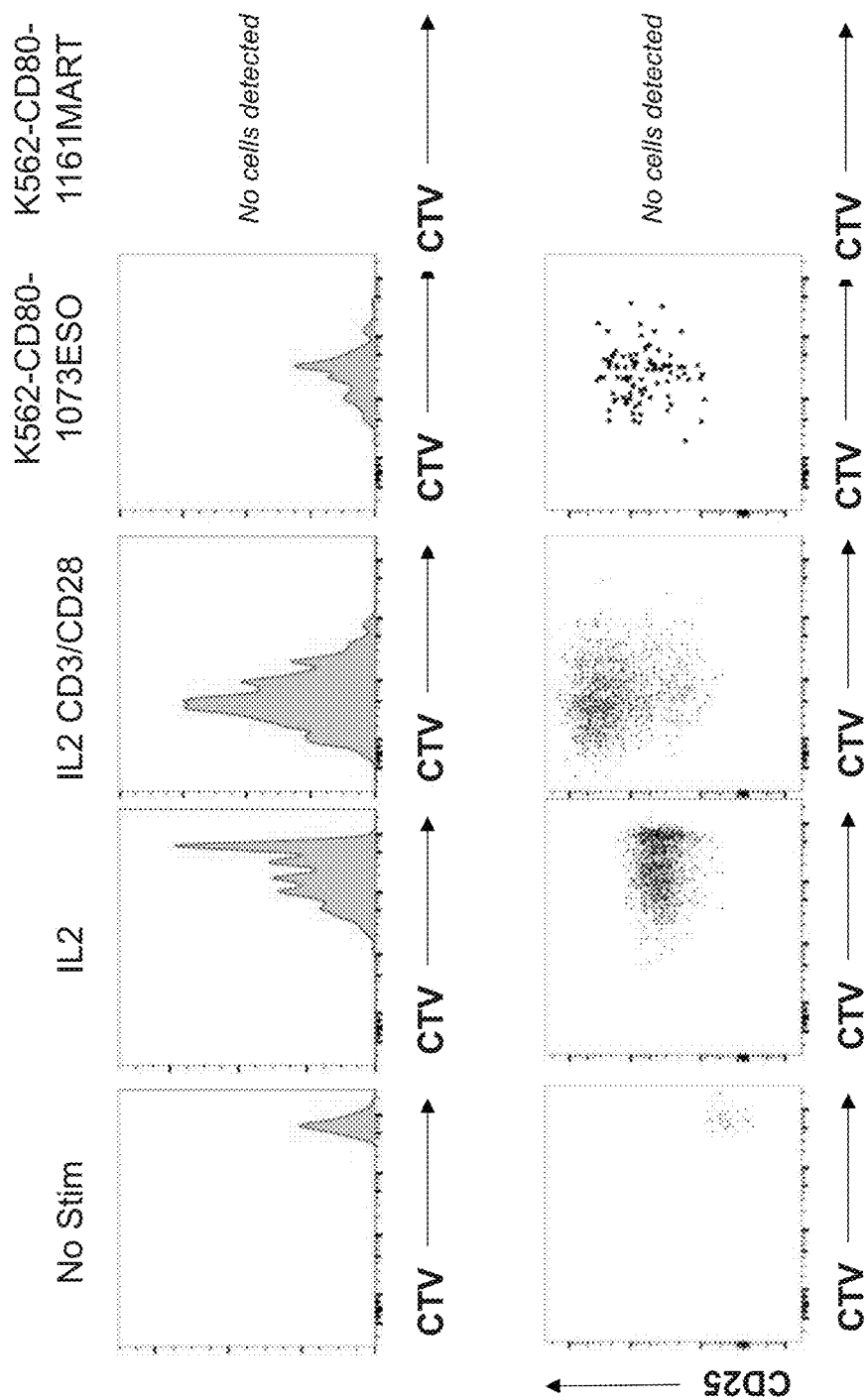
FIG. 45 shows that the isolated NY-ESO TCR CD8SP cells undergo activation upon CD3/28 or aAPC stimulation five days post ATO (week 5).
Figure 46:
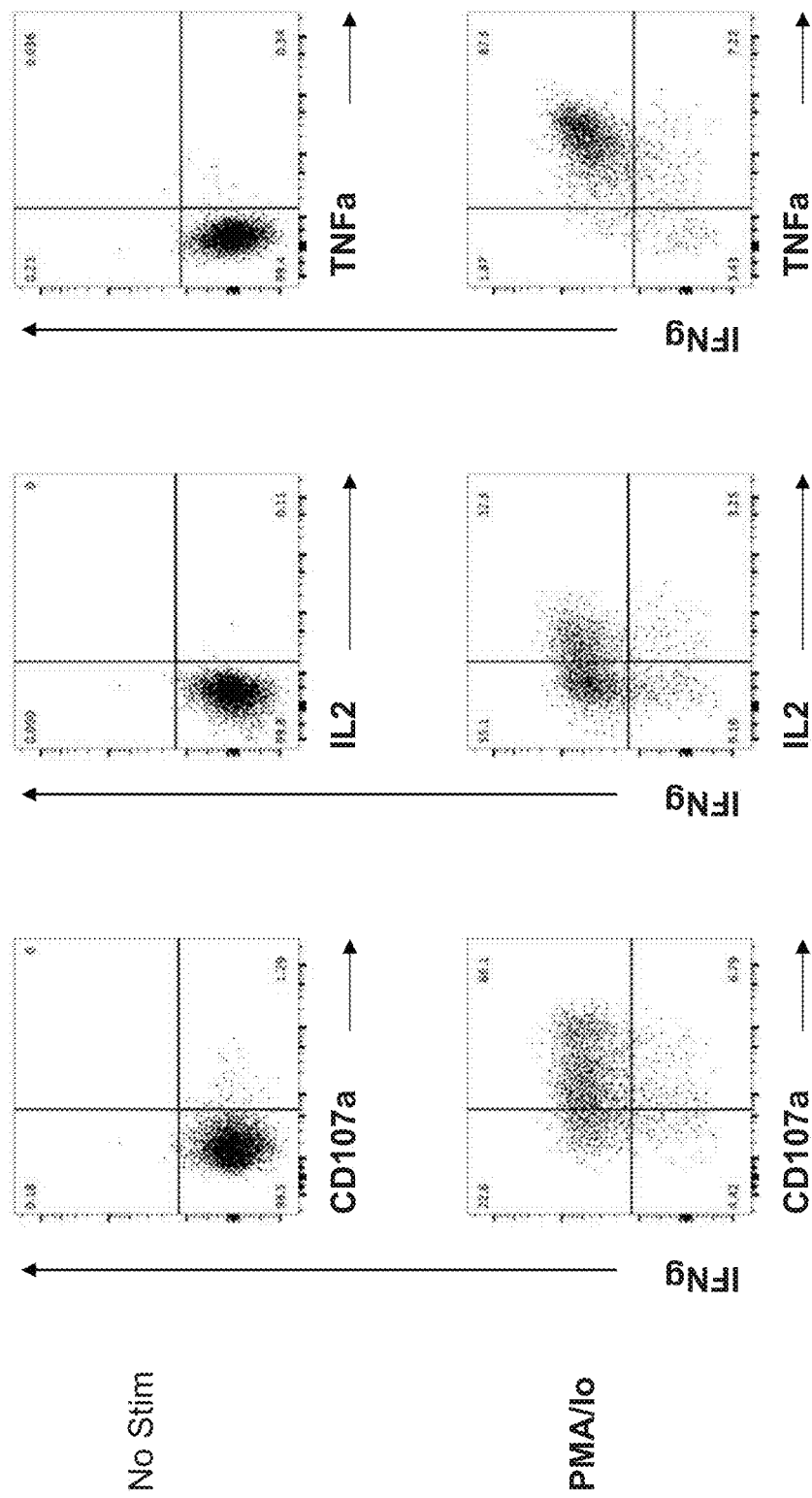
FIG. 46 shows that the isolated NY-ESO TCR CD8SP cells produced cytotoxic cytokines (IFNg, IL2, TNFa) in response to the stimulation.
Figure 47:
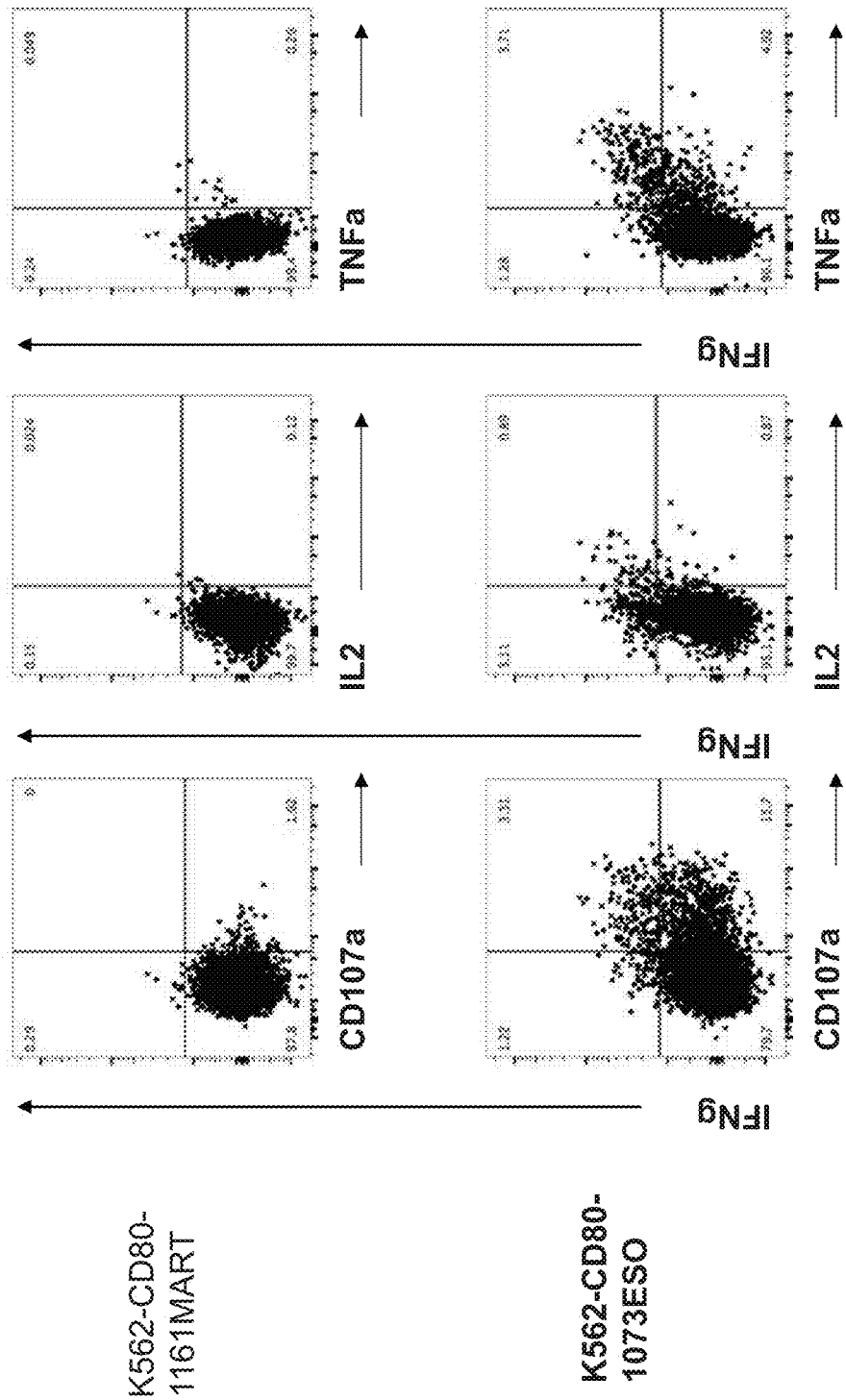
FIG. 47 demonstrates the specific activation of engineered hESC-derived (hEMP) T cells in response to artificial antigen presenting cells (K562). Analysis showed the production of cytotoxic cytokines (IFNg, IL2, TNFa) and degranulation (CD107a) in response to aAPC expressing the cognate (NY-ESO) but not the irrelevant (MART-1) peptide.
Figure 48:
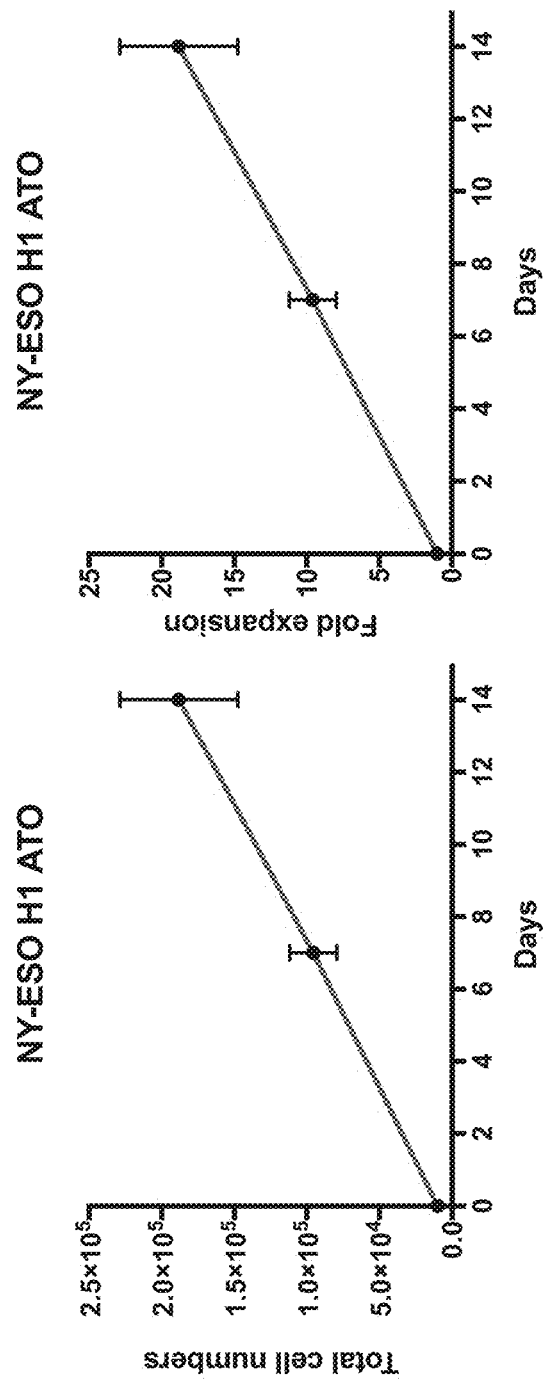
FIG. 48 shows that TCR-transduced ES-derived T cells showed a robust expansion in response to anti-CD3/CD28.

Next, it was sought to determine if T cells that were engineered to express an exogenous TCR could be generated from the ATO system with hESC cells as the starting material. H1 hESC were transduced with the opt1G4 vector (NY-ESO TCR) expressing GFP. The H1 NY-ESO TCR hESC line was created by isolating the GFP+ cells and expanding them. Cells were then submitted to them same protocol as described above to induce T-cell differentiation. This is depicted in FIG. 42. The engineered T cells generated in ATOs from hESC can be monitored by the expression of GFP and Tetramer. These cells followed the classic way of T-cell differentiation (DP, CD3+/TCR+ CD8SP) (FIG. 43). At week five, the engineered hESC-derived CD8SP T cells show a mature naïve phenotype: CD45 RA+, CD27+, CD62L+, CD31+ (FIG. 44A-B). Engineered CD8 SP T cells generated in ATOs from hESC (week 5) were tested functionally in vitro. Isolated cells were stained with CTV (Cell tracker Violet) and incubated with CD3/CD28 activation beads or in the presence of artificial antigen presenting cells (aAPC) expressing CD80 and a cognate HLA-A*02:01/NY-ESO-1 peptide-MHC single chain trimer, or an irrelevant HLA-A*02:01/MART-1 aAPC for 5 days. Cell underwent multiple cell divisions as shown by the dilution of CTV and activation as shown by the expression of CD25 in response to CD3/28 activation and the aAPC expressing the cognate peptide (FIG. 45). In this assay the cells did not survive in the presence of aAPC expressing the irrelevant peptide. In a further experiment, isolated cells were treated with PMA/Ionomycine for 6 hours. Intracellular staining showed the production of cytotoxic cytokines (IFNg, IL2, TNFa) in response to the stimulation (FIG. 46). Cells also underwent degranulation as shown by the expression of CD107a (FIG. 46). In two individual assays, isolated cells were incubated in the presence of artificial antigen presenting cells (aAPC) expressing CD80 and a cognate HLA-A*02:01/NY-ESO-1 peptide-MHC single chain trimer, or an irrelevant HLA-A*02:01/MART-1 aAPC for 6 hours. Analysis showed the production of cytotoxic cytokines (IFNg, IL2, TNFa) and degranulation (CD107a) in response to aAPC expressing the cognate peptide but not the irrelevant one. One representative experiment is shown in FIG. 47. Next, the isolated cells were tested for their proliferation capacity. They were activated with CD3/CD28 beads for 4 days and maintained for 2 weeks in AIM V medium supplemented with 5% human AB serum and IL2 (20 ng/ml). Results show a 20-fold expansion of cells at 2 weeks (FIG. 48).

Example 6: ATO Medium Supplementation

Components of the B27 supplement were tested to determine their relative contribution to the ATO system. The table below demonstrates the components of the B27 supplement:

| | |
|---|---|
| Vitamins | Biotin |
| | DL Alpha Tocopherol Acetate |
| | DL Alpha-Tocopherol |
| | Vitamin A (acetate) |
| Proteins | BSA, fatty acid free Fraction V |
| | Catalase |
| | Human Recombinant Insulin |
| | Human Transferrin |
| | Superoxide Dismutase |
| Other Components | Corticosterone |
| | D-Galactose |
| | Ethanolamine HCl |
| | Glutathione (reduced) |
| | L-Carnitine HCl |
| | Linoleic Acid |
| | Linolenic Acid |
| | Progesterone |
| | Putrescine 2HCl |
| | Sodium Selenite |
| | T3 (triodo-I-thyronine) |

Figure 49:
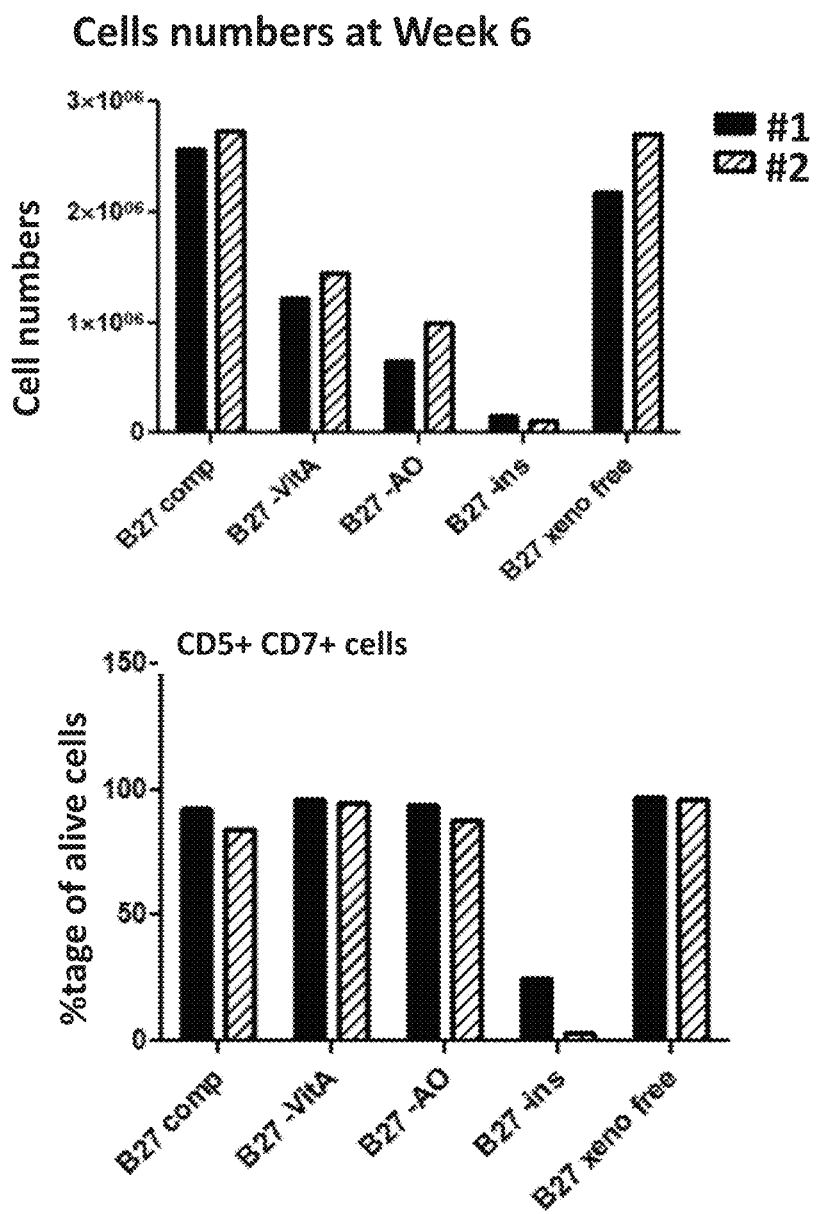
FIG. 49 shows data using different versions of the B27 supplement that are deficient in a single component (insulin (-ins), Vit A, anti-oxidants (AO)) or xenobiotic free (xeno free) compared to standard (complete) B27 (Comp). ATO cultures were initiated with CD34+CD3− cord blood HSPC and analyzed at 6 weeks. Shown are total cell numbers and % of cultures that are CD5+CD7+ T cell precursors.
Figure 50:
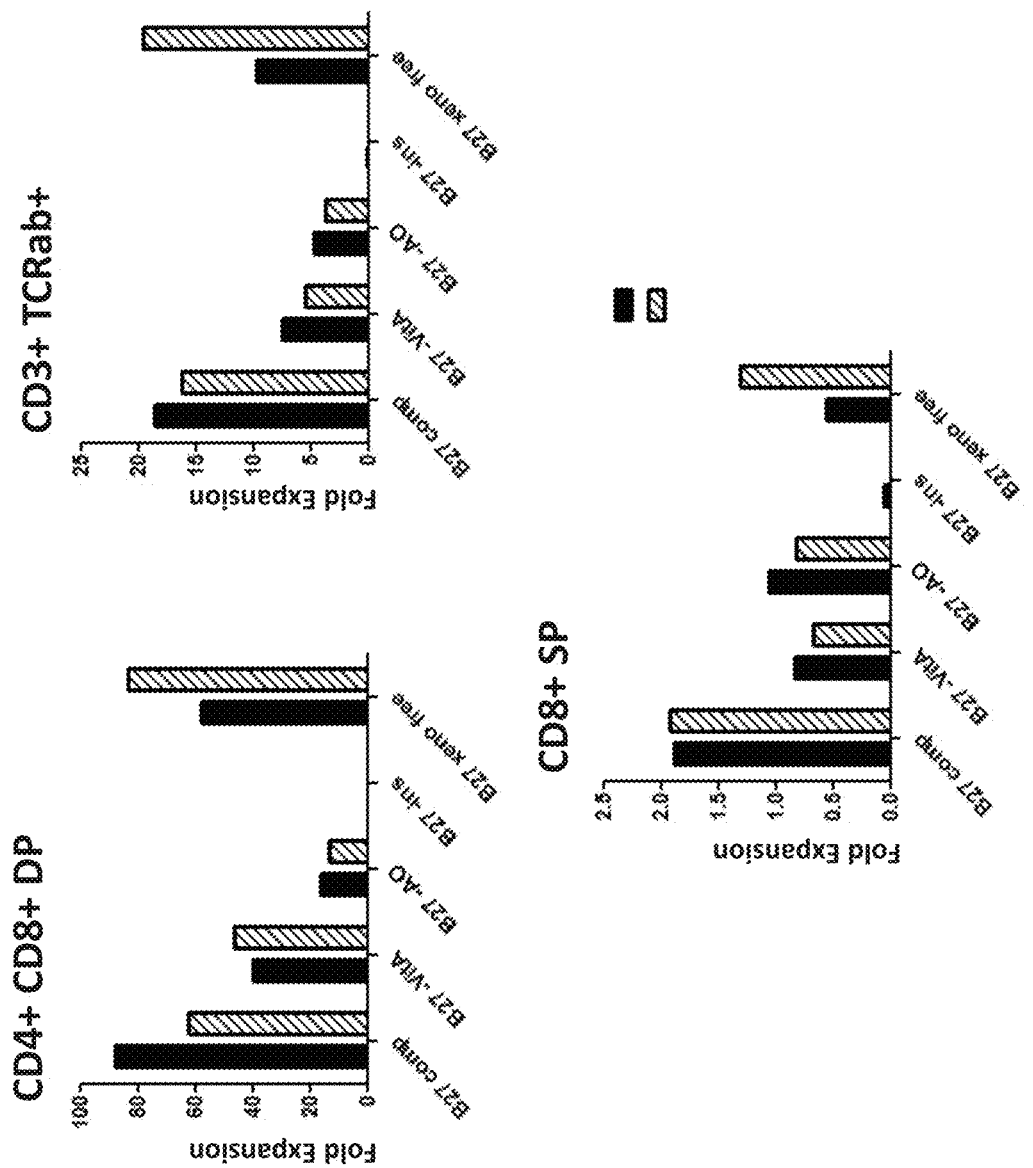
FIG. 50 shows data using different versions of the B27 supplement that are deficient in a single component (insulin (-ins), Vit A, anti-oxidants (AO)) or xenobiotic free (xeno free) compared to complete B27 (Comp). Data shows that insulin is essential for T-cell commitment and vitamin A and anti-oxidants facilitate cell output.
Figure 51:
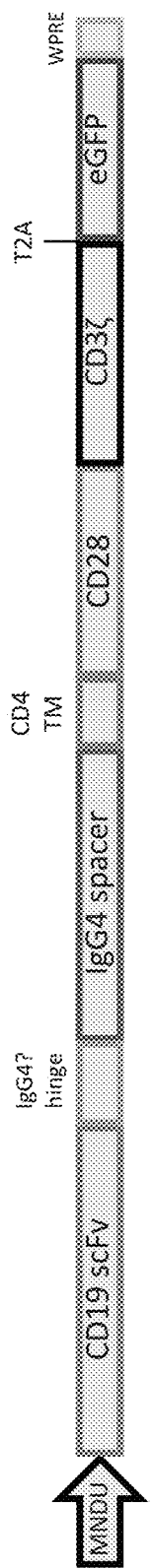
FIG. 51 depicts the design of a $2^{nd}$ generation CD19-targeted CAR used in the experiments that follow.

Cord blood ATOs (initiated with CD34+CD3− HSPC) were set up to determine what components of B27 supplement are essential. Complete (standard) B27 ("B27 comp") was compared with four supplements that are identical except for deletion of a single component (all supplied by the same manufacturer): without vitamin A (B27-Vit A), without antioxidants (B27-AO), without insulin (B27-insulin), and without xenobiotic components (B27 xeno free). The data Data shown is from two independent experiments both at 6 weeks Graphs show total cell output (top) and % of T cell committed cells (CD5+CD7+) (bottom). As shown in FIGS. 49-50, it was determined that insulin is essential for T-cell commitment in the ATO system and that vitamin A and anti-oxidants facilitate cell expansion. Furthermore, the xeno-free formula of B27 gives similar results for T cell differentiation and expansion in ATOs compared to the non xeno-free. In conclusion, Insulin is essential for T cell production in ATO, Xenobiotic free is equivalent to complete B27, and Vit A and antioxidants enhance cell output but are not essential for T cell differentiation.

Example 7: Generation of CAR-T Cells from Human Hematopoietic Stem/Progenitor Cells Using the Artificial Thymic Organoid (ATO) System In this study, the inventors sought out to determine the effects of CAR signaling on normal T cell differentiation in ATOs, determine the in vitro and in vivo function and anti-tumor efficacy of ATO-derived CAR-T cells, and to determine the ability of CARs to mediate TCR allelic exclusion. To this end, a CD19-targeted CAR transduced into cord blood CD34+CD3− HSPCs. These cells were then subjected to the ATO system for a time period of 4-6 weeks.

Figure 52:
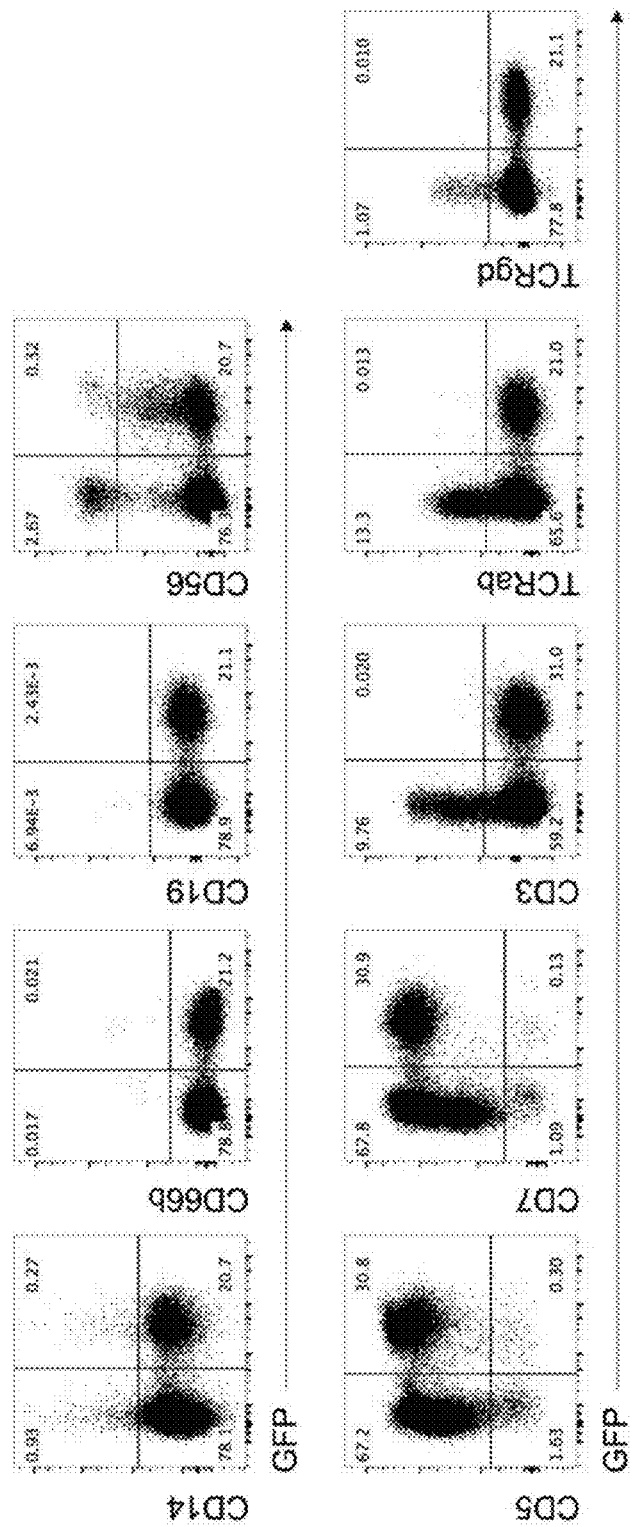
FIG. 52 shows FACS analysis of CAR-transduced CB ATOs demonstrating that CAR expression (i.e. GFP+) in ATOs is largely limited to T-lineage cells (CD5+ and CD7+) that are CD3−TCRab− and CD3−TCRgd−.

As shown in FIG. 52, CAR expression in ATOs is largely limited to T-lineage cells. As chimeric antigen receptors (CARs) are not dependent on CD3 or TCR subunits for surface expression and signaling, they may be expressed in multiple cell lineages. The lineage output of CD34+CD3− CB HSPCs transduced with a vector encoding a CD19-specific 2nd generation (CD28/CD3zeta) CAR and eGFP were tested in standard ATO cultures (i.e. MS5-hDLL1 stroma, RB27 media supplemented with 5 ng/ml FLT3L and 5 ng/ml IL-7). Briefly, 7500 transduced HSPCs were aggregated at a 1:20 HSPC:stromal cell ration and cultured as described for 4 weeks. At 4 weeks, ATOs were disrupted and total human cells analyzed for lineage markers (shown here). There were very few eGFP+ (CAR+) monocytes (CD14+), granulocytes (CD66b+), B cells (CD19+), or NK cells (CD56+). The majority of CAR+ cells were CD5+ and CD7+, consistent with the T cell lineage. Of note, CAR+ cells displayed a near complete lack of CD3, TCRab, and TCRgd expression, suggesting unconventional T cell differentiation.

Figure 53:
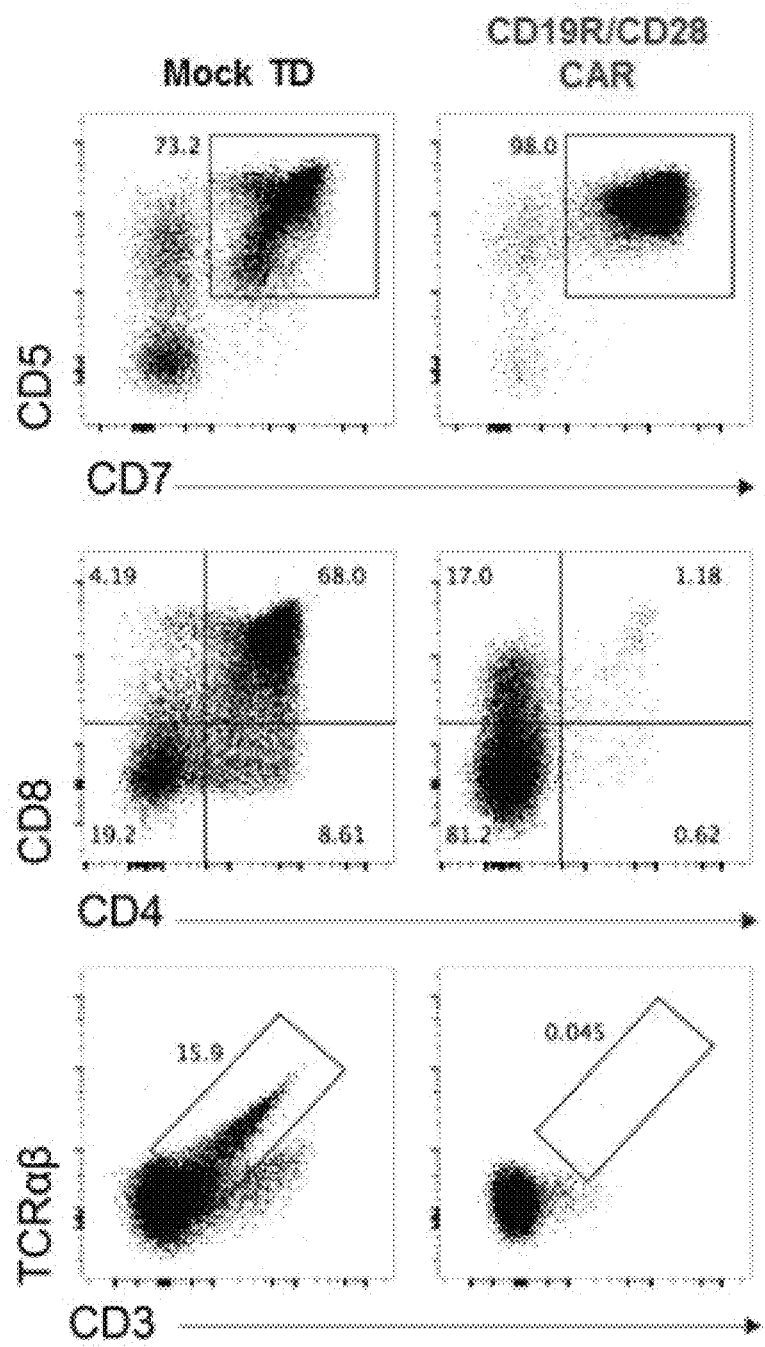
FIG. 53 shows FACS analysis of CAR-transduced CB ATOs demonstrating that ATO-derived CAR-T cells display unconventional T cell differentiation i.e. CD5+CD7+CD3−TCRab−CD4−CD8−. Mock transduced ATOs are shown for comparison.
Figure 54:
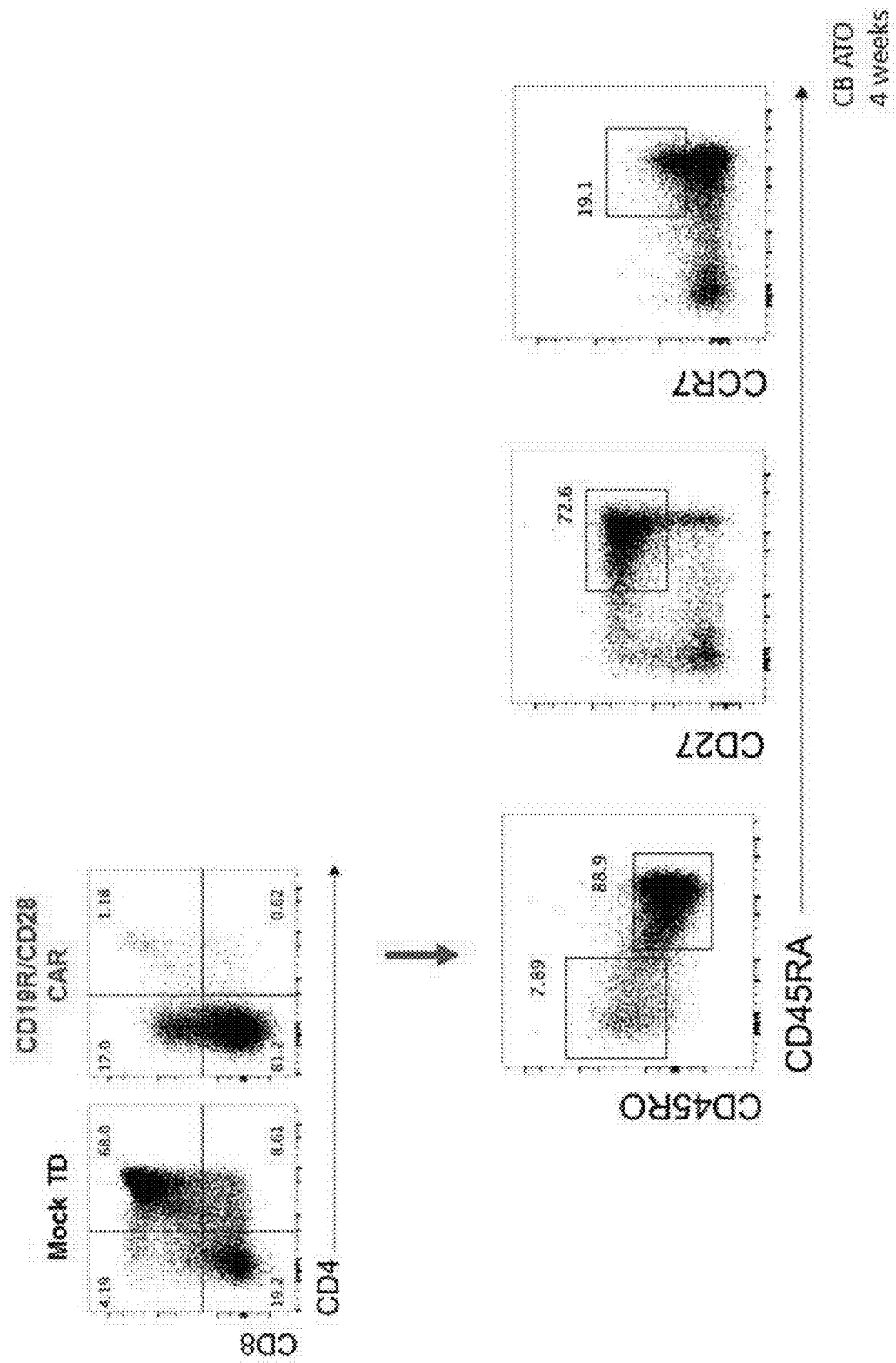
FIG. 54 shows that CB ATO-derived CAR-T cells display a naïve T cell phenotype (CD45RA+) and are phenotypically mature (CD27+CCR7+).

ATO-derived CAR-T cells display unconvention T cell differentiation. Cells from week 4 ATOs initiated with either mock or CD19-specific 2nd generation (CD28/CD3zeta) CAR-transduced CB HSPCs were analyzed for T cell markers. CAR-transduced cells (gated on GFP+) were predominantly T lineage (CD5+CD7+), but did not display the typical patter of DN to DP to SP T cell differentiation. Instead, most cells were DN or CD8SP (middle row). Furthermore, there was no evidence of CD3/TCR surface expression in ATO CAR-T cells. This is shown in FIG. 53. Despite unconventional T cell differentiation, ATO-derived CAR-T cells (from CD19-specific 2nd generation (CD28/CD3zeta) CAR-transduced CB HSPCs) displayed a normal naïve T cell phenotype characterized as CD45RA+ CD45RO− with co-expression of CD27 and CCR7 (FIG. 54). These cells also co-expressed CD62L (no shown).

Figure 55:
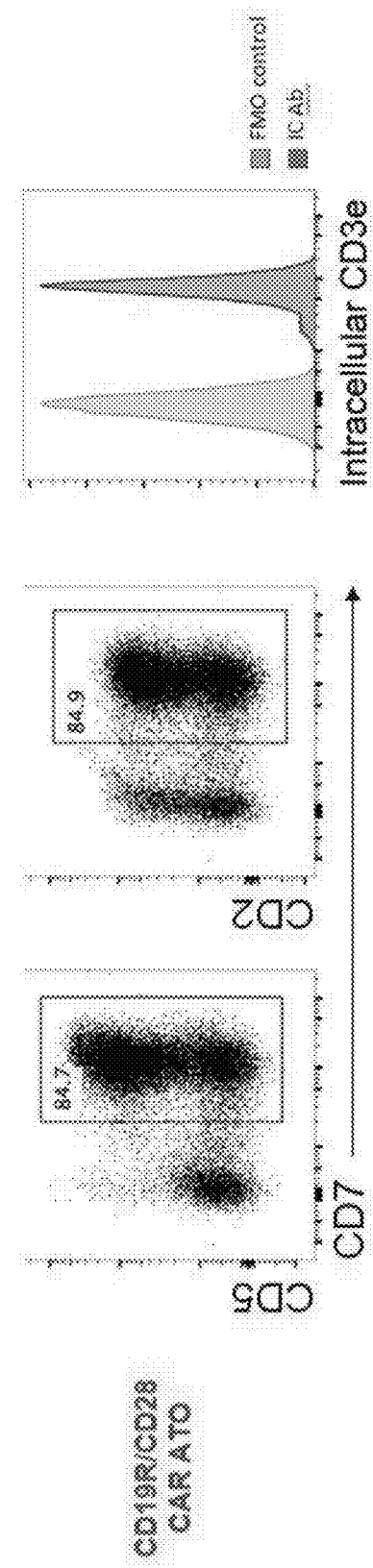
FIG. 55 shows that CB ATO-derived CAR-T cells express CD2 and intracellular CD3e

ATO-derived CAR-T cells express CD2 an intracellular CD3. As shown in FIG. 55, ATO-derived CAR-T cells (from CD19-specific 2nd generation (CD28/CD3zeta) CAR-transduced CB HSPCs) co-express CD5, CD7, CD2, and intracellular CD3, confirming their identity as T lineage cells.

Figure 56A:
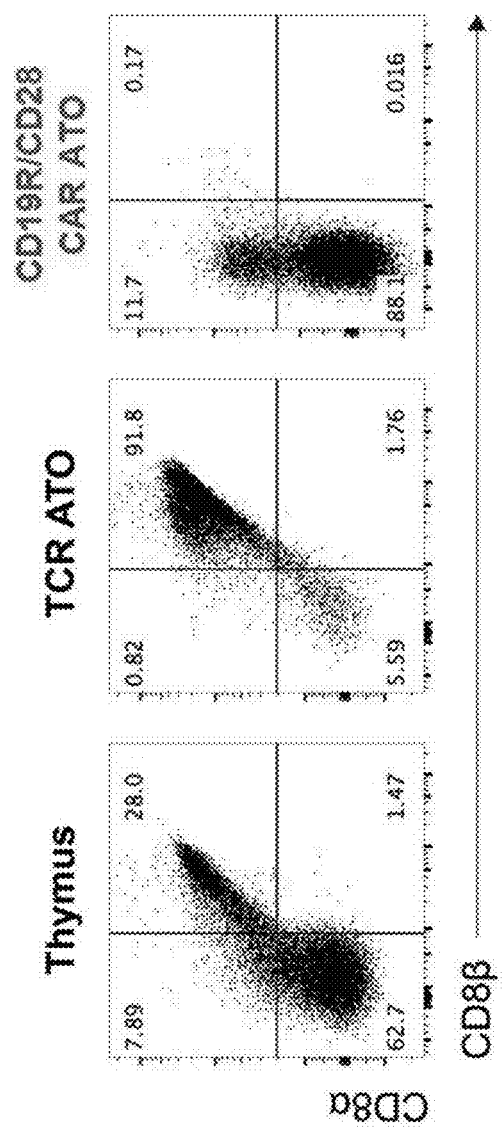
FIG. 56A-B: ATO-derived CB CAR-T cells are CD4−CD8− (DN) or express CD8αα homodimers (a) and express CD56 and CD16, associated with IELs (and NK cells) (b).
Figure 56B:
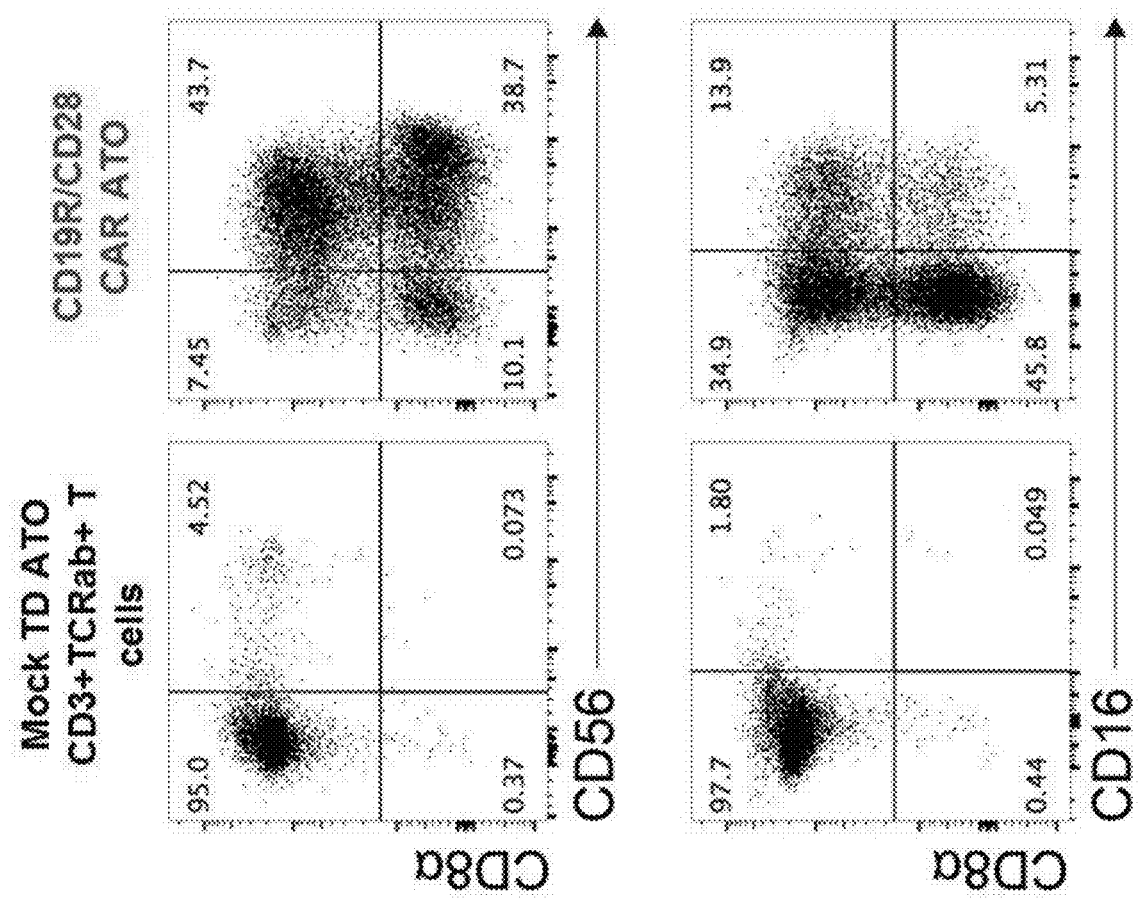

ATO-derived CAR-T cells are either DN or CD8αα+. ATO-derived CAR-T cells (from CD19-specific 2nd generation (CD28/CD3zeta) CAR-transduced CB HSPCs) do not express CD8beta (FIG. 56A), in contrast to conventional T cells from either the human thymus or ATO-derived T cells generated from TCR-transduced HSPCs. They also express markers characteristic of innate-like T cells, including CD56 and CD16 (FIG. 56B). Taken together, ATO-derived CAR-T cells resemble human intraepithelial lyphocytes (IEL).

Figure 57:
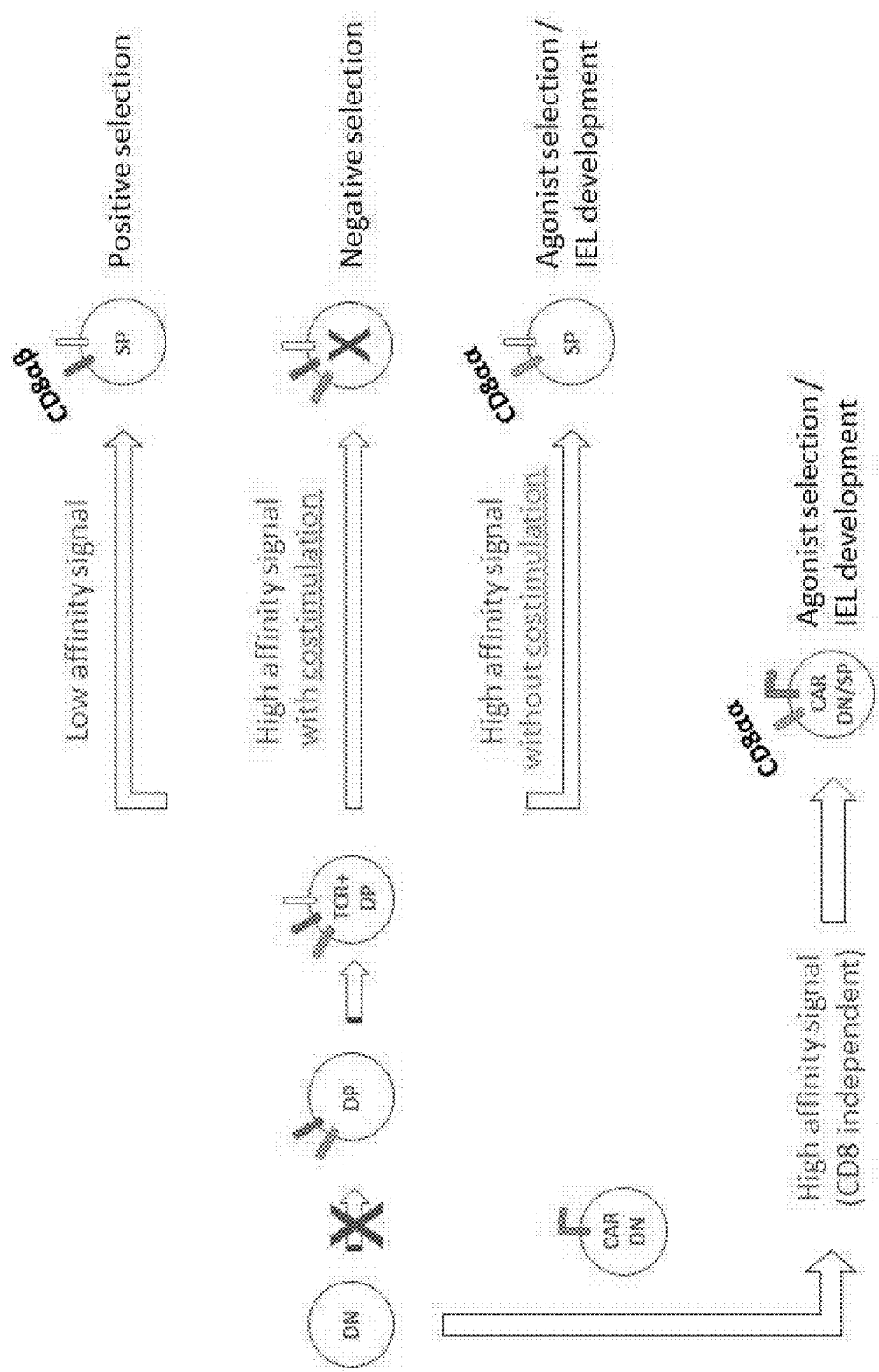
FIG. 57 shows a hypothetical model of CAR-T cell agonist selection in ATOs.

It is hypothesized that that IEL-like CAR-T cell differentiation in ATOs is driven by agonist selection (i.e. strong signaling through the CAR) that occurs through either interaction with cognate antigen in ATOs and/or tonic signaling through the CAR. A strong signaling during early T cell differentiation (e.g. at the DN stage) drives the developing T cell to bypass conventional T cell differentiation and enter non-classical differentiation to an IEL-like lineage (FIG. 57).

Figure 58:
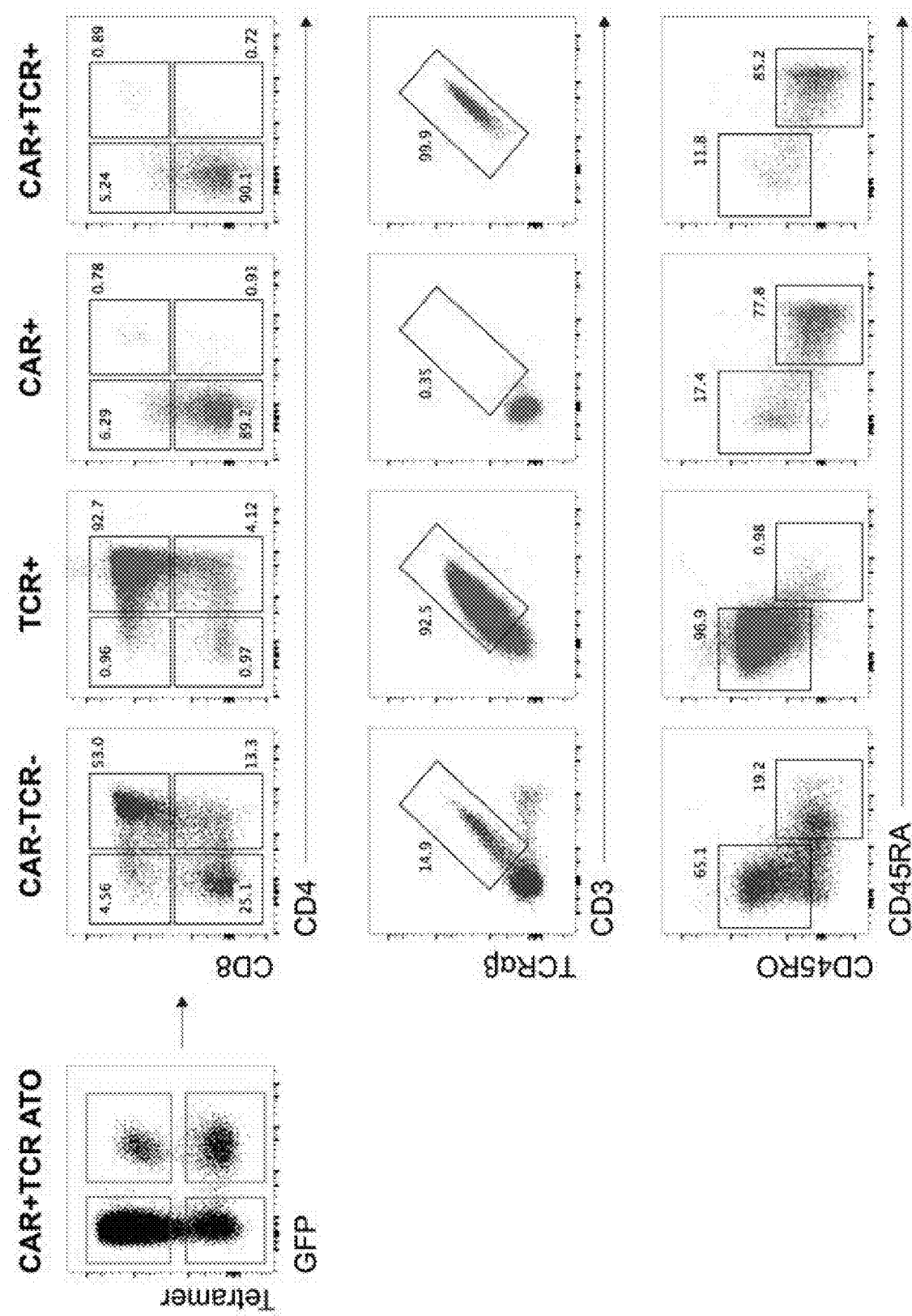
FIG. 58 demonstrates the restoration of CD3/TCR complex expression (but not CD4 or CD8 expression) in CB ATO CAR-T cells by TCR co-transduction.

ATO-derived CAR-T cells can express a TCR when it is co-transduced with a CAR. CB HSPCs co-transduced with a CAR (CD19-specific 2nd generation (CD28/CD3zeta) and/or a TCR (codon-optimized 1G4 TCR) cultured in ATOs for 4 weeks resulted in CAR+ cells (GFP+) that co-express CD3 and the transduced TCR (shown by tetramer staining) (FIG. 58). This is consistent with their identity as T cells (as CD3 subunits are required for TCR expression). Of note, transduction of a TCR does not affect the unconventional, IEL-like differentiation of CAR-T cells in ATOs.

Figure 59:
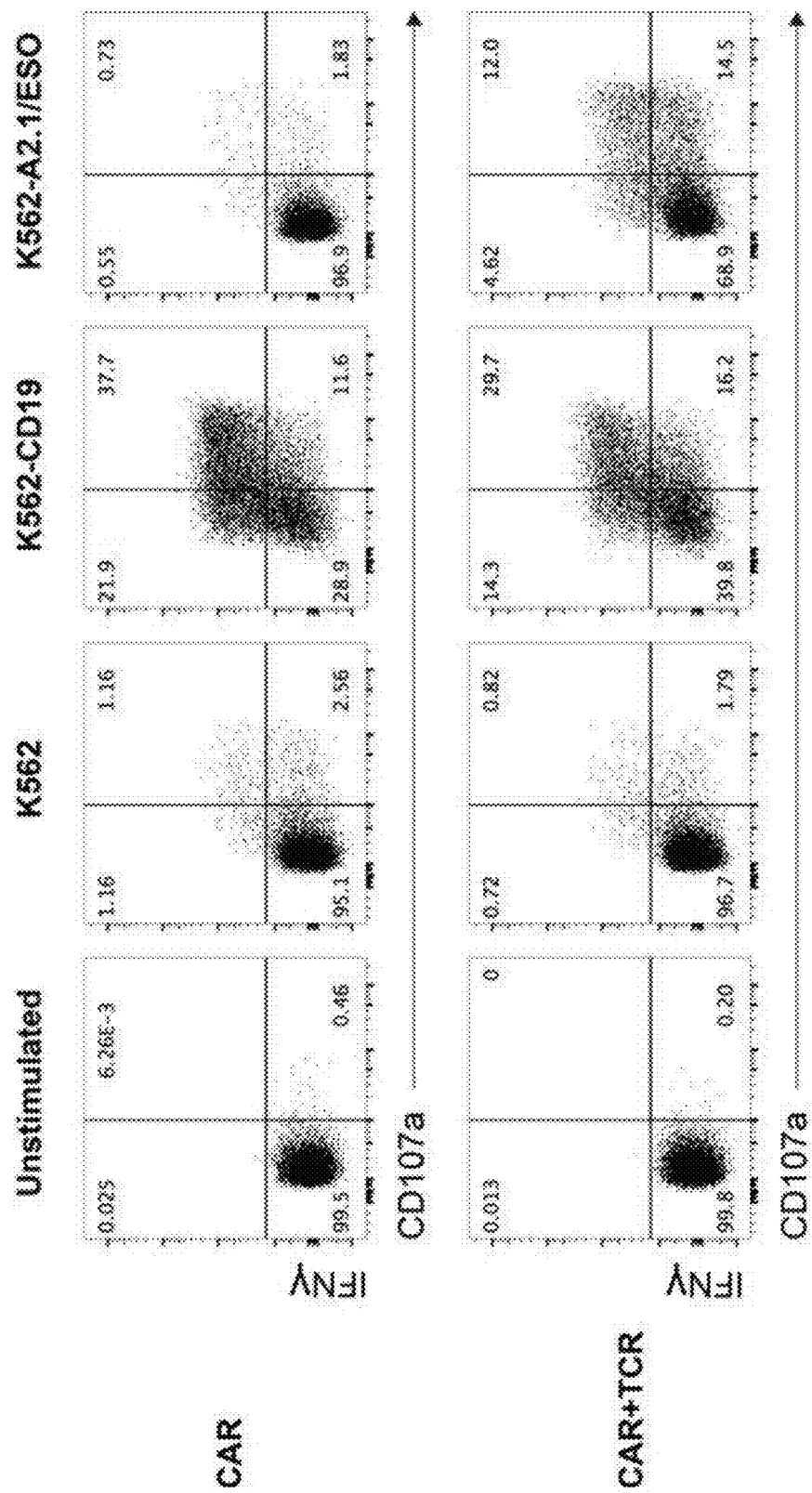
FIG. 59 shows functional TCR reconstitution in CB ATO-derived CAR+TCR+ T cells. ATO-derived CAR-T cells that co-e

ATO-derived CAR-T cells that co-express a transduced TCR are activated by CAR and TCR antigenic signaling. ATO-derived total GFP+ cells generated from CB HSPCs co-transduced with a CAR (CD19-specific 2nd generation (CD28/CD3zeta) or a CAR and TCR (codon-optimized 1G4 TCR) were isolated from week 6 ATOs and co-incubated for 6 hours with non-specific K562 cells, K562 cells transduced with CD19 (CAR targets) or a single-chain trimer of HLA-A*02:01/B2M/NYESO1157-165 (TCR targets). T cell activation was analyzed by intracellular staining for interferon gamma and surface staining for CD107a. T cells from CAR+TCR co-transduced ATOs responded to both CAR and TCR target cells (FIG. 59).

Figure 60:
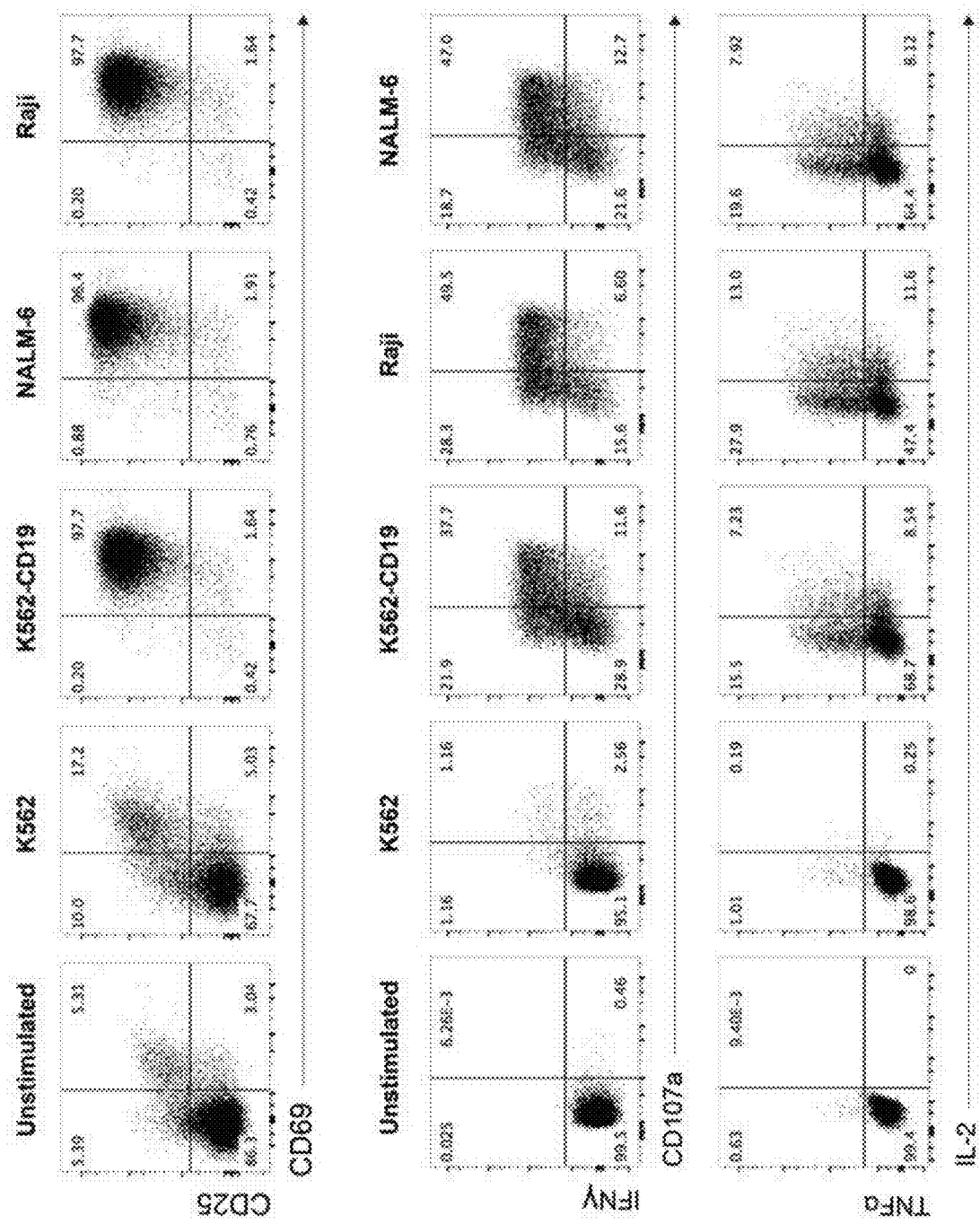
FIG. 60 shows functional analyses of CB ATO-derived CD19 CAR-T cells. Cytokine release and activation of CAR-T cells in response to CD19+ cells (K562 transduced with CD19 vector, Nalm6 and Raji cells) (analysed without additional activation/costimulation).

ATO-derived CD19 CAR-T cells are functional in response to CD19+ cells without additional activation/co-stimulation. ATO-derived total GFP+ cells generated from CB HSPCs transduced with a CAR (CD19-specific 2nd generation (CD28/CD3zeta) were isolated from week 6 ATOs and co-incubated for 6 hours with non-specific K562 cells, K562 cells transduced with CD19 (CAR targets), the CD19+ Nalm-6 leukemia cell line, or the CD19+ Raji lymphoma cell line. T cell activation was analyzed by intracellular staining for interferon gamma, TNFa, and IL-2, and surface staining for CD107a. ATO-derived CAR-T cells underwent activation in response to target cells without the addition of exogenous cytokines (FIG. 60).

Figure 61:
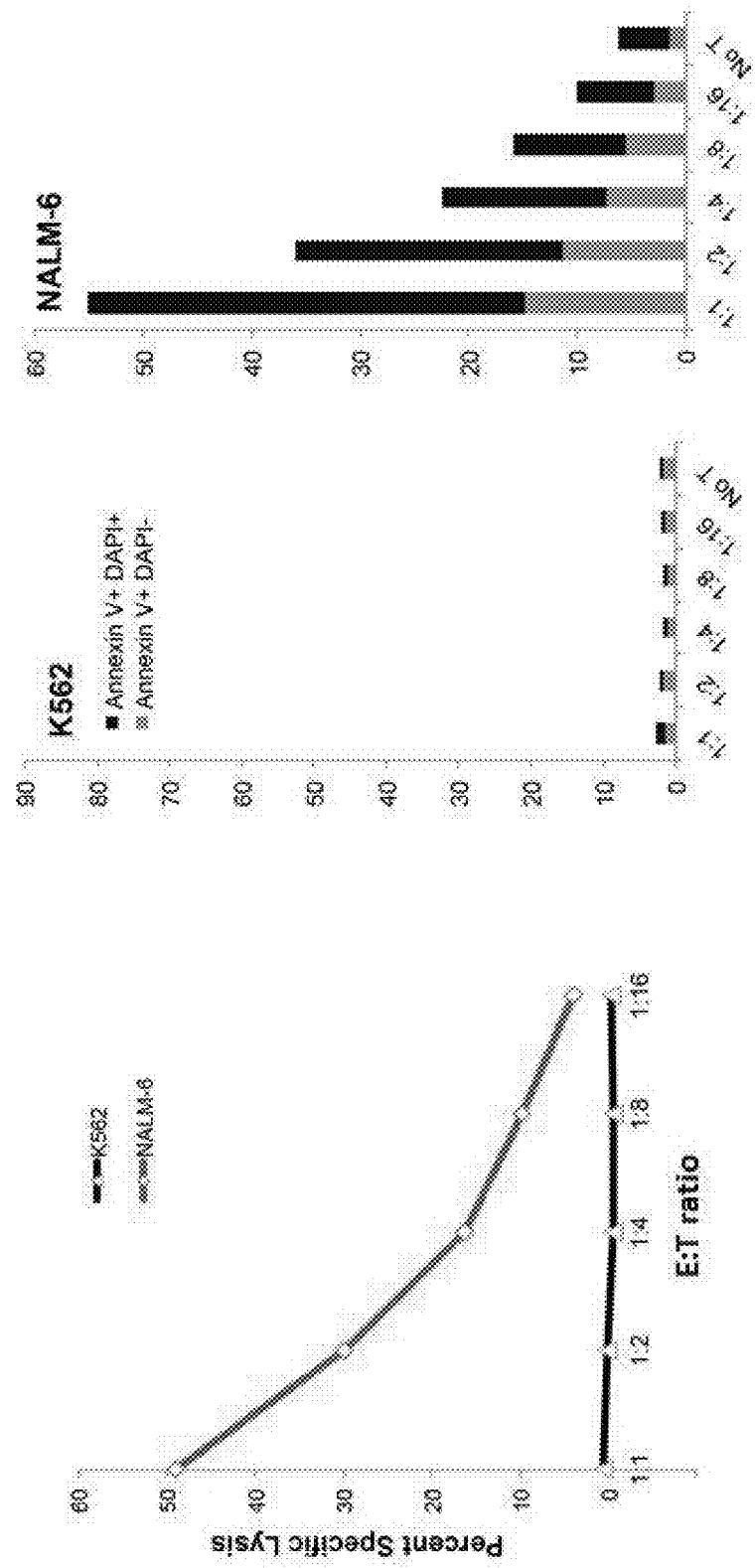
FIG. 61 shows cytotoxicity assay for CB ATO-derived CAR-T cells. CD19+ targets are Nalm6 and CD19− controls are K562 (non-transduced).

FIG. 61 shows that ATO-derived CD19 CAR-T cells are cytotoxic. ATO-derived total GFP+ cells generated from CB HSPCs transduced with a CAR (CD19-specific 2nd generation (CD28/CD3zeta) were isolated from week 6 ATOs were co-incubated for 9 hours with non-specific K562 cells or the CD19+ Nalm-6 leukemia cell line at different effector to target (E:T) ratios. Apoptosis of the tumor cell lines was measured by annexin V/DAPI staining.

Figure 62:
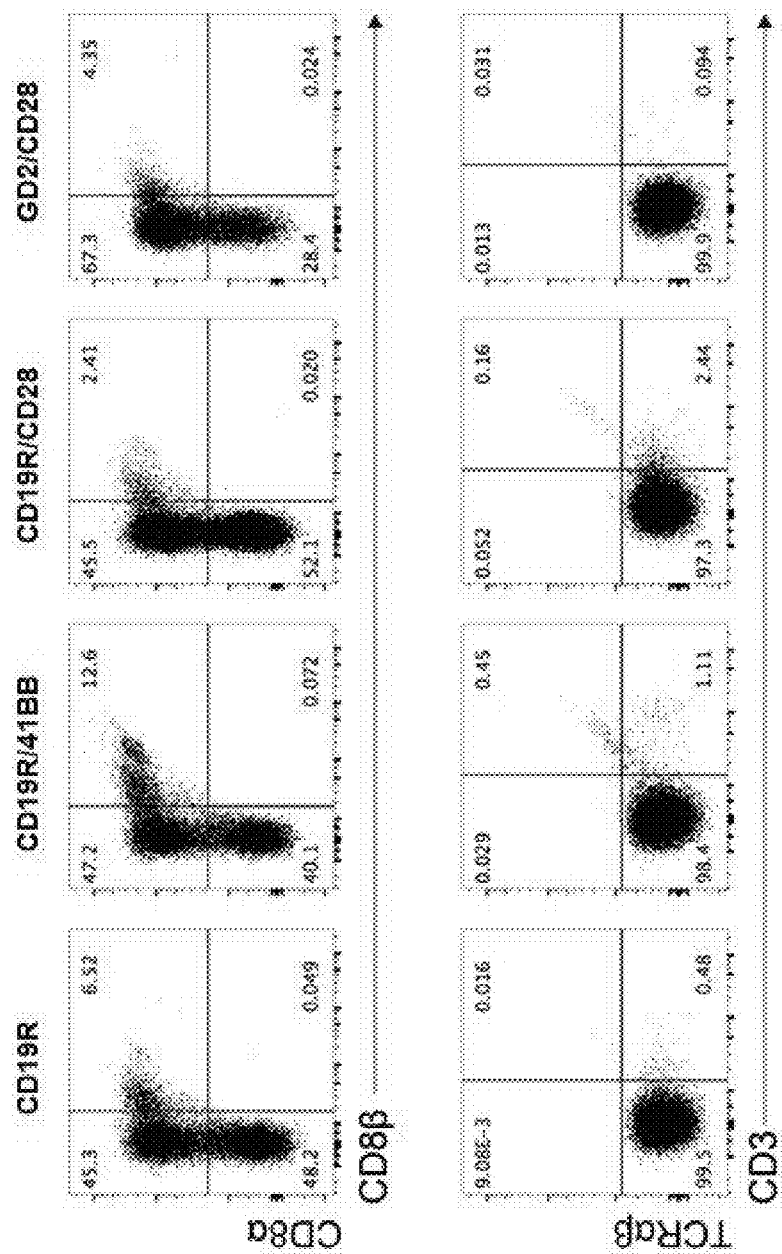
FIG. 62 shows in CB-ATOs that production of IEL-like CD8aa CAR-T cells (presumably through agonist selection) is observed across different coactivation and scFv domains of CAR constructs.

As shown in FIG. 62, IEL-like differentiation (i.e. agonist selection) in ATOs is seen with different CAR constructs. CB HSPCs transduced with different CAR constructs: CD19-specific 1st generation (CD3zeta), 2nd generation (CD28/CD3zeta or 4-1BB/CD3zeta); or a GD2-specific 2nd generation (CD28/CD3zeta) CAR. Differentiation in ATOs was evaluated at 6 weeks (gating on transduced GFP+ cells). Similar IEL-like T cell differentiation was seen with all CAR constructs.

Example 8: CAR-T Cell Differentiation from CAR-Transduced ES Cells in ATOs

ATO-derived CAR-T cells from human ES cells produce cytokines in response to PMA/ionomycin. H1 or H1-CAR derived CD45+ cells from week 5 ATOs were treated with PMA/ionomycin for 6 hours. Activation is shown by intracellular staining for interferon gamma and IL-2.

Figure 63:
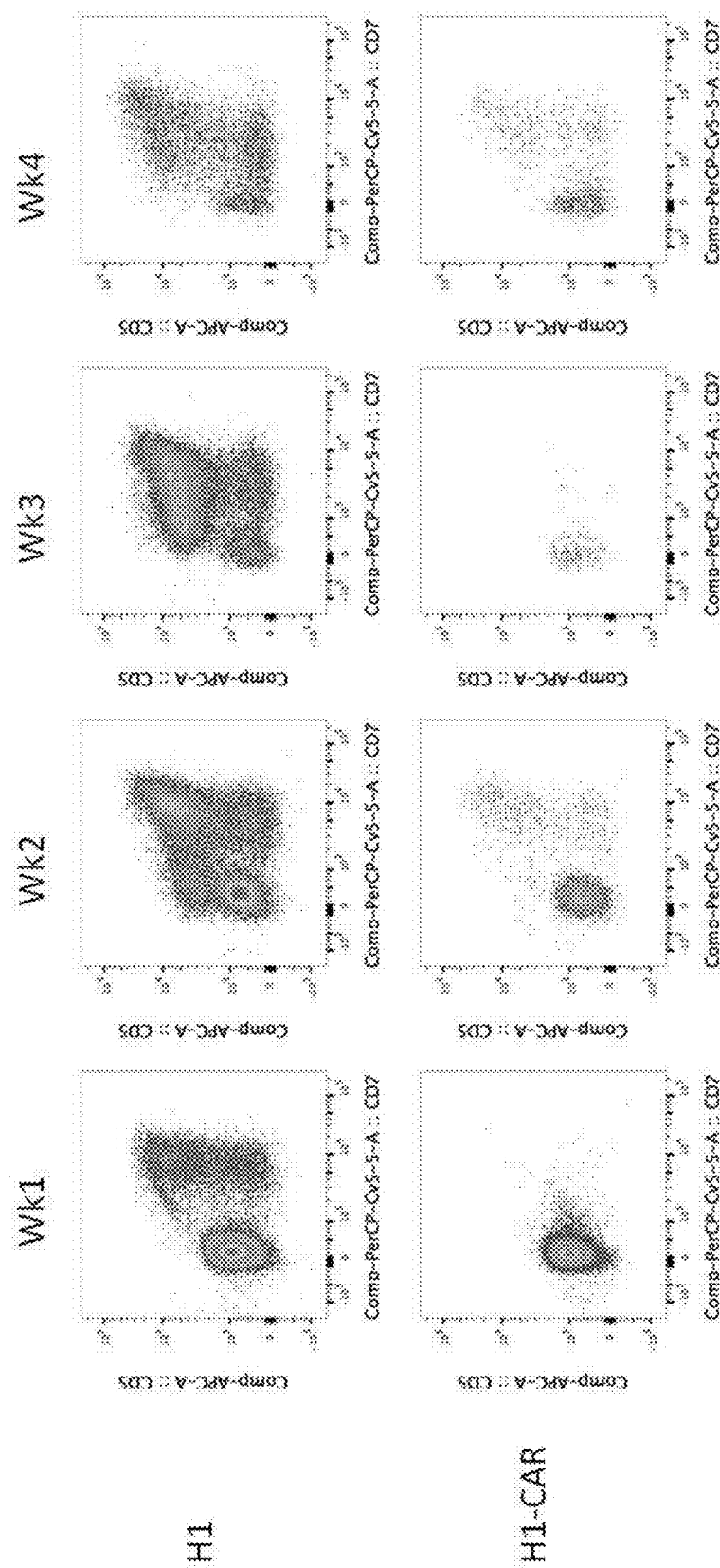
FIG. 63 shows that CAR-transduced human ES cells can generate CAR-T cells in ATOs. Cells are gated on CD45+. Shown are analyses at weeks 1-4 of ATOs from hEMP generated either from non-transduced H1 hESC or CAR-transduced hESC

T cell differentiation from either H1 or H1 cells transduced with a CD19-specific $2^{nd}$ generation (CD26/CD3zeta) CAR. The H1-CAR line was stably transduced with a lentivirus encoding the CAR and eGFP. H1 or H1-CAR cells were differentiated to the hEMP stage as described and sorted hEMPs were aggregated with MS5-hDLL1 cells and differentiated as described (briefly, in EGM2 medium+ TGFbeta inhibition for 1 week, followed by addition of SCF, FLT3L, TPO, and IL-3 for 1 week, followed by media change to RB27 with SCF, FLT3L, and IL-3 for ATO cultures for up to 6 additional weeks. CD45+ cells are shown above from weeks 1-4 following initiation of ATO culture conditions. T lineage differentiation is shown by co-expression of CD5 and CD7. It was found that CAR-transduced human ES cells can generate CAR-T cells in ATOs (FIG. 63).

Figure 64:
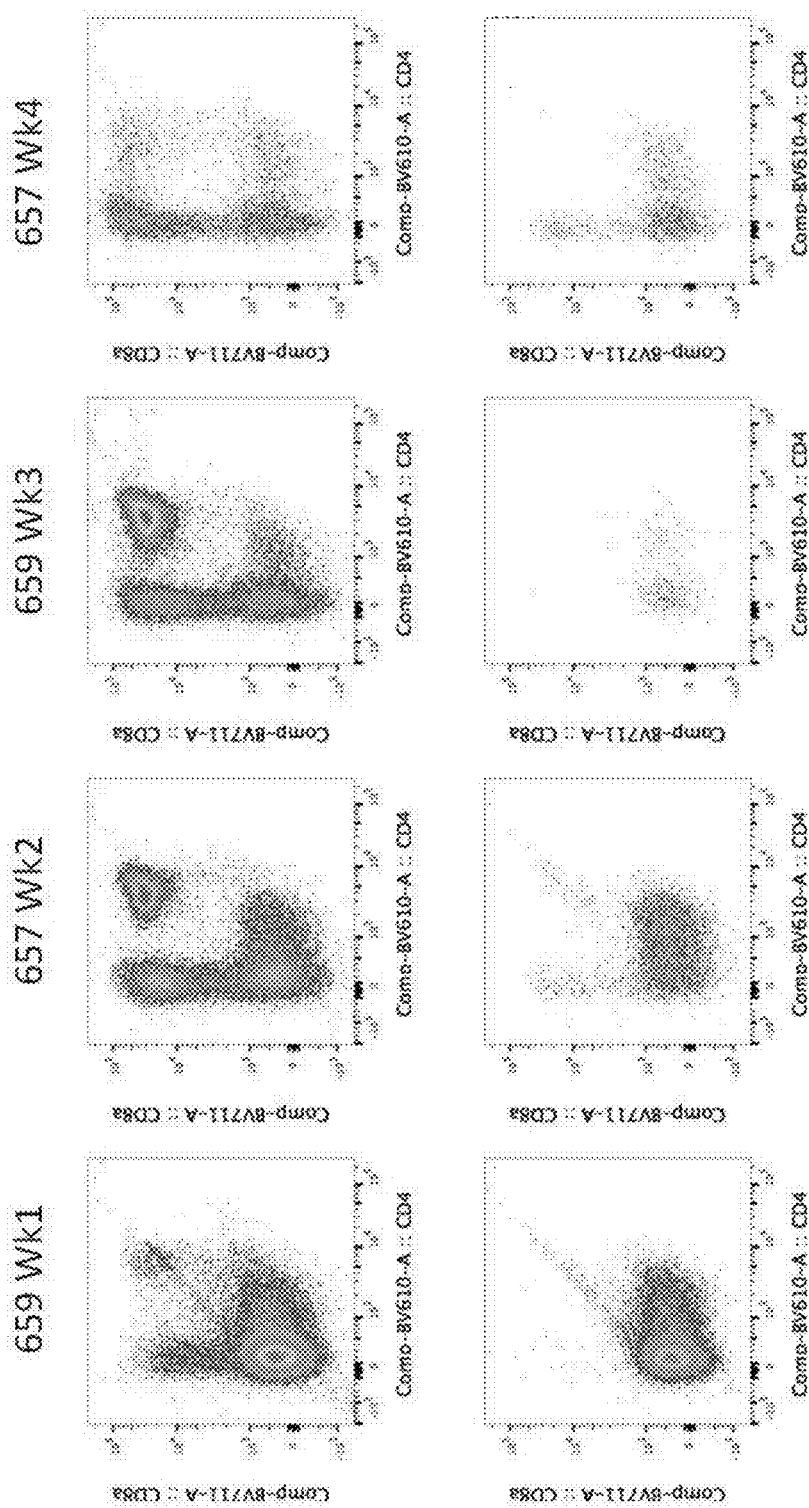
FIG. 64 shows that ATO-derived CAR-T cells from human ES cells exhibit unconventional T cell differentiation. Cells are gated on CD45+. Shown are analyses at weeks 1-4 of ATOs from hEMP generated either from non-transduced H1 hESC or CAR-transduced hESC.
Figure 65:
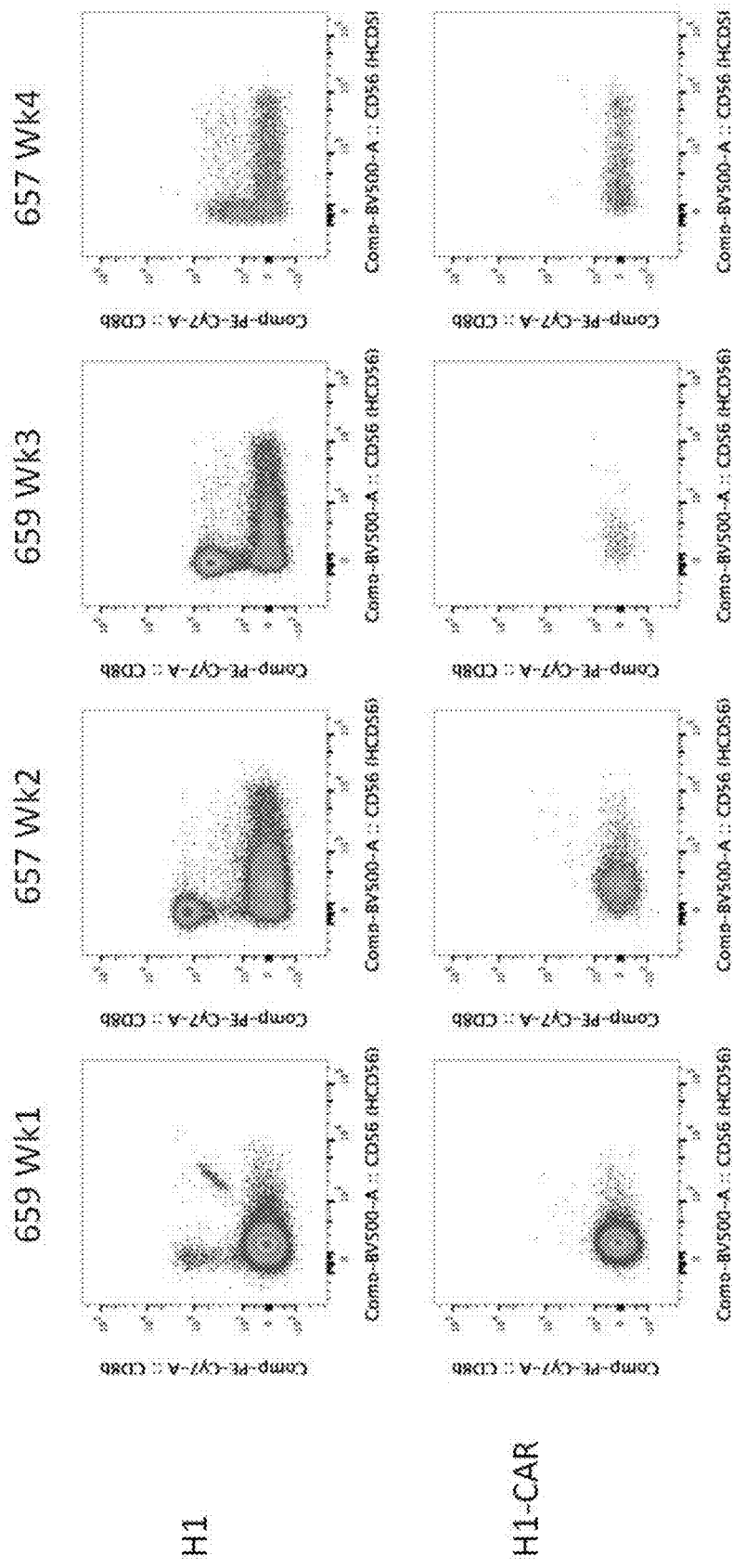
FIG. 65 shows that ATO-derived CAR-T cells from human ES cells do not express CD8beta. Shown are data from two experiments (657 and 659) at time points shown. Cells were generated from hEMP generated either from non-transduced H1 hESC or CAR-transduced hESC and are gated on CD45+
Figure 66A:
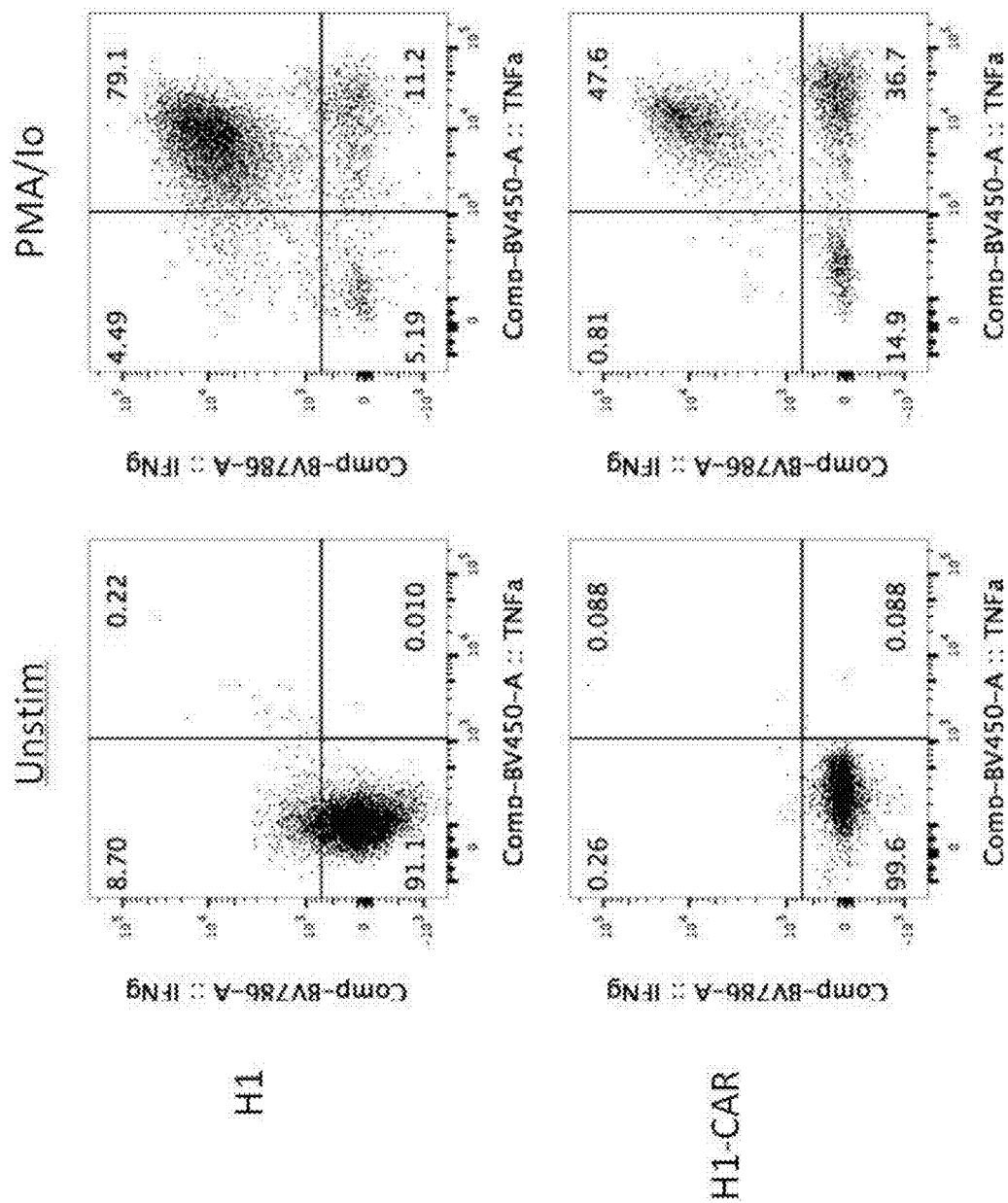
FIG. 66A-B shows that ATO-derived CAR-T cells from human ES cells produce cytokines in response to PMA/ionomycin. Activation is shown by intracellular staining for interferon gamma and TNF alpha in (a) and interferon gamma and IL-2 in (b). The data is from week 5 ATOs.
Figure 66B:
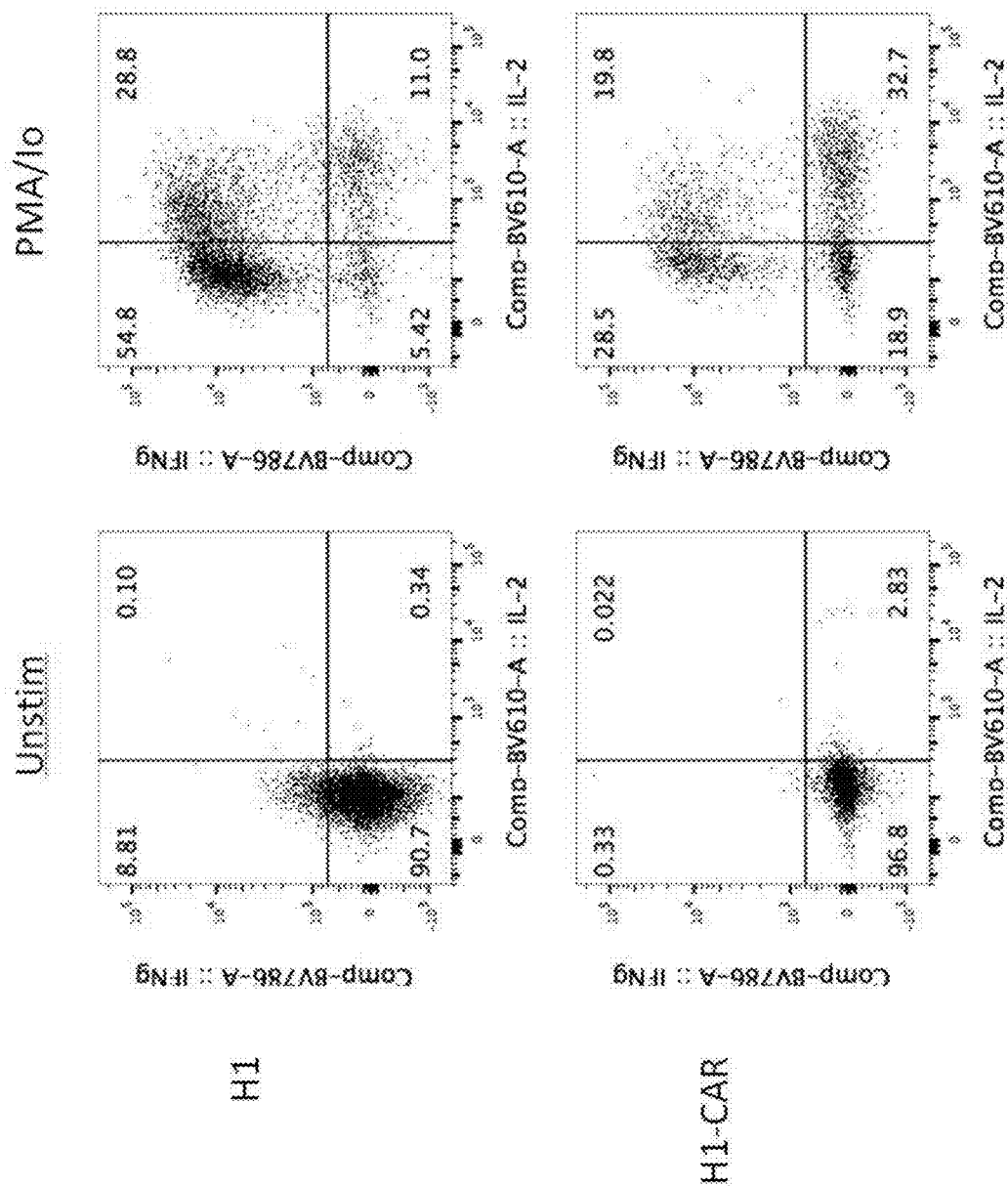
Figure 67:
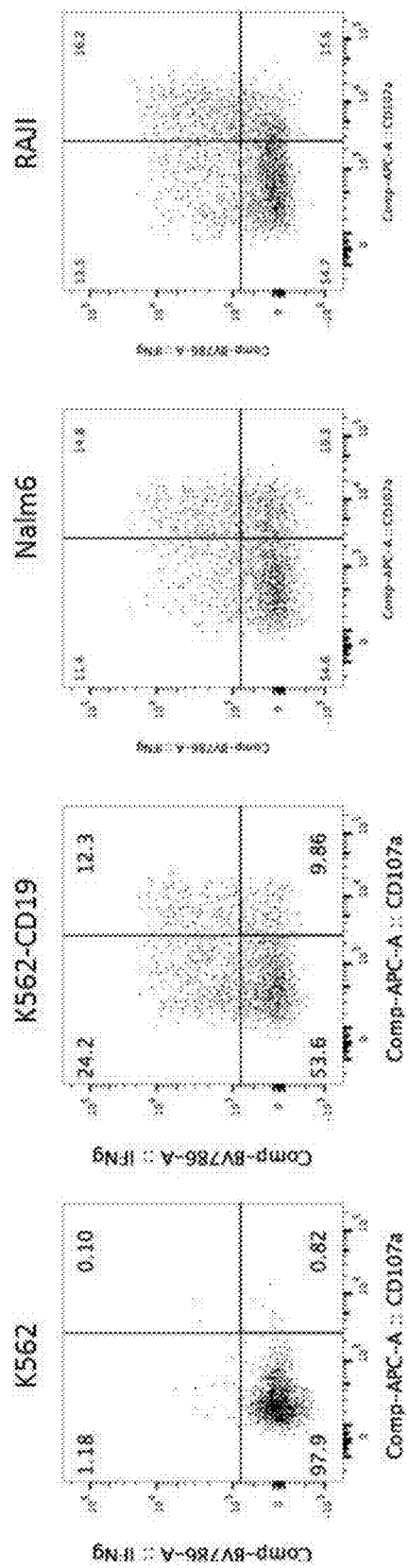
FIG. 67 shows that ATO-derived CAR-T cells from human ES cells produce cytokines and degranulate in response to CD19+ target cells (Cd19+K562, Nalm6, RAJI cells) but not parent (Cd19−) K562 cells. The data is from week 5 hESC-ATOs and cells gated as CD7+CD45RA+.

H1 or H1-CAR derived CD45+ cells from weeks 1-4 following initiation of ATO culture conditions show the absence of normal markers of T cell maturation, similar to CB HSPC ATO derived CAR-T cells. There is an absence of DP-stage T cells, with most cells being DN. $CD4^{dim}$ cells in H1 and H1-CAR ATOs are likely immature single positive CD4 (ISP4) T cell precursors. As shown in FIG. 64, ATO-derived CAR-T cells from human ES cells exhibit unconventional T cell differentiation. As shown in FIG. 65, ATO-derived CAR-T cells from human ES cells do not express CD8beta. H1 or H1-CAR derived CD45+ cells from weeks 1-4 following initiation of ATO culture conditions show the absence of CD8beta, similar to CB HSPC ATO derived CAR-T cells. It was further found that ATO-derived CAR-T cells from human ES cells produce cytokines in response to PMA/ionomycin (FIG. 66A-B). H1 or H1-CAR derived CD45+ cells from week 5 ATOs were treated with PMA/ionomycin for 6 hours. Activation is shown by intracellular staining for interferon gamma and TNF alpha (FIG. 66A) or interferon gamma and IL-2 (FIG. 66B). Last, it was found that ATO-derived CAR-T cells from human ES cells produce cytokines and degranulate in response to target cells (FIG. 67). H1-CAR derived total GFP+ cells from week 4 ATOs were co-cultured with CD19− K562 cells, K562 cells transduced with CD19, or CD19+ Nalm-6 or RAJI cell lines for 6 h. Activation was measured by surface staining for CD107a and intracellular staining for interferon gamma. For analysis, mature phenotype (CD45RA+) CAR-T cells were gated.

Example 9: Advantages of ATO System for T Cell Differentiation

A. Some Advantages of Expressing TCR in HSPC/ATOs Over the Standard Immunotherapy Approach of Transducing Peripheral Blood (PB) T Cells with TCR PB T cells have a pre-existing diverse TCR repertoire when they are transduced to express a specific anti-tumor TCR. Thus mispairing of endogenous TCR chains with the transgenic TCR can occur with autologous cells; this may result in diminished anti-tumor specificity, or the generation of novel, autoreactive mis-paired TCRs. Due to allelic exclusion of endogenous TCRβ rearrangement in ATO-derived TCR-engineered T cells, the risk of mispairing between transduced and endogenous TCR chains should be greatly reduced.

As mentioned above, the expression of a TCR during early T cell differentiation in ATOs leads to allelic exclusion of the endogenous TCRβ chains (see Seet et al). This phenomenon raises the therapeutic possibility of using allogeneic HSPC to generate T cells which will not react against the patient. In contrast, allogeneic T cells from PB could not be used therapeutically as their diverse endogenous TCR repertoire would carry the risk of graft versus host disease (GvHD). Allelic exclusion induced in the ATO system could thus allow the development of off-the-shelf products from allogeneic donors for immunotherapy B. Some Advantages of Expressing Chimeric Antigen Receptors (CARs) in HSPC/ATOs Over the Standard Immunotherapy Approach of Transducing PB T Cells with CAR The usual approach for CART cell therapy is to express CARs in PB. The CART cells so generated thus also express a diverse TCR from endogenous expression. In contrast CAR transduction of HSPC produces T cells with a CD3−TCR− phenotype similar to intra-epthelial lymphocytes (IEL). The absence of TCR expression should prevent GvHD in allogeneic recipients presenting the possibility of a universal product.

C. Advantages of ATOs Over OP9-DL1 to Generate TCR-Engineered T Cells from HSPC

The group of Bart Vandekerckhove in Belgium has used OP9-DL1 to generate immature T cell precursors from either TCR-transduced CD34+ thymic pro-T cells or CD34+ mobilized peripheral blood (MPB) HSPCs (Snauwaert, et. al, *Leukemia*, 2014). In this system, however, <1% of cells were mature CD8+ T cells at day 14 (thymic pro-T) or day 33 (MPB). The majority of TCR-transduced cells were arrested at the DP stage, consistent with the poor ability of OP9-DL1 to support T cell maturation. The present methods produce more mature CD8+ T cells.

D. Advantages of Using ATO Over OP9-DL1 for T Cell Differentiation from Human Pluripotent Stem Cells (hPSC)

OP9-DL1 (or D114) was previously the only system for T cell differentiation from hPSC (either hESC or hiPSC). On OP9-DL1 the cell yield from PSC is very poor and T cell differentiation even worse than with CB HSPC. In contrast, T cell differentiation from hPSCs (both hESC or iPSC) is highly efficient in the ATO system. Mature naïve CD8 and CD4 SP cells are produced even more rapidly from PSC than from CB HSPC. The capacity to produce mature T cells from hPSC means that a truly off-the-shelf, universal product could be readily generated through gene editing of hPSC to remove or replace immune-reactive genes. A single PSC-derived T cell product would be available to multiple potential patients, overcoming the current limitation of time and cost that exists in creating patient specific products. In addition the problem of harvesting sufficient autologous T cells from lymphopenic patients post chemotherapy would be avoided.

E. Comparison of T Cells Differentiated from Cord Blood in ATO System Vs. OP9-DLL1

Figure 68:
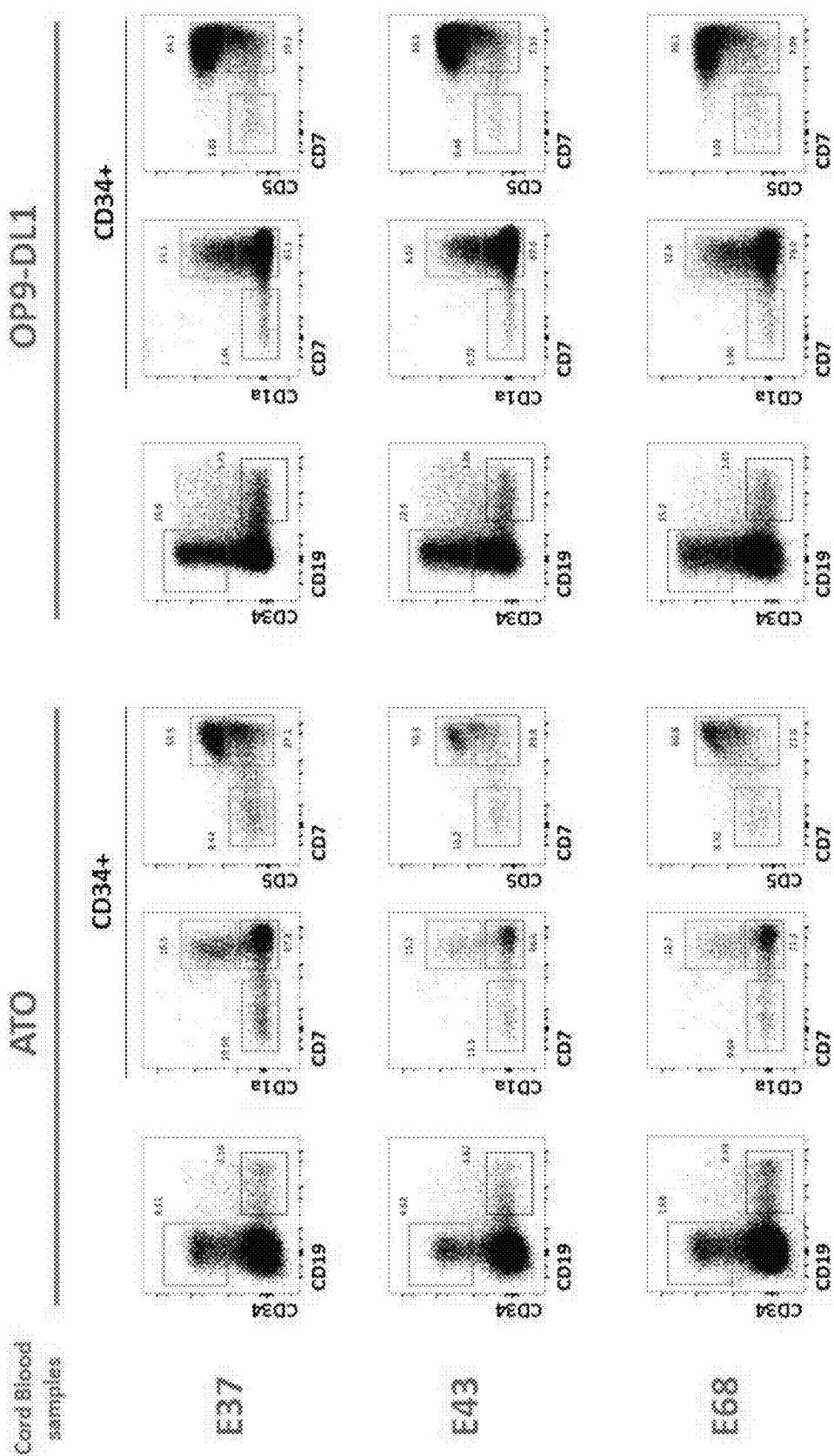
FIG. 68 shows that both the ATO (MS5-DLL1) and monolayer (OP9-DLL1) systems allow for the maintenance of CD34+ T cell progenitors and commitment to CD5+CD7+ T cell precursors. Shown are week 4 CB-ATOs, gated as shown, derived from three different CB samples (E37, E43, E68).
Figure 69:
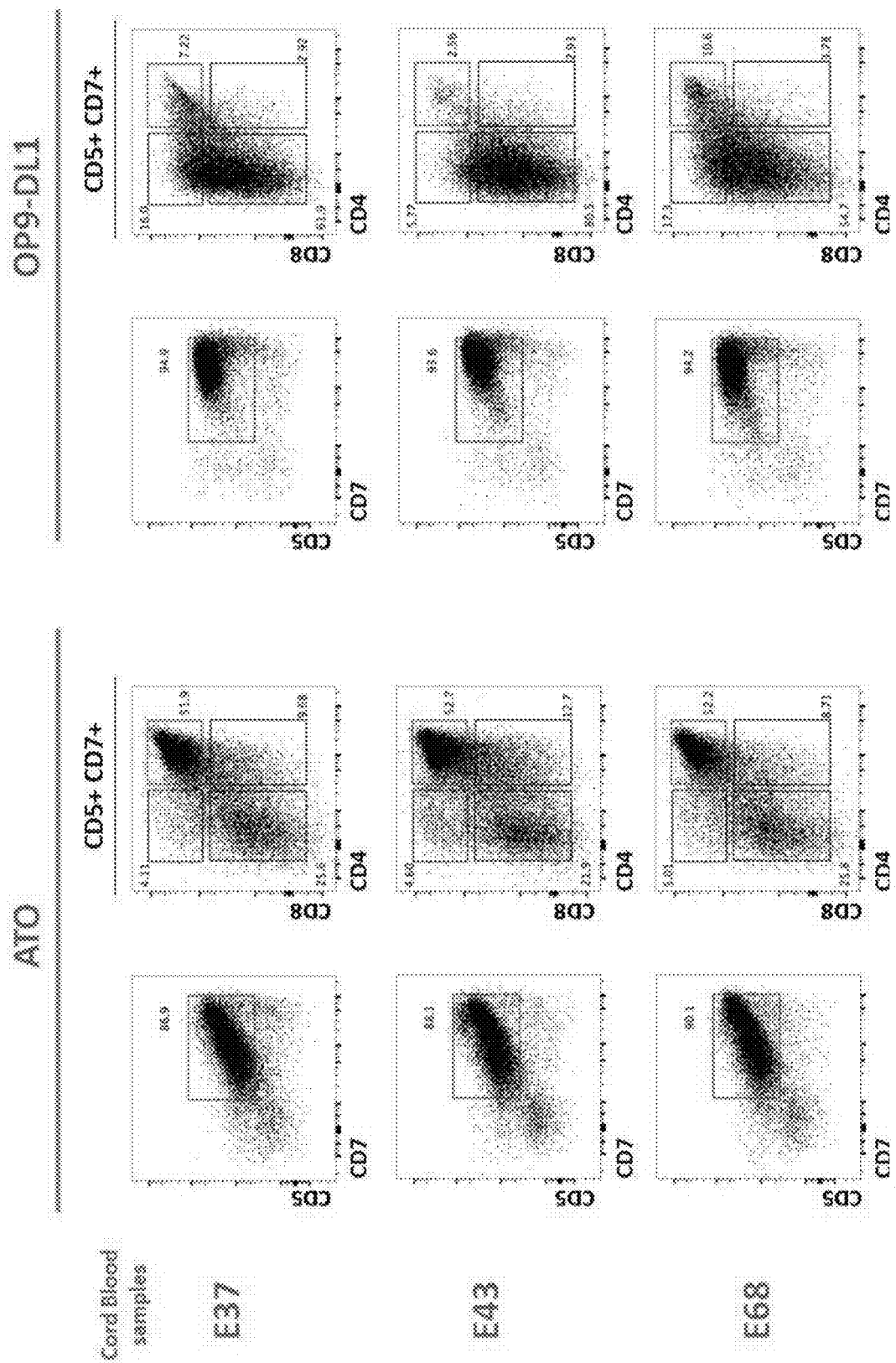
FIG. 69 shows that both the ATO and OP9-DLL1 systems allow the commitment of the cells to the T-cell lineage as sown by the expression of CD5 and CD7. However, the ATO system is highly superior in the generation of CD4+CD8+ Double Positive cells (DP). Shown are week 4 CB-ATOs, gated as shown, derived from three different CB samples (E37, E43, E68).
Figure 70:
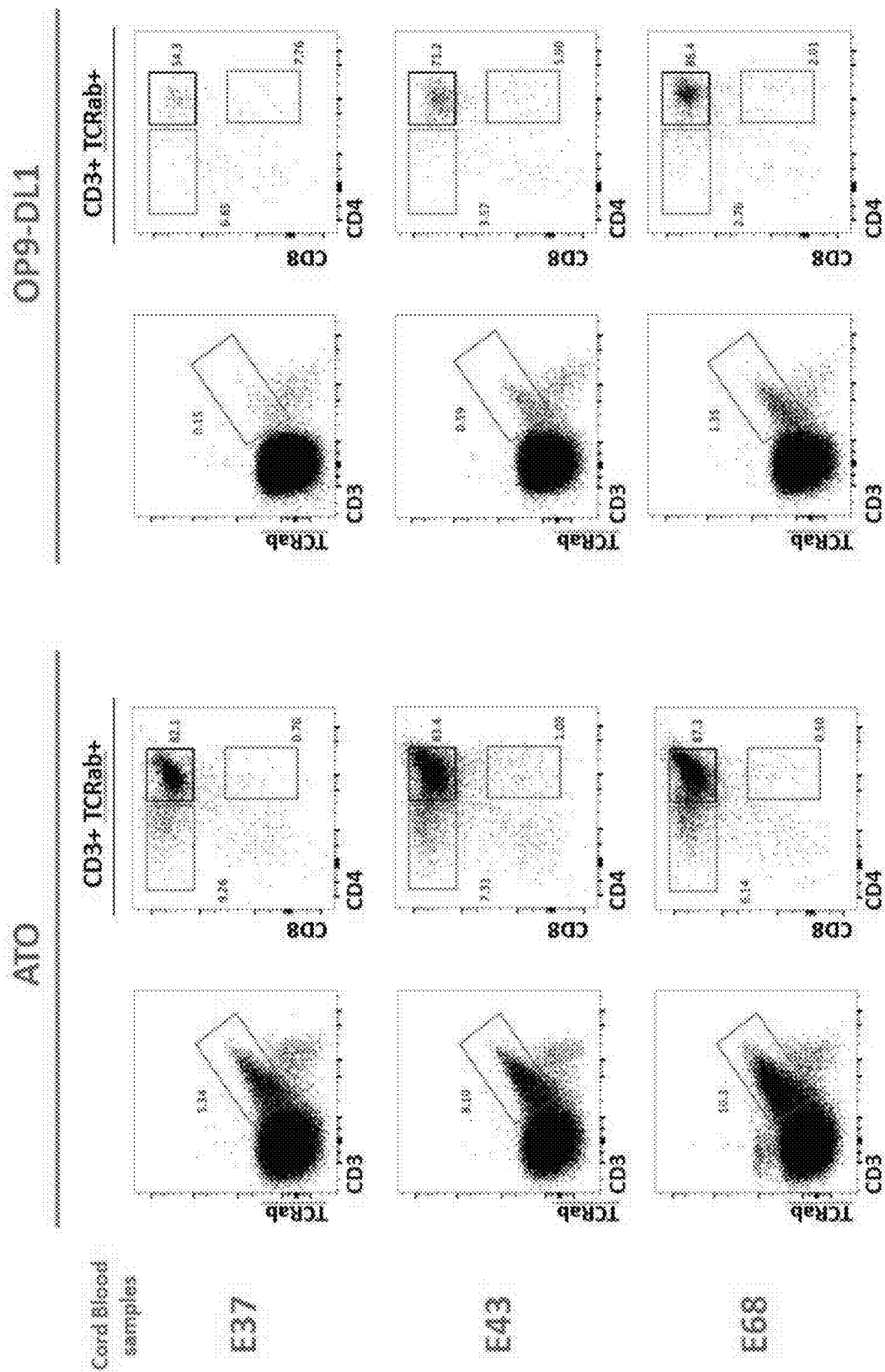
FIG. 70 shows the robust generation of a robust population of TCRab+CD3+ cells which are DP and CD8SP in the CB-ATO system, but not the OP9-DLL1 monolayer system. Shown are week 4 CB-ATOs, gated as shown, derived from three different CB samples (E37, E43, E68).
Figure 71:
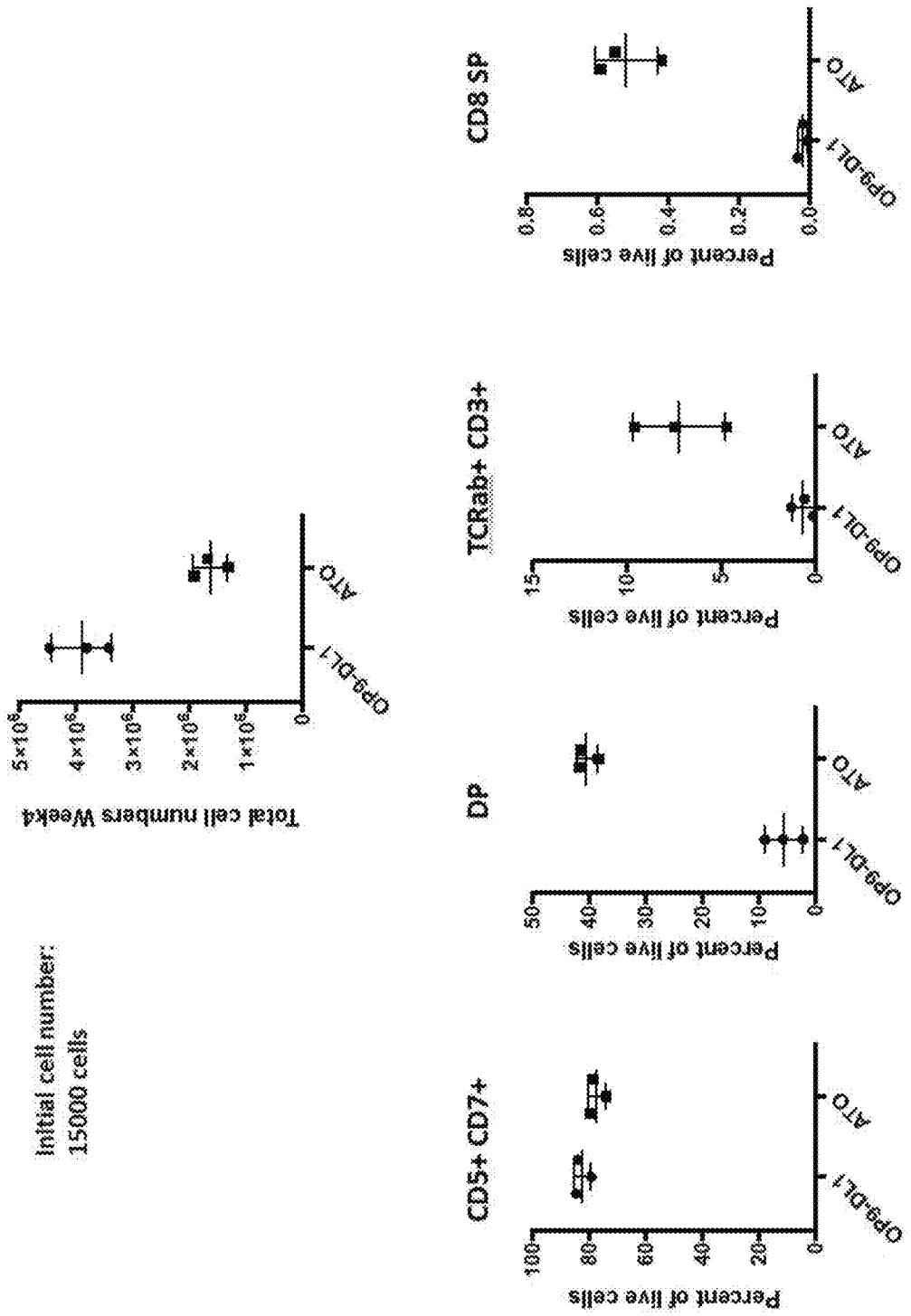
FIG. 71 shows a numerical representation of the data presented in FIG. 70.

Previous examples show the the comparison between the ATO system using CD34+ cord blood cells and MS5-hDLL1 stroma and the current state of the art protocol for in vitro human T cell differentiation: the OP9-Dll1 system. To provide further evidence of the superiority of the ATO system to OP9-DLL1, ATOs from 3 different cord blood donors (E37, E43, E68) were generated and compared to the differentiation on OP9-DLL1 stroma. FIG. 68 shows the maintenance of CD34+ and T cell progenitors in both systems at week 4 (FIG. 68). Both systems allow the commitment of the cells to the T-cell lineage as sown by the expression of CD5 and CD7. However, the ATO system is highly superior in the generation of CD4CD8 Double Positive cells (DP) (FIG. 69). Already at week 4, the ATO system allows the generation of a robust population of TCRab+ CD3+ cells and some of them are already CD8SP, while the OP9-hDLL1 is much more inefficient and the amount of viable cells produced from the OP9-hDLL1 system does not allow for the production of enough T cell for therapeutic and commercial viability (FIG. 70). The numeric representation of the data in FIG. 70 is shown in FIG. 71.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aasen and Belmonte, *Nat. Protoc.*, 5(2):371-382, 2010.
Abboud et al., *Blood*, 58:1148-1154, 1981.
Adams, *J. Virol.*, 61(5):1743-1746, 1987.
Aiyar et al., *EMBO J.*, 17(21):6394-6403, 1998.
Akkina et al., *J. Virol.*, 70(4):2581-2585, 1996.
Alexander et al., *Proc. Nat. Acad. Sci. USA*, 85:5092-5096, 1988.
Altmann et al., *Proc. Natl. Acad. Sci. USA*, 103(38):14188-14193, 2006.
Amit et al., *Dev. Bio.*, 227:271-278, 2000.
Anderson and Jenkinson, J Immunol. 2008 Dec. 1; 181(11): 7435-6.
Andrews et al., In: *Teratocarcinomas and Embryonic Stem Cells*, Robertson (Ed.), IRL Press, 207-246,1987.
*Animal Cell Culture*, Freshney (Ed.), 1987.
Aravind and Landsman, *Nucleic Acids Res.*, 26(19):4413-4421, 1998.
Ausubel et al., Current Protocols in Molecular Biology, Greene Publishing Associates and Wiley Interscience, N.Y., 1994.
Awong, et al, BMC Immunol. 2011 Mar. 23; 12:22.
Baer et al., *Biochemistry*, 39:7041-7049, 2000.
Baer et al., *Nature*, 310(5974):207-211, 1984.
Bain et al., *Biochem. J.*, 408(3):297-315, 2007.
Bennett et al, *J. Biol. Chem.*, 277:34, 2002.
Bertrand et al., *J. Mol Biol.*, 333(2):393-407, 2003.
Bingham, *Cell*, 90(3):385-387, 1997.
Biswas et al., *Annals NY Acad. Sci.*, 590:582-583, 1990.
Biswas, et al., *J. Clin. Microbiol.*, 29:2228-2233, 1991.
Bochkarev et al., *Cell*, 84(5):791-800, 1996.
Bode et al., *Biol. Chem.*, 381:801-813, 2000.
Bode et al., *Gene Ther. Mol. Biol.*, 6:33-46, 2001.
Bode et al., *Science*, 255(5041):195-197,1992.
Bublitz, *Mol. Cell Biochem.*, 108(2):141-4, 1991.
Byrne et al., *Nature*, 450(7169):497-502, 2007.
Carbonelli et al., *FEMS Microbiol. Lett.*, 177(1):75-82, 1999.
Chadwick et al., *Blood*, 102(3):906-15, 2003.
Chandler et al., *Proc. Natl. Acad. Sci. USA*, 94(8):3596-601, 1997.
Chang, et al., *Frontiers in Bioscience*, 12:4393-4401, 2007.
Chaudhuri et al., *Proc. Natl. Acad. Sci. USA*, 98(18):10085-10089, 2001.
Chen and Okayama, *Mol. Cell Biol.*, 7(8):2745-2752, 1987.
Chen et al., *Cell*, 133:1106-1117, 2008.
Chesne et al., In: *Liver Cells and Drugs*, Guillouzo (Ed.), John Libbey Eurotext, London, 343-350, 1988
Chin et al., *Molecular Brain Res.*, 137(1-2):193-201, 2005.
Chow et al., *Cytometry Commun. Clinical Cytometry*, 46:72-78, 2001.
Christ et al., *Haematologica*, 92(9):1165-72, 2007.
Chung, et al, Stem Cells, 2014 September 32:2386-96
Clark et al, J Clin Invest. 2005 November; 115(11):3239-49. Epub 2005 Oct. 13.
Cocea, *Biotechniques*, 23(5):814-816, 1997.
Current Protocols in Molecular Biology and Short Protocols in Molecular Biology, 1987 and 1995.
DaCosta et al., *Molec. Pharmacol.*, 65(3):744-752, 2004.
Davies et al., *Biochem J.*, 351:95-105, 2000.
de Gouville et al., *Drug News Perspective*, 19(2):85-90, 2006.
De Oliveira, et al, Hum Gene Ther. 2013 October; 24(10): 824-39.
deFelipe, *Prog. Brain Res.*, 136:215-38, 2002.
Delaney et al., *Nat. Med.*, 16(2):232-236, 2010.
Dhar et al., *Cell*, 106(3):287-296, 2001.
Doe et al., *J. Pharmacol. Exp. Ther.*, 32:89-98, 2007.

Doevendans et al., *J. Mol. Cell Cardiol.*, 32:839, 2000.
Downey et al., *J. Biol. Chem.*, 271(35):21005-21011, 1996.
Eliasson and Jonsson, *J. Cell Physiol.*, 222(1):17-22, 2010.
Embryonic Stem Cell Differentiation in vitro, 1993.
English et al., *Trends in Pharmac. Sci.*, 23(1):40-45, 2002.
Ercolani et al., *J. Biol. Chem.*, 263:15335-15341,1988.
Ermakova et al., *J. Biol. Chem.*, 271(51):33009-33017, 1996.
Evans et. al., *Nature*, 292:154, 1981.
Evans, et al., In: *Cancer Principles and Practice of Oncology*, Devita et al. (Eds.), Lippincot-Raven, NY, 1054-1087, 1997.
Fauser et al., *Stem Cells*, 1:73-80, 1981
Fechheimer et al., *Proc Natl. Acad. Sci. USA*, 84:8463-8467, 1987.
Fernandes et al., *Nature Cell Biology*, 6:1082-1093, 2004.
Fernandes, et al., *J. Biotechnology*, 132(2):227-236, 2007.
Fischer et al., *J. Virol.*, 71:5148-5146, 1997.
Fraley et al., *Proc. Natl. Acad. Sci. USA*, 76:3348-3352, 1979.
Frame et al, *Biochemical J.*, 359:1-16, 2001.
Frappier and O'Donnell, *Proc. Natl. Acad. Sci. USA*, 88(23): 10875-10879, 1991.
Gahn and Schildkraut, *Cell*, 58(3):527-535, 1989.
Gahn and Sugden, *J. Virol.*, 69(4):2633-2636, 1995.
Garrick et al., *Nat. Genet.*, 18:56-59, 1998.
Gebhart and Wang, *J. Cell Sci.*, 56233-244, 1982.
Gellibert, et al., *J. Med. Chem.*, 49(7):2210-2221, 2006.
Gene Targeting, A Practical Approach, IRL Press at Oxford University Press, 1993.
Gene Transfer Vectors for Mammalian Cells, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Giannoni, et al, Mol Ther. 2013 May; 21(5):1044-54.
Golde et al., *Proc. Natl. Acad. Sci. USA*, 77:593-596, 1980.
Gomez-Lechon et al., *Anal. Biochem.*, 236:296, 1996.
Gopal, *Mol. Cell Biol.*, 5:1188-1190, 1985.
Gould et al, *Intl. J. Neuropsychopharmacology*, 7:387-390, 2004.
Gould et al, *Pharmacological Res.*, 48:49-53, 2003.
Graham and Van Der Eb, *Virology*, 52:456-467, 1973.
Greber et al., *Stem Cells*, 25:455-464, 2007.
Gschweng et al, Cancer Res. 2014 Sep. 15; 74(18):5173-83.
Guide to Techniques in Mouse Development, 1993.
Harb et al., *PLoS One*, 3(8):e3001, 2008.
Harland and Weintraub, *J. Cell Biol.*, 101(3):1094-1099, 1985.
Haugland, In: *Molecular Probes: Handbook of Fluorescent Probes and Research Chemicals*, 1992-1994.
Hegde et al., *Nature*, 359(6395):505-512, 1992.
Hess et al., *Blood*, 104(6):1648-55, 2004.
Hu and Yang, Cell Mol Immunol. 2012 May; 9(3):232-6.
Hung et al., *Proc. Natl. Acad. Sci. USA*, 98(4):1865-1870, 2001.
Igelmund et al., *Pflugers Arch.*, 437:669, 1999.
In vitro Methods in Pharmaceutical Research, Guillouzo (Ed.), Academic Press, 411-431, 1997.
Inman et al., *Molec. Pharmacol.*, 62(1):65-74, 2002.
Ishizaki, et al., *Mol. Pharmacol.*, 57:976-983, 2000.
Itoh, et al, Exp Hematol. 1989 February; 17(2):145-53.
Jainchill et al., *J. Virol.*, 4:549, 1969.
Jenke et al., *Proc. Natl. Acad. Sci. USA*, 101 (31), 11322-11327, 2004.
Julien et al., *Virology*, 326(2):317-328, 0.2004.
Kadaja-Saarepuu et al., *Oncogene*, 27(12):1705-1715, 2008.
Kaeppler et al., *Plant Cell Reports* 9: 415-418, 1990.

Kaminska et al., *Acta Biochimica Polonica*, 52(2):329-337, 2005.
Kanda et al., *Mol. Cell. Biol.*, 21(10):3576-3588, 0.2001.
Kaneda et al., *Science*, 243:375-378, 1989.
Karin et al. *Cell*, 36:371-379,1989.
Kato et al, *J. Biol. Chem.*, 266:3361-3364, 1991.
Keller et al., *Curr. Opin. Cell Biol.*, 7(6):862-9, 1995.
Keller et al., *Curr. Opin. Cell Biol.*, 7:862-869, 1995.
Kennedy and Sugden, *Mol. Cell. Biol.*, 23(19):6901-6908, 2003.
Kennedy et al., *Proc. Natl. Acad. Sci. USA*, 100:14269-14274, 2003.
Kim et al., *J. Biol. Chem.*, 275(40):31245-31254, 2000.
Kim et al., *J. Virol.*, 66:3879-3882, 1992.
Kim et al., *Virology*, 239(2):340-351, 1997.
Kim et al., *Xenobiotica*, 38(3):325-339, 2008.
Kirchmaier and Sugden, *J. Virol.*, 69(2):1280-1283, 1995.
Kirchmaier and Sugden, *J. Virol.*, 72(6):4657-4666, 1998.
Kirkeby et al., *Biochem. Biophys. Meth.*, 24:225, 1992.
Klein et al, *Neoplasia*, 8:1-8, 2006.
Kleinman et al., *J. Biometer. Sci. Polymer Edn.*, 5:1-11, 1993.
Klimanskaya et al., *Lancet.*, 365:P1636-1641, 2005.
Kodama et al., *J. Cell. Physiol.*, 112:89, 1982.
La Motte-Mohs, et al, *Blood.* 2005 Feb. 15; 105(4):1431-9.
Langle-Rouault et al., *J. Virol.*, 72(7):6181-6185, 1998.
Lapenna, et al, *PLoS One.* 2013 Jul. 23; 8(7):e69572.
Leight and Sugden, *Mol. Cell Bio.*, 21:4149-61, 2001.
Levenson et al., *Hum. Gene Ther.*, 9(8):1233-1236, 1998.
Levitskaya et al., *Nature*, 375(6533):685-688, 1995.
Levitskaya et al., *Proc. Natl. Acad. Sci. USA*, 94(23):12616-12621, 1997.
Lindner and Sugden, *Plasmid*, 58:1-12, 2007.
Loh et al., *Blood*, 113(22):5476-5479, 2009.
Ludwig et al., *Nat. Biotechnol.*, 24(2):185-187, 2006b.
Ludwig et al., *Nat. Methods*, 3(8):637-46, 2006a.
Lusis, *Blood*, 57:13-21, 1981.
Macejak and Sarnow, *Nature*, 353:90-94, 1991.
Mackey and Sugden, *Mol. Cell. Biol.*, 19(5):3349-3359, 1999.
Mackey et al., *J. Virol.*, 69(10):6199-6208, 1995.
Maniatis, et al., Molecular Cloning, A Laboratory Manual, Cold Spring Harbor Press, Cold Spring Harbor, N.Y., 1988.
Manipulating the Mouse Embryo A Laboratory Manual, Second Edition, Cold Spring Harbor Laboratory Press, 1994.
Manzini et al., *Proc. Natl. Acad. Sci. USA*, 103(47):17672-17677, 2006.
Marechal et al., *J. Virol.*, 73(5):4385-4392, 1999.
Martin, et al., *Nature Immunology*, 6:111-184, 2005.
Martin, *Proc. Natl. Acad. Sci. USA*, 78:7634, 1981.
Marvin et al., *Genes Dev.*, 15:316, 2001.
Mattingly et al, *J. Pharmacol. Experimen. Therap.*, 316:456-465, 2006.
Meek et al, *BMC Immunol.* 2011 Feb. 18; 12:17.
Middleton and Sugden, *J. Virol.*, 66(1):489-495, 1992.
Miyoshi et al, *J. Biomater. Sci. Polym. Ed.*, 9:227-237, 1998.
Mohtashami et al, *Int Immunol.* 2013 October; 25(10):601-11.
Nabel et al., *Science*, 244(4910):1342-1344, 1989.
Nakajima et al., *Cancer Chemother. Pharmacol.*, 52:319-324, 2003.
Nakano et al., *Science*, 272, 722, 1996.
Nanbo and Sugden, *EMBO J.*, 26:4252-62, 2007.
Narazaki et al., *Circulation*, 118(5): 498-506, 2008.
Ng et al., *Development*, 132(5):873-84, 2005.
Ng, *Nuc. Acid Res.*, 17:601-615,1989.
Nicola, et al., *Blood*, 54:614-627, 1979.
Nicolau and Sene, *Biochim. Biophys. Acta*, 721:185-190, 1982.
Nicolau et al., *Methods Enzymol.*, 149:157-176, 1987.
Niller et al., *J. Biol. Chem.*, 270(21):12864-12868, 1995.
Noble et al, *Proc. Natl. Acad. Science, USA*, 102:6990-6995, 2005.
Ockerman, *Clin. Chim. Acta*, 17:201, 1968.
Ogawa et al., *J. Cell Sci.*, 120:55-65, 2007.
Okabe, *J. Cell. Phys.*, 110:43-49, 1982.
Omirulleh et al., *Plant Mol. Biol.*, 21(3):415-428, 1993.
Palamaro et al, *Int Immunol.* 2013 December; 25(12):703-14.
Passonneau and Lauderdale, *Anal. Biochem.*, 60:405-415, 1974.
PCT Appln. 2005/123902
PCT Appln. WO 1998/30679
PCT Appln. WO 2001/088100
PCT Appln. WO 2001/51616
PCT Appln. WO 2002/076976
PCT Appln. WO 2003/004626
PCT Appln. WO 2003/050251
PCT Appln. WO 2003/059913
PCT Appln. WO 2003/062225
PCT Appln. WO 2003/062227
PCT Appln. WO 2003/062227
PCT Appln. WO 2004/039796
PCT Appln. WO 2005/080554
PCT Appln. WO 2005/123902
PCT Appln. WO 2007113505
PCT Appln. WO 2008/006583
PCT Appln. WO 2008/094597
PCT Appln. WO 2010/0003757
PCT Appln. WO 94/09699
PCT Appln. WO 95/06128
PCT Appln. WO 98/30679
PCT Appln. WO 99/20741
Pelletier and Sonenberg, *Nature*, 334(6180):320-325, 1988.
Piechaczek et al., *Nucleic Acids Res.*, 27(2):426-428, 1999.
Potrykus et al., *Mol. Gen. Genet.*, 199(2):169-177, 1985.
Potter et al., *Proc. Natl. Acad. Sci. USA*, 81:7161-7165, 1984.
Properties and uses of Embryonic Stem Cells: Prospects for Application to Human Biology and Gene Therapy, 1998.
Quitsche et al., *J. Biol. Chem.*, 264:9539-9545,1989.
Rawlins et al., *Cell*, 42((3):859-868, 1985.
Reisman and Sugden, *Mol. Cell. Biol.*, 6(11):3838-3846, 1986.
Reisman et al., *Mol. Cell. Biol.*, 5(8):1822-1832, 1985.
Richards et al., *Cell*, 37:263-272, 1984.
Rinehart et al., *J. Clinical Oncol.*, 22:4456-4462, 2004.
Ring et al., *Diabetes*, 52:588-595, 2003.
Rippe, et al., *Mol. Cell Biol.*, 10:689-695, 1990.
Ritzi et al., *J. Cell Sci.*, 116(Pt 19):3971-3984, 2003.
Rossi et al., *Cell*, 132:681-696, 2008.
Ryan et al., *J. Gen. Virol.*, 78:(Pt 4):699-723, 1997.
Sambrook et al., In: *Molecular cloning: a laboratory manual*, $2^{nd}$ Ed., Cold Spring Harbor Laboratory Press, Cold Spring Harbor, N.Y., 1989.
Sasaki et al., *Pharmacol. Ther.*, 93:225-232, 2002.
Scalia et al., *J. Cell. Biochem.*, 82:610, 2001.
Schaarschmidt et al., *EMBO J.*, 23(1):191-201, 0.2004.
Schaffer et al.; *Gene*, 302(1-2):73-81, 2003.
Schepers et al., *EMBO J.*, 20(16):4588-4602, 2001.
Schmitt, et al, *Nat Immunol.* 2004 April; 5(4):410-7.
Schneider et al., *Genes Dev.*, 15:304, 2001.

Scymczak et al., *Nat. Biotechnol.*, 22(5):589-94 2004.
Sears et al., *J. Virol.*, 77(21):11767-11780, 2003.
Sears et al., *J. Virol.*, 78(21):11487-11505, 2004.
Sheehan and Hrapchak, In: *Theory and Practise of Histotechnology*, 2$^{nd}$ Ed., Battelle Memorial Institute, Columbus, OH, 1987.
Shiojiri, *J. Embryol. Exp. Morph.*, 62:139, 1981.
Shire et al., *J. Virol.*, 73(4):2587-2595, 1999.
Smith, In: Origins and Properties of Mouse Embryonic Stem Cells, *Annu. Rev. Cell. Dev. Biol.*, 2000.
Snauwaert, et al, Leukemia. 2014 April; 28(4):830-41.
Su et al., *Proc. Natl. Acad. Sci. USA*, 88(23):10870-19874, 1991.
Sugden and Warren, *J. Virol.*, 63(6):2644-2649, 1989.
Sun et al., *Proc. Natl. Acad. Sci. USA*, 106(37):15720-15725, 2009.
Sutherland et al., *Exp. Hematol.*, 20:590, 1992.
Suzuki et al., *Cancer Res.*, 67(5):2351-2359, 2007.
Suzuki et al., *Proc. Natl. Acad. Sci. USA*, 103:10294-10299, 2006.
Takahashi and Yamanaka, *Cell.*, 126(4):663-676, 2006.
Takahashi et al., *Cell*, 126(4):663-76, 2007.
Takahashi et al., *Cell*, 131:861-872, 2007.
Thompson, In: *Selected Histochemical and Histopathological Methods*, Tomas (Ed.), Sprungfield, I L, 1966.
Thomson and Marshall, *Curr. Top. Dev. Biol.*, 38:133-165, 1998.
Thomson and Odorico, *Trends Biotechnol.*, 18(2):53-57, 2000.
Thomson et al. *Proc. Natl. Acad. Scie. USA*, 92:7844-7848, 1995.
Thomson et al., *Science*, 282:114, 1998.
Tojo, et al., *Cancer Science*, 96(11):791-800, 2005,
Tur-Kaspa et al., *Mol. Cell Biol.*, 6:716-718, 1986.
U.S. Pat. No. 4,683,202
U.S. Pat. No. 4,684,611
U.S. Pat. No. 4,714,680
U.S. Pat. No. 4,952,500
U.S. Pat. No. 5,302,523
U.S. Pat. No. 5,322,783
U.S. Pat. No. 5,384,253
U.S. Pat. No. 5,464,765
U.S. Pat. No. 5,478,838
U.S. Pat. No. 5,538,877
U.S. Pat. No. 5,538,880
U.S. Pat. No. 5,550,318
U.S. Pat. No. 5,563,055
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,702,932
U.S. Pat. No. 5,728,581
U.S. Pat. No. 5,736,524
U.S. Pat. No. 5,780,448
U.S. Pat. No. 5,789,215
U.S. Pat. No. 5,843,780
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,624
U.S. Pat. No. 6,200,806
U.S. Pat. No. 6,602,711
U.S. Pat. No. 6,833,269
U.S. Pat. No. 7,029,913
U.S. Publn. 2002/0076976
U.S. Publn. 2002/0086005
U.S. Publn. 2002/0168766
U.S. Publn. 2003/0022367
U.S. Publn. 2003/0059913
U.S. Publn. 2003/0062225
U.S. Publn. 2003/0062227
U.S. Publn. 2003/0087919
U.S. Publn. 2003/0125344
U.S. Publn. 2003/0211603
U.S. Publn. 2004/0002507
U.S. Publn. 2004/0039796
U.S. Publn. 20040002508
U.S. Publn. 20040014755
U.S. Publn. 2005/0192304
U.S. Publn. 2005/0209261
U.S. Publn. 2007/0116680
U.S. Publn. 2007/0238170
U.S. Publn. 2008/0038820
U.S. Publn. 2008/0171385
U.S. Publn. 2008/0226558
U.S. Publn. 2008/0254003
U.S. Publn. 20080004287
U.S. Publn. 20080038820
U.S. Publn. 20080226558
U.S. Publn. 20080254003
U.S. Publn. 2009/0047739
Van Coppernolle, et al, J Immunol. 2009 Oct. 15; 183(8): 4859-70.
van der Laarse et al., *Biotech Histochem.* 67:303, 1992.
Van Lent, et al, J Immunol. 2007 Oct. 15; 179(8):4959-68.
Vatakis, et al, Proc Natl Acad Sci USA. 2011 Dec. 20; 108(51):E1408-16.
Vodyanik et al., *Blood*, 108(6):2095-105, 2006.
Wagman, *Current Pharmaceutical Design*, 10:1105-1137, 2004.
Wang et al., *Mol. Cell. Biol.*, 26(3):1124-1134, 2006.
Wang et al., *Nat. Biotechnol.*, 25(3):317-8, 2007.
Watabe and Miyazono, *Cell Res.*, 19:103-115, 2009.
Watanabe et al., *Nat. Neurosci.*, 8(3):288-96, 2005.
Wege, et al, Curr Top Microbiol Immunol. 2008; 324:149-65.
Wilson et al., *Science*, 244:1344-1346, 1989.
Wobus et al., *Ann. N.Y. Acad. Sci.*, 27:752, 1995,
Wong et al., *Gene*, 10:87-94, 1980.
Wrzesinski et al., *Clinical Cancer Res.*, 13(18):5262-5270, 2007.
Wu and Wu, Biochemistry, 27: 887-892, 1988.
Wu and Wu, *J. Biol. Chem.*, 262:4429-4432, 1987.
Wu et al., *J. Virol.*, 76(5):2480-2490, 2002.
Wysokenski and Yates, *J. Virol.*, 63(6):2657-2666, 1989.
Xu et al., *Cell Stem Cell*, 3:196-206, 2008.
Xu et al., *Nat. Biotechnol.*, 19:971-974, 2001.
Yasmineh et al., *Clin. Biochem.*, 25:109, 1992.
Yates and Guan, *J. Virol.*, 65(1):483-488, 1991.
Yates et al., *J. Virol.*, 74(10):4512-4522, 2000.
Yates et al., *Nature*, 313:812-815, 1985.
Yates et al., *Proc. Natl. Acad. Sci. USA*, 81:3806-3810, 1984.
Yates, *Cancer Cells*, (6)197-205, 1988.
Ye et al., *Blood*, 114(27):5473-5480, 2009.
Yin et al., *Science*, 301(5638):1371-1374, 2003.
Ying et al., *Cell*, 115:281-292, 2003.
Ying, *Nature*, 453:519-23, 2008.
Yoshida et al., *Cell Stem Cell*, 5(3):237-41, 2009.
Yu and Thompson, *Genes Dev.* 22(15):1987-97, 2008.

Yu et al., *Science*, 318:1917-1920, 2007.
Yu et al., *Science*, 324(5928):797-801, 2009.
Zhang et al., *Angew. Chem., Int. Ed.*, 48:2542-2545, 2009.
Zhang et al., *Bioorganic Med. Chem. Letters*; 10:2825-2828, 2000.
Zhang, et al., *Zhongguo Xiu Fu Chong Jian Wai Ke Za Zhi.*, 23(1):82-86, 2009.
Zhao, et al, Cancer Res. 2007 Mar. 15; 67(6):2425-9.
Zhou et al., *EMBO J.*, 24(7):1406-1417, 2005

The invention claimed is:

1. A method for preparing a composition of mature CD4$^+$ CD8$^-$, or CD8ab$^+$ CD4$^-$ T cells from stem or progenitor cells, the method comprising culturing a three-dimensional (3D) cell aggregate comprising:
   a) a cell line of stromal cells that express a Notch ligand; and
   b) a population of stem or progenitor cells generated in vitro from embryonic stem cells (ESCs), induced pluripotent stem cells (iPSC), or human embryonic mesodermal progenitor cells;
   wherein the 3D cell aggregate is cultured in a serum-free medium for a time period sufficient for in vitro differentiation of the stem or progenitor cells to mature T cells, wherein the 3D cell aggregate does not comprise an exogenous matrix or a scaffold.

2. The method of claim 1, wherein the Notch ligand is an exogenous Notch ligand.

3. The method of claim 1, wherein the medium further comprises one or more of externally added FLT3 ligand (FLT3L), interleukin 7 (IL-7), stem cell factor (SCF), thrombopoietin (TPO), thrombopoietin (TPO), IL-2, IL-4, IL-6, IL-15, IL-21, TNF-alpha, TGF-beta, interferon-gamma, interferon-lambda, TSLP, thymopentin, pleiotrophin, midkine, or combinations thereof.

4. The method of claim 1, wherein the stromal cells have an exogenous nucleotide sequence encoding an intact, partial or modified Notch ligand, and wherein the Notch ligand is DLL4, DLL1, JAG1, JAG2, or a combination thereof.

5. The method of claim 1, wherein the stromal cells express one or more of an exogenous human major histocompatibility complex (MHC), an exogenous antigen-specific costimulatory molecule or cytokine, an exogenous antigen, an extracellular matrix protein, or a bioactive molecule or gene that modulates T cell differentiation, proliferation, or function.

6. The method of claim 1, wherein the stem or progenitor cells comprise one or more of an exogenous T cell receptor (TCR), a chimeric antigen receptor (CAR), an exogenous invariant natural killer T cell (INKT)-associated TCR, and genetic modification of HLA expression or function.

7. The method of claim 1, wherein the T cells generated from the 3D cell aggregate do not express an endogenous TCR via allelic exclusion or genetic modification, or said T cells comprise an exogenous TCR gene inserted into endogenous TCR gene loci.

8. The method of claim 1, wherein the T cells generated from the 3D cell aggregate express one or both of an exogenous TCR and a CAR.

9. The method of claim 1, wherein the mature T cells are CD3+ TCRab+ CD4+ CD8− or CD3+ TCRab+ CD8ab+ CD4−.

10. The method of claim 1, wherein the mature T cells are CD3+ TCRgd+ CD4+ CD8− or CD3+ TCRgd+ CD8ab+ CD4−.

* * * * *

SEQUENCE LISTING

```
<160> NUMBER OF SEQ ID NOS: 5

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gccacagcac tgttgctctt gaagtcc                                           27

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(5)
<223> OTHER INFORMATION: a, c, t, g, unknown or other

<400> SEQUENCE: 2
nnnnnggcag ggtcagggtt ctggat                                            26

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccaccagctc agctccacgt g                                                 21

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(5)
<223> OTHER INFORMATION: a, c, t, g, unknown or other

<400> SEQUENCE: 4
nnnnngggaa cacsttkttc aggtcctc                                          28

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
```

```
<222> LOCATION: (32)..(32)
<223> OTHER INFORMATION: a, c, t, g, unknown or other

<400> SEQUENCE: 5
tttttttttt tttttttttt tttttttttt vn                              32
```